United States Patent
Hopkins et al.

(10) Patent No.: US 11,129,807 B2
(45) Date of Patent: Sep. 28, 2021

(54) METHODS OF TREATING SCHIZOPHRENIA

(71) Applicant: Sunovion Pharmaceuticals Inc., Marlborough, MA (US)

(72) Inventors: Seth Hopkins, Northborough, MA (US); Kenneth Koblan, Sudbury, MA (US); Antony Loebel, Larchmont, NY (US); Ajay Ogirala, Hopkinton, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

(21) Appl. No.: 16/486,257

(22) PCT Filed: Feb. 16, 2018

(86) PCT No.: PCT/US2018/000078
§ 371 (c)(1),
(2) Date: Aug. 15, 2019

(87) PCT Pub. No.: WO2018/151861
PCT Pub. Date: Aug. 23, 2018

(65) Prior Publication Data
US 2020/0129477 A1 Apr. 30, 2020

Related U.S. Application Data

(60) Provisional application No. 62/459,784, filed on Feb. 16, 2017.

(51) Int. Cl.
*A61K 31/381* (2006.01)
*A61P 25/18* (2006.01)

(52) U.S. Cl.
CPC ............ *A61K 31/381* (2013.01); *A61P 25/18* (2018.01)

(58) Field of Classification Search
CPC .... A61K 31/381; A61K 31/435; A61K 31/55; A61K 45/06; C07D 333/50; C07D 333/54; C07D 333/76; C07D 333/78; A61P 25/18
See application file for complete search history.

(56) References Cited

U.S. PATENT DOCUMENTS

| | | | |
|---|---|---|---|
| 4,021,451 A | 5/1977 | Dobson et al. | |
| 4,021,452 A | 5/1977 | Floyd, Jr. | |
| 4,036,842 A | 7/1977 | Dobson et al. | |
| 4,127,665 A | 11/1978 | Sarges et al. | |
| 4,337,343 A | 6/1982 | Maillard et al. | |
| 5,532,233 A | 7/1996 | Weber et al. | |
| 6,262,044 B1 | 7/2001 | Møller et al. | |
| 6,313,309 B1 | 11/2001 | Baxter et al. | |
| 7,019,026 B1 | 3/2006 | Andersen et al. | |
| 8,710,245 B2 | 4/2014 | Shao | |
| 9,351,954 B2 | 5/2016 | Shao et al. | |
| 10,085,968 B2 | 10/2018 | Shao et al. | |
| 2004/0180883 A1 | 9/2004 | Gilmore | |
| 2004/0220402 A1 | 11/2004 | Chow et al. | |
| 2005/0075366 A1 | 4/2005 | Heidelbaugh et al. | |
| 2005/0187281 A1 | 8/2005 | Hinze et al. | |
| 2006/0047127 A1 | 3/2006 | Arjona | |
| 2006/0148872 A1 | 7/2006 | Chow et al. | |
| 2007/0072926 A1 | 3/2007 | Chow et al. | |
| 2007/0154534 A1* | 7/2007 | Sheitman ............ | A61K 9/0019 424/449 |
| 2008/0081910 A1 | 4/2008 | Sabb et al. | |
| 2008/0113961 A1 | 5/2008 | Nishi et al. | |
| 2008/0255239 A1 | 10/2008 | Chow et al. | |
| 2009/0318690 A1 | 12/2009 | Sasaki et al. | |
| 2010/0035887 A1 | 2/2010 | Ricciardi | |
| 2012/0295881 A1 | 11/2012 | Lange et al. | |
| 2019/0256525 A1 | 8/2019 | Bauer et al. | |
| 2020/0179336 A1 | 6/2020 | Hopkins | |

FOREIGN PATENT DOCUMENTS

| | | |
|---|---|---|
| AU | 2010325925 A1 | 6/2011 |
| AU | 2016200448 A1 | 2/2016 |
| CA | 2031684 A1 | 6/1991 |
| CA | 2781716 A1 | 6/2011 |
| CN | 1300291 A | 6/2001 |
| CN | 101759710 A | 6/2010 |
| CN | 102731574 A | 10/2012 |
| CN | 104193761 A | 12/2014 |
| DE | 3827727 A1 | 2/1990 |
| DE | 4104257 A1 | 8/1992 |
| EP | 333427 A1 | 9/1989 |
| EP | 366327 A1 | 5/1990 |
| EP | 0368175 A1 | 5/1990 |
| EP | 370732 A2 | 5/1990 |
| EP | 416740 A2 | 3/1991 |
| EP | 431945 A2 | 6/1991 |
| EP | 483647 A1 | 5/1992 |
| EP | 0518805 A1 | 12/1992 |
| EP | 555824 A1 | 8/1993 |
| EP | 574313 A1 | 12/1993 |

(Continued)

OTHER PUBLICATIONS

Kay et. al., Schizophrenia Bulletin, 1987, vol. 13(2), pp. 261-276 (Year: 1987).*
Mahableshwarkar et. al., "Replication of a statistical method to reduce pseudospecificity and enhance understanding of score changes among PANSS factors", poster presented at meeting for Int. Soc. for CNS clinical trials and methodology, presented between Aug. 31, 2017-Sep. 2, 2017 (Year: 2017).*

(Continued)

*Primary Examiner* — Sarah Pihonak
(74) *Attorney, Agent, or Firm* — Philip Hansen

(57) ABSTRACT

Provided herein are methods for determining if a compound has potential efficacy for the treatment for a specific symptom domain of schizophrenia, such as for example, the treatment of a negative symptom of schizophrenia. In addition, provided herein are methods of determining the prominent symptom domain of a subject suffering from schizophrenia. Further, provided herein are various methods for the treatment of the negative symptoms, cognitive dysfunction symptoms, or both, associated with schizophrenia comprising administering to a subject a therapeutically or prophylactically effective amount of various compounds.

22 Claims, 6 Drawing Sheets

(56) References Cited

FOREIGN PATENT DOCUMENTS

Figure 1:
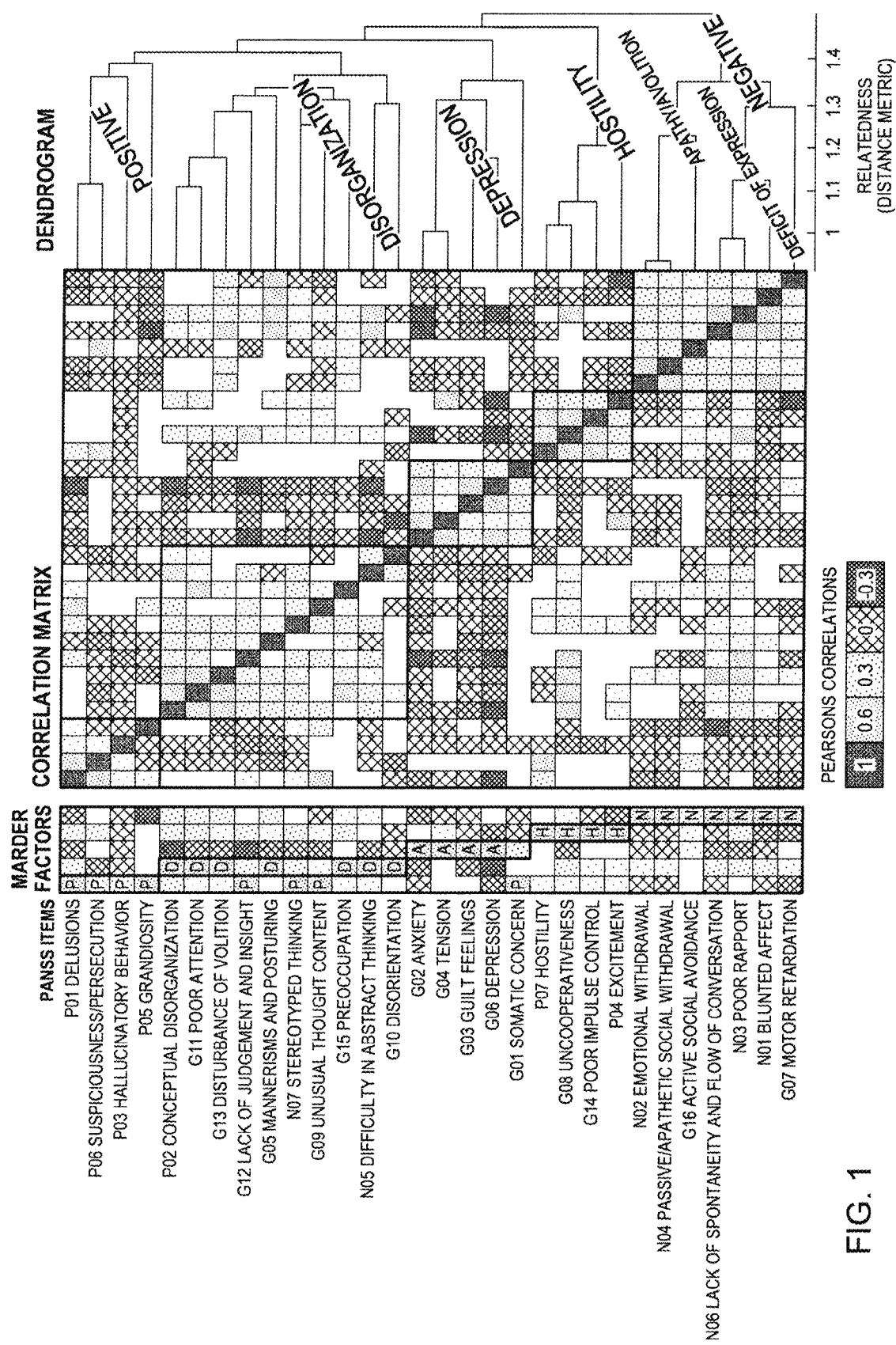

| | | |
|---|---|---|
| EP | 600836 A2 | 6/1994 |
| EP | 745598 A1 | 12/1996 |
| EP | 1634873 A1 | 3/2006 |
| EP | 1829869 A1 | 9/2007 |
| EP | 1982714 A1 | 10/2008 |
| EP | 1982987 A1 | 10/2008 |
| EP | 2377850 A1 | 10/2011 |
| FR | 2875230 A1 | 3/2017 |
| JP | 54109975 A | 8/1979 |
| JP | S567772 A | 1/1981 |
| JP | 2243691 A | 9/1990 |
| JP | 4009367 A | 1/1992 |
| JP | 03163068 B2 | 5/2001 |
| JP | 03223277 B2 | 10/2001 |
| JP | 2003261566 A | 9/2003 |
| JP | 2004269449 A | 9/2004 |
| JP | 2005145859 A | 6/2005 |
| JP | 2005523925 A | 8/2005 |
| JP | 2006117568 A | 5/2006 |
| JP | 2008530229 A | 8/2008 |
| JP | 2009505948 A | 2/2009 |
| JP | 2015227348 A | 12/2015 |
| JP | 6333382 B2 | 5/2018 |
| MX | 2012006326 A | 10/2012 |
| RU | 2128649 C1 | 4/1999 |
| SG | 181498 A1 | 7/2012 |
| WO | 9108205 A1 | 6/1991 |
| WO | 9203434 A1 | 3/1992 |
| WO | 9215592 A1 | 9/1992 |
| WO | 9400441 A1 | 1/1994 |
| WO | 9604287 A1 | 2/1996 |
| WO | 9946237 A1 | 9/1999 |
| WO | 9946267 A1 | 9/1999 |
| WO | 0023445 A1 | 4/2000 |
| WO | 2000023445 | 4/2000 |
| WO | 0035915 A1 | 6/2000 |
| WO | 2000035915 | 6/2000 |
| WO | 0043397 A1 | 7/2000 |
| WO | 2000043397 | 7/2000 |
| WO | 0068230 A1 | 11/2000 |
| WO | 2000068230 | 11/2000 |
| WO | 0117516 A2 | 3/2001 |
| WO | 0119831 A1 | 3/2001 |
| WO | 2001017516 | 3/2001 |
| WO | 2001019831 | 3/2001 |
| WO | 0132610 A1 | 5/2001 |
| WO | 0132655 A2 | 5/2001 |
| WO | 2001032610 | 5/2001 |
| WO | 0212189 A1 | 2/2002 |
| WO | 2002012189 | 2/2002 |
| WO | 0222614 A1 | 3/2002 |
| WO | 2002022614 | 3/2002 |
| WO | 02102387 A1 | 12/2002 |
| WO | 03006455 A1 | 1/2003 |
| WO | 03035065 A1 | 5/2003 |
| WO | 03092374 A2 | 11/2003 |
| WO | 2004004726 A1 | 1/2004 |
| WO | 2004035812 A2 | 4/2004 |
| WO | 2004066912 A2 | 8/2004 |
| WO | 2004078723 A1 | 9/2004 |
| WO | 2004082687 A1 | 9/2004 |
| WO | 2004087680 A1 | 10/2004 |
| WO | 2005072412 A2 | 8/2005 |
| WO | 2005073236 A2 | 8/2005 |
| WO | 2005087779 A1 | 9/2005 |
| WO | 2006014135 A1 | 2/2006 |
| WO | 2006014136 A1 | 2/2006 |
| WO | 2006015259 A2 | 2/2006 |
| WO | 2006030124 A1 | 3/2006 |
| WO | 2006053274 A2 | 5/2006 |
| WO | 2006089053 A2 | 8/2006 |
| WO | 2007001939 A1 | 1/2007 |
| WO | 2007002681 A2 | 1/2007 |
| WO | 2007006546 A1 | 1/2007 |
| WO | 2007095586 A2 | 8/2007 |
| WO | 2007102999 A2 | 9/2007 |
| WO | 2007126041 A1 | 11/2007 |
| WO | 2008042422 A2 | 4/2008 |
| WO | 2008048981 A2 | 4/2008 |
| WO | 2008058342 A1 | 5/2008 |
| WO | 2008155132 A1 | 12/2008 |
| WO | 2009009550 A1 | 1/2009 |
| WO | 2009067202 A1 | 5/2009 |
| WO | 2009068467 A1 | 6/2009 |
| WO | 2009072621 A1 | 6/2009 |
| WO | 2009085256 A1 | 7/2009 |
| WO | 2010053583 A2 | 5/2010 |
| WO | 2010092180 A1 | 8/2010 |
| WO | 2010092181 A1 | 8/2010 |
| WO | 2011036889 A1 | 3/2011 |
| WO | 2011060035 A1 | 5/2011 |
| WO | 2011060217 A1 | 5/2011 |
| WO | 2011/069063 A2 | 6/2011 |
| WO | 2011069063 A2 | 6/2011 |
| WO | 2011081205 A1 | 7/2011 |
| WO | 2011133729 A2 | 10/2011 |
| WO | 2012020133 A1 | 2/2012 |
| WO | 2012122340 A1 | 9/2012 |
| WO | 2013010453 A1 | 1/2013 |
| WO | 2018151861 | 8/2018 |
| WO | 2019161236 A1 | 8/2019 |
| WO | 2019161238 A1 | 8/2019 |
| WO | 2020118032 A1 | 6/2020 |
| ZA | 9102744 A | 2/1992 |

OTHER PUBLICATIONS

International Search Report and Written Opinion issued in PCT/US2018/000078, dated Jun. 7, 2018.
Koblan et al. "A Non-D2-Receptor-Binding Drug for the Treatment of Schizophrenia" The New England Journal of Medicine, vol. 382, No. 16, pp. 1497-1506. Apr. 16, 2020.
Dedic, Sep-363856, a Novel Psychotropic Agent with the Unique, Non-D2 Receptor Mechanism of Action, The Journal of Pharmacology and Experimental Therapeutics, htt://jpet.aspetjournals.org/content/suppl/2019/08/01/jpet.119.260281.DC1 Oct. 2019.
International Search Report and Written Opinion in International Application No. PCT/US2019/064646 dated Mar. 9, 2020.
Torrado et al. "Novel Selective and Potent 5-HT Reuptake Inhibitors with 5-HT1D Antagonist Activity: Chemistry and Pharmacological Evaluation of a Series of Thienopyran Derivatives", Bioorganic & Medicinial Chemistry, 12(20), pp. 5277-5295. Oct. 15, 2004.
Vecchietti et al. "(1 S)-1-(Aminomethyl)-2-(arylacetyl)-1,2,3,4-tetrahydroisoquinoline and Heterocycle-Condensed Tetrahydropyridine Derivatives: Members of a Novel Class of Very Potent K Opioid Analgesics", Journal of Medicinal Chemistry, vol. 34, No. 8, pp. 2624-2633. 1991.
PubChem CID 4878038 (search date Feb. 22, 2019). Sep. 17, 2005.
PubChem CID 4878041 (search date Feb. 22, 2019). Sep. 17, 2005.
Ross et al., "α2 Adrenoceptor Agonists as Potential Analgesic Agents. 2. Discovery of 4-(4-Imidazo)-1,3-dimethyl-6,7-dihydrothianaphthene as a High-Affinity Ligand for the β2D Adrenergic Receptor", J. Med. Chem., vol. 43, pp. 1423-1426. 2000.
Frohlich et al., "A Novel Synthesis of 3,3-(Spiro)Substituted Azetidines", Heterocycles, vol. 37, No. 3, pp. 1897-1891. 1994.
Datta et al., "Studies in Sulphur Heterocycles. Part 5. Further Use of 6,7-Dihydribenzo[b]thiphen-4[5H]-one in the Synthesis of Substitited Benzo[b]thiophene Derivatives", J. Chem. Research (S), pp. 72-73. 1988.
Stanetty et al., "Heterocyclische Spiroverbindungen Spiroverbindungen: Spiro [benzo[b]thiophen-4(5H),3'-pyrrolidine]", Arch. Pharm. vol. 317, pp. 168-176. 1984.
Devani et al., "Synthesis of 2-Aminothiophenes & Thieno[2,3-d]pyrimidines", Indian Journal of Chemistry, vol. 14B, pp. 357-360. May 1976.
Fujima, et al., Synthesis of (S)-3-(N-Methylamino)-1-(2-thienyl)propan-1-ol: Revisiting Eli Lilly's Resolution-Racemization-Recycle Synthesis of Duloxetine for Its Robust Processes, Organic Process Research & Development, vol. 10, No. 5 2006.

(56) References Cited

OTHER PUBLICATIONS

International Search Report and Written Opinion issued in PCT/US2019/018265 dated Jun. 18, 2019.
Caira "Crystalline Polymorphism of Organic Compounds" Topics in Current Chemistry, vol. 198. Jan. 1, 1998.
International Search Report in International Application No. PCT/US2019/018263 dated Apr. 2, 2019.
International Search Report in International Application No. PCT/US2018/000078. dated Mar. 25, 2018.
Unpublished U.S. Appl. No. 16/704,202 to Hopkins. Dec. 5, 2019.
Unpublished International Application No. PCT/US2019/064646 to Hopkins. Dec. 5, 2019.
Deakin et al. "A Phase 1 Functional Neuroimaging Study of Sep 363856 in Healthy Volunteers With High or Low Schizotype", American College of Neuropsychopharmacology, Poster. Dec. 2016.
Koblan et al. "A Phase 1 Open Label Safety and Tolerability Study of Sep-363856, A Novel Non-D2 Mechanism of Action Molecule, In Patients With Schizophrenia", American College of Neuropsychopharmacology, Poster. Dec. 2016.
Poola et al. "Pharmacokinetics, Safety, and Tolerability of Sep-363856 in Healthy Adult Male Subjects and in Adult Patients With Schizophrenia Following Oral Administration", American College of Clinical Pharmacology, Poster. Sep. 2018.
Koblan et al. "Efficacy and Safety of Sep-363856 in the Treatment of Schizophrenia: A 4-Week, Randomized, Placebo-Controlled Trial of a Novel Compound With a Non-D2 Mechanism of Action", American College of Neuropsychopharmacology, Poster. Dec. 2018.
Koblan, "Sep-363856, A Candidate Antipsychotic and Antidepressant Compound With a Noval Non-D2 Mechanism of Action", Schizophrenia International Research Society, Oral Presentation. Apr. 2018.
Koblan et al. "Sep-363856, A Novel Psychotropic Agent With a Non-D2 Mechanism of Action, for the Treatment of Schizophrenia", Schizophrenia International Research Society, Oral Presentation. Apr. 2019.
Koblan et al. "Efficacy and Safety of SEP-363856, A Novel Psychotropic Agent With a Non-D2 Mechanism of Action, In the Treatment of Schizophrenia: A 4-Week, Randomized, Placebo-Controlled Trial", American Psychiatric Association, Poster. Oct. 2019.
Koblan et al. "Efficacy and Safety of SEP-363856, A Novel Psychotropic Agent With a Non-D2 Mechanism of Action, In the Treatment of Schizophrenia: A 4-Week, Randomized, Placebo-Controlled Trial", American Society of Clinical Psychopharmacology, Poster. May 2019.
Jones et al. "Sep-0363856, A Novel Psychotropic Agent With a Unique, Non-D2 Mechanism of Action", European College of Neuropsychopharmacology, Poster. Sep. 2019.
Koblan et al. "Efficacy and Safety of SEP-363856, A Novel Non-D2 Agent, In the Treatment of Schizophrenia: A 4-Week, Randomized, Placebo-Controlled Trial", European College of Neuropsychopharmacology, Poster. Sep. 2019.
Koblan et al. "Efficacy and Safety of SEP-363856, A Novel Psychotropic Agent With a Non-D2 Mechanism of Action, In the Treatment of Schizophrenia: A 4-Week, Randomized, Placebo-Controlled Trial", US Pychiatric and Mental Health Congress, Poster. May 2019.
Koblan et al. "Efficacy and Safety of SEP-363856, A Novel Psychotropic Agent With a Non-D2 Mechanism of Action, In the Treatment of Schizophrenia: A Randomized, Placebo-Controlled Trial", Neuroscience Education Institute, Poster. Nov. 2019.
Correll et al. "Safety and Effectiveness of SEP-363856 in Schizophrenia: Results of a 6-Month, Open-Label Extension Study", American College of Neuropsychopharmacology, Poster. Dec. 2019.
Hopkins et al. "Effects of SEP-363856 on Negative Symptoms in Schizophrenia: Analysis of an Acute, Placebo-Controlled Trial of a Novel Psychotropic Agent With No Dopamine-D2/5-Ht2a Antagonist Activity", American College of Neuropsychopharmacology, Poster. Dec. 2019.

Dedic et al. "The Novel, Non-D2 Psychotropic Agent SEP-363856 Modulates Presynaptic Dopamine Function in Mice", American College of Neuropsychopharmacology, Poster. Dec. 9, 2019.
Dedic et al. "SEP-363856, A Novel Psychotropic Agent With a Unique, Non-D2 Receptor Mechanism of Action", The Journal of Pharmacology and Experimental Therapeutics, Manuscript. Oct. 2019.
Karran et al. "The Amyloid Cascade Hypothesis for Alzheimer's Disease: an Appraisal for the Development of Therapeutics", Nature, vol. 10, p. 698. 2011.
Schmitz et al. "Hippocampal Neuron Loss Exceeds Amyloid Plaque Load in a Transgenic Mouse Model of Alzheimer's Disease", American Journal of Pathology, vol. 164, p. 1495. 2004.
Hejl et al. "Prepulse Inhibition in Patients with Alzheimer's Disease", Neurobiology of Aging, vol. 25, p. 1045. 2004.
Trehan "A New Synthesis of 13-aza-18-nor-17-oxo-A-nor-3-thiaestra-1,5(10), 9(11)-triene", retrieved from STN Database Accession No. 1986:225089 and Indian Journal of Chemistry, Section 6: Organic Chemistry Including Medicinal Chemistry, vol. 24B(6), pp. 659-661. 1985.
Trehan "Synthesis of 2, 3, 13-Triaza-18-nor-17-oxo-3-phenyl-A-nor-estra-1,5(10), 9(11)-triene & 2, 3, 13-Triaza-7,7-dimethyl-18-nor-17-oxo-3-phenyl-A-nor=estra-1,5(10), 9(11)-triene", Indian Journal of Chemistry, vol. 19B, pp. 243-245. 1980.
Mashkovskiy "Drugs", Moscow, New Wave, LLC, vol. 1, p. 11 with translation. 2002.
Berardi et al. "A Multireceptorial Binding Reinvestigation on an Extended Class of s Ligands: N-[w-(Indan-1-yl and Tetralin-1-yl)alkyl] Derivatives of 3,3-Dimethylpiperidine Reveal High Affinities Towards s1 and EBP Sites", Bioorganic & Medicinial Chemistry, vol. 9, No. 5, pp. 1325-1335. 2001.
Berardi et al. "Novel Potent s1 Ligands: N-[w-(Tetralin-1-yl)alkyl] piperidine Derivatives" Journal of Medicinal Chemistry, American Chemical Society, vol. 39, No. 21, pp. 4255-4260. 1996.
Berardi et al. "4-(Tetralin-1-yl)-and 4-(Naphthalen-1-yl) alkyl Derivatives Ligands with Agonist s2 Activity", Journal of Medicinal Chemistry, American Chemical Society, vol. 47, No. 9, pp. 2308-2317. 2004.
Chihara et al. "Preparation of Benzothiophene Derivatives as Blood Platelet Aggregation Inhibitors", Retrieved from STN Database Accession No. 1992:128652 and JP03223277A, Yoshitomi Pharmaceutical Industries LTD. Oct. 2, 1991.
Corbera et al. "A Medicinal-Chemistry-Guided Approach to Selective and Druglike Sigma 1 Ligands", Chemmedchem, vol. 1, No. 1, pp. 140-154. Jan. 2006.
Dehaven-Hudkins et al. "Characterization of the Binding of [3H](+)pentazocine to O'Recognition Sites in Guinea Pig Brain" Eur. Journal Pharmacol., vol. 277, pp. 371-378. 1992.
Hanner et al. "Purification, Molecular Cloning, and Expression of the Mammalian Sigma1-Binding Site", Proc. Natl. Aca. Sci, vol. 93, pp. 8072-8077. 1996.
Krogsgaard-Larsen et al. "Textbook of Drug Design and Discovery", Taylor & Francis. Apr. 2002.
Langa et al. "Generation and Phenotypic Analysis of Sigma Receptor Type 1 (Sigma1) Knockout Mice", European Journal of Neuroscience, vol. 18, pp. 2188-2196. 2003.
Lowry et al. "Protein Measurement with the Folin Phenol Reagent", Journal Bio. Chem., vol. 193, p. 265. 1951.
Maier et al., "Novel Spiropiperidines as Highly Potent and Subtype Selective a-Receptor Ligands. Part 1", Journal Med. Chem., vol. 45, pp. 438-448. 2002.
Maier et al., "Novel σ Receptor Ligands. Part 2. SAR of Spiro[[2]benzopyran-1,4'-piperidines] and Spiro [[2] benzofuran-1,4'-piperidines] with Carbon Substituents in Position 3", Journal Med. Chem., vol. 45, pp. 4923-4930. 2002.
Quirion et al. "A Proposal for the Classification of Sigma Binding Sites", Trends Pharmacol. Sci., vol. 13, pp. 86-86. Mar. 1992.
Radesca "Synthesis adn Receptor Binding EnantiomericN-Substitutedcis-N-[2-(3,4-Dichloroph-enyl)ethyl]-2-(1-pyrrolidiny) Cyclohexylamines as High-Affinity O' Receptor Ligands", Journal Med. Chem., vol. 34, pp. 3065-3074. 1991.
Schow "Novel Sigma Receptor Ligands 2", Bioorganic and Medicinal Chemistry Letters, No. 2, pp. 221-224. 1993.

(56) References Cited

OTHER PUBLICATIONS

Snyder et al. "Receptor Mechanisms in Antipsychotic Drug Action: Focus on Sigma Receptors", Journal Neuropsychiatry, vol. 1, pp. 7-15. 1989.
Extended European Search Report for EP Application No. 10835185.9, pp. 1-15. dated Apr. 4, 2013.
Walker: Pharmacological Reviews, "Sigma Receptors: Biology and Function", vol. 42, No. 4, pp. 355-402. 1990.
Bakshi et al. "Antagonism of Phencyclidine-Induced Deficits in Prepulse Inhibition by the Putative Aytpical Antipsychotic Olanzapine", Psychopharmacology, vol. 122, No. 2, pp. 198-201. Nov. 1995.
Ghaemi et al. "Does Olanzapine have Antidepressant Properties? A Retrospective Preliminary Study", Bipolar Disorders, vol. 2, pp. 196-199. 2000.
Ghasemi et al. "The Role of NMDA Receptors in the Pathophysiology and Treatment of Mood Disorders", Neuroscience and Biobehavioral Reviews, vol. 47, pp. 336-358. Sep. 16, 2014.
Gleason et al. "Blockade of Phencyclidine-Induced Hyperlocomotion by Olanzapine, Clozapine adn Serotonin Receptor Subtype Selective Antagonists in Mice", Psyhopharmacology, vol. 129, pp. 79-84. 1997.
International Search Report and Written Opinion issued in PCT/US2010/05884, 10 pages. dated Aug 25, 2011.
Jacobs et al. "1-Imidazolyl(alkyl)-Substituted Di- and Tetrahydroquinolines and Analogues: Syntheses and Evaluation of Dual Inhibitors of Thromboxane A2 Synthase and Aromatase", Journal of Medicinal Chemistry, vol. 43, No. 9, pp. 1841-1851. Apr. 12, 2000.
Jentsch et al., "The Neuropsychopharmacology of Phencyclidine: From NMDA Receptor Hypofunction to the Dopamine Hypothesis of Schizophrenia", Neuropsychopharmacology, vol. 20, No. 3, pp. 201-225. 1999.
Jobson et al. "Pyrano Heterocycles. I. The Syntheses of Isochromans and the Novel thieno[3,2-c]pyran, benzothieno [3,2-c]pyran, benzothieno[2,3-c]pyran, and pyrano[4,3-b] benzofuran Systems", Journal of Heterocyclic Chemistry, 12 (3), pp. 591-594. Jan. 1, 1975.
Kapur et al. "NMDA Receptor Antagonist Ketamine and PCP Have Direct Effects on the Dopamine D2 adn Serotonin 5-HT2 Receptors-Implications for Models of Schizophrenia", Molecular Psychiatry, vol. 7, pp. 837-844. 2002.
Katsuki et al., "Excitotoxic Degeneration of Hypothalamic Orexin Neurons in Slice Culture", Neurobiology of Disease, vol. 15, pp. 61-69. 2004.
Kostin et al. "Lack of Hypocretin Attenuates Behavioral Changes Produced by Glutamatergic Activation of the Perifornical-Lateral Hypothalamic Area", Sleep, vol. 37, No. 5, pp. 1011-1020. 2014.
Marcus et al. "The Efficacy and Safety of Aripiprazole as Adjunctive Therapy in Major Depressive Disorder. A second Multicenterm Randomized, Double-Blind, Pacebo-Controlled Study", Journal of Clinical Psychopharmacology, vol. 28, No. 2, pp. 15-165. Apr. 2008.
Moreno et al. "Preclinical Models of Antipsychotic Drug Action", International Journal of Neuropsychopharmacology, vol. 16, pp. 2131-2144. Jun. 10, 2013.
Nordquist et al. "Effects of Aripiprazole/OPC-14597 on Motor Activity, Pharmacological Models of Psychosis, and Brain Activity in Rats", Neuropharmacology, vol. 54, pp. 405-416. 2008.
Pittenger et al. "The NMDA Receptor as a Therapeutic Target in Major Depressive Disorder", CNS & Neurological Disorders—Drug Targets, vol. 6, No. 2, pp. 101-115. Feb. 19, 2007.
Registry (STN) [online] CAS Registry No. 933704-21-3, 1 page. Apr. 30, 2007.
Singapore Search Report and Written Opinion issued in Singapore Application No. 10201401661, 10 pages. dated Jun. 15, 2015.
Singapore Written Opinion issued in Singapore Application No. 201204089-5, 12 pages. dated Sep. 20, 2013.
Swerdlow et al. "Seroquel Restores Sensorimotor Gating in Phencyclidine-Treated Rats", Journal of Pharmacology and Experimental Therapeutics, vol. 279, No. 3, pp. 1290-1299. Dec. 1996.
Sheitman et al., "Secretin for refractory schizophrenia" Elsevier, Science Direct, Schizophrenia Research 66 (2004) 177-181 2004.
Hopkins et al., "Transformed PANSS Factors Intended to Reduce Pseudospecificity Among Domains and Enhancing Understanding of Symptom Change in Antipsychotic-Treated Patients with Schizophrenia", The International Society or CNS Clinical Trials and Methodology (ISCTM) 13th Annual Scientific Meeting; Feb. 21-23, 2017 (The Fairmont, Washington DC), https://isctm.org/meeting/13th-annual-scientific-meeting/ Feb. 21, 2017.
Hopkins et al., "Transformed PANSS Factors Intended to Reduce Pseudospecificity Among Symptom Domains and Enhance Understanding of Symptom Change in Antipsychotic-Treated Patients With Schizophrenia", Schizophrenia Bulletin vol. 44 No. 3 pp. 593-602, 2018,doi:10.1093/schbul/sbx101, https://pubmed.ncbi.nlm.nih.gov/28981857/, https://academic.oup.com/schizophreniabulletin/article/44/3/593/4110338 2018.
Hopkins, "Improving the Specificity and Precision of PANSS Factors: One Approach to Facilitate Development of Novel Treatments in Schizophrenia", The International Society for CNS Clinical Trials and Methodology, (ISCTM) 14th Annual Scientific Meeting; Feb. 20-22, 2018 (The Fairmont, Washington DC), https://sctm.org/meeting/14th-annual-scientific-meeting/ Feb. 20, 2018.
Kokkinou et al., "Reproducing the Dopamine Pathophysiology of Schizophrenia and Approaches to Ameliorate It: A Translational Imaging Study with Ketamine", Molecular Psychiatry, 15 pages. May 7, 2020.
Milanovic et al., "Measures of Cognition and Social Functioning in Schizophrenia Patients Receiving SEP-363856", Poster, Schizophrenia International Research Society Congress. 2020.
Synan et al., "Preclinical Abuse Liability Assessment of SEP-363856, A Compound with a Non-D2 Receptor Mechanism of Action", Poster, College on Problems of Drug Dependence. 2020.
Synan et al., "SEP-363856, A Novel TAAR1 Agonist, Lacks Abuse Liability in Preclinical Models and Attenuates Concaine Cue-Induced Relaps in Rats", Poster, The American College of Neuropsuchopharmacology. 2020.
Dworak, "SEP-363856: A Compound with a Non-D2 Receptor Mechanism of Action for the Treatment of Schizophrenia: Update", Poster, American Society of Clinical Psychpharmacology Annual Meeting. 2021.
Dworak et al., "Effects of SEP-363856, A Novel TAAR1 Agonist, On Negative Symptoms in Schizophrenia: Results Across An Initial Double-Blind Acute Study, and a 6-Month, Open-Label Extension Study", Poster, The American College of Neuropsychopharmacology 59th Annual Meeting. 2020.
Hopkins et al., "Characterization of Sepcific and Distinct Patient Types in Clinical Trails of Acute Schizophrenia Using an Uncorrelated PANSS Score Matrix Transform (UPSM)", Psychiatry Research, vol. 294, 7 pages. 2020.
Hopkins et al., "The Safety Profile of the TAAR1 Agonist, SEP-363856, Is Distinct From Atypical Antipsychotics", Poster, American Psychiatric Association Annual Meeting. 2021.
Isaacson et al., "Efficacy and Safety of SEP-363856, A Non-D2-Receptor-Binding Drug With Antipsychotic Activity, in Patients with Parkinson's Disease Psychosis", American Academy of Neurology, Virtual Annual Meeting, 18 pages. 2021.
Koblan, "SEP-363856, A Novel Non-D2, TAAR1 Agonist for the Treatment of Schizophrenia: Current Development Status", American Society of Clinical Psychopharmacology, Annual Meeting, 15 pages. 2020.
Hopkins et al., "Effect of TAAR1/5-HT1A Agonist SEP-363856 on REM Sleep in Humans", Translational Psychiatry, vol. 11, No. 228, 10 pages. 2021.
Koblan, "SEP-363856: A Compound with a Non-D2 Receptor Mechanism of Action for the Treatment of Schizophrenia: Update", Schizophrenia International Research Society Annual Congress, Poster. 2020.
Bengi et al. "Towards Novel Treatments for Schizophrenia: Molecular and Behavioural Signature of the Psychotropic Agent SEP-363856", International Journal of Molecular Sciences, vol. 22, No. 4119, 19 pages. 2021.

(56) References Cited

OTHER PUBLICATIONS

Chen et al., "No Chiral Inversion for SEP-363856 in Humans by a Novel Chiral LC-MS/MS Analysis of Human Plasma from Clinical Trials", Poster, American Society for Mass Spectrometry. 2020.

* cited by examiner

| PANSS | MARDER PANSS Factors ||||| TRANSFORMED PANSS Factors ||||||| ITEM |
|---|---|---|---|---|---|---|---|---|---|---|---|---|---|
| | POS | DIS | NEG | HOS | DEP/ANX | POS | DIS | NAA | NDE | HOS | ANX | DEP | |
| PANSS01 | 1 | 0 | 0 | 0 | 0 | 0.58 | -0.15 | -0.08 | 0.01 | -0.06 | -0.07 | 0.00 | P01 DELUSIONS |
| PANSS06 | 1 | 0 | 0 | 0 | 0 | 0.35 | -0.06 | 0.05 | 0.00 | 0.02 | -0.02 | 0.01 | P06 SUSPICIOUSNESS/PERSECUTION |
| PANSS03 | 1 | 0 | 0 | 0 | 0 | 0.21 | -0.02 | -0.03 | -0.01 | -0.03 | 0.00 | 0.03 | P03 HALLUCINATORY BEHAVIOR |
| PANSS23 | 1 | 0 | 0 | 0 | 0 | 0.14 | 0.09 | -0.03 | -0.04 | -0.07 | -0.02 | -0.02 | G09 UNUSUAL THOUGHT CONTENT |
| PANSS26 | 1 | 0 | 0 | 0 | 0 | 0.01 | 0.15 | -0.03 | -0.03 | 0.03 | -0.06 | -0.06 | G12 LACK OF JUDGEMENT AND INSIGHT |
| PANSS14 | 1 | 0 | 0 | 0 | 0 | -0.01 | 0.15 | -0.03 | 0.00 | -0.01 | -0.01 | 0.00 | N07 STEREOTYPED THINKING |
| PANSS05 | 1 | 0 | 0 | 0 | 0 | -0.03 | -0.03 | 0.00 | -0.02 | -0.01 | -0.03 | 0.03 | P05 GRANDIOSITY |
| PANSS15 | 1 | 0 | 0 | 0 | 0 | -0.04 | 0.06 | -0.04 | 0.01 | -0.03 | 0.04 | 0.11 | G01 SOMATIC CONCERN |
| PANSS29 | 0 | 1 | 0 | 0 | 0 | -0.05 | 0.29 | 0.00 | -0.03 | -0.04 | 0.00 | 0.06 | G15 PREOCCUPATION |
| PANSS25 | 0 | 1 | 0 | 0 | 0 | -0.10 | 0.28 | -0.05 | 0.00 | 0.00 | -0.02 | 0.04 | G11 POOR ATTENTION |
| PANSS02 | 0 | 1 | 0 | 0 | 0 | 0.03 | 0.20 | -0.03 | -0.02 | -0.04 | 0.00 | -0.04 | P02 CONCEPTUAL DISORGANIZATION |
| PANSS27 | 0 | 1 | 0 | 0 | 0 | -0.06 | 0.19 | -0.01 | 0.06 | -0.01 | -0.04 | 0.05 | G13 DISTURBANCE OF VOLITION |
| PANSS12 | 0 | 1 | 0 | 0 | 0 | 0.00 | 0.11 | 0.03 | -0.03 | -0.01 | 0.01 | -0.07 | N05 DIFFICULTY IN ABSTRACT THINKING |
| PANSS19 | 0 | 1 | 0 | 0 | 0 | -0.05 | 0.05 | -0.03 | 0.10 | -0.01 | 0.03 | -0.04 | G05 MANNERISMS AND POSTURING |
| PANSS24 | 0 | 1 | 0 | 0 | 0 | -0.04 | -0.03 | -0.03 | -0.02 | -0.03 | -0.02 | -0.02 | G10 DISORIENTATION |
| PANSS11 | 0 | 0 | 1 | 0 | 0 | -0.09 | -0.09 | 0.46 | -0.03 | -0.02 | -0.02 | -0.01 | N04 PASSIVE/APATHETIC SOCIAL WITHDRAWAL |
| PANSS09 | 0 | 0 | 1 | 0 | 0 | -0.03 | -0.02 | 0.33 | -0.02 | -0.05 | -0.01 | 0.01 | N02 EMOTIONAL WITHDRAWAL |
| PANSS30 | 0 | 0 | 1 | 0 | 0 | -0.01 | 0.00 | 0.29 | -0.06 | 0.02 | -0.03 | 0.04 | G16 ACTIVE SOCIAL AVOIDANCE |
| PANSS21 | 0 | 0 | 1 | 0 | 0 | -0.03 | -0.04 | -0.08 | 0.44 | -0.01 | -0.02 | 0.05 | G07 MOTOR RETARDATION |
| PANSS13 | 0 | 0 | 1 | 0 | 0 | 0.00 | 0.01 | 0.00 | 0.26 | -0.01 | 0.02 | -0.10 | N06 LACK OF SPONTANEITY AND FLOW OF CONVERSATION |
| PANSS08 | 0 | 0 | 1 | 0 | 0 | -0.01 | -0.03 | 0.06 | 0.25 | -0.04 | 0.02 | -0.01 | N01 BLUNTED AFFECT |
| PANSS10 | 0 | 0 | 1 | 0 | 0 | -0.07 | -0.04 | -0.01 | 0.02 | 0.02 | -0.02 | -0.02 | N03 POOR RAPPORT |
| PANSS07 | 0 | 0 | 0 | 1 | 0 | -0.04 | -0.18 | -0.03 | 0.03 | 0.50 | -0.10 | 0.06 | P07 HOSTILITY |
| PANSS22 | 0 | 0 | 0 | 1 | 0 | -0.08 | 0.03 | -0.01 | -0.02 | 0.29 | -0.06 | -0.05 | G08 UNCOOPERATIVENESS |
| PANSS28 | 0 | 0 | 0 | 1 | 0 | -0.07 | 0.02 | -0.03 | 0.00 | 0.25 | -0.02 | -0.01 | G14 POOR IMPULSE CONTROL |
| PANSS04 | 0 | 0 | 0 | 1 | 0 | -0.03 | 0.01 | 0.00 | -0.07 | 0.14 | 0.11 | -0.10 | P04 EXCITEMENT |
| PANSS18 | 0 | 0 | 0 | 0 | 1 | -0.09 | -0.03 | -0.01 | 0.02 | -0.03 | 0.51 | -0.03 | G04 TENSION |
| PANSS16 | 0 | 0 | 0 | 0 | 1 | -0.03 | -0.08 | -0.03 | -0.05 | -0.04 | 0.46 | 0.12 | G02 ANXIETY |
| PANSS20 | 0 | 0 | 0 | 0 | 1 | -0.03 | -0.07 | -0.04 | 0.04 | 0.00 | -0.06 | 0.45 | G06 DEPRESSION |
| PANSS17 | 0 | 0 | 0 | 0 | 1 | -0.04 | 0.00 | 0.00 | -0.04 | -0.03 | -0.03 | 0.25 | G03 GUILT FEELINGS |

FIG. 4

| Data set | Study | Design | Subjects | Duration | Nfactors vs. PANSS total | Nfactors vs. POS | | | | Subtotals vs. Pos | | |
|---|---|---|---|---|---|---|---|---|---|---|---|---|
| | | | | | | DIS | AA | DE | HOS | Dis | Neg | Hos |
| Analysis | D1050006 | RCT | 132 | Week 6 | 0.91 | 0.21 | -0.03 | 0.03 | 0.00 | 0.72 | 0.50 | 0.52 |
| | D1050196 | | 174 | | 0.94 | 0.25 | 0.00 | -0.02 | 0.17 | 0.76 | 0.51 | 0.59 |
| | D1050229 | | 471 | | 0.93 | 0.15 | 0.09 | 0.02 | 0.27 | 0.71 | 0.54 | 0.67 |
| | D1050231 | | 456 | | 0.95 | 0.20 | 0.13 | -0.02 | 0.17 | 0.74 | 0.56 | 0.62 |
| | D1050233 | | 477 | | 0.94 | 0.20 | 0.16 | 0.13 | 0.22 | 0.75 | 0.62 | 0.67 |
| Validation | D1001002 | RCT | 455 | Week 6 | 0.95 | 0.06 | -0.04 | -0.08 | 0.24 | 0.72 | 0.56 | 0.74 |
| | D1001056 | | 450 | | 0.96 | 0.16 | 0.07 | 0.08 | 0.18 | 0.75 | 0.65 | 0.68 |
| | D1050049 | | 325 | | 0.93 | 0.11 | 0.09 | 0.01 | 0.04 | 0.69 | 0.54 | 0.56 |
| | D1050301 | | 326 | | 0.92 | 0.00 | 0.13 | -0.02 | 0.13 | 0.63 | 0.55 | 0.60 |
| | D1050303 | | 402 | | 0.94 | 0.14 | 0.09 | -0.02 | 0.17 | 0.70 | 0.56 | 0.59 |
| | D1050307 | | 191 | Week 12 | 0.94 | -0.06 | 0.16 | -0.02 | 0.11 | 0.61 | 0.59 | 0.54 |
| | D1050237 | | 615 | Week 28 | 0.86 | -0.08 | -0.09 | -0.09 | -0.07 | 0.40 | 0.28 | 0.28 |
| | D1050290 | | 145 | Month 6 | 0.88 | 0.06 | 0.04 | -0.30 | -0.14 | 0.48 | 0.28 | 0.34 |
| | D1050234 | | 292 | Month 12 | 0.91 | 0.13 | 0.16 | -0.03 | 0.17 | 0.68 | 0.51 | 0.62 |
| | D1050238 | RWS - DB | 284 | Week 28 | 0.94 | 0.07 | 0.14 | 0.05 | 0.24 | 0.70 | 0.61 | 0.64 |
| | D1050238 | RWS - OL | 655 | Week 24 | 0.91 | 0.08 | 0.16 | 0.02 | 0.09 | 0.65 | 0.55 | 0.59 |
| | D1050289 | OL | 236 | Week 6 | 0.86 | -0.01 | -0.03 | -0.12 | -0.02 | 0.40 | 0.31 | 0.32 |
| | D1001057 | | 281 | Week 26 | 0.95 | 0.10 | 0.01 | -0.08 | 0.18 | 0.75 | 0.61 | 0.72 |

FIG. 5

METHODS OF TREATING SCHIZOPHRENIA

I. CROSS REFERENCE TO RELATED APPLICATIONS

This application is a national phase entry under 35 USC 371 of PCT International Application PCT/US2018/00078, filed Feb. 16, 2018. PCT/US2018/00078 claims priority to U.S. Provisional Patent Application No. 62/459,784, filed Feb. 16, 2017, the content of both of which is hereby incorporated by reference herein in its entirety.

II. FIELD

Provided herein are methods for treating schizophrenia, and various compounds and compositions comprising the compounds, for use therein.

III. BACKGROUND

Central nervous system disorders affect a wide range of the population with differing severity. Generally, the major feature of this class of disorders includes the significant impairment of cognition or memory that represents a marked deterioration from a previous level of functioning.

Schizophrenia is a psychopathic disorder of unknown origin, which usually appears for the first time in early adulthood and is marked by characteristics such as, psychotic symptoms, phasic progression and development, and/or deterioration in social behavior and professional capability. Schizophrenia is also a chronic and disabling disorder with a heterogeneous clinical presentation characterized by symptoms across a range of psychological, behavioral, and cognitive domains. A DSM-5 diagnosis of schizophrenia requires the presence of at least 3 criteria in the domains of positive symptoms (delusions or hallucinations), negative symptoms (diminished emotional expression or avolition), or disorganized thinking/behavior (disorganized speech or grossly disorganized behavior or catatonia). Associated symptoms supporting the diagnosis include symptoms occurring in 2 additional domains of depression/anxiety and hostility/excitement. See, e.g., *Diagnostic and Statistical Manual of Mental Disorders*, 5$^{th}$ Ed., American Psychiatric Association (2013) (DSM-V™, aka DSM-5).

Since its introduction in 1987, the Positive and Negative Syndrome Scale (PANSS), consisting of 30 items, has been the most widely used measure of schizophrenia illness severity, and the PANSS total score is the gold standard primary efficacy measure in acute treatment studies of schizophrenia. Factor analyses of the PANSS have consistently identified 5 factors, which are frequently used as secondary efficacy measures, and which map on to DSM-5 core, and associated, diagnostic criteria: positive symptoms, negative symptoms, disorganized thinking, hostility/excitement, and symptoms of depression/anxiety.

Positive symptoms are those, which represent an "excess" of normal experiences, such as hallucinations and delusions. Negative symptoms are those where the patient suffers from a lack of normal experiences, such as anhedonia and lack of social interaction. The cognitive symptoms relate to cognitive impairment in schizophrenics, such as lack of sustained attention and deficits in decision making. The current antipsychotics may be successful in treating the positive symptoms but fare less well for the negative and cognitive symptoms.

A significant impediment to establishing the efficacy of new drugs for the treatment of specific symptom domains (e.g., negative symptoms or cognitive dysfunction) is the extent to which PANSS factors are correlated with each other. As a consequence, it has not been possible to determine whether improvement in the severity of symptoms in the five PANSS factors is a domain-specific treatment effect, or is a non-specific effect secondary to observed improvement in correlated PANSS items.

Accordingly, although both first and second generation antipsychotic medications have demonstrated significant efficacy in the treatment of positive symptoms of schizophrenia, hostility/excitement, and (to a lesser degree) symptoms of depression/anxiety. However, comparably effective treatment of negative symptoms and cognitive dysfunction remains an unmet need.

Therefore, there is a great need for effective treatments for the negative symptoms and cognitive dysfunction symptoms of schizophrenia.

IV. SUMMARY

Provided herein are various methods for the treatment of the negative symptoms, cognitive dysfunction symptoms, or both, associated with schizophrenia. In various aspects, provided herein are methods of identifying compounds with potential efficacy in the treatment of the negative symptoms, cognitive dysfunction symptoms, or both, associated with schizophrenia. In various aspects, provided herein are methods of treating the negative symptom domain of schizophrenia in prominently negative symptom type subjects. In addition, provided herein are methods of treating the negative symptoms, cognitive dysfunction symptoms, or both, associated with schizophrenia comprising administering to a subject a therapeutically or prophylactically effective amount of a therapeutic agent or a pharmaceutically acceptable salt or stereoisomer thereof.

In various aspects provided herein are various methods for the treatment of one or more of: a symptom domain of schizophrenia, a symptom sub-domain of schizophrenia, a subject sub-population with symptoms prominently in a symptom domain of schizophrenia; and/or a subject sub-population with symptoms prominently in symptom sub-domain of schizophrenia.

In various aspects provided herein are various methods for the treatment of one or more of: a symptom domain of schizophrenia, a symptom sub-domain of schizophrenia, a subject sub-population with symptoms prominently in a symptom domain of schizophrenia; and/or a subject sub-population with symptoms prominently in symptom sub-domain of schizophrenia, comprising administering to a subject a therapeutically or prophylactically effective amount of a therapeutic agent or a pharmaceutically acceptable salt or stereoisomer thereof.

In various embodiments, the schizophrenia symptom domain is one or more of the positive domain, the negative domain, the disorganized domain, the affective domain, and the hostility domain. In various embodiments, the schizophrenia symptom sub-domain is one or more of apathy/avolition; and deficit of expression. In various embodiments, the schizophrenia symptom sub-domain is one or more of depression and anxiety.

In various aspects provided herein are methods of identifying compounds with potential efficacy in the treatment of a symptom domain of schizophrenia, a symptom sub-domain of schizophrenia, or both. In various aspects provided herein are methods of identifying subjects with symptoms prominently in a symptom domain of schizophrenia, a symptom prominently in a symptom sub-domain of schizophrenia, or both. In various embodiments, provided are methods of identifying compounds with potential efficacy in the treatment of the negative symptoms. In various embodiments, provided herein are methods of identifying subjects with prominently negative symptoms, and methods of treating such subjects comprising administering to such a subject a therapeutically or prophylactically effective amount of a therapeutic agent or a pharmaceutically acceptable salt or stereoisomer thereof.

In various embodiments of the methods provided herein the therapeutic agent comprises a compound of formula (I), or pharmaceutically acceptable salts or stereoisomers thereof:

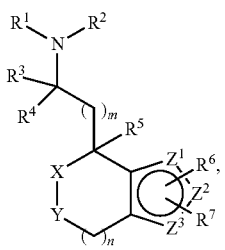

(I)

wherein $R^1$, $R^2$, $R^3$, $R^4$, $R^5$, $R^6$, $R^7$, X, Y, $Z^1$, $Z^2$, $Z^3$, m, and n are defined herein elsewhere.

In various embodiments of the methods provided herein the therapeutic agent comprises a compound of formula (IIa):

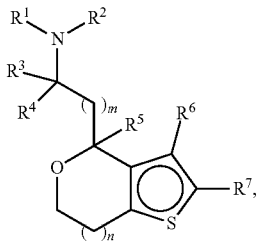

(IIa)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In various embodiments of the methods provided herein the therapeutic agent comprises a compound of the formula:

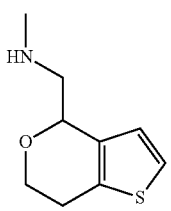

In various embodiments of the methods provided herein the therapeutic agent comprises a compound comprising one or more compounds of the formulas:

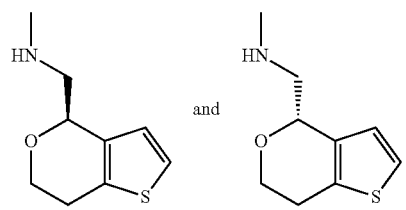

In various embodiments of the methods provided herein the therapeutic agent comprises a compound of the formula:

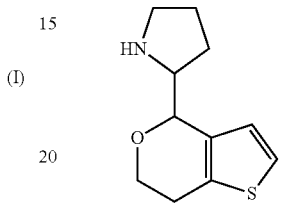

In various embodiments of the methods provided herein the therapeutic agent comprises a compound comprising one or more compounds of the formulas:

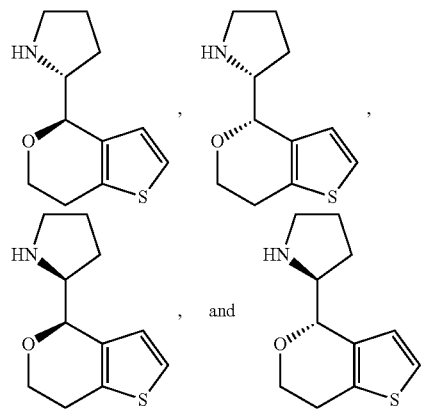

In various embodiments of the methods provided herein the therapeutic agent comprises a compound of formula (IIb):

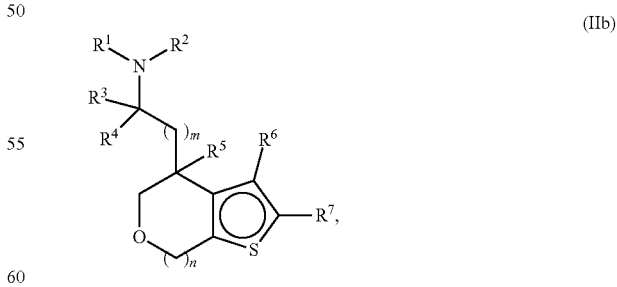

(IIb)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In various embodiments of the methods provided herein the therapeutic agent comprises a compound of formula (IIc):

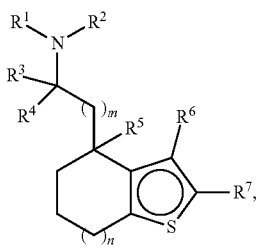

(IIc)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In various embodiments of the methods provided herein the therapeutic agent comprises a compound of the formula:

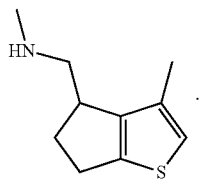

In various embodiments of the methods provided herein the therapeutic agent comprises a compound comprising one or more compounds of the formulas:

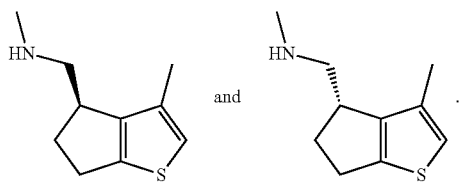

In various embodiments of the methods provided herein the therapeutic agent comprises a compound of formula (IIIa):

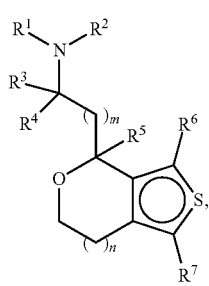

(IIIa)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In various embodiments of the methods provided herein the therapeutic agent comprises a compound of formula (IIIb):

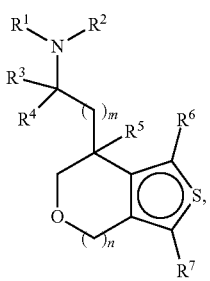

(IIIb)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In various embodiments of the methods provided herein the therapeutic agent comprises a compound of formula (IIIc):

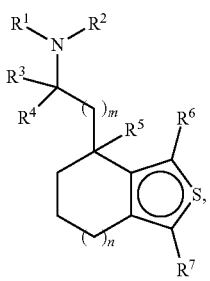

(IIIc)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In various embodiments of the methods provided herein the therapeutic agent comprises a compound of formula (IVa):

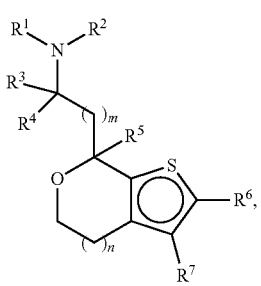

(IVa)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In various embodiments of the methods provided herein the therapeutic agent comprises a compound of the formula:

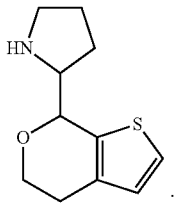

In various embodiments of the methods provided herein the therapeutic agent comprises a compound comprising one or more compounds of the formulas:

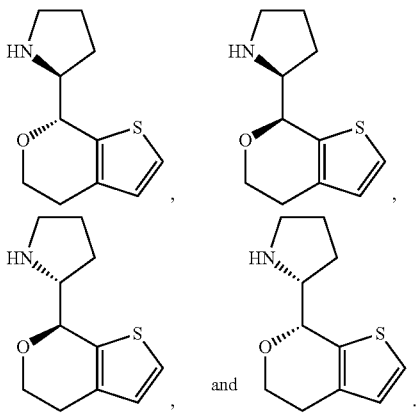

In various embodiments of the methods provided herein the therapeutic agent comprises a compound of the formula:

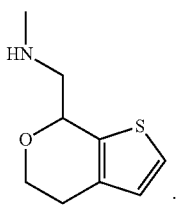

In various embodiments of the methods provided herein the therapeutic agent comprises a compound comprising one or more compounds of the formulas:

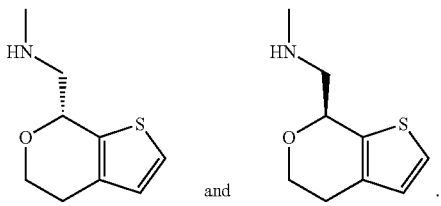

In various embodiments of the methods provided herein the therapeutic agent comprises a compound of formula (IVb):

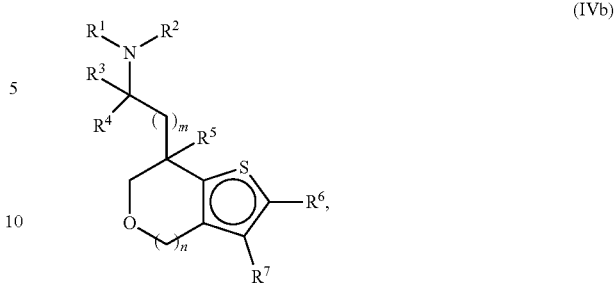

(IVb)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In various embodiments of the methods provided herein the therapeutic agent comprises a compound of formula (IVc):

(IVc)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In various embodiments of the methods provided herein the therapeutic agent comprises a compound of formula (V):

(V)

or a pharmaceutically acceptable salt or stereoisomer thereof, wherein $R^1$, $R^2$, $R^3$, $R^4$, $R^5$, $R^6$, $Z^1$, $Z^3$, X, Y, m and n are as defined herein elsewhere.

In various embodiments of the methods provided herein the therapeutic agent comprises a compound of formula (VI):

(VI)

or a pharmaceutically acceptable salt or stereoisomer thereof, wherein $R^1$, $R^2$, $R^3$, $R^4$, $R^5$, $R^6$, $R^7$, $Z^1$, $Z^2$, $Z^3$, and m are as defined herein elsewhere.

In various aspects provided are methods of treating specific symptoms, domains of symptoms and/or sub-domains of symptoms of schizophrenia comprising administering to a subject a therapeutically or prophylactically effective amount of a therapeutic agent or a pharmaceutically acceptable salt or stereoisomer thereof. As used herein, a "symptom domain" of schizophrenia refers to one of the five generally recognized domains of schizophrenia: (1) positive, (2) negative, (3) disorganized, (4) affective, and (5) hostility. See, e.g., Marder S R, Davis J M, Chouinard G., *J. Clin. Psychiatry.* 1997; 58:538-546). In addition, the negative symptom domain and the affective symptom domain each have two recognized symptom sub-domains. The negative domain symptom sub-domains are (a) apathy/avolition; and (b) deficit of expression. The affective domain symptom sub-domains are (a) depression; and (b) anxiety.

In addition, it is to be understood that schizophrenia subject populations can be classified by their prominent symptomology. For example, schizophrenia subject can be classified as having prominently positive, prominently hostile, prominently disorganized, prominently affective, or prominently negative symptoms.

In various embodiments, the therapeutic agent of a method of the present invention is an antipsychotic agent. In various embodiments, the antipsychotic agent is selected from typical antipsychotic agents and atypical antipsychotic agents. In various embodiments, the therapeutic agent is a typical antipsychotic agent. In various embodiments, the therapeutic agent is an atypical antipsychotic agent. In various embodiments, the therapeutic agent is a dopamine antagonist. In various embodiments, the therapeutic agent is a D2 receptor antagonist.

In various aspects provided are methods of treating the negative symptoms, cognitive dysfunction symptoms, or both, associated with schizophrenia comprising administering to a subject a therapeutically or prophylactically effective amount of lurasidone.

In various aspects provided are methods of treating the negative symptoms, cognitive dysfunction symptoms, or both, associated with schizophrenia comprising administering to a subject a therapeutically or prophylactically effective amount of one or more of: aripiprazole cholorpromazine, promazine, thioridazine, haloperidol, clopenthixol, thiothixene, sulpride, spiperone, pimozide, clozapine, fluphenazine, carpipramine, bromperidol, zotepine, amisulpride, levosulpride, emonapride, risperidone, olanzapine, quetiapine, ziprasidone, perospirone, sertindole, paliperidone, blonanserin, asennapine, iloperidone, brexpiprazole, and cariprazine.

Provided herein in various embodiments are methods of treating schizophrenia in a subject in need thereof, comprising administering a therapeutic agent wherein the subject exhibits a schizophrenia domain characterized by a transformed PANSS score and wherein the schizophrenia domain is selected from the group consisting of prominently positive, prominently disorganized thinking/cognitive dysfunction, prominently affective (depression/anxiety), prominently hostility/excitement, and prominently negative symptoms (apathy/avolition and deficit of expression).

In various aspects provided are methods of treating a subject that is part of a schizophrenic symptom sub-population (that is, subjects with symptoms prominently in a specific symptom domain, sub-domain or sub-domains), the methods comprising administering to a subject a therapeutically or prophylactically effective amount of a therapeutic agent or a pharmaceutically acceptable salt or stereoisomer thereof. In various preferred embodiments, the symptom domain, sub-domain and/or sub-domains are determined using transformed PANSS factors in accord with an embodiments of a method provided herein.

In various embodiments, the schizophrenia subject sub-population is selected from the group consisting of subjects with prominently positive, prominently hostile, prominently disorganized, prominently affective, or prominently negative symptoms. In various embodiments, the subject is part of a schizophrenic symptom sub-population having symptoms primarily in the positive symptom domain, the hostile domain, the disorganized thought or thinking symptom domain, the affective symptom domain, or the negative symptom domain. In various embodiments, the subject is part of a schizophrenic symptom sub-population having symptoms prominently in one or more of the negative symptom sub-domains of apathy/avolition and deficit of expression. In various embodiments, the subject is part of a schizophrenic symptom sub-population having symptoms prominently in one or more of the depression/anxiety symptom sub-domains depression and anxiety.

The present inventors have discovered methods which can be used to minimize the correlation or decorrelate the PANSS factors and thus ascertain the potential efficacy of a compound and/or treatment for a specific symptom of schizophrenia, and in various particular embodiments, the potential efficacy of a compound and/or treatment for a negative symptom of schizophrenia.

In various aspects, the present inventions utilize existing PANSS data and transform that data with score matrix weighting coefficients to generate transformed PANSS factors with minimal between-factor correlation (enhanced orthogonality) while preserving the correspondence to Marder PANSS factors (Marder S R, Davis J M, Chouinard G., *J. Clin. Psychiatry.* 1997; 58:538-546).

Accordingly, in various aspects provided are methods for determining if a drug has potential efficacy for the treatment for a specific symptom of schizophrenia, and in various particular embodiments, the potential efficacy of a compound for treatment of a negative symptom of schizophrenia.

In addition, the present inventors have discovered that in various aspects embodiments of the methods used to minimize the correlation or decorrelate the PANSS factors, can be used to classify subjects by their prominent symptomology. Accordingly, in various embodiments provided are methods of identifying subjects with prominently positive, prominently hostile, prominently disorganized, prominently affective, or prominently negative symptoms, and methods of treating such subjects comprising administering to such a subject a therapeutically or prophylactically effective amount of a therapeutic agent or a pharmaceutically acceptable salt or stereoisomer thereof.

Also provided herein are compositions and dosage forms, comprising a compound provided herein, and one or more pharmaceutically acceptable excipients. Compositions and dosage forms provided herein may further comprise one or more additional active ingredients.

In various embodiments, provided herein is a method of treating, preventing, and/or managing the negative symptoms, cognitive dysfunction symptoms, or both, associated with schizophrenia. In various embodiments, provided herein are methods of treating, preventing, and/or managing negative symptoms, cognitive dysfunction symptoms, or both, associated with schizophrenia in a subject, such as a mammal, such as, e.g., human, rodent (such as, e.g., mice and rats), cat, dog, non-human primate, among others. In various embodiments, the methods comprises contacting a compound (provided herein and/or selected employing the methods provided herein) with one or more receptors of the central nervous system. In various embodiments, the methods comprise contacting a cell, where in various embodiments the cell is a brain cell, such as, e.g., a neuronal cell or a glial cell.

V. BRIEF DESCRIPTION OF THE DRAWINGS

In the accompanying drawings like reference numerals indicate like elements and features in the various figures. For clarity, not every element may be labeled in every figure. In addition, the drawings are not necessarily complete when viewed without reference to the text, emphasis instead being placed upon illustrating the principles of the inventions.

FIG. 1 presents a correlation matrix heat map of PANSS item scores for all patients at baseline (N=1710). The dendrogram (far right) displays clustering of related items according to a distance metric ($1-r^2$), where closely related items were more correlated than distantly related items (x-axis). The branches are labeled according to the clustering of items. Each row corresponds to an item in PANSS (labeled on far left) with identity to each column in the correlation matrix along the diagonal. The columns under heading MARDER FACTORS collect correlations between each item rating and each of 5 Marder PANSS factor scores vs rows. Items identified by the Marder model are labeled with letters as follows: P for positive, D for disorganized, A for anxiety/depression, H for hostility, and N for negative. The CORRELATION MATRIX is shaded according to Pearson's r value between each item (higher absolute values of r having a darker shading) and is symmetrical across the diagonal. Boxed areas identify clusters of items with higher correlations (darker shading) and correspond to the clustering in the dendrogram branches.

Figure 2:
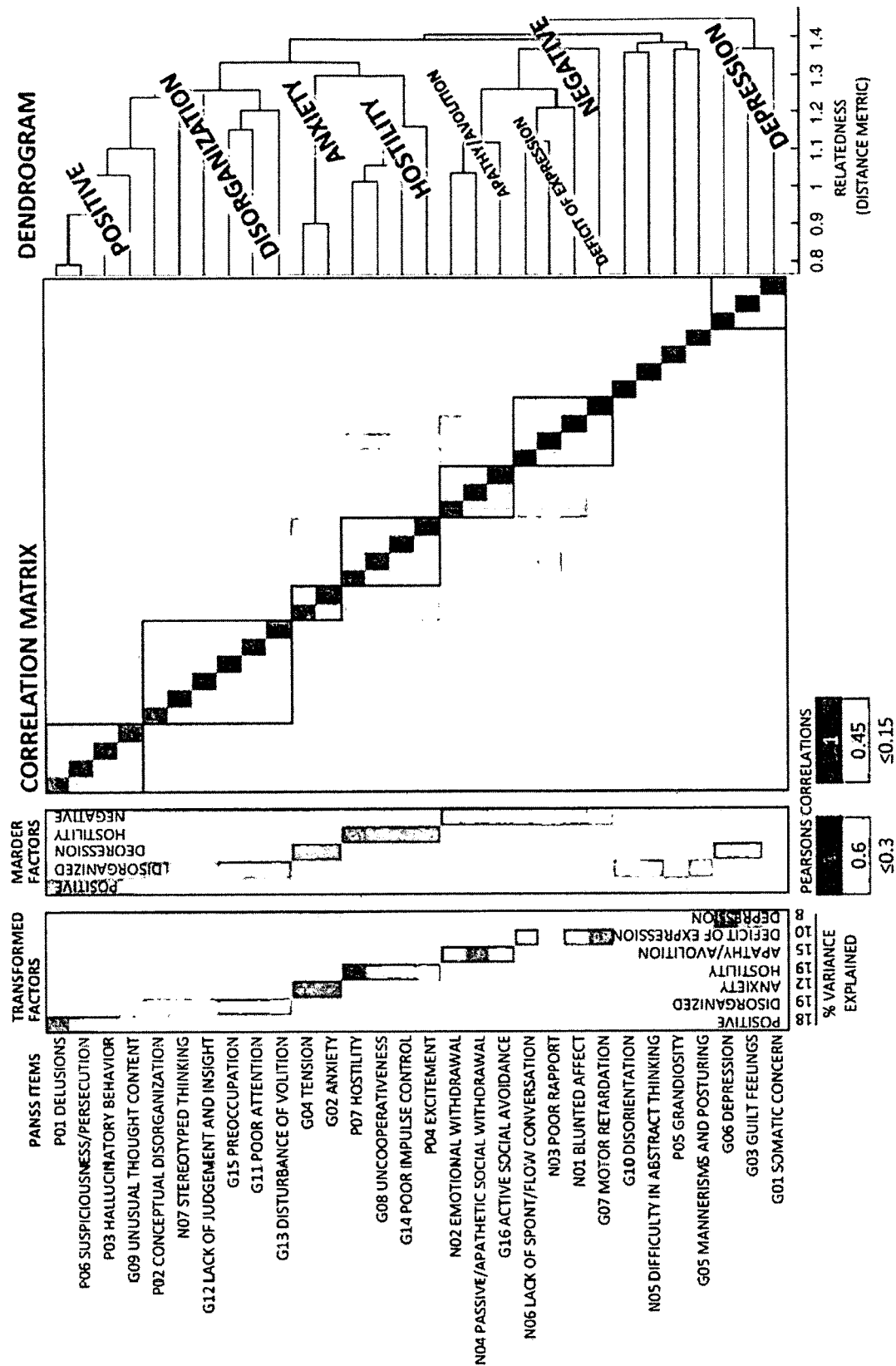

FIG. 2 presents a correlation matrix heat map of PANSS item scores for all observations' change from baseline. Correlations of individual item change scores (rows) are shown relative to the transformed PANSS factor change scores (columns under heading TRANSFORMED FACTORS), or relative to the Marder PANSS factors. Transformed PANSS factors were calculated using the coefficients of the score matrix (see FIG. 4 and Table 4A). The relatively low correlations among items outside of their respective (transformed) factor illustrates specific associations of items with distinct transformed PANSS factors, relative to Marder PANSS factor scores which have substantial correlations outside of their respective PANSS factors. The amount of variance explained by each PANSS factor was identified and labeled for each transformed PANSS factor. The CORRELATION MATRIX is shaded according to Pearson's r value between each item, and corresponds by row to the dendrogram at the far right. Branches in the dendrogram are labeled according to clustering of items, and correspond to boxes along the diagonal of the correlation matrix.

Figure 3A:
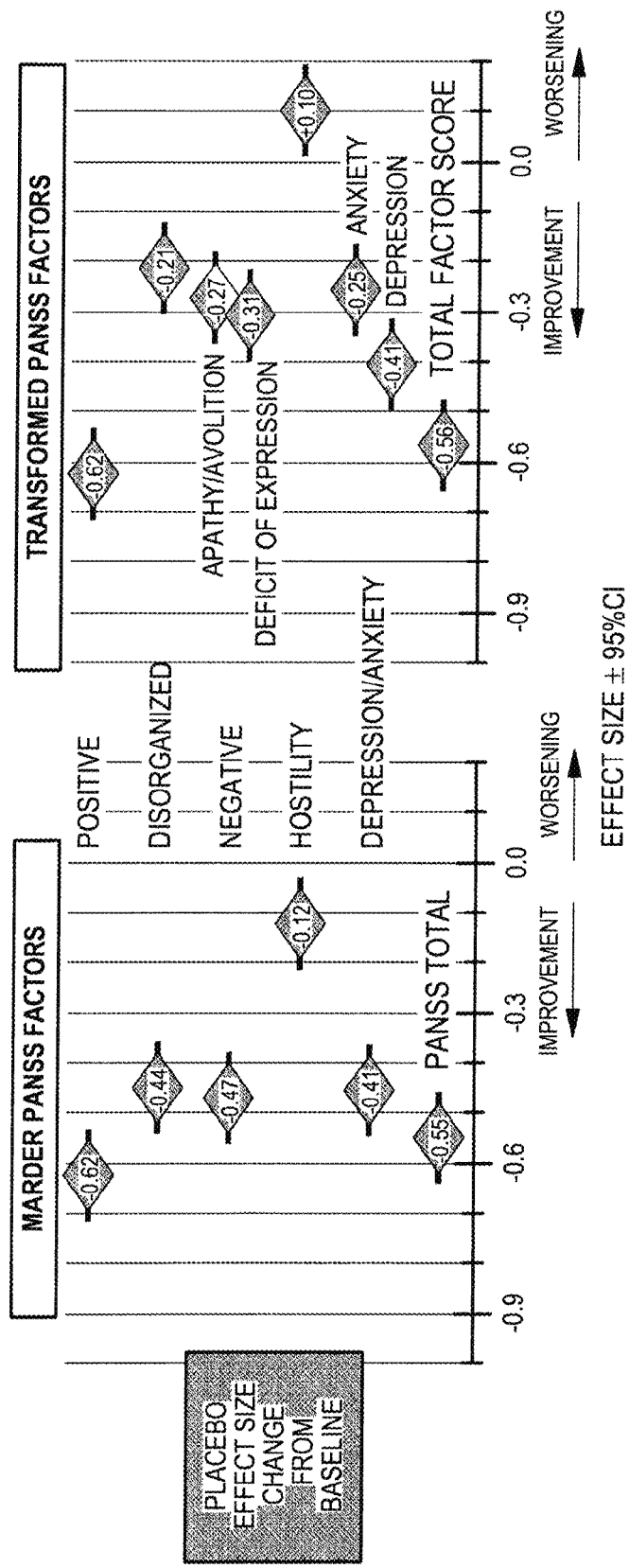

FIG. 3A shows a Forest plot of the effect size change from baseline for placebo. Profile of improvements (change from baseline) in schizophrenia symptoms estimated using PANSS factors. In the left panel of FIG. 3A, shown are within-treatment effect sizes (with 95% CI) for placebo for change from baseline at week 6 endpoint, based on the Marder PANSS factors. In the right panel of FIG. 3A, the same within-treatment effect sizes at endpoint are shown based on the transformed PANSS factors. Transformed PANSS factors were calculated using the coefficients of the score matrix (see FIG. 4 and Table 4A).

Figure 3B:
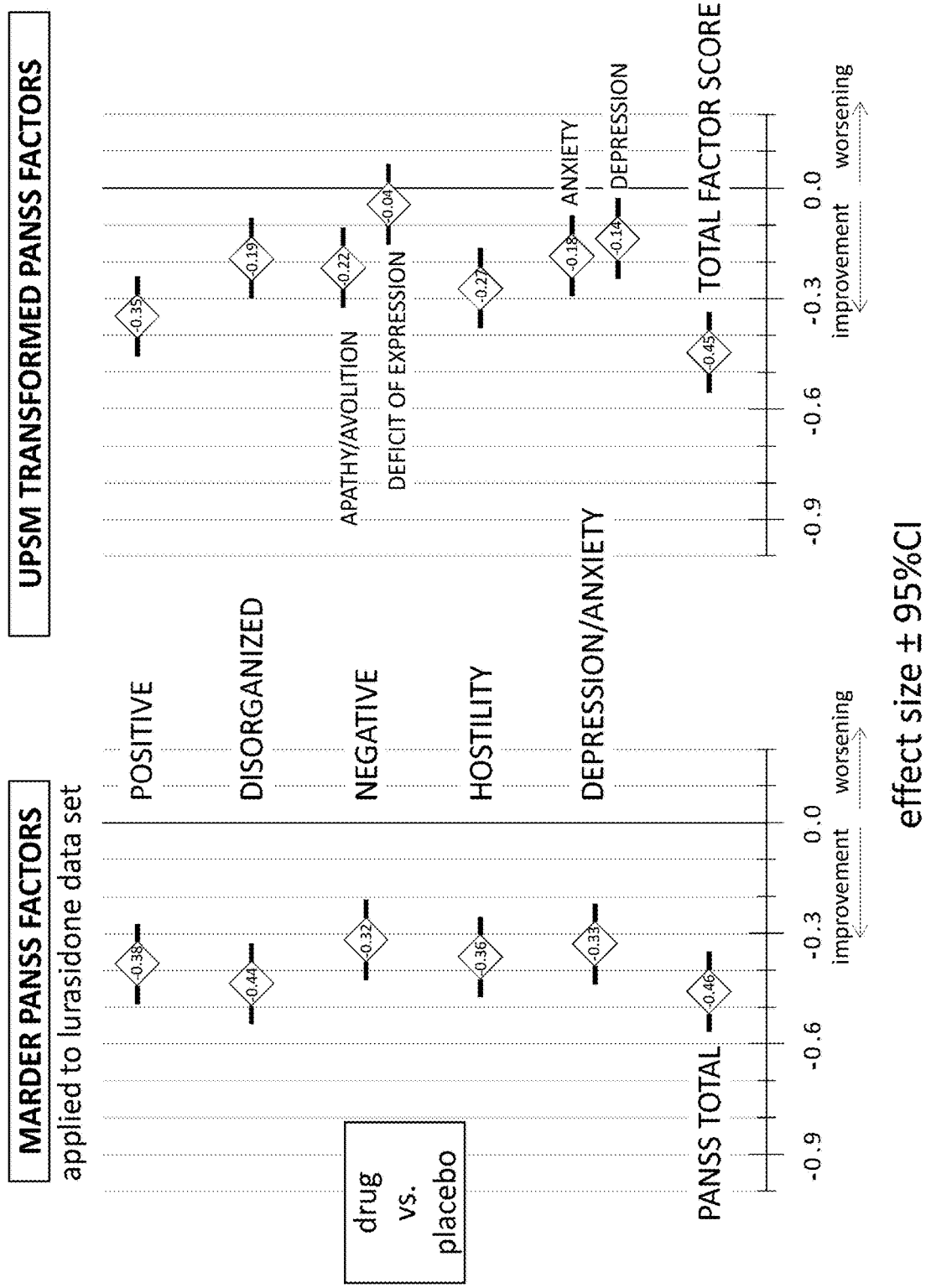

FIG. 3B shows a Forest plot of the effect size change from baseline for treatment with lurasidone. Profile of active drug effects on schizophrenia symptom domains. In the left panel of FIG. 3B, shown are lurasidone vs placebo effect sizes (with 95% CI) for change from baseline at week 6 endpoint, based on the Marder PANSS factors. In the right panel of FIG. 3B, the same lurasidone vs placebo effect sizes at endpoint are shown based on the transformed PANSS factors. Drug effects were constructed using a pool of all lurasidone doses (40, 80, 120, or 160 mg/day, total N=993) and excluded active comparators (olanzapine, quetiapine-XR). To examine placebo effects on PANSS factors, placebo treated patients (N=484) were pooled across all studies. Transformed PANSS factors were calculated using the coefficients of the score matrix (see FIG. 4 and Table 4A).

FIG. 4 presents the transformation matrix, also referred to herein as the score matrix and Uncorrelated PANSS Score Matrix (UPSM), that was used to transform Marder PANSS factor data to transformed PANSS factor data. The score matrix itself comprises the matrix from Columns 7 to 13 (inclusive) and rows 2 to 30 (inclusive), and is also presented in Table 4A. Column 1 provides the PANSS factor transformed (e.g. provide the order of the PANSS column vector) and column 14 the name for this PANSS factor. Columns 2 to 6 illustrate the correspondence between the PANSS factors and the associated Marder PANSS factors (here also diagnostic symptom domains), and the traditional weighting of PANSS factors as either "0" or "1." In FIG. 4, the following abbreviations are used: "POS" means positive symptoms; "DIS" means disorganized thoughts; "NAA" means negative symptoms of apathy/avolition; "NDE" means negative symptom of deficit of expression; "HOS" means hostility; "NEG" means, negative symptoms; "ANX" means anxiety; and "DEP" means depression; "DEP/ANX" means depression/anxiety.

FIG. 5 presents the correlation coefficients among the transformed PANSS factor scores for the validation data of Example 1. Column of the table of FIG. 5 indicates if the study used was from the analysis or validation data set; column 2 the study; column 3 the study design; column 4 the number of subjects; column 5 the study duration; column 6 the transformed PANSS factors (Nfactor) total versus the PANSS factor total; columns 7-10 the Pearson's correlation coefficients between the transformed PANSS factor scores for Positive symptoms (POS) and the other transformed PANSS factor scores (e.g. DIS, AA, DE and HOS); and columns 11-13 the transformed PANSS factor subtotals versus the transformed PANSS factor scores for Positive symptoms. Correlations are presented for change scores to study endpoint for the indicated duration of column 5. The following abbreviations are used: "RCT" means Randomized placebo-Controlled Trial in acute schizophrenia; "RWS" means Randomized Withdrawal Study at endpoint of Open Label ("OL") or Double Blind ("DB") period; "POS" means positive symptoms; "DIS" or "Dis" means disorganized thoughts; "AA" also "NAA" means negative symptoms of apathy/avolition; "DE" also "NDE" means negative symptom of deficit of expression; "HOS" or "Hos" means hostility; and "NEG" or "Neg" means, negative symptoms.

VI. DETAILED DESCRIPTION

A. Definitions

Unless defined otherwise, all technical and scientific terms used herein have the same meaning as those commonly understood by one of ordinary skill in the art. In certain embodiments, abbreviations are as defined in *J. Org. Chem.* 2007, 72, 23A. All publications and patents referred to herein are incorporated by reference herein in their entireties. As used in the specification and the accompanying claims, the indefinite articles "a" and "an" and the definite article "the" include plural as well as singular referents, unless the context clearly dictates otherwise.

As used herein, and unless otherwise specified, the terms "drug" and "therapeutic agent" refer to a compound, or a pharmaceutical composition thereof, which is administered to a subject for treating, preventing, managing, or ameliorating one or more symptoms of a condition, disorder, or disease.

As used herein, and unless otherwise specified, the terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

As used herein, the term "subject," to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

As used herein, the terms "treatment," "treat," and "treating" refer to reversing, alleviating, delaying the onset of, or inhibiting the progress of a disease or disorder, or one or more symptoms thereof, including but not limited to therapeutic benefit. In various embodiments, treatment may be administered after one or more symptoms have developed. In other embodiments, treatment may be administered in the absence of symptoms. For example, treatment may be administered to a subject prior to the onset of symptoms (e.g., in light of a history of symptoms and/or in light of genetic or other susceptibility factors). Treatment may also be continued after symptoms have resolved, for example to prevent or delay their recurrence.

Therapeutic benefit includes eradication and/or amelioration of the underlying disorder being treated; it also includes the eradication and/or amelioration of one or more of the symptoms associated with the underlying disorder such that an improvement is observed in the subject, notwithstanding that the subject may still be afflicted with the underlying disorder. In various embodiments, "treatment" or "treating" includes one or more of the following: (a) inhibiting the disorder (for example, decreasing one or more symptoms resulting from the disorder, and/or diminishing the extent of the disorder); (b) slowing or arresting the development of one or more symptoms associated with the disorder (for example, stabilizing the disorder and/or delaying the worsening or progression of the disorder); and/or (c) relieving the disorder (for example, causing the regression of clinical symptoms, ameliorating the disorder, delaying the progression of the disorder, and/or increasing quality of life.)

As used herein, the term "therapeutically effective amount" or "effective amount" refers to an amount that is effective to elicit the desired biological or medical response, including the amount of a compound that, when administered to a subject for treating a disorder, is sufficient to effect such treatment of the disorder. The effective amount will vary depending on the compound, the disorder, and its severity, and the age, weight, etc. of the subject to be treated. The effective amount may be in one or more doses (for example, a single dose or multiple doses may be required to achieve the desired treatment endpoint). An effective amount may be considered to be given in an effective amount if, in conjunction with one or more other agents, a desirable or beneficial result may be or is achieved. Suitable doses of any co-administered compounds may optionally be lowered due to the combined action, additive or synergistic, of the compound.

As used herein, an "at risk" individual is an individual who is at risk of developing a disorder to be treated. This may be shown, for example, by one or more risk factors, which are measurable parameters that correlate with development of a disorder and are known in the art.

As used herein, "prevention" or "preventing" refers to a regimen that protects against the onset of the disorder such that the clinical symptoms of the disorder do not develop. Accordingly, "prevention" relates to administration of a therapy, including administration of a compound disclosed herein, to a subject before signs of the diseases are detectable in the subject (for example, administration of a compound disclosed herein to a subject in the absence of a detectable syndrome of the disorder). The subject may be an individual at risk of developing the disorder. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the terms "manage," "managing," and "management" refer to preventing or slowing the progression, spread or worsening of a disease or disorder, or of one or more symptoms associated with the disease or disorder. In one embodiment, such symptoms are those known to a person of skill in the art to be associated with the disease or disorder being managed. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, the various PANSS factors terms: (P01) delusions, (P02) conceptual disorganization, (P03) hallucinations, (P04) excitement, (P05) grandiosity, (P06) suspiciousness/persecution, and (P07) hostility, (N01) blunted affect, (N02) emotional withdrawal, (N03) poor rapport, (N04) passive/apathetic social withdrawal, (N05) difficulty in abstract thinking, (N06) lack of spontaneity and flow of conversation, and (N07) stereotyped thinking, (G01) somatic concern, (G02) anxiety, (G03) guilt feelings, (G04) tension, (G05) mannerisms and posturing, (G06) depression, (G07) motor retardation, (G08) uncooperativeness, (G09) unusual thought content, (G10) disorientation, (G11) poor attention, (G12) lack of judgment and insight, (G13) disturbance of volition, (G14) poor impulse control, (G15) preoccupation, and (G16) active social avoidance; are used herein in a manner consistent with their accepted meanings in the art. See, e.g., Marder S R, Davis J M, Chouinard G., J. Clin. Psychiatry. 1997; 58:538-546). It is to be understood that the notations in parenthesis, for example (P01), (N05), (G12), etc., are used for ease of reference and convenience.

The general psychopathology factors are (G01) somatic concern, (G02) anxiety, (G03) guilt feelings, (G04) tension, (G05) mannerisms and posturing, (G06) depression, (G07) motor retardation, (G08) uncooperativeness, (G09) unusual thought content, (G10) disorientation, (G11) poor attention, (G12) lack of judgment and insight, (G13) disturbance of volition, (G14) poor impulse control, (G15) preoccupation, and (G16) active social avoidance.

The Marder PANSS factor domains are positive, disorganized, affective, hostility, and negative. The Marder PANSS factor domain of negative comprises two subdomains: apathy/avolition and deficit of expression. The Marder PANSS factor domain of affective comprises two subdomains: depression and anxiety. In various embodiments, an untransformed Marder PANSS positive factor is based on the Marder PANSS positive factor domain comprised of PANSS factors: (P01) delusions, (P03) hallucinatory behavior, (P05) grandiosity, (P06) suspiciousness/persecution, (N07) stereotyped thinking, (G01) somatic concern, (G09) unusual thought content, and (G12) lack of judgment and insight. In various embodiments, an untransformed Marder PANSS disorganized factor is based on the Marder PANSS disorganized factor domain comprised of PANSS factors: (P02) conceptual disorganization, (N05) difficulty in abstract thinking, (G05) mannerisms and posturing, (G10) disorientation, (G11) poor attention, (G13) disturbance of volition, and (G15) preoccupation. In various embodiments, an untransformed Marder PANSS affective factor is based on the Marder PANSS affective factor domain comprised of PANSS factors: (G02) anxiety, (G03) guilt feelings, (G04) tension, and (G06) depression. In various embodiments, an untransformed Marder PANSS hostility factor is based on the Marder PANSS hostility factor domain comprised of PANSS factors: (P04) excitement, (P07) hostility, (G08) uncooperativeness, and (G14) poor impulse control. In various embodiments, an untransformed Marder PANSS negative factor is based on the Marder PANSS negative factor domain comprised of PANSS factors: (N01) blunted affect, (N02) emotional withdrawal, (N03) poor rapport, (N04) passive/apathetic social withdrawal, (N06) lack of spontaneity and flow of conversation, (G07) motor retardation, and (G16) active social avoidance. In various embodiments, an untransformed Marder PANSS depression subdomain factor is based on the PANSS factors: (G03) guilt feelings, and (G06) depression. In various embodiments, an untransformed Marder PANSS anxiety subdomain factor is based on the PANSS factors: (G02) anxiety, and (G04) tension. In various embodiments, an untransformed Marder PANSS apathy/avolition subdomain factor is based on the PANSS factors: (N02) emotional withdrawal, (N04) passive/apathetic social withdrawal, and (G16) active social avoidance. In various embodiments, an untransformed Marder PANSS deficit of expression subdomain factor is based on the PANSS factors: (N01) blunted affect, (N03) poor rapport, (N06) lack of spontaneity and flow of conversation, and (G07) motor retardation.

It is to be understood that an untransformed Marder PANSS factor is also referred to herein simply as a PANSS factor, or untransformed PANSS factor, as will be evident to those of ordinary skill in the art based on context.

It is to be understood that typical positive schizophrenia symptoms are: (1) delusions, (2) conceptual disorganization, (3) hallucinations, (4) excitement, (5) grandiosity, (6) suspiciousness/persecution, and (7) hostility.

It is to be understood that typical negative schizophrenia symptoms are: (1) blunted affect, (2) emotional withdrawal, (3) poor rapport, (4) passive/apathetic social withdrawal, (5) difficulty in abstract thinking, (6) lack of spontaneity and flow of conversation, and (7) stereotyped thinking.

As used herein, and unless otherwise specified, the terms "psychosis," "schizophrenia," "blunted affect," "emotional withdrawal," "poor rapport," "passive/apathetic social withdrawal," "difficulty in abstract thinking," "lack of spontaneity and flow of conversation," "stereotyped thinking," "delusions," "conceptual disorganization," "hallucinations," "excitement," "grandiosity," "suspiciousness/persecution," "hostility," and other CNS or neurological disorders or symptoms described herein elsewhere are used herein in a manner consistent with their accepted meanings in the art. See, e.g., *Diagnostic and Statistical Manual of Mental Disorders*, 5$^{th}$ Ed., American Psychiatric Association (2013) (DSM-V™).

As used herein, and unless otherwise specified, the term "seizure" refers to a neurological disorder and may be used interchangeably with "convulsion," although there are many types of seizure, some of which have subtle or mild symptoms instead of convulsions. In one embodiment, the term "seizure" as used herein is intended to encompass "convulsion." In various embodiments, seizures may be caused by disorganized and sudden electrical activity in the brain. In various embodiments, convulsions are a rapid and uncontrollable shaking during which the muscles contract and relax repeatedly. Unless otherwise specified, the terms "convulsion" and "seizure" are used herein in accordance with the accepted meanings as found in the *Diagnostic and Statistical Manual of Mental Disorders*, 5$^{th}$ Ed., American Psychiatric Association (2013) (DSM-V™).

As used herein, and unless otherwise specified, the term "affective disorder" includes depression, attention deficit disorder, attention deficit disorder with hyperactivity, bipolar disorder, and manic disorder, and the like.

As used herein, and unless otherwise specified, the term "depression" includes all forms of depression, including, but not limited to, major depressive disorder (MDD) or unipolar depressive disorder, dysthymia, seasonal affective disorder (SAD), and bipolar depressive disorder. "Major depressive disorder" is used herein interchangeably with "unipolar depression", "unipolar depressive disorder", and "major depression." "Depression" may also include any condition commonly associated with depression, such as all forms of fatigue (e.g., chronic fatigue syndrome) and cognitive deficits.

As used herein, and unless otherwise indicated, the term "alkyl" refers to a linear or branched saturated monovalent hydrocarbon radical, wherein the alkyl may optionally be substituted with one or more substituents. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$, or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms, e.g., n-propyl and isopropyl), butyl (including all isomeric forms, e.g., n-butyl, isobutyl, and t-butyl), pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is optionally substituted as described herein elsewhere.

As used herein, and unless otherwise specified, the term "alkenyl" refers to a linear or branched monovalent hydrocarbon radical, which contains one or more, in one embodiment, one to five, carbon-carbon double bonds. The alkenyl may be optionally substituted with one or more substituents. The term "alkenyl" also encompasses radicals having "cis" and "trans" configurations, or alternatively, "E" and "Z" configurations, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl. In certain embodiments, the alkenyl is optionally substituted as described herein elsewhere.

As used herein, and unless otherwise specified, the term "alkynyl" refers to a linear or branched monovalent hydrocarbon radical, which contains one or more, in one embodiment, one to five, carbon-carbon triple bonds. The alkynyl may be optionally substituted with one or more substituents. In certain embodiments, the alkynyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkynyl groups include, but are not limited to, ethynyl (—C≡CH) and propargyl (—$CH_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is optionally substituted as described herein elsewhere.

As used herein, and unless otherwise specified, the term "cycloalkyl" refers to a cyclic fully or partially saturated bridged and/or non-bridged hydrocarbon radical or ring system, which may be optionally substituted with one or more substituents. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl. In certain embodiments, the cycloalkyl is optionally substituted as described herein elsewhere.

As used herein, and unless otherwise specified, the term "heteroalkyl" refers to a stable straight or branched chain, or cyclic hydrocarbon radical, or combinations thereof, consisting of the stated number of carbon atoms and from one or more, in one embodiment, one to three, heteroatoms selected from the group consisting of O, N, Si, and S, and wherein the nitrogen and sulfur atoms are optionally oxidized and the nitrogen heteroatom can optionally be quaternized. In one embodiment, the heteroatom(s) O, N and S can be placed at any interior position of the heteroalkyl group. In one embodiment, the heteroatom Si can be placed at any position of the heteroalkyl group (e.g., interior or terminal position), including the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms can be consecutive, such as, for example, —$CH_2$—NH—O—$CH_3$ and —$CH_2$—O—Si($CH_3$)$_3$. In certain embodiments, the heteroalkyl is optionally substituted as described herein elsewhere.

As used herein, and unless otherwise specified, the term "alkoxyl" refers to a stable straight or branched chain, or cyclic hydrocarbon radical, or combinations thereof, consisting of the stated number of carbon atoms and from one or more, in one embodiment, one to three, O atoms. Examples of alkoxyl include, but are not limited to, —O—$CH_3$, —O—$CF_3$, —O—$CH_2$—$CH_3$, —O—$CH_2$—$CH_2$—$CH_3$, —O—CH—($CH_3$)$_2$, and —O—$CH_2$—$CH_2$—O—$CH_3$. In one embodiment, the alkoxyl is optionally substituted as described herein elsewhere.

As used herein, and unless otherwise specified, the term "aminoalkyl" refers to a stable straight or branched chain, or cyclic hydrocarbon radical, or combinations thereof, consisting of the stated number of carbon atoms and from one or more, in one embodiment, one to three, N atoms. Examples of aminoalkyl include, but are not limited to, —NH—$CH_3$, —N($CH_3$)$_2$, —NH—$CH_2$—$CH_3$, —N($CH_3$)—$CH_2$—$CH_3$, —NH—CH—($CH_3$)$_2$, —$CH_2$—$CH_2$—NH—$CH_3$, and —$CH_2$—$CH_2$—N($CH_3$)$_2$. In one embodiment, the aminoalkyl is optionally substituted as described herein elsewhere. In various embodiments, the aminoalkyl is optionally substituted with one or more halo.

As used herein, and unless otherwise specified, the term "aryl" refers to an optionally substituted monocyclic or multicyclic radical or ring system that contains at least one aromatic hydrocarbon ring. In certain embodiments, the aryl has from 6 to 20, from 6 to 15, or from 6 to 10 ring atoms. Examples of aryl groups include, but are not limited to, phenyl, naphthyl, fluorenyl, azulenyl, anthryl, phenanthryl, pyrenyl, biphenyl, and terphenyl. In certain embodiments, aryl also refers to bicyclic, tricyclic, or tetracyclic carbon rings, where one of the rings is aromatic and the other(s) of the rings may be saturated, partially unsaturated, or aromatic, for example, dihydronaphthyl, indenyl, indanyl, or tetrahydronaphthyl (tetralinyl). In certain embodiments, aryl may be a bicyclic, tricyclic, or tetracyclic ring system, where at least one of the rings is aromatic and one or more of the ring(s) is/are saturated or partially unsaturated containing one or more heteroatoms independently selected from O, S, and N. In certain embodiments, the aryl is optionally substituted with one or more substituents as described herein elsewhere.

As used herein, and unless otherwise specified, the term "arylalkyl" or "aralkyl" refers to a monovalent alkyl group substituted with aryl. Example of aralkyl includes, but is not limited to, benzyl. In certain embodiments, both alkyl and aryl may be optionally substituted with one or more substituents as described herein elsewhere.

As used herein, and unless otherwise specified, the term "cycloalkylalkyl" refers to a monovalent alkyl group substituted with cycloalkyl. In certain embodiments, both the alkyl and cycloalkyl may be optionally substituted with one or more substituents as described herein elsewhere.

As used herein, and unless otherwise specified, the term "heteroaryl" refers to an optionally substituted monocyclic or multicyclic radical or ring system which contains at least one aromatic ring having one or more heteroatoms independently selected from O, S, and N. In one embodiment, each ring of a heteroaryl group can contain one or two 0 atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. In certain embodiments, heteroaryl also refers to bicyclic, tricyclic, or tetracyclic rings, where one of the rings is aromatic having one or more heteroatoms independently selected from O, S, and N, and the other(s) of the rings may be saturated, partially unsaturated, or aromatic and may be carbocyclic or contain one or more heteroatoms independently selected from O, S, and N. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents as described herein elsewhere.

As used herein, and unless otherwise specified, the term "heterocycloalkyl" or "heterocyclyl" refers to an optionally substituted monocyclic or multicyclic radical or ring system which contains at least one non-aromatic ring having one or more heteroatoms independently selected from O, S, and N, and the remaining ring atoms are carbon atoms. In certain embodiments, the heterocyclyl or heterocycloalkyl group has from 3 to 20, from 3 to 15, from 3 to 10, from 3 to 8, from 4 to 7, or from 5 to 6 ring atoms. In certain embodiments, the heterocyclyl or heterocycloalkyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, the ring carbon atoms may be optionally substituted with oxo, and some rings may be partially or fully saturated, or aromatic. The heterocycloalkyl or heterocyclyl may be attached to the main structure at a heteroatom or a carbon atom which results in the creation of a stable compound. Examples include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, when the heterocyclyl or heterocycloalkyl ring contains one or more 0, the heterocyclyl or heterocycloalkyl may also be referred to as "cycloalkoxyl." In certain embodiments, the heterocyclyl or heterocycloalkyl is optionally substituted with one or more substituents as described herein elsewhere.

As used herein, and unless otherwise specified, the term "halogen", "halide" or "halo" refers to fluorine, chlorine, bromine, and iodine.

As used herein, and unless otherwise specified, the term "hydrogen" encompasses proton ($^1$H), deuterium ($^2$H), tritium ($^3$H), and/or mixtures thereof. In a compound described herein, one or more positions occupied by hydrogen may be enriched with deuterium and/or tritium. Such isotopically enriched analogs may be prepared from suitable isotopically labeled starting material obtained from a commercial source or prepared using known literature procedures.

As used herein, and unless otherwise specified, the term "optionally substituted" is intended to mean that a group, such as an alkyl, alkenyl, alkynyl, cycloalkyl, heteroalkyl, aryl, aralkyl, cycloalkylalkyl, heteroaryl, or heterocyclyl, may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (b) halo, cyano (—CN), nitro (—NO$_2$), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) R$^b$ and R$^c$ together with the N atom to which they are attached form heteroaryl or heterocyclyl, optionally substituted with one or more, in one embodiment, one, two, three, or four, substituents $Q^1$. As used herein, all groups that can be substituted are "optionally substituted," unless otherwise specified.

In one embodiment, each $Q^1$ is independently selected from the group consisting of (a) cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^f$ and R$^g$ together with the N atom to which they are attached form heteroaryl or heterocyclyl.

As used herein, and unless otherwise specified, the term "pharmaceutically acceptable salts" refers to salts prepared from pharmaceutically acceptable non-toxic acids, including inorganic acids and organic acids. Suitable non-toxic acids include inorganic and organic acids, such as, including but not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, and p-toluenesulfonic.

As used herein, and unless otherwise specified, the term "solvate" refers to a compound provided herein or a salt thereof, which further includes a stoichiometric or non-stoichiometric amount of solvent bound by non-covalent intermolecular forces. Where the solvent is water, the solvate is a hydrate.

As used herein, and unless otherwise specified, the term "stereoisomer" encompasses all enantiomerically/diastereomerically/stereomerically pure and enantiomerically/diastereomerically/stereomerically enriched compounds provided herein.

As used herein and unless otherwise specified, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

As used herein, and unless otherwise indicated, the term "enantiomerically pure" means a stereomerically pure composition of a compound having one chiral center. Similarly, the term "enantiomerically enriched" means a stereomerically enriched composition of a compound having one chiral center.

In certain embodiments, as used herein, and unless otherwise specified, "optically active" and "enantiomerically active" refer to a collection of molecules, which has an enantiomeric excess or diastereomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer or diastereomer and about 5% or less of the less preferred enantiomer or diastereomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 30%, 25%, 20%, 15%, 10%, 9%, 8%, 7%, 6%, 5%, 4%, 3%, 2%, 1%, 0.5%, 0.1%, or 0.05% of a given value or range.

As used herein, and unless otherwise specified, the term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy*, 21st Edition, Lippincott Williams & Wilkins: Philadelphia, Pa., 2005; *Handbook of Pharmaceutical Excipients*, 5th Edition, Rowe et al., Eds., The Pharmaceutical Press and the American Pharmaceutical Association: 2005; and *Handbook of Pharmaceutical Additives*, 3rd Edition, Ash and Ash Eds., Gower Publishing Company: 2007; *Pharmaceutical Preformulation and Formulation*, 2nd Edition, Gibson Ed., CRC Press LLC: Boca Raton, Fla., 2009.

B. Methods

For decades, the PANSS has been the most widely used measure for evaluating efficacy in randomized clinical trials of acute schizophrenia. However, attribution of specific treatment-related improvements among the various symptom domains within PANSS is limited by the high degree of correlation between PANSS factors. As a consequence, apparent improvement in key clinical domains (e.g., negative symptoms, disorganized thinking/behavior) may largely be attributable to scoring of a correlated clinical domain, such as positive symptoms, a problem frequently referred to as pseudospecificity.

Previous attempts at targeting specific symptom domains, sub-domains or patient sub-populations (e.g. patients with symptoms prominently in a specific symptom sub-domain or sub-domains) have not resulted in regulatory approval, in large measure because multidimensional scales such as the PANSS have not overcome the hurdle of pseudospecificity, i.e., the strong correlation between traditional PANSS factors.

The present inventors have discovered methods which can be used to minimize the correlation or decorrelate the PANSS factors and thus ascertain the potential efficacy of a compound and/or treatment for a specific symptom of schizophrenia, and in various particular embodiments, the potential efficacy of a compound and/or treatment for a negative symptom of schizophrenia.

In various embodiments, methods of the present inventions provide a solution to the problem of pseudospecificity, by validating orthogonal, minimally correlated measures of key clinical domains.

Traditional PANSS factors can be significantly correlated, as a consequence, it has not been possible to determine whether improvement in the severity of symptoms in the five PANSS factors is a domain-specific treatment effect, or is a non-specific effect secondary to observed improvement in correlated PANSS items. The inventors have conducted an analysis of PANSS data from a 6-week treatment study of lurasidone that illustrates such correlation.

The analysis sample consisted of PANSS data derived from 5 similarly-designed, randomized, double-blind, placebo-controlled, 6-week treatment studies of lurasidone or active comparator for the treatment of patients with an acute exacerbation of schizophrenia. Patients (N=1,710) were included in this analysis if they had received at least one dose of study drug, and had at least one post-baseline PANSS assessment. The analysis pooled all lurasidone doses (40, 80, 120, or 160 mg/d, total N=993), and excluded active comparators (olanzapine, quetiapine-XR). To examine placebo effects on PANSS factors, placebo treated patients (N=484) were pooled across all studies. Herein also referred to as the "PANSS Analysis Study."

To visualize the relatedness among PANSS items, dendrograms were calculated using correlations between items at baseline, and separately using correlations between items in change post baseline. Items with more correlation were considered more closely related and were shown with shorter pairwise branch distances in a dendrogram. Dendrograms were calculated based on the unweighted average distance method in MATLAB R2016a2, and using a distance metric of $1-r^2$, where r is the Pearson correlation between two items.

FIG. 1 presents the correlation matrix heat map of PANSS item scores calculated for all patients at baseline. Schizophrenia symptoms, present at baseline in the pooled sample (N=1,710), were clustered according to the relative correlations among the 30 PANSS items. The baseline correlation matrix identified substantial correlations among PANSS items. To identify clustering of related items, a dendrogram of baseline symptoms was plotted using the correlation matrix as a distance metric. The dendrogram of FIG. 1 (far right), displays clustering of related items according to the distance metric $1-r^2$, where closely related items are more correlated than distantly related items (x-axis). Clusters of items visible as 5 major branches in the dendrogram were identified as 5 domains of psychopathology. The branches are labeled according to the clustering of items.

Ratings on items identified by the original PANSS factor model of Marder (Marder S R, Davis J M, Chouinard G., J. Clin. Psychiatry. 1997; 58:538-546) were summed (with equal weighting) to show correlations between individual PANSS items and the 5 Marder PANSS factors (see FIG. 1). A correspondence was found between the Marder PANSS factors, and branches in the dendrogram.

The change-from-baseline was then examined in the 30 PANSS items. The correlation matrix identified substantial correlations among individual PANSS item change scores. Referring to FIG. 2, a second dendrogram of the PANSS item change scores was plotted to identify clustering of related items using the correlation matrix of change scores as a distance metric, shown in FIG. 2. The dendrogram of FIG. 2 suggested that change-from-baseline in PANSS items exhibited a clustering that was similar to that observed for PANSS items at baseline. In the branch of negative symptoms, for example, the same two distinct subfactors (apathy/avolition and deficit of expression) were evident in both change-from-baseline, and at baseline. Table 1 shows the Pearson's correlation coefficients between the Marder PANSS factors, where the following abbreviations are used: POS, positive symptoms; DIS, disorganized thoughts; Neg, negative symptoms; Hos/Exc, hostility/excitement; Anx/Dep, anxiety/depression; Tot, total.

TABLE 1

Correlations Among Marder PANSS Factor Scores
(Week 6 Change from Baseline)

| Marder PANSS factors | Pos | Neg | Anx/Dep | Dis | Hos/Exc | Tot |
|---|---|---|---|---|---|---|
| Positive Symptoms | 1 | | | | | |
| Negative Symptoms | 0.57 | 1 | | | | |
| Anxiety/Depression | 0.52 | 0.40 | 1 | | | |
| Disorganized Thought | 0.74 | 0.62 | 0.45 | 1 | | |
| Hostility/Excitement | 0.64 | 0.43 | 0.46 | 0.59 | 1 | |
| PANSS Total | 0.90 | 0.77 | 0.66 | 0.86 | 0.77 | 1 |

The analysis of baseline-to-endpoint change in the current pooled data set revealed substantial correlations among the Marder PANSS factors as can be seen in Table 1. For example, endpoint (week 6) change in the Marder PANSS positive factor score was highly correlated with endpoint change in the Marder PANSS negative (r=0.57), PANSS disorganized (r=0.74), PANSS hostile (r=0.64), and PANSS depressed (r=0.52) factor scores.

The present inventors have discovered methods which can be used to minimize the correlation or decorrelate PANSS factors. Despite the availability of dozens of agents across two generations of antipsychotic drugs, there is broad consensus that there remains an unmet need for effective treatments of key clinical dimensions of schizophrenia, most notably negative symptoms and cognitive dysfunction. In various aspects and embodiments, the present inventions provide orthogonal, minimally correlated measures of severity across key symptom domains and/or patient sub-populations, which, for example, could be used by clinicians to more clearly delineate the efficacy of drugs in treating symptom domain, symptom sub-domains and/or patient sub-populations (e.g. patients with symptoms prominently in a specific symptom sub-domain or sub-domains).

In various embodiments, the methods provide transformed PANSS factor score estimates by differentially weighting each PANSS item to optimize its contribution to the relevant factor, while minimizing the contribution of the item to other PANSS factors.

In various embodiments, a score matrix (also referred to herein as an Uncorrelated PANSS Score Matrix, abbreviated UPSM) is used to transform PANSS factor data into transformed PANSS factor data, where the transformed PANSS factors have reduced or minimal correlation between them.

In various embodiments, the methods transform a PANSS data set comprising 30 PANSS factors (see. e.g., Table 4A, column 8, and Table 4B) to produce a data set described by 7 transformed PANSS factors. For example, in various embodiments, the PANSS factors are as listed in Table 4B and the score matrix portion of Table 4A is used to transform the PANSS data substantially as follows:

$$[\text{PANSS Data}]_{(N \times 30)} * [\text{UPSM}]_{(30 \times 7)} = [\text{Transformed PANSS Factor Data}]_{(N \times 7)}$$

where $[\text{PANSS Data}]_{(N \times 30)}$ is a matrix with N PANSS assessments and 30 columns for 30 PANSS factors to be transformed; $[\text{UPSM}]_{(30 \times 7)}$ is a matrix with 30 rows (one for each PANSS item) and 7 columns (one for each of the 7 Transformed PANSS Factors); and $[\text{Transformed PANSS Factor Data}]_{(N \times 7)}$ is the transformed matrix with N PANSS assessments in the 7 columns for 7 Transformed PANSS factors. That is, the coefficients of the uncorrelated PANSS score matrix (the UPSM is a matrix of 30 rows, one of r each PANSS item, ×7 columns, one for each transformed PANSS Factor) are used to transform individual PANSS assessments (ratings expressed either as change from baseline, or as absolute ratings) to reduce 30 items into 7 factor scores (transformed PANSS factor scores) for each PANSS assessment. Each column of the UPSM contains coefficients to multiply the corresponding item scores of PANSS.

In various embodiments, a score matrix for any set of PANSS factors is determined by a maximum likelihood factor analysis upon a matrix of untransformed factors followed by an orthogonal rotation, e.g. a varimax rotation, to produce the score matrix. Communalities greater than 1 in the maximum likelihood factor analysis are compensated for using Heywood criteria (that is, communalities greater than 1 are set to 1, thus no communality is allowed to exceed 1) without a limit on the number of factors produced.

It is to be understood that maximum likelihood factor analysis can have issues with commonalities (which can arise from the interactive way in which communalities are estimated), in addition, maximum likelihood factor analysis is far more computationally intensive than principal factor analysis by two or more orders of magnitude. Further, it is to be understood that rotating a set of factors does not change the statistical explanatory power of the factors. Therefore, there is no a prior choice for orthogonal rotation and choice of rotation cannot be based on statistical grounds. However, the inventors have unexpectedly discovered that a UPSM generated by maximum likelihood factor analysis with a varimax rotation, despite issues communalities has general applicability as further discussed in the Examples.

For example, the UPSM of Table 4A was generated from PANSS data derived from the 5 similarly-designed, randomized, double-blind, placebo-controlled, 6-week treatment studies of lurasidone or active comparator for the treatment of patients with an acute exacerbation of schizophrenia described above (the PANSS Analysis Study) and discussed in the context of Table 1 and FIG. 1 and FIG. 2.

The Uncorrelated PANSS Score Matrix (UPSM) of FIG. 4 and Table 4A was derived using PROC FACTOR procedure of SAS 9.4 with maximum likelihood method (maximum likelihood factor analysis), rotated using the varimax algorithm and compensated for communality greater than 1 using Heywood criteria without a limit on the number of factors produced. A last observation carried forward (LOCF) data imputation method was applied for missing post-baseline PANSS assessments.

An analysis of PANSS assessments as pooled over all post-baseline observations was conducted on the PANSS Analysis Study data. The factoring of change scores was weighted both by repeated measures within-patients as well as by the between-patient measures, and was utilized to increase statistical confidence in the output of the factor analysis. The change-from-baseline transformation of PANSS items (the score matrix) was intentionally derived from an analysis of PANSS over time (study visits) across the study population such that items changing together (vs changing separately) were captured in the structure and coefficients of the score matrix. Remarkably it was discovered that a fixed score matrix applied to disparate patient samples, different trial designs and durations, still retained the properties of orthogonality and high total variance explained with respect to the known factor structure of PANSS.

The ratings of 30 items in the PANSS data of the PANSS Analysis Study were transformed to transformed PANSS factor scores using a score matrix identified by the maximum likelihood method factor analysis conducted on all change from baseline PANSS data from the 5 short-term clinical trials in the pooled analysis sample. The score matrix, also referred to here as the UPSM, consisted of coefficients multiplying the numerical ratings of each PANSS item differentially for each of the factor scores.

The change-from-baseline PANSS data for all patients and all observations N was a matrix of dimensions (N observations×30 items). To increase precision, the score matrix coefficients were determined using all change-from-baseline observations at Weeks 1-6. The resultant score matrix (30 items×7 factors), or UPSM, was used to transform individual PANSS item change scores (without standardization) to reduce the dimensionality into 7-factor values for each PANSS assessment. FIG. 4 and Table 4A summarize the score matrix (UPSM) weights for individual PANSS items used to generate the transformed PANSS factors.

The weighted score matrix transformation was performed on each of the PANSS item baseline-to-endpoint change scores. This transformation yielded 5 transformed PANSS factors that corresponded to the Marder PANSS factors, with two of the factors (negative symptoms and depression/anxiety) further subdivided into sub-factors (corresponding to the symptom sub-domains of: apathy/avolition and deficit of expression; and depression and anxiety, respectively).

Each transformed PANSS factor corresponded preferentially with each of the Marder PANSS factors, as illustrated in Table 2. The transformed PANSS positive symptom factor (POS) correlated well with the Marder positive symptom factor (r=0.79) (see Table 2). The transformed PANSS factor for negative, disorganized, and hostile symptoms were each preferentially correlated with their respective Marder PANSS factors. The transformed PANSS anxiety and depression sub-factors (representing symptom sub-domains) were each well-correlated with the combined Marder PANSS depression/anxiety factor (r=0.74 and r=0.76, respectively).

The amount of variance explained by each transformed PANSS factor is noted in FIG. 2 with 8 to 19% variance explained by each of the 7 transformed PANSS factor scores. PANSS total scores were well-described by sums of the 7 transformed PANSS factor scores, with estimates from regression analysis yielding $r^2$ value goodness of fit for $p<0.0001$ at 0.93.

The transformed PANSS factors resulted in a marked reduction in correlations between the different factors when compared to the substantial correlations observed between the Marder PANSS factors, see for example Table 1. The off-diagonal item correlations evident in the Marder PANSS factors (see Table 1) were substantially reduced in the transformed PANSS factor correlations (see Table 3). In Table 3 the orthogonality of the transformed PANSS factors is evidenced by the lower correlations between the transformed PANSS factors when compared with the higher off-diagonal correlations of the Marder PANSS factors shown in Table 1.

In various aspects, the present inventions utilize existing PANSS data and transform that data with score matrix weighting coefficients to generate transformed PANSS factors with minimal between-factor correlation (enhanced orthogonality) while preserving the correspondence to Marder PANSS factors.

The low between-factor correlations between transformed PANSS factors (see Table 3) indicates that the transformed PANSS factors are measuring independent symptom domains and/or sub-domains, thereby reducing or eliminating pseudospecificity concerns. In addition, the strong correspondence between the transformed PANSS factors and the Marder PANSS factors confirms that each factor is measuring similar, established symptom domains of schizophrenia without substantial loss of statistical validity. These results were further validated as discussed in Examples 1-3, and it has been unexpectedly discovered that various embodiments of these methods provide a robust and generalizable means to address the challenge of pseudospecificity that has, to date, been a limitation in the usefulness of PANSS factors as efficacy measures.

Accordingly, in various aspects provided are methods for determining if a drug has potential efficacy for the treatment for a specific symptom of schizophrenia, and in various particular embodiments, the potential efficacy of a compound for treatment of a negative symptom of schizophrenia.

TABLE 2

Correlations Between Marder vs Transformed PANSS Factor Scores

| Marder PANSS factors | Transformed PANSS factors | | | | | | | |
|---|---|---|---|---|---|---|---|---|
| | POS | DIS | NAA | NDE | HOS | ANX | DEP | TOT |
| Positive Symptoms | 0.79 | 0.52 | 0.24 | 0.15 | 0.44 | 0.28 | 0.28 | 0.85 |
| Disorganized Thought | 0.44 | 0.79 | 0.30 | 0.27 | 0.39 | 0.24 | 0.20 | 0.79 |
| Negative Symptoms | 0.32 | 0.33 | 0.75 | 0.65 | 0.28 | 0.13 | 0.23 | 0.78 |
| Hostility/ Excitement | 0.38 | 0.30 | 0.16 | 0.02 | 0.94 | 0.29 | 0.12 | 0.73 |
| Anxiety/ Depression | 0.26 | 0.14 | 0.17 | 0.10 | 0.30 | 0.74 | 0.76 | 0.73 |
| PANSS Total | 0.59 | 0.55 | 0.42 | 0.31 | 0.57 | 0.37 | 0.36 | 0.97 |

TABLE 3

Correlations Among the Transformed PANSS Factor Scores

| Transformed PANSS factors | (Week 6 Change from Baseline) | | | | | | |
|---|---|---|---|---|---|---|---|
| | POS | DIS | NAA | NDE | HOS | ANX | DEP |
| Positive | 1 | | | | | | |
| Disorganized | 0.20 | 1 | | | | | |
| Neg Apathy/Avolition | 0.10 | 0.08 | 1 | | | | |
| Neg Deficit of Expression | 0.04 | 0.12 | 0.22 | 1 | | | |
| Hostility | 0.21 | 0.12 | 0.07 | −0.02 | 1 | | |
| Anxiety | 0.09 | 0.04 | −0.01 | −0.08 | 0.13 | 1 | |
| Depression | 0.10 | 0.00 | 0.12 | 0.13 | 0.04 | 0.27 | 1 |
| PANSS Total Score | 0.59 | 0.55 | 0.42 | 0.31 | 0.57 | | 0.36 |

In various aspects, the present inventions utilize existing PANSS data and transform that data with score matrix weighting coefficients to generate transformed PANSS factors with minimal between-factor correlation (enhanced orthogonality) while preserving the correspondence to Marder PANSS factors.

The low between-factor correlations between transformed PANSS factors (see Table 3) indicates that the transformed PANSS factors are measuring independent symptom domains and/or sub-domains, thereby reducing or eliminating pseudospecificity concerns. In addition, the strong correspondence between the transformed PANSS factors and the Marder PANSS factors confirms that each factor is measuring similar, established symptom domains of schizophrenia without substantial loss of statistical validity. These results were further validated as discussed in Examples 1-3, and it has been unexpectedly discovered that various embodiments of these methods provide a robust and generalizable means to address the challenge of pseudospecificity that has, to date, been a limitation in the usefulness of PANSS factors as efficacy measures.

Accordingly, in various aspects provided are methods for determining if a drug has potential efficacy for the treatment for a specific symptom of schizophrenia, and in various particular embodiments, the potential efficacy of a compound for treatment of a negative symptom of schizophrenia.

In Table 4A, the following abbreviations are used: "POS" means positive symptoms; "DIS" means disorganized thoughts; "NAA" means negative symptoms of apathy/avolition; "NDE" means negative symptom of deficit of expression; "HOS" means hostility; "ANX" means anxiety; and "DEP" means depression. Table 4B provides the PANSS item names for the 30 PANSS factors transformed.

TABLE 4A

Score Matrix (UPSM) & PANSS Factor

| HOS | DIS | POS | NAA | ANX | NDE | DEP | PANSS Factor |
|---|---|---|---|---|---|---|---|
| −0.059303151 | −0.154712684 | 0.57927306 | −0.082893265 | −0.073544962 | 0.007192722 | 0.002048441 | 01 |
| −0.036875601 | 0.197582458 | 0.029244439 | −0.026017326 | −0.001239624 | −0.02347538 | −0.036164505 | 02 |

TABLE 4A-continued

Score Matrix (UPSM) & PANSS Factor

| HOS | DIS | POS | NAA | ANX | NDE | DEP | PANSS Factor |
|---|---|---|---|---|---|---|---|
| −0.030050707 | −0.017941982 | 0.206578833 | −0.025066345 | 0.000150601 | −0.013303188 | 0.029300172 | 03 |
| 0.137935863 | 0.011528435 | −0.033679063 | 0.001165239 | 0.110819466 | −0.072389146 | −0.104522446 | 04 |
| −0.0069204 | −0.030187543 | −0.034150858 | −0.004101956 | −0.031327706 | −0.02334591 | 0.030828842 | 05 |
| 0.019206744 | −0.062627075 | 0.353725463 | 0.047732995 | −0.016139814 | 0.001212671 | 0.006326424 | 06 |
| 0.50254111 | −0.176791937 | −0.038346899 | −0.02993407 | −0.09971212 | 0.031465286 | 0.057360408 | 07 |
| −0.0388464 | −0.029140028 | −0.005423027 | 0.056870294 | 0.018823539 | 0.247417621 | −0.009152487 | 08 |
| −0.050709628 | −0.024392585 | −0.031576569 | 0.331790758 | −0.014565383 | −0.022820458 | 0.011268907 | 09 |
| 0.024553635 | −0.040131302 | −0.074207289 | −0.009748512 | −0.017616152 | 0.016151367 | −0.017221804 | 10 |
| −0.018906239 | −0.085636419 | −0.094353259 | 0.46115038 | −0.018582518 | −0.02868251 | −0.013043389 | 11 |
| −0.013349757 | 0.106249635 | 0.004333869 | 0.025591059 | 0.009606579 | −0.030147041 | −0.068680239 | 12 |
| −0.008500464 | 0.00515219 | 0.00412747 | 0.000955886 | 0.019423501 | 0.25768135 | −0.103745952 | 13 |
| −0.005529127 | 0.146226869 | −0.01112673 | −0.027641626 | −0.01184278 | 0.002301719 | 0.004012879 | 14 |
| −0.030917629 | 0.055250829 | −0.035627201 | −0.038262772 | 0.044494408 | 0.011015249 | 0.105984519 | 15 |
| −0.038647338 | −0.082189447 | −0.033105283 | −0.032737664 | 0.457657982 | −0.053317814 | 0.11978003 | 16 |
| −0.027217213 | −0.00043631 | −0.03688546 | −0.00206815 | −0.025316364 | −0.040797646 | 0.245965461 | 17 |
| −0.028752975 | −0.03326176 | −0.093136769 | −0.013294393 | 0.512385016 | 0.02319047 | −0.031252256 | 18 |
| −0.013667619 | 0.049411355 | −0.045519943 | −0.032417456 | 0.029350727 | 0.102625566 | −0.044173526 | 19 |
| 0.004221962 | −0.068819767 | −0.034475189 | −0.041273835 | −0.063510109 | 0.038179376 | 0.451442685 | 20 |
| −0.007324041 | −0.036613781 | −0.034889002 | −0.077978283 | −0.019265529 | 0.440989521 | 0.046413188 | 21 |
| 0.285870078 | 0.033402594 | −0.080369092 | −0.008848889 | −0.056716786 | −0.020048317 | −0.053107613 | 22 |
| −0.067585698 | 0.09392137 | 0.142896674 | −0.03261436 | −0.020907284 | −0.036752464 | −0.017789007 | 23 |
| −0.02661807 | −0.032458408 | −0.038304777 | −0.025539389 | −0.021006853 | −0.018011534 | −0.017602911 | 24 |
| 0.003765645 | 0.281436726 | −0.103631152 | −0.047891864 | −0.022652024 | 0.002998624 | 0.040135105 | 25 |
| 0.026229599 | 0.154863574 | 0.014298759 | −0.030608933 | −0.057629355 | −0.033158169 | −0.062618049 | 26 |
| −0.014549433 | 0.186791423 | −0.057351327 | −0.014348916 | −0.037178831 | 0.058153415 | 0.045541208 | 27 |
| 0.254666994 | 0.016627203 | −0.074838781 | −0.026749802 | −0.020124919 | −0.003163278 | −0.007642028 | 28 |
| −0.044233735 | 0.29122955 | −0.052081246 | 0.002977548 | −0.004799129 | −0.032435046 | 0.056719123 | 29 |
| 0.018359839 | −0.000724698 | −0.011203099 | 0.286013681 | −0.030234777 | −0.060620143 | 0.037074873 | 30 |

TABLE 4B

PANSS Factor (Item) Names

| PANSS Factor | PANSS FACTOR NAME |
|---|---|
| 01 | P01 DELUSIONS |
| 02 | P02 CONCEPTUAL DISORGANIZATION |
| 03 | P03 HALLUCINATORY BEHAVIOR |
| 04 | P04 EXCITEMENT |
| 05 | P05 GRANDIOSITY |
| 06 | P06 SUSPICIOUSNESS/PERSECUTION |
| 07 | P07 HOSTILITY |
| 08 | N01 BLUNTED AFFECT |
| 09 | N02 EMOTIONAL WITHDRAWAL |
| 10 | N03 POOR RAPPORT |
| 11 | N04 PASSIVE/APATHETIC SOCIAL WITHDRAWAL |
| 12 | N05 DIFFICULTY IN ABSTRACT THINKING |
| 13 | N06 LACK OF SPONTANEITY AND FLOW OF CONVERSATION |
| 14 | N07 STEREOTYPED THINKING |
| 15 | G01 SOMATIC CONCERN |
| 16 | G02 ANXIETY |
| 17 | G03 GUILT FEELINGS |
| 18 | G04 TENSION |
| 19 | G05 MANNERISMS AND POSTURING |
| 20 | G06 DEPRESSION |
| 21 | G07 MOTOR RETARDATION |
| 22 | G08 UNCOOPERATIVENESS |
| 23 | G09 UNUSUAL THOUGHT CONTENT |
| 24 | G10 DISORIENTATION |
| 25 | G11 POOR ATTENTION |
| 26 | G12 LACK OF JUDGEMENT AND INSIGHT |
| 27 | G13 DISTURBANCE OF VOLITION |
| 28 | G14 POOR IMPULSE CONTROL |
| 29 | G15 PREOCCUPATION |
| 30 | G16 ACTIVE SOCIAL AVOIDANCE |

In various aspects provided herein are methods of identifying subjects with symptoms prominently in a symptom domain of schizophrenia, a symptom prominently in a symptom sub-domain of schizophrenia, or both. In various embodiments, provided are methods of identifying compounds with potential efficacy in the treatment of the negative symptoms. In various embodiments, provided herein are methods of identifying subjects with prominently negative symptoms, and methods of treating such subjects comprising administering to such a subject a therapeutically or prophylactically effective amount of a therapeutic agent or a pharmaceutically acceptable salt or stereoisomer thereof.

In various aspects provided are methods for identifying subjects with prominently positive, prominently hostile, prominently disorganized, prominently affective, or prominently negative symptoms, and methods of treating such subjects comprising administering to such a subject a therapeutically or prophylactically effective amount of a therapeutic agent or a pharmaceutically acceptable salt or stereoisomer thereof.

In various embodiments, the methods comprise treating the positive symptom domain of a subject with prominently positive symptoms comprising administering to such a subject a therapeutically or prophylactically effective amount of a therapeutic agent or a pharmaceutically acceptable salt or stereoisomer thereof. In various embodiments, the methods comprise treating the hostile symptom domain of a subject with prominently hostile symptoms comprising administering to such a subject a therapeutically or prophylactically effective amount of a therapeutic agent or a pharmaceutically acceptable salt or stereoisomer thereof. In various embodiments, the methods comprise treating the disorganized symptom domain of a subject with prominently disorganized symptoms comprising administering to such a subject a therapeutically or prophylactically effective amount of a therapeutic agent or a pharmaceutically acceptable salt or stereoisomer thereof.

In various embodiments, the methods comprise treating the affective symptom domain of a subject with prominently affective symptoms comprising administering to such a subject a therapeutically or prophylactically effective amount of a therapeutic agent or a pharmaceutically acceptable salt or stereoisomer thereof. In various embodiments, the methods comprise treating one or more of the apathy/avolition sub-domain and the deficit of expression sub-domain of a subject with prominently affective symptoms comprising administering to such a subject a therapeutically or prophylactically effective amount of a therapeutic agent or a pharmaceutically acceptable salt or stereoisomer thereof.

In various embodiments, the methods comprise treating the negative symptom domain of a subject with prominently negative symptoms comprising administering to such a subject a therapeutically or prophylactically effective amount of a therapeutic agent or a pharmaceutically acceptable salt or stereoisomer thereof. In various embodiments, the methods comprise treating one or more of the depression sub-domain and the anxiety sub-domain of a subject with prominently negative symptoms comprising administering to such a subject a therapeutically or prophylactically effective amount of a therapeutic agent or a pharmaceutically acceptable salt or stereoisomer thereof.

In various embodiments, subjects can be classified using the UPSM (score matrix) (see FIG. 4 and Table 4A) on the PANSS factors assessed at baseline ("BL") to produce transformed PANSS factors from which subject classification can be made. In various embodiments, subject PANSS scores are transformed using a score matrix (see FIG. 4 and Table 4A) and clustering the subjects by k-means to identify distinct clusters, each characterized by distinctly prominent baseline transformed PANSS factor scores. A SVM (Support Vector Machine) classifier is then trained on these cluster assignments at baseline, and subsequently used to identify subject sub-population types post-baseline and in external data sets.

For example, in various embodiments, a liner support vector machine classifier is determined substantially as follow, where the score matrix (e.g. UPSM) transforms PANSS data into seven factors. For each cluster in the trainer data (transformed PANSS factors), calculate all possible distance between each Cartesian coordinate point within the cluster and outside the cluster, where the number of Cartesian coordinate points is equal to the number of transformed factors. In this example embodiment, the PANSS factor data is transformed into seven transformed PANSS factors so the coordinate points a 7D (seven dimensional).

Distance between two 7D Cartesian coordinate points $(a_i, b_i, c_i, d_i, e_i, f_i, g_i)$ and $(a_j, b_j, c_j, d_j, e_j, f_j, g_j)$ can be calculated using, $$d_k = \sqrt{\begin{array}{c}(a_i - a_j)^2 + (b_i - b_j)^2 + (c_i - c_j)^2 + (d_i - d_j)^2 + \\ (e_i - e_j)^2 + (f_i - f_j)^2 + (g_i - g_j)^2\end{array}}$$

The process continues with the selection of two of the coordinate points, for example purposes called A and B, that give the give a minimum distance, min $(d_k)$, where point A is within the cluster and point B is outside the cluster.

A hyperplane (of one less dimension than the coordinate dimension, here a 6D hyperplane) is determined where all the points on the hyperplane are equidistant from A and B. That is, if P is on the hyperplane, $$|AP| = |BP|$$

$$\sqrt{\begin{array}{c}(a_i - a_k)^2 + (b_i - b_k)^2 + (c_i - c_k)^2 + (d_i - d_k)^2 + \\ (e_i - e_k)^2 + (f_i - f_k)^2 + (g_i - g_k)^2\end{array}} =$$

$$\sqrt{\begin{array}{c}(a_j - a_k)^2 + (b_j - b_k)^2 + (c_j - c_k)^2 + (d_j - d_k)^2 + \\ (e_j - e_k)^2 + (f_j - f_k)^2 + (g_j - g_k)^2\end{array}}$$

Where the above equation can be used to provide the hyperplane, and where |AP| is the distance between A and P; |BP| is the distance between B and P; A is $(a_i, b_i, c_i, d_i, e_i, f_i, g_i)$; B is $(a_j, b_j, c_j, d_j, e_j, f_j, g_j)$; and P is $(a_k, b_k, c_k, d_k, e_k, f_k, g_k)$.

The 7 axis of the 7D Cartesian coordinate system (or N axis for an N dimensional coordinate system, e.g., a 5 axis for a 5D coordinate system) along with the 7 hyperplanes (or N hyperplanes for an N dimensional coordinate system) that separate each cluster give the margins (boundaries) of each cluster. Based on the maximum value along each axis, new axis constants (lines x=k or y=t) can be defined to complete polygon margins. These cluster margins complete the training, or cluster margin, and thus classifier determination, for, in this example, Linear SVM. Accordingly, any new Cartesian coordinate (here 7D), i.e. transformed PANSS factor vector, that is the seven transformed PANSS factors of a given subject, can be classified into the clusters based on the cluster margins so defined.

In various embodiments, a comparison of transformed PANSS symptom domain score is used to determine which symptom domain is prominent. In various embodiments, the symptom domain with the highest domain score is determined to be prominent.

In various embodiments, provided herein are methods for treating positive domain symptoms of schizophrenia in a subject comprise administering to the subject a therapeutically or prophylactically effective amount of a composition or a compound provided herein or a pharmaceutically acceptable salt or stereoisomer thereof, to treat a positive domain symptom.

In various embodiments, provided herein are methods for treating hostile domain symptoms of schizophrenia in a subject comprise administering to the subject a therapeutically or prophylactically effective amount of a composition or a compound provided herein or a pharmaceutically acceptable salt or stereoisomer thereof, to treat a hostile domain symptom.

In various embodiments, provided herein are methods for treating disorganized domain symptoms of schizophrenia in a subject comprise administering to the subject a therapeutically or prophylactically effective amount of a composition or a compound provided herein or a pharmaceutically acceptable salt or stereoisomer thereof, to treat a disorganized domain symptom.

In various embodiments, provided herein are methods for treating affective domain symptoms of schizophrenia in a subject comprise administering to the subject a therapeutically or prophylactically effective amount of a composition or a compound provided herein or a pharmaceutically acceptable salt or stereoisomer thereof, to treat a affective domain symptom.

In various embodiments, provided herein are methods for treating one or more of the sub-domain symptoms of apathy/avolition and deficit of expression of the affective symptom domain of schizophrenia comprising administering to the subject a therapeutically or prophylactically effective amount of a composition or a compound provided herein or a pharmaceutically acceptable salt or stereoisomer thereof, to treat the one or more sub-domain symptoms.

In various embodiments, provided herein are methods for treating negative domain symptoms of schizophrenia in a subject comprising administering to the subject a therapeutically or prophylactically effective amount of a composition or a compound provided herein or a pharmaceutically acceptable salt or stereoisomer thereof, to treat a negative domain symptom.

In various embodiments, provided herein are methods for treating one or more of the sub-domain symptoms of depression and anxiety of the negative symptom domain of schizophrenia comprising administering to the subject a therapeutically or prophylactically effective amount of a composition or a compound provided herein or a pharmaceutically acceptable salt or stereoisomer thereof, to treat the one or more sub-domain symptoms.

In certain embodiments, the efficacious concentration of a compound provided herein is less than 10 nM, less than 100 nM, less than 1 μM, less than 10 μM, less than 100 μM, or less than 1 mM. In one embodiment, a compound's activity may be assessed in various art-recognized animal models.

In other embodiments, provided herein is a method of effecting a therapeutic effect as described herein elsewhere. The method comprises administering to a subject (e.g., a mammal) a therapeutically or prophylactically effective amount of a compound or composition provided herein. The particular therapeutic effects may be measured using any model system known in the art or described herein, such as those involving an animal model of schizophrenia.

In various embodiments, the particular therapeutic effects are measured using transformed PANSS total scores as provided herein. In various embodiments, the particular therapeutic effects are measured using transformed PANSS domain scores as provided herein. In various embodiments where the therapeutic effect of a therapeutic agent on a symptom domain (and/or sub-domain) is being measured, the transformed PANSS score for that domain (and/or sub-domain) is used to measure the therapeutic effect. For example, in various embodiments where the therapeutic effect of a therapeutic agent on a negative symptom domain is being measured, the negative domain transformed PANSS score is used. As is understood in the art, when using PANSS scores to assess therapeutic effect, scores after treatment are compared to the corresponding baseline score.

In various embodiments, the untransformed PANSS score total is used to measure the therapeutic effect of a therapeutic agent. In various preferred embodiments, the untransformed PANSS score total is used to assess the therapeutic effect of a therapeutic agent used in a method to treat a subject with symptoms prominently in a symptom domain of schizophrenia, a symptom prominently in a symptom sub-domain of schizophrenia, or both.

In various embodiments, provided herein are methods of treating schizophrenia in a subject in need thereof, comprising administering a therapeutic agent wherein the subject exhibits a prominently positive schizophrenia domain characterized by a transformed PANSS score.

In various embodiments, the transformed PANSS positive domain score comprises PANSS factors (P01) delusions, (P03) hallucinatory behavior, (P05) grandiosity, and (P06) suspiciousness/persecution. In various embodiments, the subject exhibits a prominently positive schizophrenia domain when the transformed PANSS score for the positive domain comprises PANSS factors (P01) delusions, (P03) hallucinatory behavior, (P05) grandiosity, and (P06) suspiciousness/persecution, and the domain score is greater than 2.5, greater than about 3.8, greater than about 5.1, and/or greater than about 6.3.

In various embodiments, the transformed PANSS positive domain score comprises PANSS factors (P01) delusions, (P03) hallucinatory behavior, (P05) grandiosity, (P06) suspiciousness/persecution, (N07) stereotyped thinking, (G01) somatic concern, (G09) unusual thought content and (G12) lack of judgement and insight. In various embodiments, the subject exhibits a prominently positive schizophrenia domain when the transformed PANSS score for the positive domain comprises PANSS factors (P01) delusions, (P03) hallucinatory behavior, (P05) grandiosity, (P06) suspiciousness/persecution, (N07) stereotyped thinking, (G01) somatic concern, (G09) unusual thought content and (G12) lack of judgement and insight, and the domain score is greater than 2.4, greater than about 3.6, greater than about 4.8, and/or greater than about 6.0.

In various embodiments, provided herein are methods of treating schizophrenia in a subject in need thereof, comprising administering a therapeutic agent wherein the subject exhibits a prominently disorganized schizophrenia domain characterized by a transformed PANSS score.

In various embodiments, the transformed PANSS disorganized domain score comprises PANSS factors (P02) conceptual disorganization, (N05) difficulty in abstract thinking, (N07) stereotyped thinking, (G09) unusual thought content and (G12) lack of judgement and insight, (G11) poor attention, (G13) disturbance of volition, and (G15) preoccupation. In various embodiments, the subject exhibits a prominently disorganized schizophrenia domain when the transformed PANSS score for the disorganized domain comprises PANSS factors (P02) conceptual disorganization, (N05) difficulty in abstract thinking, (N07) stereotyped thinking, (G09) unusual thought content and (G12) lack of judgement and insight, (G11) poor attention, (G13) disturbance of volition, and (G15) preoccupation, and the domain score is greater than 2.6, greater than about 4.0, greater than about 5.3, and/or greater than about 6.7.

In various embodiments, the transformed PANSS disorganized domain score comprises PANSS factors (P02) conceptual disorganization, (N05) difficulty in abstract thinking, (G05) mannerisms and posturing, (G10) disorientation, (G11) poor attention, (G13) disturbance of volition, and (G15) preoccupation. In various embodiments, the subject exhibits a prominently disorganized schizophrenia domain when the transformed PANSS score for the disorganized domain comprises PANSS factors (P02) conceptual disorganization, (N05) difficulty in abstract thinking, (G05) mannerisms and posturing, (G10) disorientation, (G11) poor attention, (G13) disturbance of volition, and (G15) preoccupation, and the domain score is greater than 2.1, greater than about 3.2, greater than about 4.3, and/or greater than about 5.4.

In various embodiments, provided herein are methods of treating schizophrenia in a subject in need thereof, comprising administering a therapeutic agent wherein the subject exhibits a prominently affective schizophrenia domain characterized by a transformed PANSS score.

In various embodiments, the transformed PANSS affective domain score comprises PANSS factors (G02) anxiety, (G03) guilt feelings, (G04) tension, and (G06) depression. In various embodiments, the subject exhibits a prominently disorganized schizophrenia domain when the transformed PANSS score for the disorganized domain comprises PANSS factors G02) anxiety, (G03) guilt feelings, (G04) tension, and (G06) depression, and the domain score is greater than 1.5, greater than about 2.3, greater than about 3.1, and/or greater than about 3.9.

In various embodiments, provided herein are methods of treating schizophrenia in a subject in need thereof, comprising administering a therapeutic agent wherein the subject exhibits a prominently anxiety schizophrenia sub-domain characterized by a transformed PANSS score. In various embodiments, the transformed PANSS anxiety schizophrenia sub-domain score comprises PANSS factors (G02) anxiety and (G04) tension.

In various embodiments, provided herein are methods of treating schizophrenia in a subject in need thereof, comprising administering a therapeutic agent wherein the subject exhibits a prominently hostile schizophrenia domain characterized by a transformed PANSS score.

In various embodiments, the transformed PANSS hostile domain score comprises PANSS factors (P04) excitement, (P07) hostility, (G08) uncooperativeness, and (G14) poor impulse control. In various embodiments, the subject exhibits a prominently disorganized schizophrenia domain when the transformed PANSS score for the disorganized domain comprises PANSS factors, (P04) excitement, (P07) hostility, (G08) uncooperativeness, and (G14) poor impulse control, and the domain score is greater than 2.3, greater than about 3.5, greater than about 4.7, and/or greater than about 5.9.

In various embodiments, provided herein are methods of treating schizophrenia in a subject in need thereof, comprising administering a therapeutic agent wherein the subject exhibits a prominently negative schizophrenia domain characterized by a transformed PANSS score.

In various embodiments, the transformed PANSS negative domain score comprises PANSS factors (N01) blunted affect, (N02) emotional withdrawal, (N03) poor rapport, (N04) passive/apathetic social withdrawal, (N06) lack of spontaneity and flow of conversation, (G07) motor retardation, and (G16) active social avoidance. In various embodiments, the subject exhibits a prominently disorganized schizophrenia domain when the transformed PANSS score for the disorganized domain comprises PANSS factors, (N01) blunted affect, (N02) emotional withdrawal, (N03) poor rapport, (N04) passive/apathetic social withdrawal, (N06) lack of spontaneity and flow of conversation, (G07) motor retardation, and (G16) active social avoidance, and the domain score is greater than 1.7, greater than about 2.5, greater than about 3.5, and/or greater than about 4.2.

In various embodiments, provided herein are methods of treating schizophrenia in a subject in need thereof, comprising administering a therapeutic agent wherein the subject exhibits a prominently apathy/avolition schizophrenia sub-domain characterized by a transformed PANSS score. In various embodiments, the transformed PANSS apathy/avolition schizophrenia sub-domain score comprises PANSS factors (N02) emotional withdrawal, (N04) passive/apathetic social withdrawal, and (G16) active social avoidance.

In various embodiments, provided herein are methods of treating schizophrenia in a subject in need thereof, comprising administering a therapeutic agent wherein the subject exhibits a prominently deficit of expression schizophrenia sub-domain characterized by a transformed PANSS score. In various embodiments, the transformed PANSS deficit of expression schizophrenia sub-domain score comprises PANSS factors (N01) blunted affect, (N03) poor rapport, (N06) lack of spontaneity and flow of conversation, and (G07) motor retardation.

In various embodiments, provided is a method of treating schizophrenia in a subject in need thereof comprising administering an antipsychotic agent, wherein the subject is part of a schizophrenia sub-population as characterized by a transformed PANSS score. In various embodiments, the schizophrenia sub-population is selected from the group consisting of prominently positive, prominently disorganized thinking/cognitive dysfunction, prominently affective (depression/anxiety), prominently hostility/excitement, and prominently negative (apathy/avolition and deficit of expression). In various embodiments, the schizophrenia sub-population is prominently positive, prominently disorganized thinking/cognitive dysfunction, prominently affective (depression/anxiety), prominently hostility/excitement, or prominently negative (apathy/avolition and deficit of expression). In various embodiments, the schizophrenia sub-population is prominently positive. In various embodiments, the schizophrenia sub-population is prominently disorganized thinking/cognitive dysfunction. In various embodiments, the schizophrenia sub-population is prominently affective (depression/anxiety). In various embodiments, the schizophrenia sub-population is prominently hostility/excitement. In various embodiments, the schizophrenia sub-population is prominently negative (apathy/avolition and deficit of expression).

In various embodiments, the subject is part of a schizophrenia sub-population selected from the group consisting of prominently positive, prominently disorganized thinking/cognitive dysfunction, prominently affective (depression/anxiety), prominently hostility/excitement, and prominently negative (apathy/avolition and deficit of expression).

In various embodiments, the subject is part of a schizophrenia sub-population wherein the schizophrenia sub-population is prominently positive, prominently disorganized thinking/cognitive dysfunction, prominently affective (depression/anxiety), prominently hostility/excitement, or prominently negative (apathy/avolition and deficit of expression). In various embodiments, the subject is part of a prominently positive schizophrenia sub-population. In various embodiments, the subject is part of a prominently disorganized thinking/cognitive dysfunction schizophrenia sub-population. In various embodiments, the subject is part of a prominently affective (depression/anxiety) schizophrenia sub-population. In various embodiments, the subject is part of a prominently hostility/excitement schizophrenia sub-population. In various embodiments, the subject is part of a prominently negative schizophrenia sub-population.

In various embodiments, provided is a method of treating schizophrenia in a subject in need thereof comprising administering an antipsychotic agent, wherein the subject preferentially exhibits a schizophrenia domain characterized a transformed PANSS score.

In various embodiments, the schizophrenia domain is selected from the group consisting of positive symptoms, negative symptoms, disorganized thinking/cognitive dysfunction, hostility/excitement, and affective (depression/anxiety). In various embodiments, the schizophrenia domain is positive symptoms, negative symptoms, disorganized thinking/cognitive dysfunction, hostility/excitement, or depression/anxiety. In various embodiments, the schizophrenia domain is positive symptoms. In various embodiments, the schizophrenia domain is negative symptoms. In various embodiments, the schizophrenia domain is disorganized thinking/cognitive dysfunction. In various embodiments, the schizophrenia domain is hostility/excitement. In various embodiments, the schizophrenia domain is affective (depression/anxiety).

In various embodiments, the subject preferentially exhibits a schizophrenia domain selected from the group consisting of positive symptoms, negative symptoms, disorganized thinking/cognitive dysfunction, hostility/excitement, and depression/anxiety. In various embodiments, the subject preferentially exhibits a schizophrenia domain wherein the schizophrenia domain is positive symptoms, negative symptoms, disorganized thinking/cognitive dysfunction, hostility/excitement, or depression/anxiety. In various embodiments, the subject preferentially exhibits positive symptoms. In various embodiments, the subject preferentially exhibits negative symptoms. In various embodiments, the subject preferentially exhibits disorganized thinking/cognitive dysfunction. In various embodiments, the subject preferentially exhibits hostility/excitement. In various embodiments, the subject preferentially exhibits affective (depression/anxiety).

In various embodiments, provided is a method of treating schizophrenia in a subject in need thereof comprising administering an antipsychotic agent, wherein the antipsychotic agent treats a transformed PANSS schizophrenia domain.

In various embodiments, the transformed PANSS schizophrenia domain is selected from the group consisting of a positive domain, a hostile domain, a disorganized domain, an affective domain, and a negative domain. In various embodiments, the transformed PANSS schizophrenia domain is a positive domain, a hostile domain, a disorganized domain, an affective domain, or a negative domain. In various embodiments, the transformed PANSS schizophrenia domain is a positive domain. In various embodiments, the transformed PANSS schizophrenia domain is a hostile domain. In various embodiments, the transformed PANSS schizophrenia domain is a disorganized domain. In various embodiments, the transformed PANSS schizophrenia domain is an affective domain. In various embodiments, the transformed PANSS schizophrenia domain is a negative domain.

In various embodiments, the antipsychotic agent treats a transformed PANSS schizophrenia domain selected from the group consisting of a positive domain, a hostile domain, a disorganized domain, an affective domain, and a negative domain. In various embodiments, the antipsychotic agent treats a transformed PANSS schizophrenia domain wherein the transformed PANSS schizophrenia domain is a positive domain, a hostile domain, a disorganized domain, an affective domain, or a negative domain. In various embodiments, the antipsychotic agent treats a transformed PANSS schizophrenia positive domain. In various embodiments, the antipsychotic agent treats a transformed PANSS schizophrenia hostile domain. In various embodiments, the antipsychotic agent treats a transformed PANSS schizophrenia disorganized domain. In various embodiments, the antipsychotic agent treats a transformed PANSS schizophrenia affective domain. In various embodiments, the antipsychotic agent treats a transformed PANSS schizophrenia negative domain.

In various embodiments, provided is a method of treating schizophrenia in a subject in need thereof comprising administering an antipsychotic agent, wherein the antipsychotic agent is determined by transformed PANSS.

In various embodiments, provided is a method of treating schizophrenia in a subject in need thereof comprising administering an antipsychotic agent, wherein the antipsychotic agent treats any one or more of positive symptoms, hostile symptoms, disorganized symptoms, affective symptoms, or negative symptoms.

In various embodiments, provided is a method of treating schizophrenia in a subject in need thereof comprising: (a) determining the subjects' PANSS score; (b) transforming the PANSS score to a transformed PANSS score using an Uncorrelated PANSS Score Matrix (UPSM); and (c) administering an antipsychotic agent to the subject relative to the transformed PANSS score.

In various embodiments, provided is a method of treating schizophrenia in a subject in need thereof comprising: (a) determining the subjects' PANSS score; (b) transforming the PANSS score to a transformed PANSS score using an Uncorrelated PANSS Score Matrix (UPSM); and (c) administering an antipsychotic agent to the subject relative to the transformed PANSS score, wherein the subject is part of a schizophrenia sub-population as characterized by transformed PANSS.

In various embodiments, provided is a method of treating schizophrenia in a subject in need thereof comprising: (a) determining the subjects' PANSS score; (b) transforming the PANSS score to a transformed PANSS score using an Uncorrelated PANSS Score Matrix (UPSM); and (c) administering an antipsychotic agent to the subject relative to the transformed PANSS score, wherein the antipsychotic agent treats a transformed PANSS schizophrenia domain.

In various embodiments, provided is a method of treating schizophrenia in a subject in need thereof comprising: (a) determining the subjects' PANSS score; (b) transforming the PANSS score to a transformed PANSS score using an Uncorrelated PANSS Score Matrix (UPSM); and (c) administering an antipsychotic agent to the subject relative to the transformed PANSS score, wherein: the subject is part of a schizophrenia sub-population as characterized by transformed PANSS, and the antipsychotic agent treats a transformed PANSS schizophrenia domain.

In various embodiments, the transformed PANSS uses an Uncorrelated PANSS Score Matrix (UPSM).

In various embodiments, the Uncorrelated PANSS Score Matrix (UPSM) weights each PANSS factor rating individually across five domains selected from the group consisting of positive symptoms, negative symptoms, disorganized thinking/cognitive dysfunction, hostility/excitement, and depression/anxiety.

In various embodiments, provided herein are methods for treating specific symptoms, domains of symptoms and/or sub-domains of symptoms of schizophrenia in a subject comprising administering to the subject (e.g., a human) a therapeutically or prophylactically effective amount of a composition or a compound provided herein or a pharmaceutically acceptable salt or stereoisomer thereof.

In one embodiment, without being limited by a particular theory, the treatment, prevention, and/or management is done by administering a compound provided herein that has shown in vivo efficacy in an animal model predictive of antipsychotic activity in humans. The phenotypic approach to develop antipsychotics has been used in psychopharmacology, with the antipsychotic chlorpromazine developed in this way. The phenotypic approach may also offer advantages over compounds developed by traditional in vitro based drug discovery approach, because the compounds developed using the phenotypic approach have established pharmaceutical properties and in vivo activity, rather than activity toward a given molecular target, which may be less predictive and lead to attrition at later stages of, for example, clinical development.

In one embodiment, provided herein is a method of treating, preventing, and/or managing a neurological disorder, including schizophrenia, schizophrenia spectrum disorder, acute schizophrenia, chronic schizophrenia, NOS schizophrenia, schizoid personality disorder, schizotypal personality disorder, delusional disorder, psychosis, psychotic disorder, brief psychotic disorder, shared psychotic disorder, psychotic disorder due to a general medical condition, drug-induced psychosis (e.g., cocaine, alcohol, amphetamine), psychoaffective disorder, aggression, delirium, Parkinson's psychosis, excitative psychosis, Tourette's syndrome, organic or NOS psychosis, seizure, agitation, post-traumatic stress disorder, behavior disorder, neurodegenerative disease, Alzheimer's disease, Parkinson's disease, dyskinesias, Huntington's disease, dementia, mood disorder, anxiety, affective disorders (e.g., depression, e.g., major depressive disorder and dysthymia; bipolar disorder, e.g., biopolar depressive disorder; manic disorder; seasonal affective disorder; and attention deficit disorder (ADD) and attention deficit hyperactivity disorder (ADHD)), obsessive-compulsive disorder, vertigo, epilepsy, pain (e.g., neuropathic pain, sensitization accompanying neuropathic pain, and inflammatory pain), fibromyalgia, migraine, cognitive impairment, movement disorder, restless leg syndrome (RLS), multiple sclerosis, sleep disorder, sleep apnea, narcolepsy, excessive daytime sleepiness, jet lag, drowsy side effect of medications, insomnia, substance abuse or dependency (e.g., nicotine, cocaine), addiction, eating disorder, sexual dysfunction, hypertension, emesis, Lesche-Nyhane disease, Wilson's disease, autism, Huntington's chorea, and premenstrual dysphoria, comprising administering to a subject an effective amount of a compound provided herein, or a pharmaceutically acceptable salt or stereoisomer thereof.

In one embodiment, provided herein is a method of treating, preventing, and/or managing a disorder related to psychosis, schizophrenia, ADHD, mood disorder or affective disorder such as depression and anxiety, comprising administering to a subject an effective amount of a compound provided herein. For example, without being limited by a particular theory, the compounds provided herein may improve the gating deficits of DBA/2 mice seen in the pre-pulse inhibition (PPI) test and reverse the methamphetamine-induced hyperlocomotor activity. Without being limited to a particular theory, the compounds provided herein may: 1) reverse the amphetamine-induced hyper-locomotor activity; 2) be useful as antipsychotic agents and dosed sparing; 3) improve attention and modulate impulsivity; 4) improve learning parameters in ADHD; 5) enhance learning ability and reduce anxiety in behavioral tests; and/or 6) have an anti-depressant effect.

Any suitable route of administration can be employed for providing the patient with a therapeutically or prophylactically effective dose of an active ingredient. For example, oral, mucosal (e.g., nasal, sublingual, buccal, rectal, vaginal), parenteral (e.g., intravenous, intramuscular), transdermal, and subcutaneous routes can be employed. Exemplary routes of administration include oral, transdermal, and mucosal. Suitable dosage forms for such routes include, but are not limited to, transdermal patches, ophthalmic solutions, sprays, and aerosols. Transdermal compositions can also take the form of creams, lotions, and/or emulsions, which can be included in an appropriate adhesive for application to the skin or can be included in a transdermal patch of the matrix or reservoir type as are conventional in the art for this purpose. An exemplary transdermal dosage form is a "reservoir type" or "matrix type" patch, which is applied to the skin and worn for a specific period of time to permit the penetration of a desired amount of active ingredient. The patch can be replaced with a fresh patch when necessary to provide constant administration of the active ingredient to the patient.

The amount to be administered to a patient to treat, prevent, and/or manage the disorders described herein will depend upon a variety of factors including the activity of the particular compound employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount required. For example, the physician or veterinarian could start doses of the compounds employed at levels lower than that required in order to achieve the desired therapeutic effect and gradually increase the dosage until the desired effect is achieved.

In general, a suitable daily dose of a compound provided herein will be that amount of the compound which is the lowest dose effective to produce a therapeutic or prophylactic effect. Such an effective dose will generally depend upon the factors described above. Generally, oral, intravenous, intracerebroventricular and subcutaneous doses of the compounds provided herein for a patient will range from about 0.005 mg per kilogram to about 5 mg per kilogram of body weight per day. In one embodiment, the oral dose of a compound provided herein will range from about 10 mg to about 300 mg per day. In another embodiment, the oral dose of a compound provided herein will range from about 20 mg to about 250 mg per day. In another embodiment, the oral dose of a compound provided herein will range from about 100 mg to about 300 mg per day. In another embodiment, the oral dose of a compound provided herein will range from about 10 mg to about 100 mg per day. In another embodiment, the oral dose of a compound provided herein will range from about 25 mg to about 50 mg per day. In another embodiment, the oral dose of a compound provided herein will range from about 50 mg to about 200 mg per day. Each of the above-recited dosage ranges may be formulated as a single or multiple unit dosage formulations.

In various embodiments, the compounds disclosed herein may be used in combination with one or more second active agents to treat, prevent, and/or manage disorders described herein.

C. Therapeutic Compounds

In various embodiments, provided herein are methods for the treatment of one or more of: a symptom domain of schizophrenia, a symptom sub-domain of schizophrenia, a subject sub-population with symptoms prominently in a symptom domain of schizophrenia; and/or a subject sub-population with symptoms prominently in symptom sub-domain of schizophrenia comprising administering to a subject a therapeutically or prophylactically effective amount of a therapeutic agent, the therapeutic agent comprising a compound of formula (I):

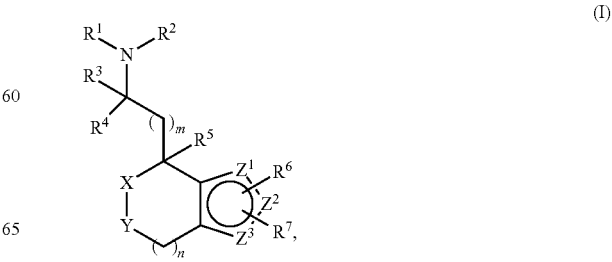

or a pharmaceutically acceptable salt or stereoisomer thereof, wherein one of X and Y is O, and the other is $CH_2$; or both X and Y are $CH_2$;

one of $Z^1$, $Z^2$, and $Z^3$ is S; and (i) two of $Z^1$, $Z^2$, and $Z^3$ are C; or (ii) one of $Z^1$, $Z^2$, and $Z^3$ is C and one of $Z^1$, $Z^2$, and $Z^3$ is N;

$R^1$ and $R^2$ are each independently (i) hydrogen, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^8$, wherein $R^8$ is $SO_2$alkyl or $SO_2$aryl, each of which is optionally substituted; or (iii) $R^1$ and $R^2$ together with the nitrogen atom to which they are attached form an optionally substituted heterocyclyl or heteroaryl;

$R^3$ and are each independently (i) hydrogen, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^9$, wherein $R^9$ is $CF_3$, CN, nitro, amino, hydroxyl, or cycloalkoxyl, each of which is optionally substituted; or (iii) $R^3$ and together with the carbon atom to which they are attached form an optionally substituted cycloalkyl or heterocyclyl; or (iv) $R^3$ and $R^1$ together with the atoms to which they are attached form an optionally substituted heterocyclyl, and IV is (i) or (ii); or (v) $R^3$ and $R^4$ are combined together to form a double bond and together with $R^1$ and/or $R^2$ and the atoms to which they are attached form an optionally substituted heteroaryl (e.g., imidazolyl or thiazolyl);

$R^5$ is (i) hydrogen, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^{10}$, wherein $R^{10}$ is $CF_3$, CN, nitro, amino, hydroxyl, or cycloalkoxyl, each of which is optionally substituted; or (iii) $R^5$ and $R^1$ together with the atoms to which they are attached form an optionally substituted heterocyclyl;

$R^6$ and $R^7$ are each independently (i) hydrogen, halo, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^{11}$, wherein $R^{11}$ is $CF_3$, CN, nitro, amino, hydroxyl, cycloalkoxyl, heteroaryl, or heterocyclyl, each of which is optionally substituted; or (iii) $R^6$ and $R^7$ together with the atoms to which they are attached form an optionally substituted aryl, heteroaryl, cycloalkyl or heterocyclyl ring; with the proviso that when one of $Z^1$, $Z^2$, and $Z^3$ is N, $R^7$ is absent;

m is 0, 1, or 2;

n is 0, 1, or 2; and each occurrence of p is independently 0, 1, or 2.

In one embodiment, provided herein is a compound of formula (I), as defined herein elsewhere, or a pharmaceutically acceptable salt or stereoisomer thereof, wherein:

one of X and Y is O, and the other is $CH_2$; or both X and Y are $CH_2$;

two of $Z^1$, $Z^2$, and $Z^3$ are C, and one of $Z^1$, $Z^2$, and $Z^3$ is S;

$R^1$ and $R^2$ are each independently (i) hydrogen, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^8$, wherein $R^8$ is $SO_2$alkyl or $SO_2$aryl, each of which is optionally substituted; or (iii) $R^1$ and $R^2$ together with the nitrogen atom to which they are attached form an optionally substituted heterocyclyl or heteroaryl;

$R^3$ and $R^4$ are each independently (i) hydrogen, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^9$, wherein $R^9$ is $CF_3$, CN, nitro, amino, hydroxyl, or cycloalkoxyl, each of which is optionally substituted; or (iii) $R^3$ and $R^4$ together with the carbon atom to which they are attached form an optionally substituted cycloalkyl or heterocyclyl; or (iv) $R^3$ and $R^1$ together with the atoms to which they are attached form an optionally substituted heterocyclyl, and $R^4$ is (i) or (ii); or (v) $R^3$ and $R^4$ are combined together to form a double bond and together with $R^1$ and/or $R^2$ and the atoms to which they are attached form an optionally substituted heteroaryl (e.g., imidazolyl or thiazolyl);

$R^5$ is (i) hydrogen, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^{10}$, wherein $R^{10}$ is $CF_3$, CN, nitro, amino, hydroxyl, or cycloalkoxyl, each of which is optionally substituted; or (iii) $R^5$ and $R^1$ together with the atoms to which they are attached form an optionally substituted heterocyclyl;

$R^6$ and $R^7$ are each independently (i) hydrogen, halo, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^{11}$, wherein $R^{11}$ is $CF_3$, CN, nitro, amino, hydroxyl, cycloalkoxyl, heteroaryl, or heterocyclyl, each of which is optionally substituted; or (iii) $R^6$ and $R^7$ together with the atoms to which they are attached form an optionally substituted aryl, heteroaryl, cycloalkyl or heterocyclyl ring;

m is 0, 1, or 2;

n is 0, 1, or 2; and each occurrence of p is independently 0, 1, or 2.

In one embodiment, X is O and Y is $CH_2$. In one embodiment, X is $CH_2$ and Y is O. In one embodiment, both X and Y are $CH_2$.

In one embodiment, $Z^1$ is S. In one embodiment, $Z^2$ is S. In one embodiment, $Z^3$ is S. In one embodiment, $Z^1$ and $Z^2$ are C, and $Z^3$ is S. In one embodiment, $Z^1$ and $Z^3$ are C, and $Z^2$ is S. In one embodiment, $Z^2$ and $Z^3$ are C, and $Z^1$ is S. In one embodiment, $Z^1$ is N, $Z^2$ is C, and $Z^3$ is S. In one embodiment, $Z^1$ is C, $Z^2$ is N, and $Z^3$ is S. In one embodiment, $Z^1$ is N, $Z^2$ is S, and $Z^3$ is C. In one embodiment, $Z^1$ is C, $Z^2$ is S, and $Z^3$ is N. In one embodiment, $Z^1$ is S, $Z^2$ is N, and $Z^3$ is C. In one embodiment, $Z^1$ is S, $Z^2$ is C, and $Z^3$ is N. In one embodiment, when one of $Z^1$, $Z^2$, and $Z^3$ is N, $R^7$ is absent and $R^6$ substitutes a carbon ring atom.

In one embodiment, $R^1$ is hydrogen. In one embodiment, $R^1$ is optionally substituted alkyl. In one embodiment, $R^1$ is alkyl. In one embodiment, $R^1$ is optionally substituted alkoxyl. In one embodiment, $R^1$ is alkoxyl. In one embodiment, $R^1$ is optionally substituted aminoalkyl. In one embodiment, $R^1$ is aminoalkyl. In one embodiment, $R^1$ is optionally substituted alkenyl. In one embodiment, $R^1$ is alkenyl. In one embodiment, $R^1$ is optionally substituted alkynyl. In one embodiment, $R^1$ is alkynyl. In one embodiment, $R^1$ is optionally substituted cycloalkyl. In one embodiment, $R^1$ is cycloalkyl. In one embodiment, $R^1$ is optionally substituted cycloalkylalkyl. In one embodiment, $R^1$ is cycloalkylalkyl. In one embodiment, $R^1$ is optionally substituted aryl. In one embodiment, $R^1$ is aryl. In one embodiment, $R^1$ is optionally substituted aralkyl. In one embodiment, $R^1$ is aralkyl. In one embodiment, $R^1$ is —$(CH_2)_p$—$SO_2$alkyl, wherein the alkyl is optionally substituted. In one embodiment, $R^1$ is —$(CH_2)_p$—$SO_2$alkyl. In one embodiment, $R^1$ is —$(CH_2)_p$—$SO_2$aryl, wherein the aryl is optionally substituted. In one embodiment, $R^1$ is —$(CH_2)_p$—$SO_2$aryl. In one embodiment, $R^1$ is $C_1$-$C_4$ alkyl optionally substituted with —$SO_2$alkyl or —$SO_2$aryl, each of which is further optionally substituted. In one embodiment, $R^1$ is $C_1$-$C_4$ alkyl optionally substituted with —$SO_2$alkyl or —$SO_2$aryl. In one embodiment, the alkyl, alkoxyl, aminoalkyl, alkenyl, alkynyl, and cycloalkyl are optionally substituted with one or more halo.

In one embodiment, $R^2$ is hydrogen. In one embodiment, $R^2$ is optionally substituted alkyl. In one embodiment, $R^2$ is alkyl. In one embodiment, $R^2$ is optionally substituted alkoxyl. In one embodiment, $R^2$ is alkoxyl. In one embodiment, $R^2$ is optionally substituted aminoalkyl. In one embodiment, $R^2$ is aminoalkyl. In one embodiment, $R^2$ is optionally substituted alkenyl. In one embodiment, $R^2$ is alkenyl. In one embodiment, $R^2$ is optionally substituted alkynyl. In one embodiment, $R^2$ is alkynyl. In one embodiment, $R^2$ is optionally substituted cycloalkyl. In one embodiment, $R^2$ is cycloalkyl. In one embodiment, $R^2$ is optionally substituted cycloalkylalkyl. In one embodiment, $R^2$ is cycloalkylalkyl. In one embodiment, $R^2$ is optionally substituted aryl. In one embodiment, $R^2$ is aryl. In one embodiment, $R^2$ is optionally substituted aralkyl. In one embodiment, $R^2$ is aralkyl. In one embodiment, $R^2$ is —$(CH_2)_p$—$SO_2$alkyl, wherein the alkyl is optionally substituted. In one embodiment, $R^2$ is —$(CH_2)_p$—$SO_2$alkyl. In one embodiment, $R^2$ is —$(CH_2)_p$—$SO_2$aryl, wherein the aryl is optionally substituted. In one embodiment, $R^2$ is —$(CH_2)_p$—$SO_2$aryl. In one embodiment, $R^2$ is $C_1$-$C_4$ alkyl optionally substituted with —$SO_2$alkyl or —$SO_2$aryl, each of which is further optionally substituted. In one embodiment, $R^2$ is $C_1$-$C_4$ alkyl optionally substituted with —$SO_2$alkyl or —$SO_2$aryl. In one embodiment, the alkyl, alkoxyl, aminoalkyl, alkenyl, alkynyl, and cycloalkyl are optionally substituted with one or more halo.

In one embodiment, $R^1$ and $R^2$ together with the nitrogen atom to which they are attached form an optionally substituted heterocyclyl. In one embodiment, $R^1$ and $R^2$ together with the nitrogen atom to which they are attached form a heterocyclyl. In one embodiment, $R^1$ and $R^2$ together with the nitrogen atom to which they are attached form an optionally substituted heteroaryl. In one embodiment, $R^1$ and $R^2$ together with the nitrogen atom to which they are attached form a heteroaryl.

In one embodiment, $R^3$ and $R^4$ are each independently (i) hydrogen, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^9$, wherein $R^9$ is $CF_3$, CN, nitro, amino, hydroxyl, or cycloalkoxyl, each of which is optionally substituted; or (iii) $R^3$ and $R^4$ together with the carbon atom to which they are attached form an optionally substituted cycloalkyl or heterocyclyl; or (iv) $R^3$ and $R^1$ together with the atoms to which they are attached form an optionally substituted heterocyclyl, and $R^4$ is (i) or (ii); or (v) $R^3$ and $R^4$ are combined together to form a double bond and together with $R^1$ and the atoms to which they are attached form an optionally substituted heteroaryl (e.g., imidazolyl).

In one embodiment, $R^3$ is hydrogen. In one embodiment, $R^3$ is optionally substituted alkyl. In one embodiment, $R^3$ is alkyl. In one embodiment, $R^3$ is optionally substituted alkoxyl. In one embodiment, $R^3$ is alkoxyl. In one embodiment, $R^3$ is optionally substituted aminoalkyl. In one embodiment, $R^3$ is aminoalkyl. In one embodiment, $R^3$ is optionally substituted alkenyl. In one embodiment, $R^3$ is alkenyl. In one embodiment, $R^3$ is optionally substituted alkynyl. In one embodiment, $R^3$ is alkynyl. In one embodiment, $R^3$ is optionally substituted cycloalkyl. In one embodiment, $R^3$ is cycloalkyl. In one embodiment, $R^3$ is optionally substituted cycloalkylalkyl. In one embodiment, $R^3$ is cycloalkylalkyl. In one embodiment, $R^3$ is optionally substituted aryl. In one embodiment, $R^3$ is aryl. In one embodiment, $R^3$ is optionally substituted aralkyl. In one embodiment, $R^3$ is aralkyl. In one embodiment, $R^3$ is —$(CH_2)_p$—$CF_3$. In one embodiment, $R^3$ is —$(CH_2)_p$—CN. In one embodiment, $R^3$ is —$(CH_2)_p$-nitro. In one embodiment, $R^3$ is —$(CH_2)_p$-amino, wherein the amino is optionally substituted. In one embodiment, $R^3$ is —$(CH_2)_p$-amino. In one embodiment, $R^3$ is —$(CH_2)_p$-hydroxyl, wherein the hydroxyl is optionally substituted. In one embodiment, $R^3$ is —$(CH_2)_p$-hydroxyl. In one embodiment, $R^3$ is —$(CH_2)_p$-cycloalkoxyl, wherein the cycloalkoxyl is optionally substituted. In one embodiment, $R^3$ is —$(CH_2)_p$-cycloalkoxyl. In one embodiment, $R^3$ is $C_1$-$C_4$ alkyl optionally substituted with $CF_3$, CN, nitro, amino, hydroxyl, or cycloalkoxyl, each of which is further optionally substituted. In one embodiment, $R^3$ is $C_1$-$C_4$ alkyl optionally substituted with $CF_3$, CN, nitro, amino, hydroxyl, or cycloalkoxyl. In one embodiment, the alkyl, alkoxyl, aminoalkyl, alkenyl, alkynyl, and cycloalkyl are optionally substituted with one or more halo.

In one embodiment, $R^4$ is hydrogen. In one embodiment, $R^4$ is optionally substituted alkyl. In one embodiment, $R^4$ is alkyl. In one embodiment, $R^4$ is optionally substituted alkoxyl. In one embodiment, $R^4$ is alkoxyl. In one embodiment, $R^4$ is optionally substituted aminoalkyl. In one embodiment, $R^4$ is aminoalkyl. In one embodiment, $R^4$ is optionally substituted alkenyl. In one embodiment, $R^4$ is alkenyl. In one embodiment, $R^4$ is optionally substituted alkynyl. In one embodiment, $R^4$ is alkynyl. In one embodiment, $R^4$ is optionally substituted cycloalkyl. In one embodiment, $R^4$ is cycloalkyl. In one embodiment, $R^4$ is optionally substituted cycloalkylalkyl. In one embodiment, $R^4$ is cycloalkylalkyl. In one embodiment, $R^4$ is optionally substituted aryl. In one embodiment, $R^4$ is aryl. In one embodiment, $R^4$ is optionally substituted aralkyl. In one embodiment, $R^4$ is aralkyl. In one embodiment, $R^4$ is —$(CH_2)_p$—$CF_3$. In one embodiment, $R^4$ is —$(CH_2)_p$—CN. In one embodiment, $R^4$ is —$(CH_2)_p$-nitro. In one embodiment, $R^4$ is —$(CH_2)_p$-amino, wherein the amino is optionally substituted. In one embodiment, $R^4$ is —$(CH_2)_p$-amino. In one embodiment, $R^4$ is —$(CH_2)_p$-hydroxyl, wherein the hydroxyl is optionally substituted. In one embodiment, $R^4$ is —$(CH_2)_p$-hydroxyl. In one embodiment, $R^4$ is —$(CH_2)_p$-cycloalkoxyl, wherein the cycloalkoxyl is optionally substituted. In one embodiment, $R^4$ is —$(CH_2)_p$-cycloalkoxyl. In one embodiment, $R^4$ is $C_1$-$C_4$ alkyl optionally substituted with $CF_3$, CN, nitro, amino, hydroxyl, or cycloalkoxyl, each of which is further optionally substituted. In one embodiment, $R^4$ is $C_1$-$C_4$ alkyl optionally substituted with $CF_3$, CN, nitro, amino, hydroxyl, or cycloalkoxyl. In one embodiment, the alkyl, alkoxyl, aminoalkyl, alkenyl, alkynyl, and cycloalkyl are optionally substituted with one or more halo.

In one embodiment, $R^3$ and together with the carbon atom to which they are attached form an optionally substituted cycloalkyl. In one embodiment, $R^3$ and together with the carbon atom to which they are attached form a cycloalkyl. In one embodiment, $R^3$ and together with the carbon atom to which they are attached form an optionally substituted heterocyclyl. In one embodiment, $R^3$ and together with the carbon atom to which they are attached form a heterocyclyl.

In one embodiment, $R^3$ and IV together with the atoms to which they are attached form an optionally substituted heterocyclyl, and is (i) hydrogen, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^9$, wherein $R^9$ is $CF_3$, CN, nitro, amino, hydroxyl, or cycloalkoxyl, each of which is optionally substituted. In one embodiment, $R^3$ and IV together with the atoms to which they are attached form a heterocyclyl, and is (i) hydrogen, alkyl, alkoxyl, aminoalkyl, alkenyl, alkynyl, cycloalkyl, cycloalkylalkyl, aryl, or aralkyl; or (ii) —(CH$_2$)$_p$—R$^9$, wherein R$^9$ is CF$_3$, CN, nitro, amino, hydroxyl, or cycloalkoxyl.

In one embodiment, $R^3$ and are combined together to form a double bond and together with IV and the atoms to which they are attached form an optionally substituted heteroaryl (e.g., imidazole). A skilled person will understand that when $R^3$ and are combined together to form a double bond and together with IV and the atoms to which they are attached form an optionally substituted heteroaryl, this embodiment could also be described as: one of $R^3$ and is absent and the other of $R^3$ and together with IV and the atoms to which they are attached form an optionally substituted heteroaryl (e.g., imidazole), which is substituted by $R^2$ (e.g., substituent on ring nitrogen atom). In one embodiment, $R^3$ and are combined together to form a double bond and together with IV and the atoms to which they are attached form a heteroaryl. Examples of the heteroaryl include, but are not limited to, imidazolyl, pyrrolyl, benzimidazolyl, or indazolyl. In various embodiments, IV and $R^2$ are also combined to form a double bond and together with $R^3$ and and the atoms to which they are attached form an optionally substituted heteroaryl (e.g., thiazole). A skilled person will understand that when $R^1$ and $R^2$ are also combined together to form a double bond and together with $R^3$ and the atoms to which they are attached form an optionally substituted heteroaryl, this embodiment could also be described as: one of $R^3$ and is absent and one of IV and $R^2$ is absent, and the other of $R^3$ and together with the other of IV and $R^2$ and the atoms to which they are attached form an optionally substituted heteroaryl (e.g., thiazole). In various embodiments, IV and $R^2$ are also combined to form a double bond and together with $R^3$ and $R^4$ and the atoms to which they are attached form a heteroaryl. Examples of the heteroaryl include, but are not limited to, oxazolyl, isoxazolyl, thiazolyl, pyridyl, or benzoxazolyl. In one embodiment, $R^1$, $R^2$, $R^3$, and $R^4$ are combined together with the atoms to which they are attached form an optionally substituted heteroaryl (e.g., imidazole or thiazole).

In one embodiment, $R^5$ is hydrogen. In one embodiment, $R^5$ is optionally substituted alkyl. In one embodiment, $R^5$ is alkyl. In one embodiment, $R^5$ is optionally substituted alkoxyl. In one embodiment, $R^5$ is alkoxyl. In one embodiment, $R^5$ is optionally substituted aminoalkyl. In one embodiment, $R^5$ is aminoalkyl. In one embodiment, $R^5$ is optionally substituted alkenyl. In one embodiment, $R^5$ is alkenyl. In one embodiment, $R^5$ is optionally substituted alkynyl. In one embodiment, $R^5$ is alkynyl. In one embodiment, $R^5$ is optionally substituted cycloalkyl. In one embodiment, $R^5$ is cycloalkyl. In one embodiment, $R^5$ is optionally substituted cycloalkylalkyl. In one embodiment, $R^5$ is cycloalkylalkyl. In one embodiment, $R^5$ is optionally substituted aryl. In one embodiment, $R^5$ is aryl. In one embodiment, $R^5$ is optionally substituted aralkyl. In one embodiment, $R^5$ is aralkyl. In one embodiment, $R^5$ is —(CH$_2$)$_p$—CF$_3$. In one embodiment, $R^5$ is —(CH$_2$)$_p$—CN. In one embodiment, $R^5$ is —(CH$_2$)$_p$-nitro. In one embodiment, $R^5$ is —(CH$_2$)$_p$-amino, wherein the amino is optionally substituted. In one embodiment, $R^5$ is —(CH$_2$)$_p$-amino. In one embodiment, $R^5$ is —(CH$_2$)$_p$-hydroxyl, wherein the hydroxyl is optionally substituted. In one embodiment, $R^5$ is —(CH$_2$)$_p$-hydroxyl. In one embodiment, $R^5$ is —(CH$_2$)$_p$-cycloalkoxyl, wherein the cycloalkoxyl is optionally substituted. In one embodiment, $R^5$ is —(CH$_2$)$_p$-cycloalkoxyl. In one embodiment, $R^5$ is C$_1$-C$_4$ alkyl optionally substituted with CF$_3$, CN, nitro, amino, hydroxyl, or cycloalkoxyl, each of which is further optionally substituted. In one embodiment, $R^5$ is C$_1$-C$_4$ alkyl optionally substituted with CF$_3$, CN, nitro, amino, hydroxyl, or cycloalkoxyl. In one embodiment, the alkyl, alkoxyl, aminoalkyl, alkenyl, alkynyl, and cycloalkyl are optionally substituted with one or more halo.

In one embodiment, $R^5$ and $R^1$ together with the atoms to which they are attached form an optionally substituted heterocyclyl. In one embodiment, $R^5$ and $R^1$ together with the atoms to which they are attached form a heterocyclyl.

In one embodiment, $R^6$ is hydrogen. In one embodiment, $R^6$ is halo. In one embodiment, $R^6$ is optionally substituted alkyl. In one embodiment, $R^6$ is alkyl. In one embodiment, $R^6$ is optionally substituted alkoxyl. In one embodiment, $R^6$ is alkoxyl. In one embodiment, $R^6$ is optionally substituted aminoalkyl. In one embodiment, $R^6$ is aminoalkyl. In one embodiment, $R^6$ is optionally substituted alkenyl. In one embodiment, $R^6$ is alkenyl. In one embodiment, $R^6$ is optionally substituted alkynyl. In one embodiment, $R^6$ is alkynyl. In one embodiment, $R^6$ is optionally substituted cycloalkyl. In one embodiment, $R^6$ is cycloalkyl. In one embodiment, $R^6$ is optionally substituted cycloalkylalkyl. In one embodiment, $R^6$ is cycloalkylalkyl. In one embodiment, $R^6$ is optionally substituted aryl. In one embodiment, $R^6$ is aryl. In one embodiment, $R^6$ is optionally substituted aralkyl. In one embodiment, $R^6$ is aralkyl. In one embodiment, $R^6$ is —(CH$_2$)$_p$—CF$_3$. In one embodiment, $R^6$ is —(CH$_2$)$_p$—CN. In one embodiment, $R^6$ is —(CH$_2$)$_p$-nitro. In one embodiment, $R^6$ is —(CH$_2$)$_p$-amino, wherein the amino is optionally substituted. In one embodiment, $R^6$ is —(CH$_2$)$_p$-amino. In one embodiment, $R^6$ is —(CH$_2$)$_p$-hydroxyl, wherein the hydroxyl is optionally substituted. In one embodiment, $R^6$ is —(CH$_2$)$_p$-hydroxyl. In one embodiment, $R^6$ is —(CH$_2$)$_p$-cycloalkoxyl, wherein the cycloalkoxyl is optionally substituted. In one embodiment, $R^6$ is —(CH$_2$)$_p$-cycloalkoxyl. In one embodiment, $R^6$ is —(CH$_2$)$_p$-heteroaryl, wherein the heteroaryl is optionally substituted. In one embodiment, $R^6$ is —(CH$_2$)$_p$-heteroaryl. In one embodiment, $R^6$ is —(CH$_2$)$_p$-heterocyclyl, wherein the heterocyclyl is optionally substituted. In one embodiment, $R^6$ is —(CH$_2$)$_p$-heterocyclyl. In one embodiment, the alkyl, alkoxyl, aminoalkyl, alkenyl, alkynyl, and cycloalkyl are optionally substituted with one or more halo.

In one embodiment, $R^7$ is hydrogen. In one embodiment, $R^7$ is halo. In one embodiment, $R^7$ is optionally substituted alkyl. In one embodiment, $R^7$ is alkyl. In one embodiment, $R^7$ is optionally substituted alkoxyl. In one embodiment, $R^7$ is alkoxyl. In one embodiment, $R^7$ is optionally substituted aminoalkyl. In one embodiment, $R^7$ is aminoalkyl. In one embodiment, $R^7$ is optionally substituted alkenyl. In one embodiment, $R^7$ is alkenyl. In one embodiment, $R^7$ is optionally substituted alkynyl. In one embodiment, $R^7$ is alkynyl. In one embodiment, $R^7$ is optionally substituted cycloalkyl. In one embodiment, $R^7$ is cycloalkyl. In one embodiment, $R^7$ is optionally substituted cycloalkylalkyl. In one embodiment, $R^7$ is cycloalkylalkyl. In one embodiment, $R^7$ is optionally substituted aryl. In one embodiment, $R^7$ is aryl. In one embodiment, $R^7$ is optionally substituted aralkyl. In one embodiment, $R^7$ is aralkyl. In one embodiment, $R^7$ is —(CH$_2$)$_p$—CF$_3$. In one embodiment, $R^7$ is —(CH$_2$)$_p$—CN. In one embodiment, $R^7$ is —(CH$_2$)$_p$-nitro. In one embodiment, $R^7$ is —(CH$_2$)$_p$-amino, wherein the amino is optionally substituted. In one embodiment, $R^7$ is —(CH$_2$)$_p$-amino. In one embodiment, $R^7$ is —(CH$_2$)$_p$-hydroxyl, wherein the hydroxyl is optionally substituted. In one embodiment, $R^7$ is —(CH$_2$)$_p$-hydroxyl. In one embodiment, $R^7$ is —$(CH_2)_p$-cycloalkoxyl, wherein the cycloalkoxyl is optionally substituted. In one embodiment, $R^7$ is —$(CH_2)_p$-cycloalkoxyl. In one embodiment, $R^7$ is —$(CH_2)_p$-heteroaryl, wherein the heteroaryl is optionally substituted. In one embodiment, $R^7$ is —$(CH_2)_p$-heteroaryl. In one embodiment, $R^7$ is —$(CH_2)_p$-heterocyclyl, wherein the heterocyclyl is optionally substituted. In one embodiment, $R^7$ is —$(CH_2)_p$-heterocyclyl. In one embodiment, the alkyl, alkoxyl, aminoalkyl, alkenyl, alkynyl, and cycloalkyl are optionally substituted with one or more halo.

In one embodiment, $R^6$ and $R^7$ together with the atoms to which they are attached form an optionally substituted aryl. In one embodiment, $R^6$ and $R^7$ together with the atoms to which they are attached form an aryl. In one embodiment, $R^6$ and $R^7$ together with the atoms to which they are attached form an optionally substituted heteroaryl. In one embodiment, $R^6$ and $R^7$ together with the atoms to which they are attached form a heteroaryl. In one embodiment, $R^6$ and $R^7$ together with the atoms to which they are attached form a partially saturated optionally substituted cycloalkyl. In one embodiment, $R^6$ and $R^7$ together with the atoms to which they are attached form a partially saturated cycloalkyl. In one embodiment, $R^6$ and $R^7$ together with the atoms to which they are attached form an optionally substituted heterocyclyl. In one embodiment, $R^6$ and $R^7$ together with the atoms to which they are attached form a heterocyclyl.

In one embodiment, m is 0. In one embodiment, m is 1. In one embodiment, m is 2.

In one embodiment, n is 0. In one embodiment, n is 1. In one embodiment, n is 2.

In one embodiment, p is 0. In one embodiment, p is 1. In one embodiment, p is 2.

In one embodiment, at least one of $R^1$, $R^2$, $R^3$, $R^4$, $R^5$, $R^6$, and $R^7$ is not hydrogen. In one embodiment, at least one of $R^1$, $R^2$, $R^3$, $R^4$, $R^5$, and $R^6$ is not hydrogen (e.g., when $R^7$ is absent). In one embodiment, at least one of $R^1$, $R^2$, $R^3$, $R^4$, $R^6$, and $R^7$ is not hydrogen. In one embodiment, at least one of $R^1$, $R^2$, $R^3$, $R^4$, and $R^6$ is not hydrogen (e.g., when $R^7$ is absent). In one embodiment, at least one of $R^1$ and $R^2$ is not hydrogen. In one embodiment, at least one of $R^3$ and $R^4$ is not hydrogen. In one embodiment, at least one of $R^6$ and $R^7$ is not hydrogen. In one embodiment, when $R^5$ is not hydrogen, at least one of $R^1$, $R^2$, $R^3$, $R^4$, $R^6$, and $R^7$ is not hydrogen. In one embodiment, when $R^5$ is not hydrogen, at least one of $R^1$, $R^2$, $R^3$, $R^4$, and $R^6$ is not hydrogen (e.g., when $R^7$ is absent). In one embodiment, $R^5$ is not hydroxyl. In one embodiment, $R^5$ is not substituted hydroxyl (e.g., alkoxyl). In one embodiment, $R^5$ is not alkyl. In one embodiment, $R^5$ is not methyl.

In one embodiment, $R^1$ and $R^2$ are not optionally substituted acyl. In one embodiment, $R^6$ and $R^7$ are not optionally substituted amide. In one embodiment, $R^{11}$ is not optionally substituted amide. In one embodiment, $R^6$ and $R^7$ are not optionally substituted acyl. In one embodiment, $R^{11}$ is not optionally substituted acyl.

In one embodiment, when X and Y are $CH_2$, $R^3$ and $R^4$ are not combined together with $R^1$ or $R^2$ and the atoms to which they are attached to form a ring (e.g., imidazole or imidazoline). In one embodiment, when X and Y are $CH_2$, $R^3$ and $R^4$ are not combined together with $R^1$ and $R^2$ and the atoms to which they are attached to form a ring (e.g., thiazole).

In one embodiment, when X and Y are $CH_2$, $R^1$ (or $R^2$) and $R^5$ are not combined together with the atoms to which they are attached form a ring (e.g., pyrrolidine or azetidine).

In one embodiment, when any one of $R^1$, $R^2$, $R^3$, $R^4$, $R^5$, $R^6$ or $R^7$ is alkyl or cycloalkyl, the alkyl or cycloalkyl is optionally substituted with one or more halo (e.g., fluoro).

Any of the combinations of X, Y, $Z^1$, $Z^2$, $Z^3$, $R^1$, $R^2$, $R^3$, $R^4$, $R^5$, $R^6$, $R^7$, m, n, and p are encompassed by this disclosure and specifically provided herein.

In various embodiments, provided herein are methods for the treatment of one or more of: a symptom domain of schizophrenia, a symptom sub-domain of schizophrenia, a subject sub-population with symptoms prominently in a symptom domain of schizophrenia; and/or a subject sub-population with symptoms prominently in symptom sub-domain of schizophrenia comprising administering to a subject a therapeutically or prophylactically effective amount of a therapeutic agent, the therapeutic agent comprising a compound of formula (IIa):

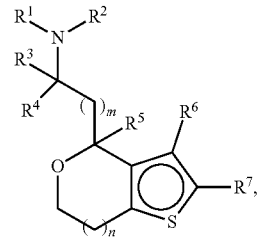

(IIa)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In one embodiment, m is 0 or 1. In one embodiment, n is 1 or 2. In one embodiment, m is 0 and n is 1. In one embodiment, n is 0 or 1. In one embodiment, n is 0.

In one embodiment, $R^5$ is hydrogen.

In one embodiment, $R^1$ and $R^2$ are each independently hydrogen, $C_1$-$C_4$ alkyl (e.g., methyl, ethyl, or propyl (e.g., n-propyl or i-propyl)), or $C_3$-$C_6$ cycloalkyl (e.g., cyclopropyl). In one embodiment, $R^1$ and $R^2$ are each independently hydrogen or $C_1$-$C_4$ alkyl (e.g., methyl, ethyl, or propyl (e.g., n-propyl or i-propyl)). In one embodiment, $R^1$ and $R^2$ are each independently $C_1$-$C_4$ alkyl, wherein one or more hydrogen(s) in the alkyl are replaced with deuterium (e.g., $CD_3$).

In one embodiment, $R^3$ and $R^4$ are hydrogen or $C_1$-$C_4$ alkyl (e.g., methyl, ethyl, or propyl (e.g., n-propyl or i-propyl)). In one embodiment, $R^3$ and $R^4$ are hydrogen.

In one embodiment, $R^6$ and $R^7$ are each independently hydrogen, halo (e.g., F or Cl), $C_1$-$C_4$ alkyl (e.g., methyl, ethyl, propyl, or $CF_3$), aryl (e.g., phenyl), heteroaryl (e.g., pyridyl), heterocyclyl (e.g., pyrrolidinyl, piperidinyl, or morpholinyl), alkoxyl (e.g., OMe), or aminoalkyl (e.g., $NMe_2$), each of which is optionally substituted. In one embodiment, $R^6$ and $R^7$ are each independently hydrogen, halo, $C_1$-$C_4$ alkyl, aryl, heteroaryl, heterocyclyl, alkoxyl, or aminoalkyl. In one embodiment, the $C_1$-$C_4$ alkyl is optionally substituted with one or more fluoro. In one embodiment, $R^6$ and $R^7$ are each independently hydrogen, fluoro, chloro, methyl, $CF_3$, ethyl, propyl, isopropyl, phenyl, pyridyl, pyrrolidinyl, piperidinyl, morpholinyl, methoxyl, or dimethylamino.

Specific examples include, but are not limited to, the following compounds:

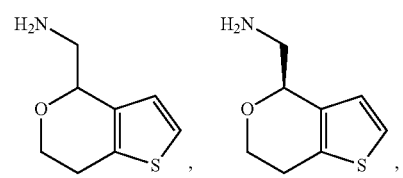

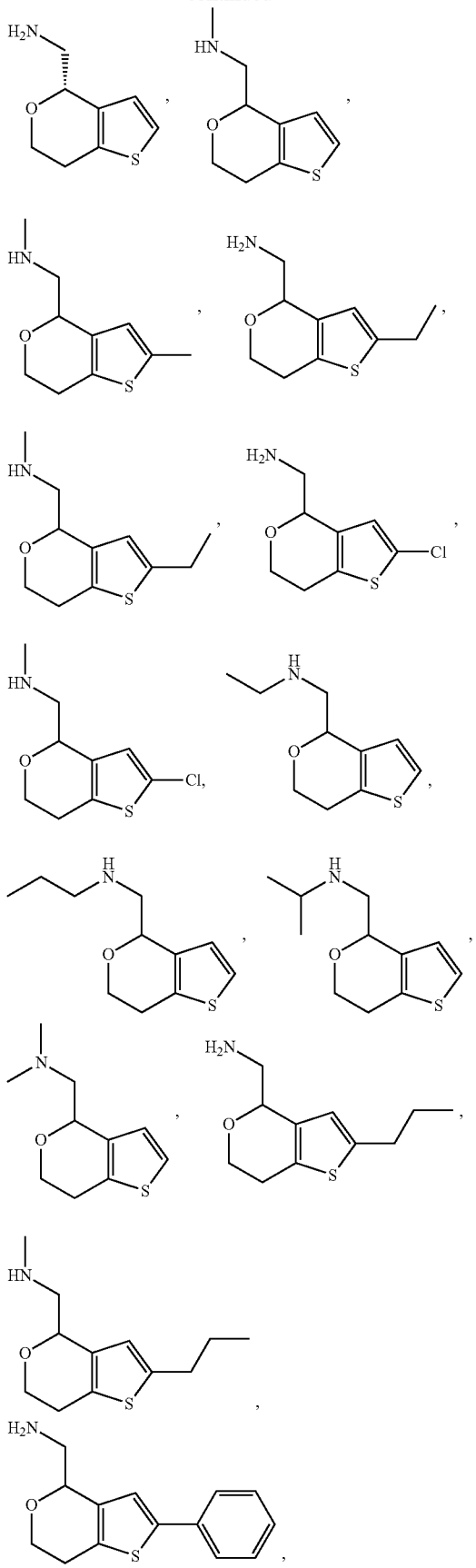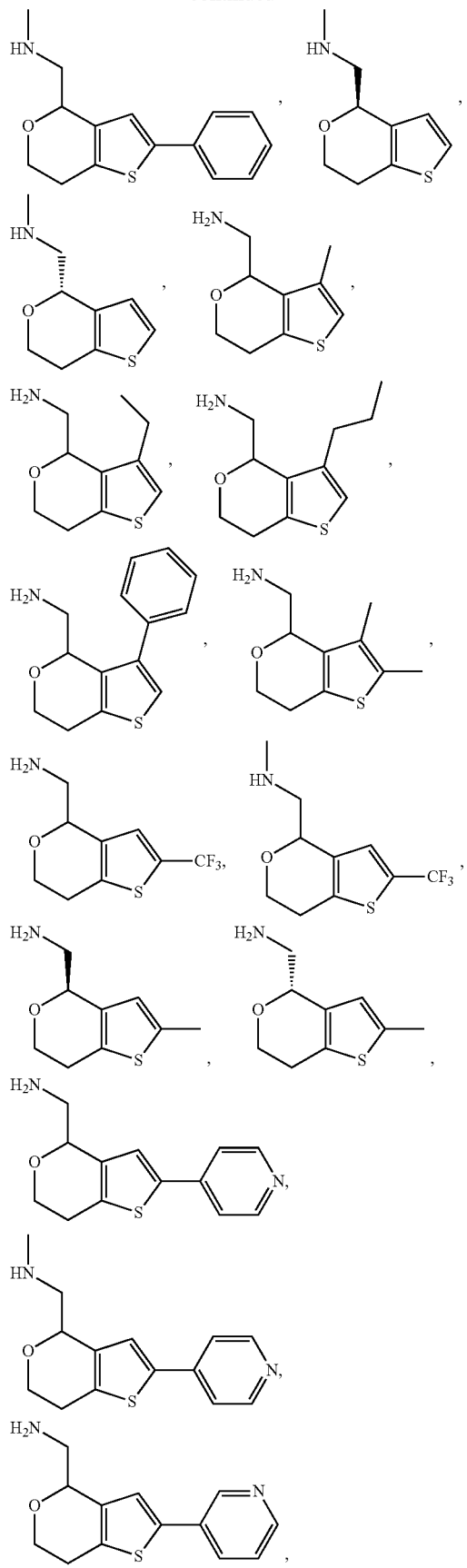

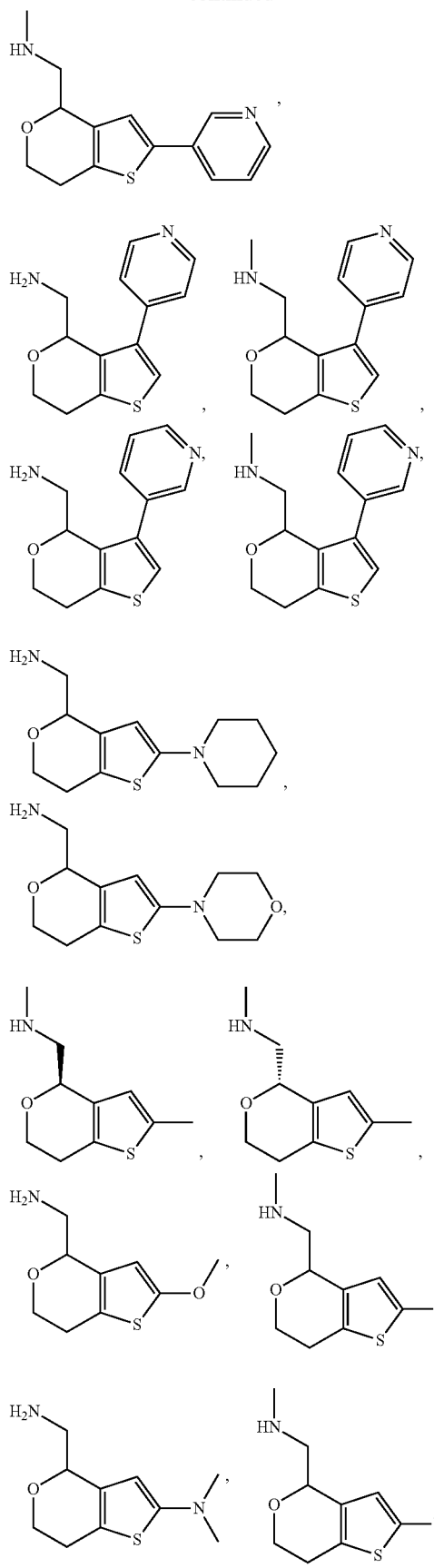
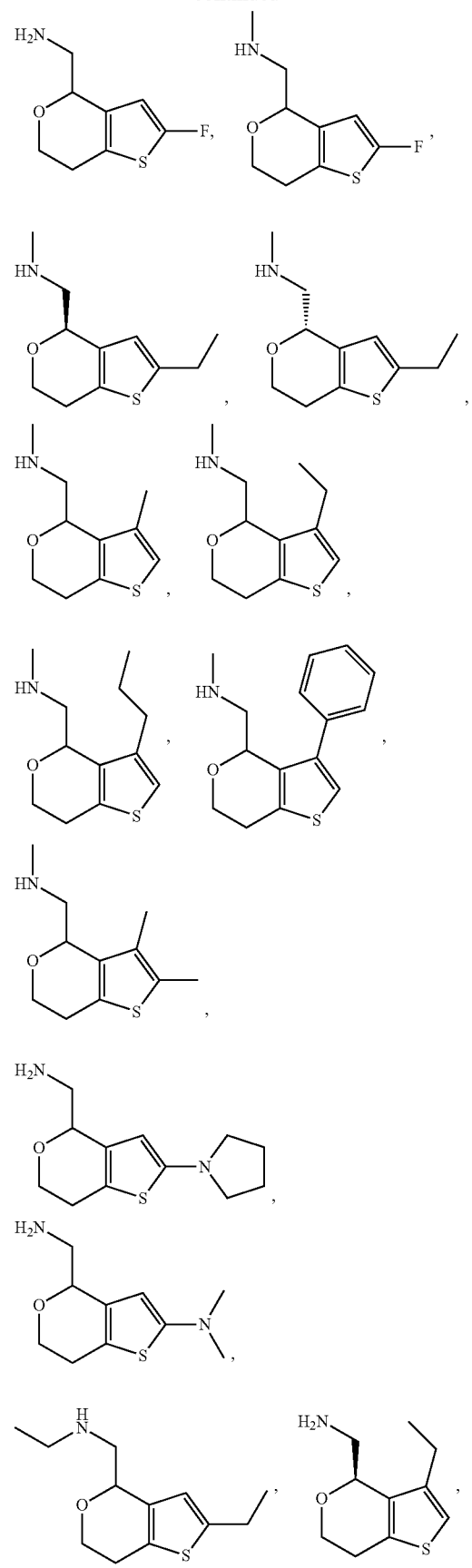

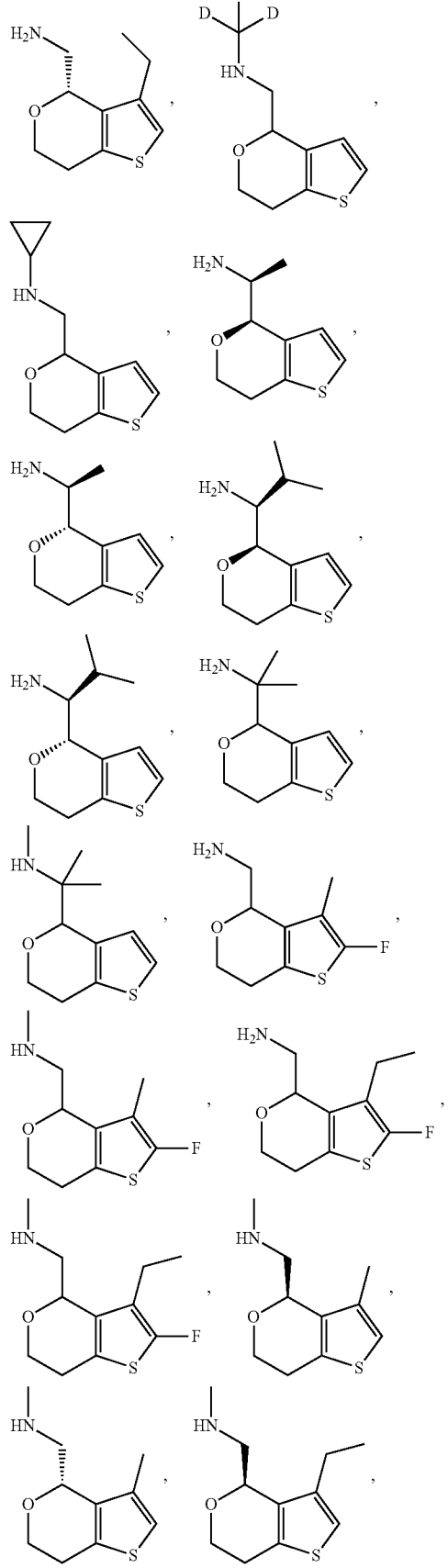

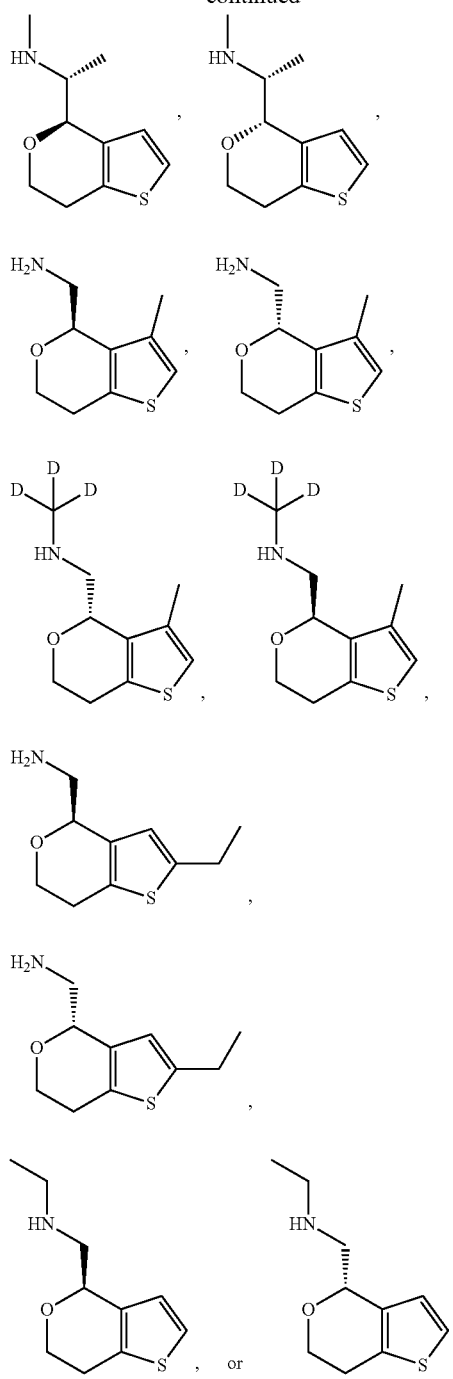

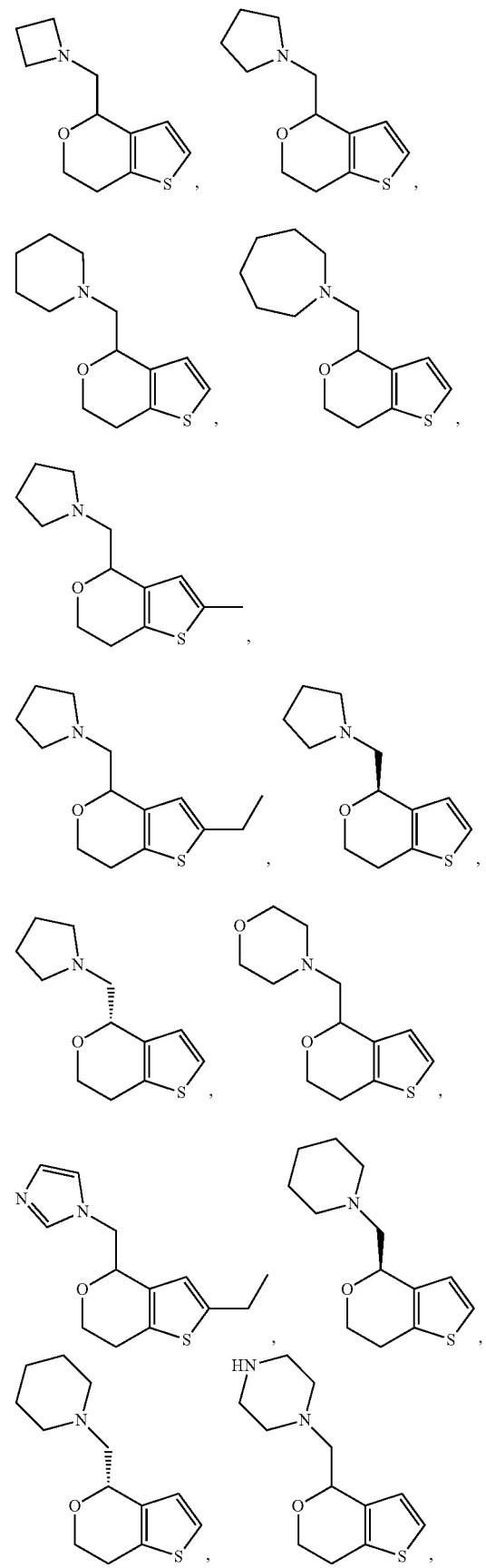

In one embodiment, R¹ and R² together with the nitrogen atom to which they are attached form a heteroaryl or heterocyclyl, each of which is optionally substituted. In one embodiment, R¹ and R² together with the nitrogen atom to which they are attached form an optionally substituted heterocyclyl. In one embodiment, R¹ and R² together with the nitrogen atom to which they are attached form a heteroaryl or heterocyclyl. Examples include, but are not limited to, azetidinyl, pyrrolidinyl, piperidinyl, azepanyl, morpholinyl, imidazolyl, piperazinyl, and N-methylpiperazinyl. Specific examples include, but are not limited to, the following compounds:

-continued

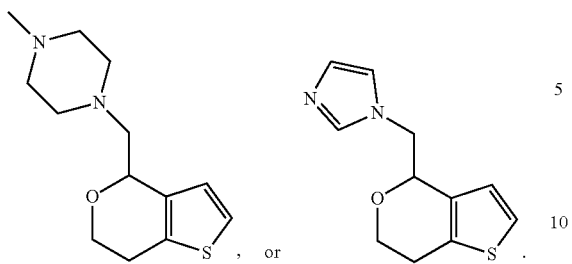

In one embodiment, $R^1$ and $R^3$ together with the atoms to which they are attached form an optionally substituted heterocyclyl ring (e.g., pyrrolidine, including, e.g., unsubstituted pyrrolidine and N-methyl-pyrrolidine). Specific examples include, but are not limited to, the following compounds:

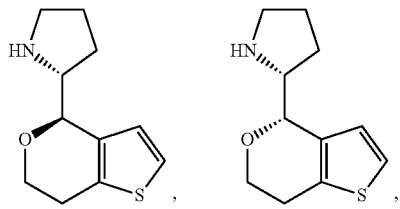

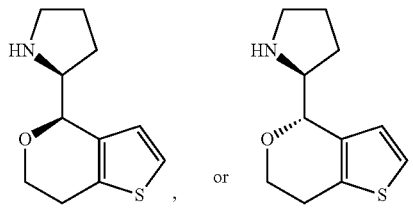

In one embodiment, $R^3$ and together with the atom to which they are attached form a cycloalkyl (e.g., cyclopropyl, cyclobutyl, cyclopentyl, or cyclohexyl) or heterocyclyl (e.g., tetrahydrofuranyl) ring, each of which is optionally substituted. Specific examples include, but are not limited to, the following compounds:

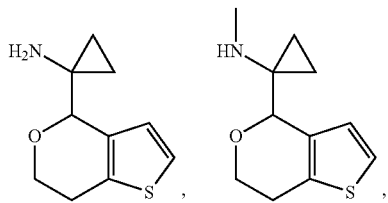

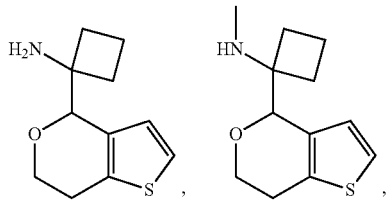

-continued

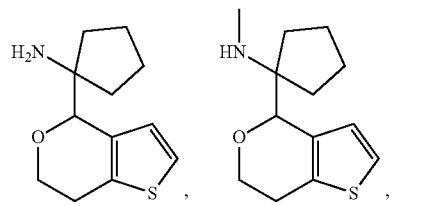

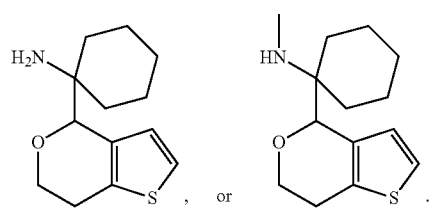

In one embodiment, $R^6$ and $R^7$ together with the atoms to which they are attached form an aryl (e.g., phenyl) or cycloalkyl (e.g., 5-, 6-, or 7-membered) ring, each of which is optionally substituted (e.g., by one or more halo or phenyl). In one embodiment, $R^6$ and $R^7$ together with the atoms to which they are attached form an optionally substituted aryl. In one embodiment, $R^6$ and $R^7$ together with the atoms to which they are attached form an aryl. Examples include, but are not limited to, phenyl, cyclopentenyl, cyclohexenyl, and cycloheptenyl. Specific examples include, but are not limited to, the following compounds:

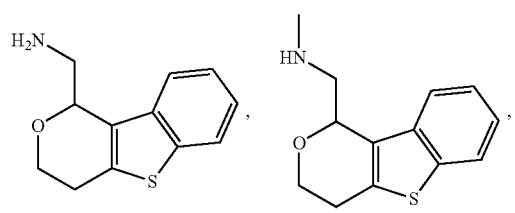

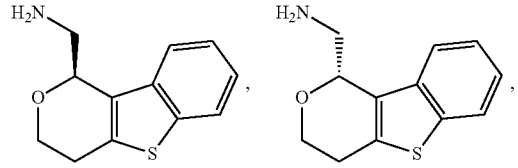

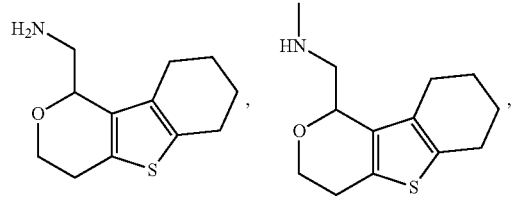

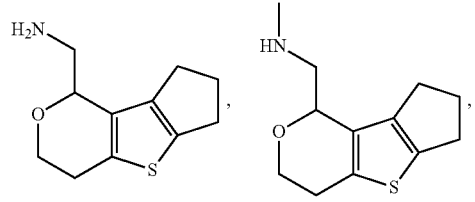

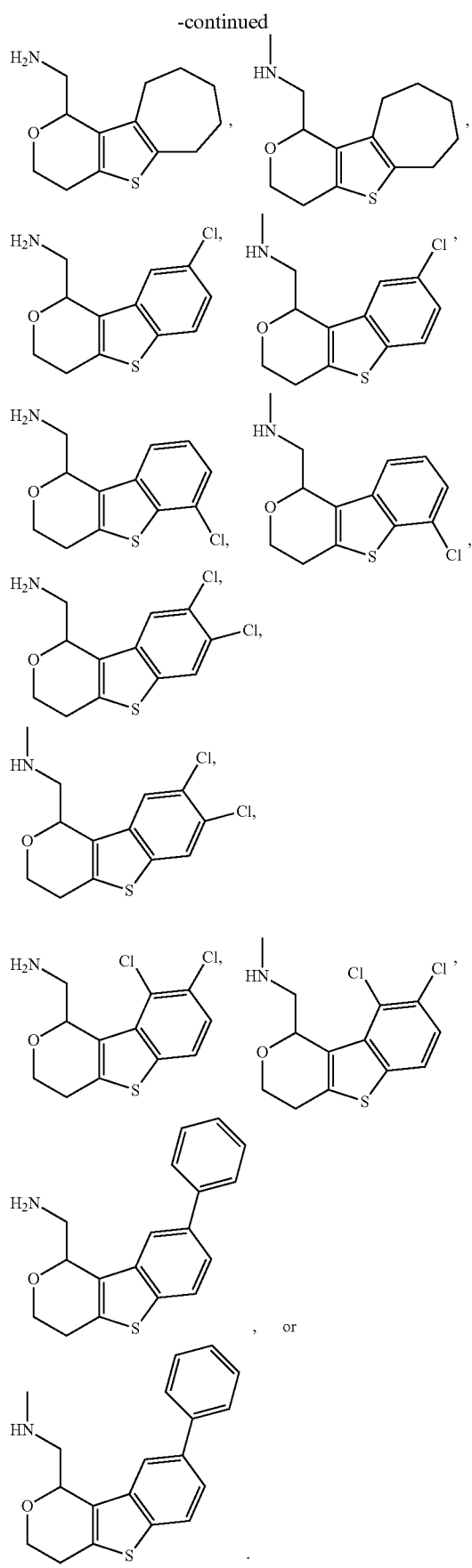

In one embodiment, $R^1$ and $R^5$ together with the atoms to which they are attached form an optionally substituted heterocyclyl. In one embodiment, $R^1$ and $R^5$ together with the atoms to which they are attached form a heterocyclyl. Examples include, but are not limited to, pyrrolidinyl and piperidinyl. Specific examples include, but are not limited to, the following compounds:

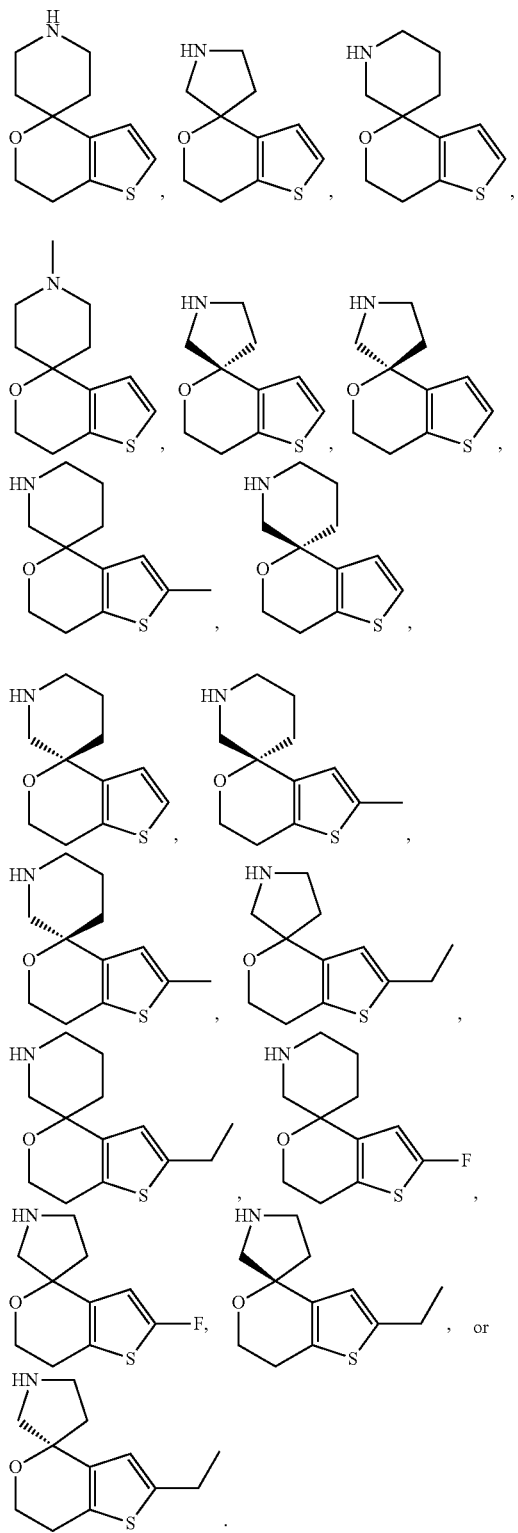

In one embodiment, $R^1$ and $R^5$ together with the atoms to which they are attached form an optionally substituted heterocyclyl (e.g., piperidinyl) and $R^6$ and $R^7$ together with the atoms to which they are attached form an optionally substituted aryl (e.g., phenyl). In one embodiment, $R^1$ and $R^5$ together with the atoms to which they are attached form a heterocyclyl and $R^6$ and $R^7$ together with the atoms to which they are attached form an aryl. Specific examples include, but are not limited to, the following compound:

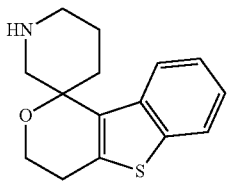

In one embodiment, m is 0 and $R^3$ and $R^4$ are combined together to form a double bond and together with $R^1$ and/or $R^2$ and the atoms to which they are attached form an optionally substituted heteroaryl. In one embodiment, the heteroaryl contains one or more heteroatoms selected from N, O, and S. Examples include, but are not limited to, imidazolyl, pyrazolyl, or thiazolyl. Specific examples include, but are not limited to, the following compounds:

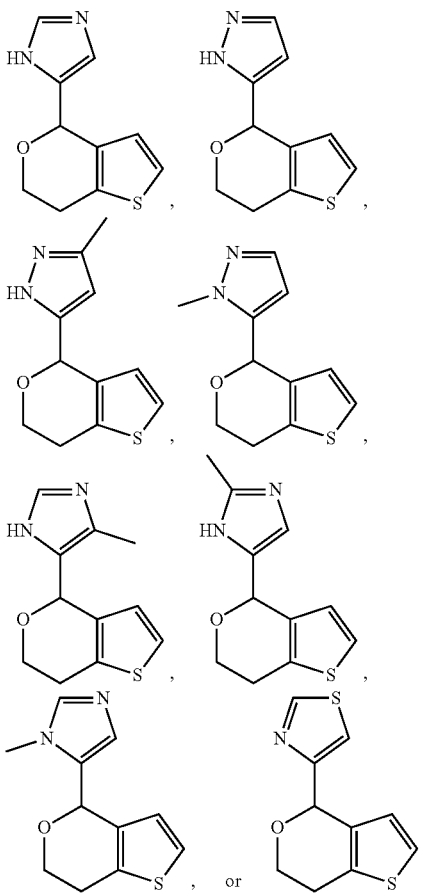

In one embodiment, m is 1. Specific examples include, but are not limited to, the following compound:

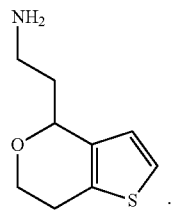 [SMILES: NCCC1OCCc2sccc21]

In one embodiment, n is 2. In one embodiment, $R^1$, $R^2$, $R^6$, and $R^7$ are each independently hydrogen or optionally substituted $C_1$-$C_4$ alkyl (e.g., methyl or ethyl). Specific examples include, but are not limited to, the following compounds:

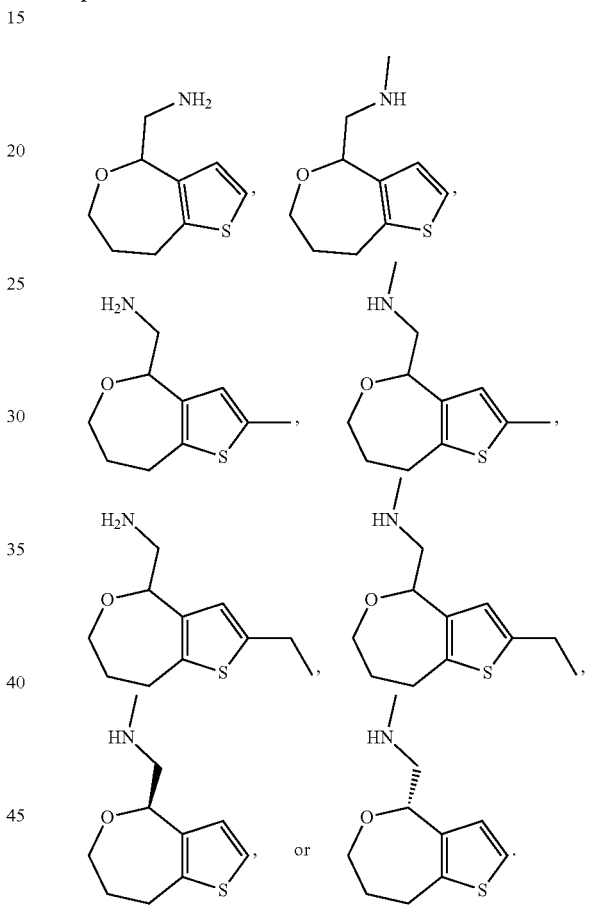

In one embodiment, $R^5$ is alkyl. In one embodiment, $R^5$ is $C_1$-$C_4$ alkyl. In one embodiment, $R^5$ is methyl. Specific examples include, but are not limited to, the following compound:

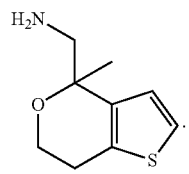

In various embodiments, provided herein are methods for the treatment of one or more of: a symptom domain of schizophrenia, a symptom sub-domain of schizophrenia, a subject sub-population with symptoms prominently in a symptom domain of schizophrenia; and/or a subject sub-population with symptoms prominently in symptom subdomain of schizophrenia comprising administering to a subject a therapeutically or prophylactically effective amount of a therapeutic agent, the therapeutic agent comprising a compound of formula (IIb):

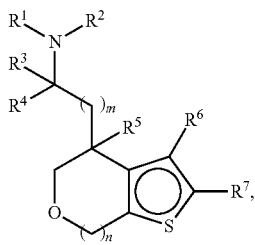
(IIb)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In various embodiments, provided herein are methods for the treatment of one or more of: a symptom domain of schizophrenia, a symptom sub-domain of schizophrenia, a subject sub-population with symptoms prominently in a symptom domain of schizophrenia; and/or a subject sub-population with symptoms prominently in symptom sub-domain of schizophrenia comprising administering to a subject a therapeutically or prophylactically effective amount of a therapeutic agent, the therapeutic agent comprising a compound of formula (IIc):

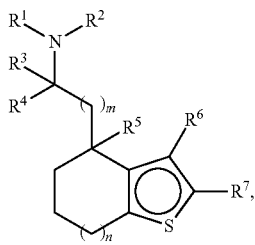
(IIc)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In one embodiment, $R^5$ is OH. Specific examples include, but are not limited to, the following compound:

In one embodiment, $R^5$ is hydrogen.

In one embodiment, n is 0. In one embodiment, $R^1$ and $R^2$ are each independently hydrogen or optionally substituted $C_1$-$C_4$ alkyl (e.g., methyl or ethyl). In one embodiment, $R^6$ and $R^7$ are each independently hydrogen, halo (e.g., F or Cl), or optionally substituted $C_1$-$C_4$ alkyl (e.g., methyl or ethyl). Specific examples include, but are not limited to, the following compounds:

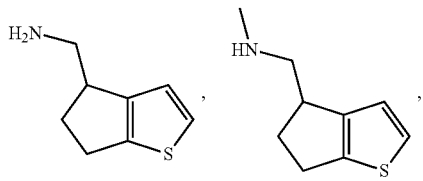

-continued

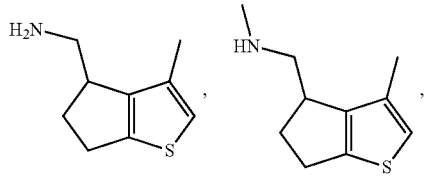

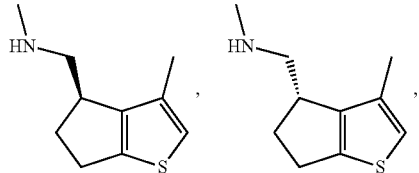

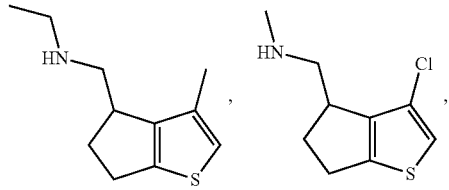

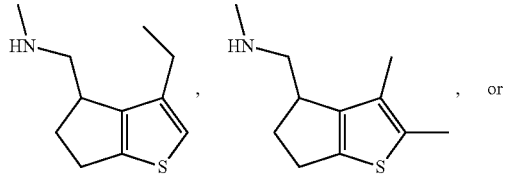

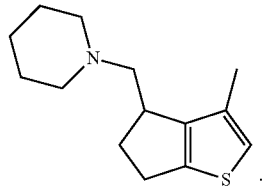
, or

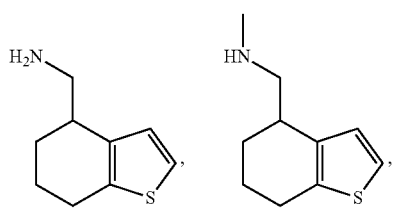

In one embodiment, n is 1. In one embodiment, $R^1$ and $R^2$ are each independently hydrogen or optionally substituted $C_1$-$C_4$ alkyl (e.g., methyl or ethyl). In one embodiment, $R^1$ and $R^2$ together with the atom to which they are attached form an optionally substituted heterocyclyl (e.g., piperidinyl). In one embodiment, $R^6$ and $R^7$ are each independently hydrogen or optionally substituted $C_1$-$C_4$ alkyl (e.g., methyl or ethyl). Specific examples include, but are not limited to, the following compounds:

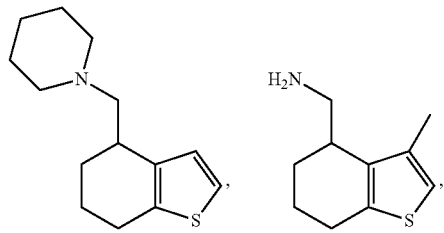

-continued

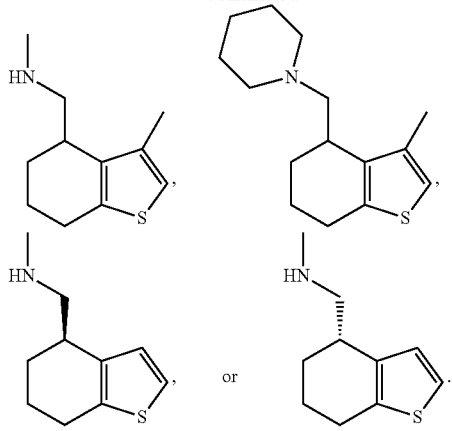

In various embodiments, provided herein are methods for the treatment of one or more of: a symptom domain of schizophrenia, a symptom sub-domain of schizophrenia, a subject sub-population with symptoms prominently in a symptom domain of schizophrenia; and/or a subject sub-population with symptoms prominently in symptom sub-domain of schizophrenia comprising administering to a subject a therapeutically or prophylactically effective amount of a therapeutic agent, the therapeutic agent comprising a compound of formula (IIIa):

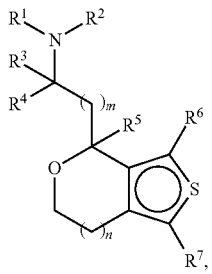

(IIIa)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In one embodiment, $R^1$, $R^2$, $R^6$, and $R^7$ are each independently hydrogen or optionally substituted $C_1$-$C_4$ alkyl (e.g., methyl or ethyl). Specific examples include, but are not limited to, the following compounds:

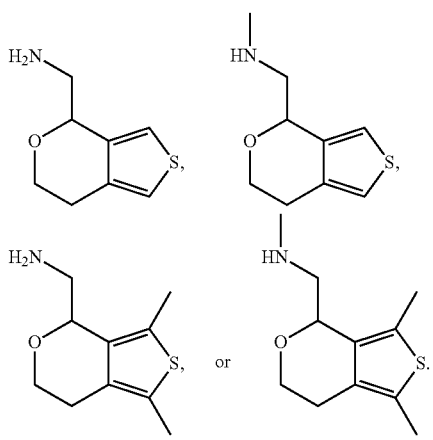

In various embodiments, provided herein are methods for the treatment of one or more of: a symptom domain of schizophrenia, a symptom sub-domain of schizophrenia, a subject sub-population with symptoms prominently in a symptom domain of schizophrenia; and/or a subject sub-population with symptoms prominently in symptom sub-domain of schizophrenia comprising administering to a subject a therapeutically or prophylactically effective amount of a therapeutic agent, the therapeutic agent comprising a compound of formula (IIIb):

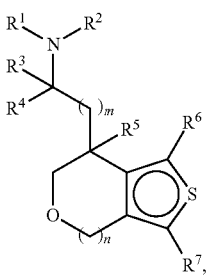

(IIIb)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In various embodiments, provided herein are methods for the treatment of one or more of: a symptom domain of schizophrenia, a symptom sub-domain of schizophrenia, a subject sub-population with symptoms prominently in a symptom domain of schizophrenia; and/or a subject sub-population with symptoms prominently in symptom sub-domain of schizophrenia comprising administering to a subject a therapeutically or prophylactically effective amount of a therapeutic agent, the therapeutic agent comprising a compound of formula (IIIc):

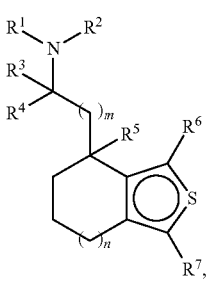

(IIIc)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In various embodiments, provided herein are methods for the treatment of one or more of: a symptom domain of schizophrenia, a symptom sub-domain of schizophrenia, a subject sub-population with symptoms prominently in a symptom domain of schizophrenia; and/or a subject sub-population with symptoms prominently in symptom sub-domain of schizophrenia comprising administering to a subject a therapeutically or prophylactically effective amount of a therapeutic agent, the therapeutic agent comprising a compound of formula (IVa):

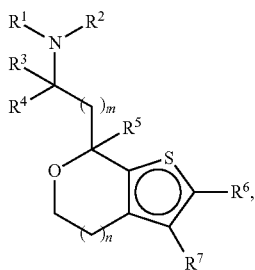

(IVa)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In one embodiment, m is 0 or 1. In one embodiment, n is 1 or 2. In one embodiment, m is 0 and n is 1. In one embodiment, n is 0 or 1. In one embodiment, n is 0.

In one embodiment, $R^5$ is hydrogen.

In one embodiment, $R^1$ and $R^2$ are each independently hydrogen, $C_1$-$C_4$ alkyl (e.g., methyl, ethyl, or propyl (e.g., n-propyl or i-propyl)), or $C_3$-$C_6$ cycloalkyl (e.g., cyclopropyl). In one embodiment, $R^1$ and $R^2$ are each independently hydrogen or $C_1$-$C_4$ alkyl (e.g., methyl, ethyl, or propyl (e.g., n-propyl or i-propyl)). In one embodiment, $R^1$ and $R^2$ are each independently $C_1$-$C_4$ alkyl, wherein one or more hydrogen(s) in the alkyl are replaced with deuterium (e.g., $CD_3$).

In one embodiment, $R^3$ and $R^4$ are hydrogen or $C_1$-$C_4$ alkyl (e.g., methyl, ethyl, or propyl (e.g., n-propyl or i-propyl)). In one embodiment, $R^3$ and $R^4$ are hydrogen.

In one embodiment, $R^6$ and $R^7$ are each independently hydrogen, halo (e.g., F or Cl), $C_1$-$C_4$ alkyl (e.g., methyl, ethyl, propyl, or $CF_3$), aryl (e.g., phenyl), heteroaryl (e.g., pyridyl), heterocyclyl (e.g., pyrrolidinyl, piperidinyl, or morpholinyl), alkoxyl (e.g., OMe), or aminoalkyl (e.g., $NMe_2$), each of which is optionally substituted. In one embodiment, $R^6$ and $R^7$ are each independently hydrogen, halo, $C_1$-$C_4$ alkyl, aryl, heteroaryl, heterocyclyl, alkoxyl, or aminoalkyl. In one embodiment, the $C_1$-$C_4$ alkyl is optionally substituted with one or more fluoro. In one embodiment, $R^6$ and $R^7$ are each independently hydrogen, fluoro, chloro, methyl, $CF_3$, ethyl, propyl, isopropyl, phenyl, pyridyl, pyrrolidinyl, piperidinyl, morpholinyl, methoxyl, or dimethylamino.

Specific examples include, but are not limited to, the following compounds:

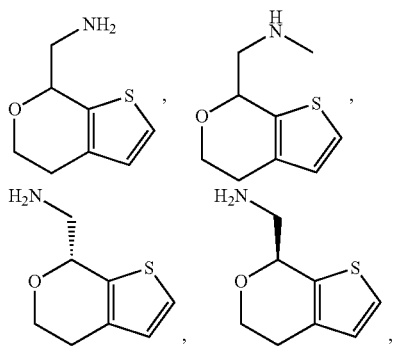

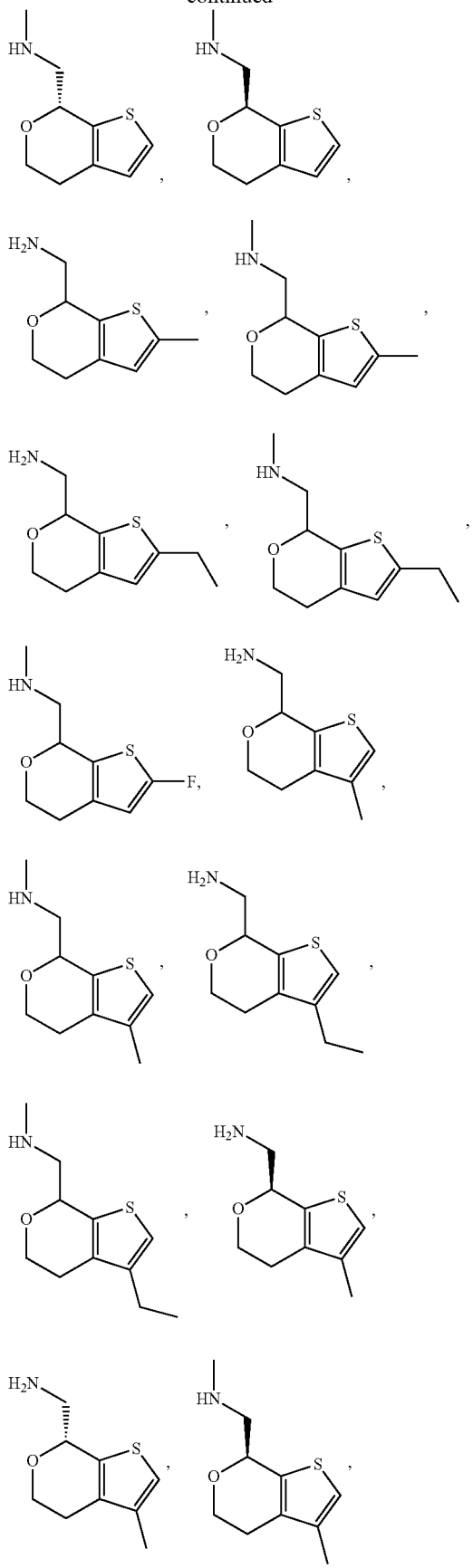

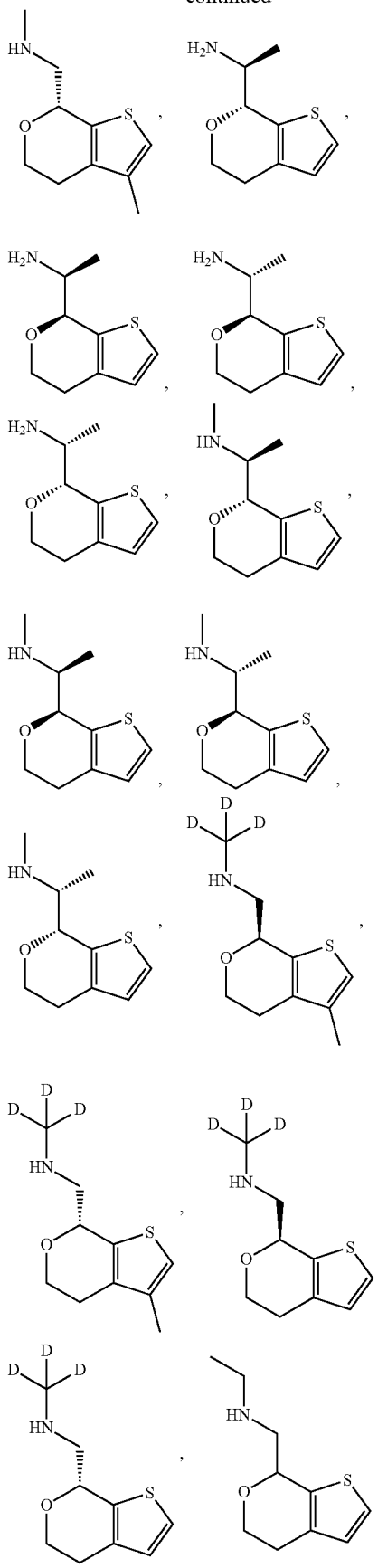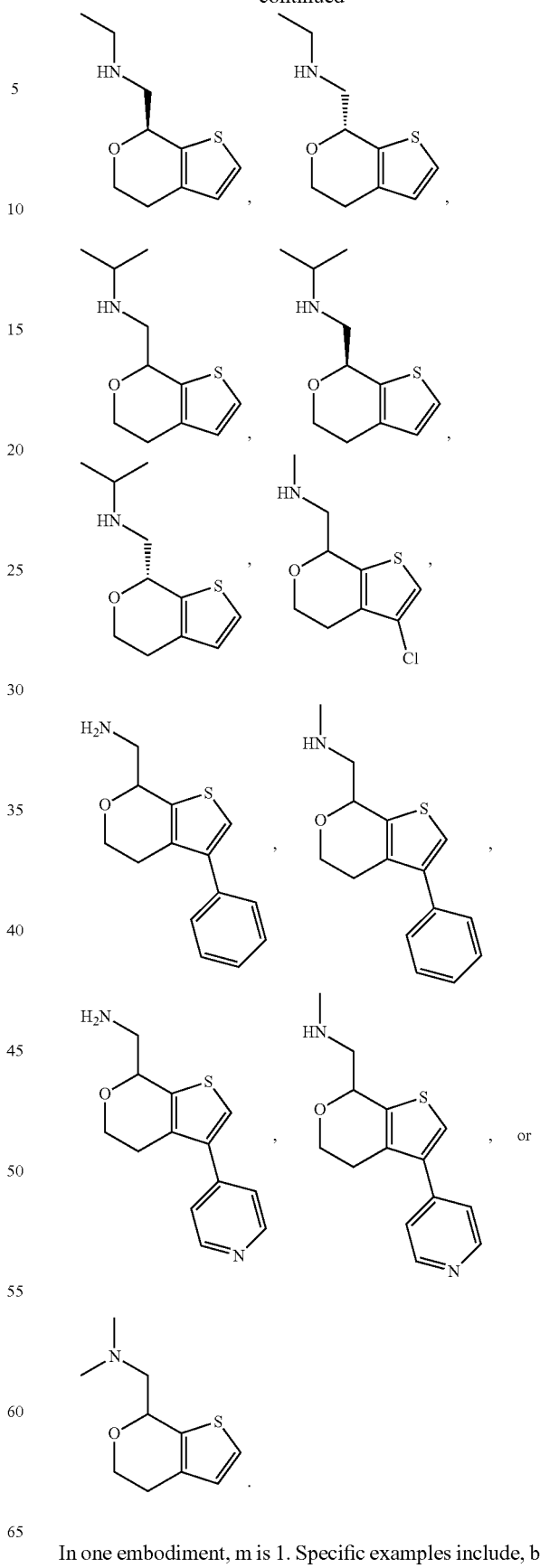
In one embodiment, m is 1. Specific examples include, but are not limited to, the following compounds:

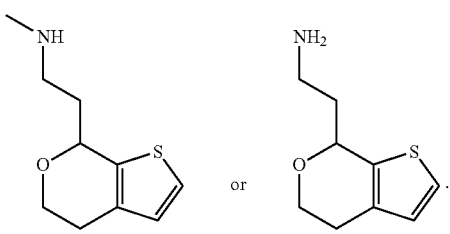 or

In one embodiment, $R^1$ and $R^2$ together with the nitrogen atom to which they are attached form a heteroaryl or heterocyclyl, each of which is optionally substituted. In one embodiment, $R^1$ and $R^2$ together with the nitrogen atom to which they are attached form an optionally substituted heterocyclyl (e.g., pyrrolidinyl or piperidinyl). Examples include, but are not limited to, azetidinyl, pyrrolidinyl, piperidinyl, azepanyl, morpholinyl, imidazolyl, piperazinyl, and N-methyl-piperazinyl. Specific examples include, but are not limited to, the following compounds:

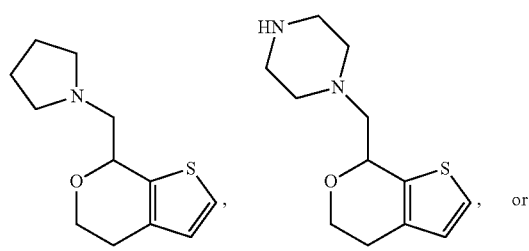 or

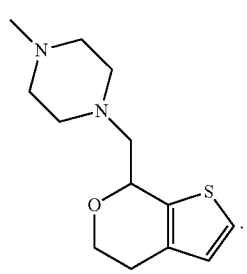.

In one embodiment, $R^1$ and $R^3$ together with the atoms to which they are attached form an optionally substituted heterocyclyl ring (e.g., pyrrolidine, including, e.g., unsubstituted pyrrolidine and N-methyl-pyrrolidine). Specific examples include, but are not limited to, the following compounds:

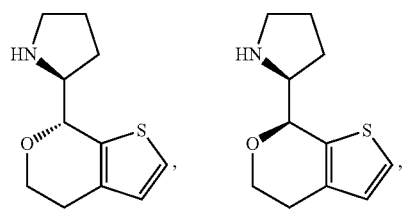

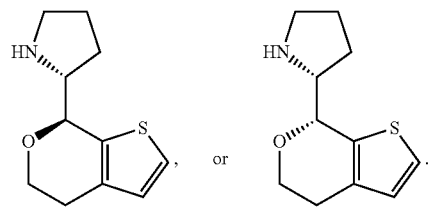 or

In one embodiment, $R^1$ and $R^5$ together with the atoms to which they are attached form an optionally substituted heterocyclyl. Examples include, but are not limited to, pyrrolidinyl and piperidinyl. Specific examples include, but are not limited to, the following compounds:

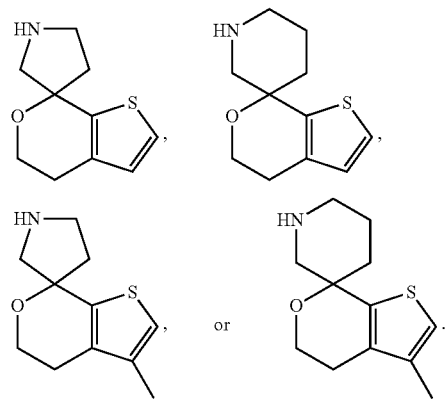

In one embodiment, $R^6$ and $R^7$ together with the atoms to which they are attached form an aryl (e.g., phenyl) or cycloalkyl (e.g., 5-, 6-, or 7-membered) ring, each of which is optionally substituted (e.g., by one or more halo or phenyl). In one embodiment, $R^6$ and $R^7$ together with the atoms to which they are attached form an optionally substituted aryl. Examples include, but are not limited to, phenyl, cyclopentenyl, cyclohexenyl, and cycloheptenyl. Specific examples include, but are not limited to, the following compounds:

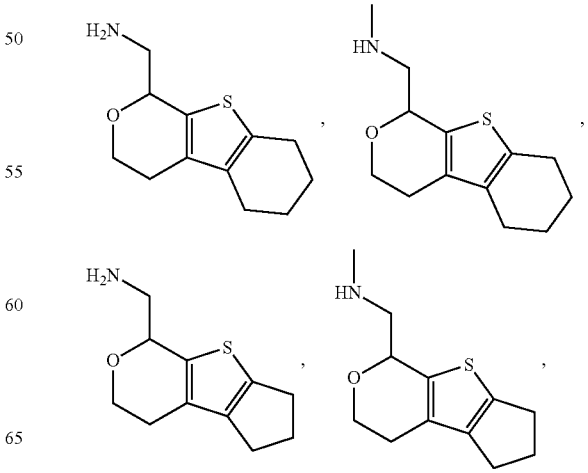

-continued

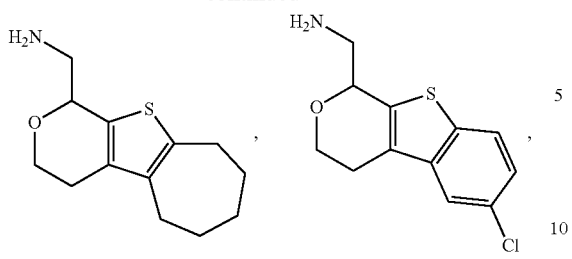

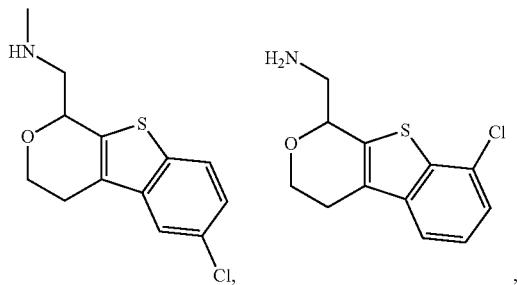

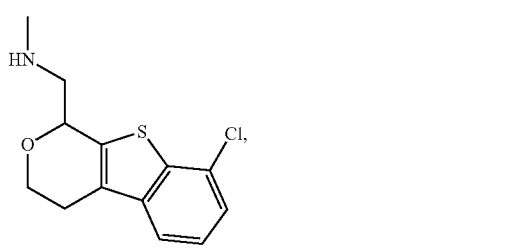

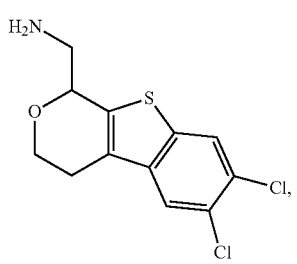

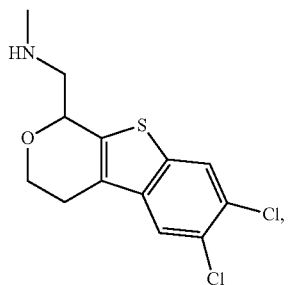

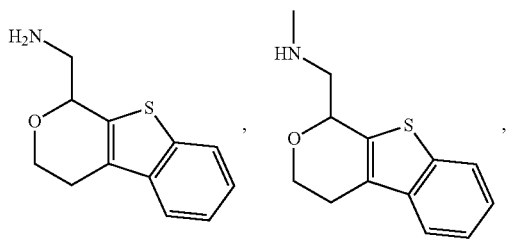

-continued

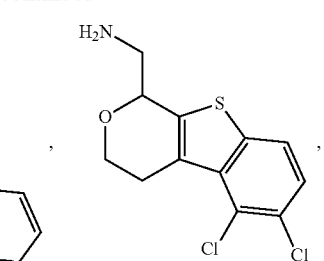

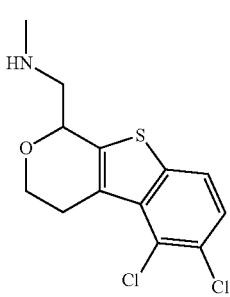

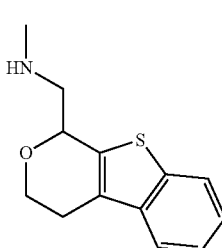, or

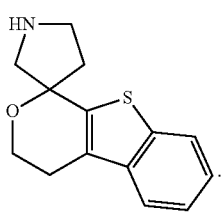 [SMILES: c1ccc2c3c(sc2c1)C1(CCNC1)OCC3]

In one embodiment, $R^1$ and $R^5$ together with the atoms to which they are attached form an optionally substituted heterocyclyl (e.g., pyrrolidinyl) and $R^6$ and $R^7$ together with the atoms to which they are attached form an optionally substituted aryl (e.g., phenyl). Specific examples include, but are not limited to, the following compound:

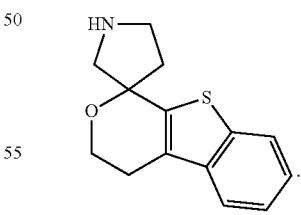

In one embodiment, m is 0 and $R^3$ and are combined together to form a double bond and together with IV and/or $R^2$ and the atoms to which they are attached form an optionally substituted heteroaryl. In one embodiment, the heteroaryl contains one or more heteroatoms selected from N, O, and S. Examples include, but are not limited to, imidazolyl, pyrazolyl, or thiazolyl. Specific examples include, but are not limited to, the following compounds:

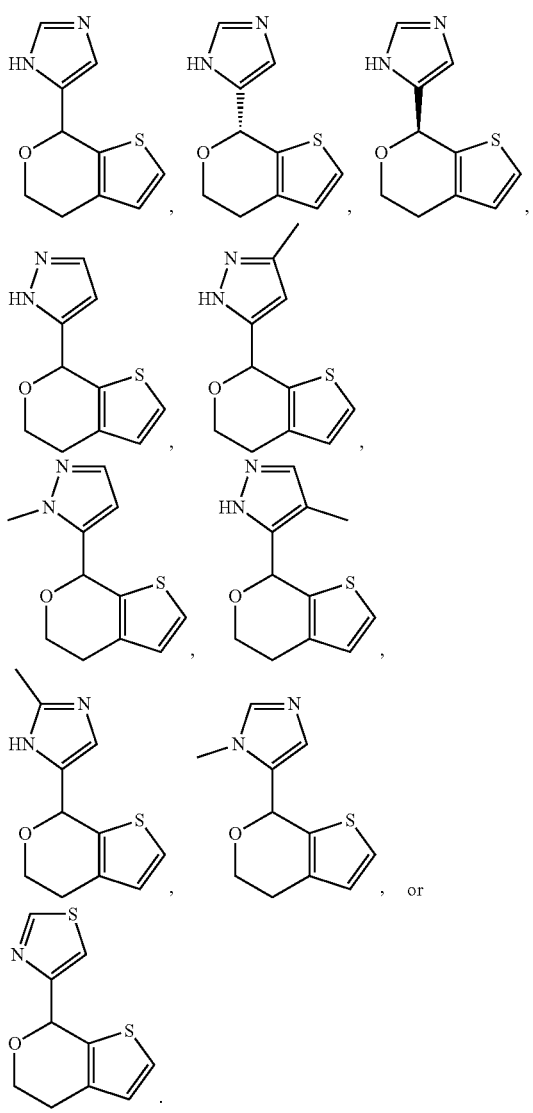

In various embodiments, provided herein are methods for the treatment of one or more of: a symptom domain of schizophrenia, a symptom sub-domain of schizophrenia, a subject sub-population with symptoms prominently in a symptom domain of schizophrenia; and/or a subject sub-population with symptoms prominently in symptom sub-domain of schizophrenia comprising administering to a subject a therapeutically or prophylactically effective amount of a therapeutic agent, the therapeutic agent comprising a compound of formula (IVb):

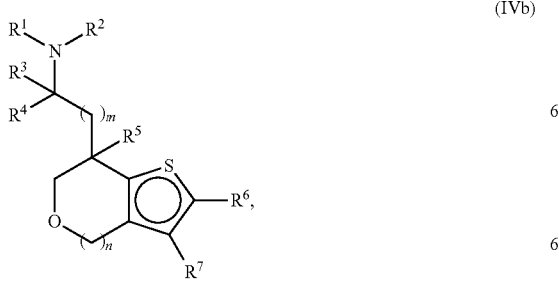
(IVb)

or a pharmaceutically acceptable salt or stereoisomer thereof, wherein IV, $R^2$, $R^3$, $R^4$, $R^5$, $R^6$, $R^7$, m and n are as defined herein elsewhere.

In various embodiments, provided herein are methods for the treatment of one or more of: a symptom domain of schizophrenia, a symptom sub-domain of schizophrenia, a subject sub-population with symptoms prominently in a symptom domain of schizophrenia; and/or a subject sub-population with symptoms prominently in symptom sub-domain of schizophrenia comprising administering to a subject a therapeutically or prophylactically effective amount of a therapeutic agent, the therapeutic agent comprising a compound of formula (IVc):

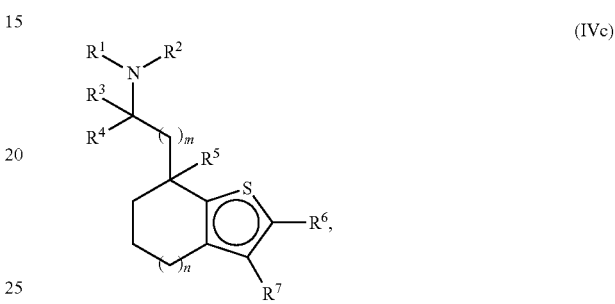
(IVc)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In one embodiment, n is 0. In one embodiment, $R^1$ and $R^2$ are each independently hydrogen or optionally substituted $C_1$-$C_4$ alkyl (e.g., methyl or ethyl). In one embodiment, $R^6$ and $R^7$ are each independently hydrogen, halo (e.g., F or Cl), or optionally substituted $C_1$-$C_4$ alkyl (e.g., methyl or ethyl). Specific examples include, but are not limited to, the following compounds:

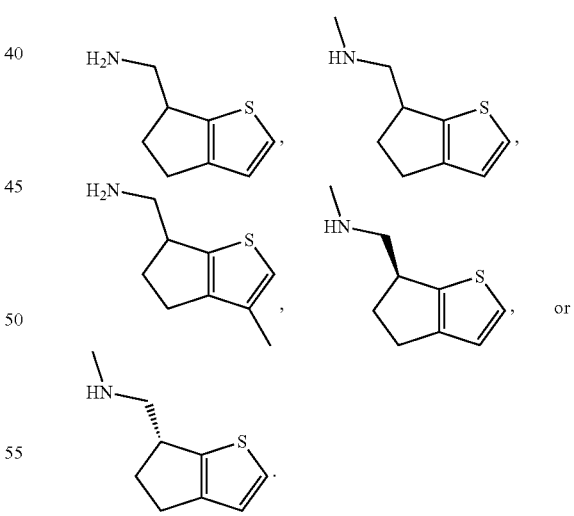

In one embodiment, n is 1. In one embodiment, $R^1$ and $R^2$ are each independently hydrogen or optionally substituted $C_1$-$C_4$ alkyl (e.g., methyl or ethyl). In one embodiment, $R^1$ and $R^2$ together with the atom to which they are attached form an optionally substituted heterocyclyl (e.g., piperidinyl). In one embodiment, $R^6$ and $R^7$ are each independently hydrogen or optionally substituted $C_1$-$C_4$ alkyl (e.g., methyl or ethyl). Specific examples include, but are not limited to, the following compounds:

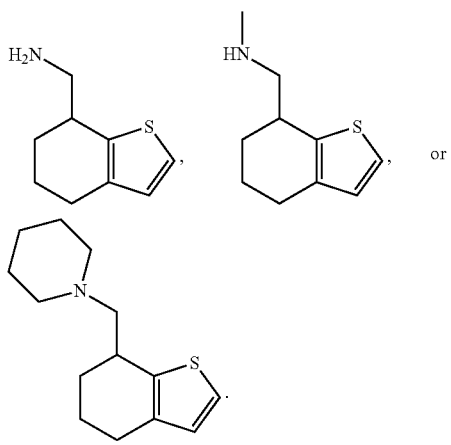

In one embodiment, $R^6$ and $R^7$ together with the atoms to which they are attached form an aryl (e.g., phenyl) or cycloalkyl (e.g., 5-, 6-, or 7-membered) ring, each of which is optionally substituted (e.g., by one or more halo or phenyl). In one embodiment, $R^6$ and $R^7$ together with the atoms to which they are attached form an optionally substituted aryl. Examples include, but are not limited to, phenyl, cyclopentenyl, cyclohexenyl, and cycloheptenyl. Specific examples include, but are not limited to, the following compounds:

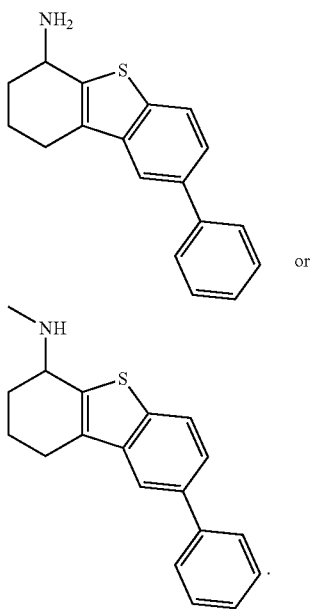

In various embodiments, provided herein are methods for the treatment of one or more of: a symptom domain of schizophrenia, a symptom sub-domain of schizophrenia, a subject sub-population with symptoms prominently in a symptom domain of schizophrenia; and/or a subject sub-population with symptoms prominently in symptom sub-domain of schizophrenia comprising administering to a subject a therapeutically or prophylactically effective amount of a therapeutic agent, the therapeutic agent comprising a compound of formula (V):

(V)

or a pharmaceutically acceptable salt or stereoisomer thereof, wherein $R^1$, $R^2$, $R^3$, $R^4$, $R^5$, $R^6$, $Z^1$, $Z^3$, X, Y, m and n are as defined herein elsewhere. In one embodiment, $Z^1$ is N and $Z^3$ is S. In one embodiment, $Z^1$ is S and $Z^3$ is N. In one embodiment, X and Y is $CH_2$. In one embodiment, m is 0 and n is 1. In one embodiment, $R^1$ and $R^2$ are each independently hydrogen or optionally substituted $C_1$-$C_4$ alkyl (e.g., methyl or ethyl). In one embodiment, $R^3$, $R^4$, and $R^5$ are hydrogen. In one embodiment, $R^6$ is hydrogen, halo (e.g., F or Cl), optionally substituted $C_1$-$C_4$ alkyl (e.g., methyl or ethyl), or optionally substituted amino (e.g., aminoalkyl, such as methylamino). Specific examples include, but are not limited to, the following compounds:

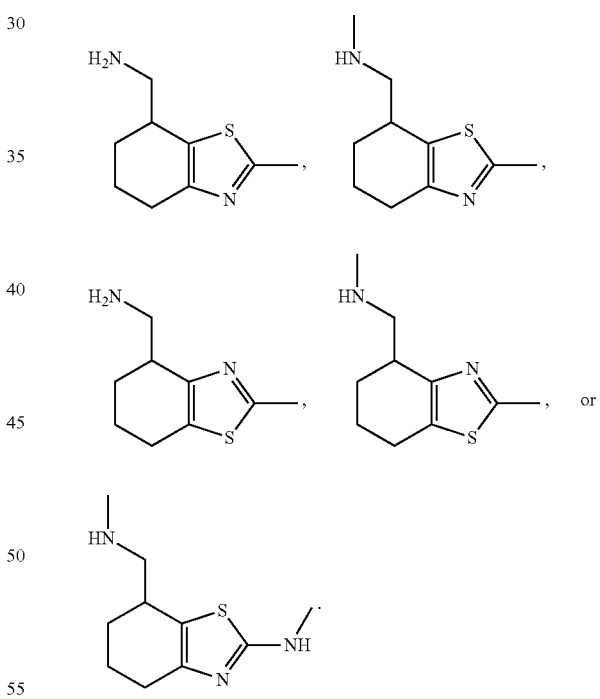

In various embodiments, provided herein are methods for the treatment of one or more of: a symptom domain of schizophrenia, a symptom sub-domain of schizophrenia, a subject sub-population with symptoms prominently in a symptom domain of schizophrenia; and/or a subject sub-population with symptoms prominently in symptom sub-domain of schizophrenia comprising administering to a subject a therapeutically or prophylactically effective amount of a therapeutic agent, the therapeutic agent comprising a compound of formula (VI):

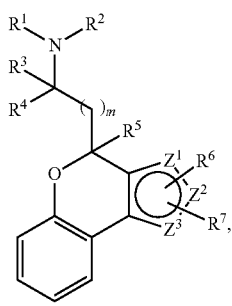

(VI)

or a pharmaceutically acceptable salt or stereoisomer thereof, wherein two of $Z^1$, $Z^2$, and $Z^3$ are C, and one of $Z^1$, $Z^2$, and $Z^3$ is S;

$R^1$ and $R^2$ are each independently (i) hydrogen, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^8$, wherein $R^8$ is $SO_2$alkyl or $SO_2$aryl, each of which is optionally substituted; or (iii) $R^1$ and $R^2$ together with the nitrogen atom to which they are attached form an optionally substituted heterocyclyl or heteroaryl;

$R^3$ and are each independently (i) hydrogen, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^9$, wherein $R^9$ is $CF_3$, CN, nitro, amino, hydroxyl, or cycloalkoxyl, each of which is optionally substituted; or (iii) $R^3$ and $R^4$ together with the carbon atom to which they are attached form an optionally substituted cycloalkyl or heterocyclyl; or (iv) $R^3$ and $R^1$ together with the atoms to which they are attached form an optionally substituted heterocyclyl, and $R^4$ is (i) or (ii); or (v) $R^3$ and $R^4$ are combined together to form a double bond and together with R' and/or $R^2$ and the atoms to which they are attached form an optionally substituted heteroaryl;

$R^5$ is (i) hydrogen, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^{10}$, wherein $R^{10}$ is $CF_3$, CN, nitro, amino, hydroxyl, or cycloalkoxyl, each of which is optionally substituted; or (iii) $R^5$ and $R^1$ together with the atoms to which they are attached form an optionally substituted heterocyclyl;

$R^6$ and $R^7$ are each independently (i) hydrogen, halo, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^{11}$, wherein $R^{11}$ is $CF_3$, CN, nitro, amino, hydroxyl, cycloalkoxyl, heteroaryl, or heterocyclyl, each of which is optionally substituted; or (iii) $R^6$ and $R^7$ together with the atoms to which they are attached form an optionally substituted aryl, heteroaryl, cycloalkyl or heterocyclyl ring; and m is 0, 1, or 2;

each occurrence of p is independently 0, 1, or 2.

In one embodiment, $R^1$, $R^2$, $R^3$, $R^4$, $R^5$, $R^6$, $R^7$, $Z^1$, $Z^2$, $Z^3$, and m are as defined herein elsewhere. In one embodiment, $Z^1$ and $Z^2$ are C, and $Z^3$ is S. In one embodiment, $Z^1$ is S, and $Z^2$ and $Z^3$ are C. In one embodiment, m is 0. In one embodiment, $R^1$ and $R^2$ are each independently hydrogen or optionally substituted $C_1$-$C_4$ alkyl (e.g., methyl or ethyl). In one embodiment, $R^3$ and $R^4$ are hydrogen. In one embodiment, $R^5$ is hydrogen. In one embodiment, $R^1$ and $R^5$ together with the atoms to which they are attached form an optionally substituted heterocyclyl (e.g., pyrrolidinyl). In one embodiment, $R^6$ and $R^7$ are each independently hydrogen, halo (e.g., F or Cl), or optionally substituted $C_1$-$C_4$ alkyl (e.g., methyl or ethyl). Specific examples include, but are not limited to, the following compounds:

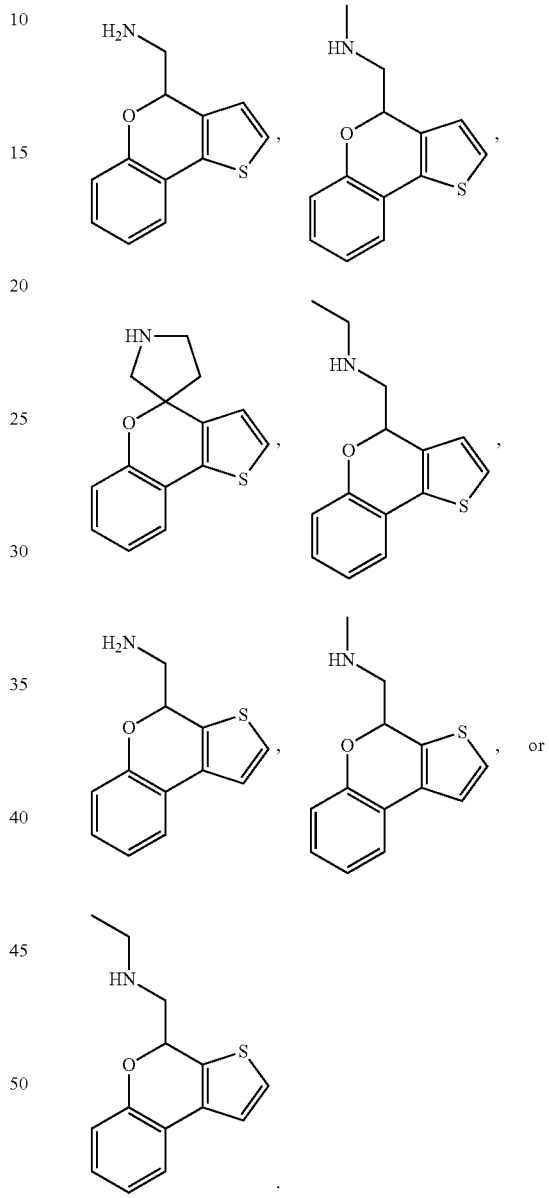

In various embodiments, provided herein are methods for the treatment of one or more of: a symptom domain of schizophrenia, a symptom sub-domain of schizophrenia, a subject sub-population with symptoms prominently in a symptom domain of schizophrenia; and/or a subject sub-population with symptoms prominently in symptom sub-domain of schizophrenia comprising administering to a subject a therapeutically or prophylactically effective amount of a therapeutic agent, the therapeutic agent comprising one or more of the following compounds:

| Compd. No. | Structure | Salt or FB* | Analytical Data |
|---|---|---|---|
| 1 | 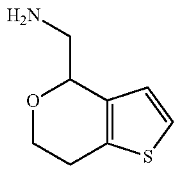 [SMILES: NCC1OCCc2sccc21] | HCl | $^1$H NMR (CD$_3$OD): 7.29 (d, J = 5.0 Hz, 1H), 6.89 (d, J = 5.0 Hz, 1H), 4.94 (d, J = 8.0 Hz, 1H), 4.29-4.23 (m, 1H), 3.85-3.78 (m, 1H), 3.46 (d, J = 13.0 Hz, 1H), 3.14 (dd, J = 9.5, 11.5 Hz, 1H), 3.05-2.97 (m, 1H), 2.80 (d, J = 16.0 Hz, 1H). |
| 2 | 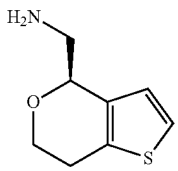 [SMILES: NC[C@@H]1OCCc2sccc21] | HCl | $^1$H NMR (CD$_3$OD): 7.29 (d, J = 5.0 Hz, 1H), 6.89 (d, J = 5.0 Hz, 1H), 4.94 (d, J = 8.0 Hz, 1H), 4.29-4.23 (m, 1H), 3.85-3.78 (m, 1H), 3.46 (d, J = 13.0 Hz, 1H), 3.14 (dd, J = 9.5, 11.5 Hz, 1H), 3.05-2.97 (m, 1H), 2.80 (d, J = 16.0 Hz, 1H). |
| 3 | 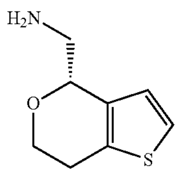 | HCl | $^1$H NMR (CD$_3$OD): 7.29 (d, J = 5.0 Hz, 1H), 6.89 (d, J = 5.0 Hz, 1H), 4.94 (d, J = 8.0 Hz, 1H), 4.29-4.23 (m, 1H), 3.85-3.78 (m, 1H), 3.46 (d, J = 13.0 Hz, 1H), 3.14 (dd, J = 9.5, 11.5 Hz, 1H), 3.05-2.97 (m, 1H), 2.80 (d, J = 16.0 Hz, 1H). |
| 4 | 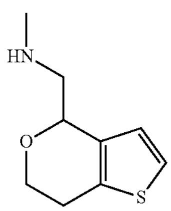 | HCl | LC-MS (6 min method): 0.24 minute, M$^+$ 184 @ 0.26 min.; $^1$H NMR (CD$_3$OD): 7.30 (d, J = 5.50 Hz, 1H), 6.90 (d, J = 5.50 Hz, 1H), 5.00 (dd, J = 2.57, 8.80 Hz, 1H), 4.30-4.26 (m, 1H), 3.89-3.80 (m, 1H), 3.57-3.53 (m, 1H), 3.28-3.21 (m, 1H), 3.05-3.01 (m, 1H), 2.84-2.79 (m, 1H), 2.74 (s, 3H). |
| 5 | 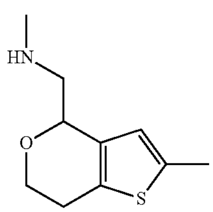 | HCl | $^1$H NMR (CD$_3$OD): δ 6.54 (s, 1H), 4.91-4.85 (m, 1H), 4.26-4.21 (m, 1H), 3.80 (td, J = 3.5, 10.0 Hz, 1H), 3.47 (dd, J = 3.0, 13.0 Hz, 1H), 3.20 (dd, J = 8.5, 13.0 Hz, 1H), 2.93-2.88 (m, 1H), 2.72 (s, 3H), 2.71-2.66 (m, 1H), 2.42 (s, 3H). |
| 6 | 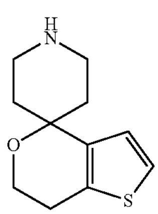 [SMILES: c1cc2c(s1)CCOC21CCNCC1] | HCl | $^1$H NMR (CD$_3$OD): δ 7.22 (d, J = 5.10 Hz, 1H), 6.87 (d, J = 5.10 Hz, 1H), 3.97 (t, J = 5.50 Hz, 2H), 3.40-3.25 (m, 4H), 2.84 (t, J = 5.5 Hz, 2H), 2.22-2.14 (m, 2H), 2.06-2.02 (m, 2H). |
| 7 | 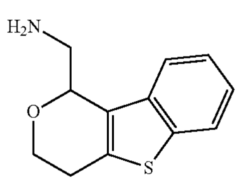 [SMILES: NCC1OCCc2sc3ccccc3c21] | HCl | LC-MS (3.0 min method): 0.98 minute, M$^+$ 220; $^1$H-NMR (400 MHz, CD$_3$OD) δ 7.86 (d, J = 7.6 Hz, 1H), 7.68 (d, J = 8.0 Hz, 1H), 7.40 (td, J = 7.2, 0.8 Hz, 1H), 7.34 (t, J = 7.2 Hz, 1H), 5.27 (dd, J = 8.4, 2.0 Hz, 1H), 4.25 (m, 1H), 3.94 (m, 1H), 3.62 (dd, J = 13.2, 2.0 Hz, 1H), 3.35 (m, 1H), 3.00 (m, 2H). |
| 8 | 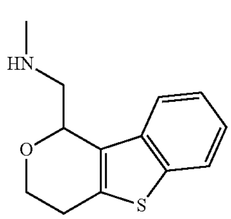 [SMILES: CNCC1OCCc2sc3ccccc3c21] | HCl | LC-MS (3.0 min method): 1.00 minute, M$^+$ 234; $^1$H-NMR (400 MHz, CD$_3$OD) δ 7.85 (d, J = 8.0 Hz, 1H), 7.20 (d, J = 8.0 Hz, 1H), 7.40 (t, J = 7.6 Hz, 1H), 7.33 (t, J = 7.6 Hz, 1H), 5.34 (d, J = 8.8 Hz, 1H), 4.26 (m, 1H), 3.94 (m, 1H), 3.68 (dd, J = 13.2, 2.0 Hz, 1H), 3.42 (m, 1H), 2.98 (m, 2H), 2.77 (s, 3H). |

| Compd. No. | Structure | Salt or FB* | Analytical Data |
|---|---|---|---|
| 9 | (structure) | HCl | $^1$H NMR (DMSO-d$^6$): δ 8.22 (br s, 3H), 6.70 (s, 1H), 4.85-4.83 (d, J = 8.01 Hz, 1H), 4.13-4.07 (m, 1H), 3.78-3.70 (m, 1H), 3.29 (s, 1H), 2.91-2.67 (m, 5H), 1.22-1.18 (t, J = 7.50 Hz, 3H). |
| 10 | (structure) | HCl | $^1$H NMR (DMSO-d$^6$): δ 9.07 (br s, 1H), 8.67 (br s, 1H), 6.60 (s, 1H), 4.94-4.92 (d, J = 8.0 Hz, 1H), 4.15-4.08 (m, 1H), 3.80-3.72 (m, 1H), 3.46-3.42 (d, J = 12.3 Hz, 1H), 3.13-3.09 (m, 1H), 2.87-2.68 (m, 4H), 2.57 (s, 3H), 1.24-1.19 (t, J = 7.5 Hz, 3H). |
| 11 | (structure) | HCl | $^1$H NMR (DMSO-d$^6$ + D$_2$O): δ 7.02 (s, 1H), 4.81-4.78 (dd, J$_1$ = 2.1 Hz, J$_2$ = 6.5 Hz, 1H), 4.15-4.08 (m, 1H), 3.80-3.72 (m, 1H), 3.35-3.29 (dd, J$_1$ = 2.9 Hz, J$_2$ = 13.3 Hz, 1H), 3.02-2.95 (m, 1H), 2.81-2.72 (m, 2H). |
| 12 | (structure) | HCl | $^1$H NMR (DMSO-d$^6$): δ 9.26 (br s, 1H), 8.80 (br s, 1H), 7.04 (s, 1H), 4.98-4.94 (dd, J$_1$ = 1.8 Hz, J$_2$ = 9.2 Hz, 1H), 4.16-4.09 (m, 1H), 3.82-3.74 (m, 1H), 3.47-3.36 (d, J = 29.1 Hz, 1H), 3.13 (m, 1H), 2.87-2.69 (m, 2H), 2.56 (s, 3H). |
| 13 | (structure) | HCl | GC-MS m/z 139 (M$^+$); $^1$H NMR (DMSO-d$^6$): δ 9.02 (s, 1H), 8.65 (s, 1H), 7.41-7.40 (d, J = 5.19 Hz 1H), 6.99-6.97 (d, J = 5.19 Hz 1H), 5.03-5.00 (d, J = 8.13 Hz, 1H), 4.21-4.12 (m, 1H), 3.83-3.75 (m, 1H), 3.52-3.48 (d, J = 12.43 Hz, 1H), 3.13-2.72 (m, 5H), 1.25-1.20 (t, J = 7.26 Hz, 3H). |
| 14 | (structure) | FB | GC-MS m/z 211 (M$^+$); $^1$H NMR (CDCl$_3$): δ 7.12-7.11 (d, J = 5.13 Hz, 1H), 6.79-6.78 (d, J = 5.13 Hz, 1H), 4.85-4.82 (dd, J$_1$ = 2.04 Hz, J$_2$ = 8.82 Hz, 1H), 4.26-4.20 (m, 1H), 3.84-3.75 (m, 1H), 3.06-2.95 (m, 2H), 2.90-2.83 (m, 1H), 2.79-2.72 (m, 1H), 2.69-2.58 (m, 2H), 1.61-1.50 (m, 2H), 0.97-0.92 (t, J = 14.80 Hz, 3H). |
| 15 | (structure) | FB | $^1$H NMR (CDCl$_3$): δ 7.12-7.10 (d, J = 5.16 Hz, 1H), 6.79-6.78 (d, J = 5.16 Hz, 1H), 4.82-4.79 (dd, J$_1$ = 2.34 Hz, J$_2$ = 9.18 Hz, 1H), 4.25-4.19 (m, 1H), 3.83-3.75 (m, 1H), 3.08-2.99 (m, 2H), 2.87-2.73 (m, 3H), 1.11 (s, 3H), 1.09 (s, 3H). |

| Compd. No. | Structure | Salt or FB* | Analytical Data |
|---|---|---|---|
| 16 | 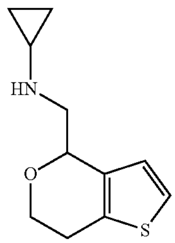 [SMILES: c1cc2c(s1)CCOC2CNC1CC1] | HCl | GC-MS m/z 209 (M⁺); ¹H NMR (DMSO-d⁶): δ 9.35 (br s, 1H), 9.03 (br s, 9.03, 1H), 7.41-7.40 (d, J = 5.20 Hz, 1H), 7.04-7.02 (d, J = 5.20 Hz, 1H), 5.08-5.05 (d, J = 8.49 Hz, 1H), 4.18-4.12 (m, 1H), 3.82-3.74 (m, 1H), 3.62-3.58 (d, J = 12.82 Hz, 1H), 3.22-3.14 (t, J = 11.65 Hz, 1H), 2.96-2.72 (m, 3H), 0.99-0.82 (m, 2H), 0.79-0.72 (m, 2H). |
| 17 | 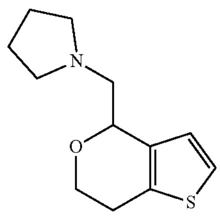 [SMILES: c1cc2c(s1)CCOC2CN1CCCC1] | FB | GC-MS m/z 223 (M⁺); ¹H NMR (CDCl₃): δ 7.10-7.08 (d, J = 4.95 Hz, 1H), 6.86-6.84 (d, J = 4.95 Hz, 1H), 4.87-4.82 (m, 1H), 4.28-4.22 (m, 1H), 3.82-3.74 (m, 1H), 3.04-2.94 (m, 1H), 2.85-2.70 (m, 3H), 2.67-2.56 (m, 4H), 1.89-1.76 (m, 4H). |
| 18 | 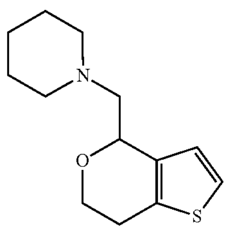 [SMILES: c1cc2c(s1)CCOC2CN1CCCCC1] | FB | ¹H NMR (CDCl₃): δ 7.10-7.09 (d, J = 5.1 Hz, 1H), 6.91-6.89 (d, J = 5.1 Hz, 1H), 4.90-4.84 (m, 1H), 4.27-4.21 (m, 1H), 3.81-3.73 (m, 1H), 3.04-2.94 (m, 1H), 2.78-2.70 (m, 1H), 2.67-2.62 (m, 2H), 2.55-2.52 (m, 4H), 1.69-1.59 (m, 4H), 1.50-1.43 (m, 2H). |
| 19 | 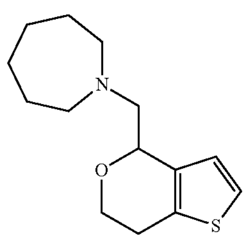 [SMILES: c1cc2c(s1)CCOC2CN1CCCCCC1] | FB | GC-MS m/z 251 (M⁺); ¹H NMR (DMSO-d⁶): δ 7.28-7.27 (d, J = 5.16 Hz, 1H), 7.03-7.02 (d, J = 5.16 Hz, 1H), 4.68-4.64 (t, J = 5.82 Hz, 1H), 4.11-4.04 (m, 1H), 3.70-3.61 (m, 1H), 2.83-2.64 (m, 8H), 1.55 (s, 8H). |
| 20 | 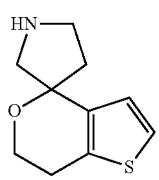 [SMILES: c1cc2c(s1)CCOC21CCNC1] | HCl | ¹H NMR (CD₃OD): δ 7.26 (d, J = 5.1, Hz, 1H), 6.96 (d, J = 5.1 Hz, 1H), 4.01-3.97 (m, 2H), 3.59-3.53 (m, 3H), 3.38 (d, J = 6.8 Hz, 1H), 2.89 (brs, 2H), 2.38-2.36 (m, 2H). |
| 21 | 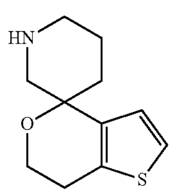 [SMILES: c1cc2c(s1)CCOC21CCCNC1] | HCl | ¹H NMR (CD₃OD): δ 7.26 (d, J = 5.0 Hz, 1H), 6.94 (d, J = 5.0 Hz, 1H), 4.00 (t, J = 5.1 Hz, 2H), 3.33-3.21 (m, 3H), 3.08 (apt, J = 2.8 Hz, 1H), 2.87 (t, J = 5.1 Hz, 2H), 2.18-2.11 (m, 1H), 2.04-1.97 (m, 2H), 1.84-1.80 (m, 1H). |
| 22 | 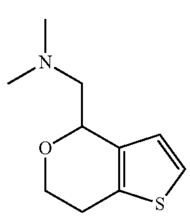 | formate | ¹H NMR (CD₃OD): δ 7.29 (d, J = 5.0 Hz, 1H), 6.88 (d, J = 5.0 Hz, 1H), 5.14 (apd, J = 6.0 Hz, 1H), 4.27 (m, 1H), 3.85 (dr, J = 11.0, 3.0 Hz, 1H), 3.67 (m, 1H), 3.38-3.25 (m, 1H), 3.04-2.77 (m, 2H), 3.00 (s, 3H), 2.92 (s, 3H). |

| Compd. No. | Structure | Salt or FB* | Analytical Data |
|---|---|---|---|
| 23 | H2N, propyl-substituted pyrano-thiophene | HCl | ¹H NMR (DMSO-d⁶): δ 8.18 (br s, 3H), 6.69 (s, 1H), 4.84-4.82 (d, J = 7.5 Hz, 1H), 4.14-4.07 (m, 1H), 3.78-3.70 (m, 1H), 3.29 (s, 1H), 2.95-2.66 (m, 5H), 1.65-1.53 (m, 2H), 1.04-0.92 (t, J = 7.32 Hz, 3H). |
| 24 | HN(Me), propyl-substituted pyrano-thiophene | HCl | ¹H NMR (DMSO-d⁶): δ 9.11 (br s, 1H), 9.69 (br, s, 1H), 6.65 (s, 1H), 4.95-4.92 (d, J = 7.9 Hz, 1H), 4.15-4.08 (m, 1H), 3.80-3.72 (m, 1H), 3.4 (m, 1H), 3.1 (m, 1H), 2.87-2.78 (m, 1H), 2.73-2.67 (m, 3H), 2.57 (s, 3H), 1.66-1.53 (m, 2H), 0.94-0.89 (m, 3H). |
| 25 | H2N, phenyl-substituted pyrano-thiophene | HCl | ¹H NMR (DMSO-d⁶ + D₂O): δ 7.59-7.57 (d, J = 7.5 Hz, 2H), 7.43-7.38 (t, 3H), 7.32-7.27 (t, 1H), 4.90-4.87 (d, J = 7.1 Hz, 1H), 4.19-4.15 (m, 1H), 3.82-3.79 (m, 1H), 3.45-3.40 (dd, J₁ = 2.8 Hz, J₂ = 13.3 Hz, 1H), 3.09-3.02 (m, 1H), 2.92-2.82 (m, 2H). |
| 26 | HN(Me), phenyl-substituted pyrano-thiophene | HCl | ¹H NMR (DMSO-d⁶): δ 9.01 (br s, 1H), 8.69 (br, s, 1H), 7.60-7.58 (d, J = 7.2 Hz, 2H), 7.45-7.38 (m, 3H), 7.33-7.28 (t, J = 7.20 Hz, 1H), 5.03-5.00 (d, J = 7.7 Hz, 1H), 4.22-4.09 (m, 1H), 3.86-3.78 (m, 1H), 3.59-3.52 (m, 1H), 3.29-3.17 (m, 1H), 2.93-2.79 (m, 2H), 2.53-2.48 (t, J = 5.31 Hz, 3H). |
| 27 | HN(Me), pyrano-thiophene | HCl | LC-MS (6 minute method on lab 209 instrument): 0.24 minute, M⁺ 184 @ 0.26 min.; ¹H NMR (CD₃OD): δ 7.30 (d, J = 5.50 Hz, 1H), 6.90 (d, J = 5.50 Hz, 1H), 5.00 (dd, J = 2.57, 8.80 Hz, 1H), 4.30-4.26 (m, 1H), 3.89-3.80 (m, 1H), 3.57-3.53 (m, 1H), 3.28-3.21 (m, 1H), 3.05-3.01 (m, 1H), 2.84-2.79 (m, 1H), 2.74 (s, 3H). |
| 28 | HN(Me), pyrano-thiophene (stereoisomer) | HCl | LC-MS (6 min method): 0.24 minute, M⁺ 184 @ 0.26 min.; ¹H NMR (CD₃OD): δ 7.30 (d, J = 5.50 Hz, 1H), 6.90 (d, J = 5.50 Hz, 1H), 5.00 (dd, J = 2.57, 8.80 Hz, 1H), 4.30-4.26 (m, 1H), 3.89-3.80 (m, 1H), 3.57-3.53 (m, 1H), 3.28-3.21 (m, 1H), 3.05-3.01 (m, 1H), 2.84-2.79 (m, 1H), 2.74 (s, 3H). |
| 29 | H2N, methyl-substituted pyrano-thiophene | HCl | ¹H NMR (DMSO-d⁶): δ 8.14 (br s, 3H), 7.00 (s, 1H), 4.97-4.90 (m, 1H), 4.02-3.94 (m, 1H), 3.85-3.78 (m, 1H), 3.11-3.08 (t, J = 10.66 Hz, 2H), 2.88-2.73 (m, 2H), 2.13-2.12 (d, J = 0.8 Hz, 3H). |
| 30 | H2N, ethyl-substituted pyrano-thiophene | HCl | ¹H NMR (DMSO-d⁶): δ 8.06 (br s, 3H), 7.02 (s, 1H), 4.97-4.93 (dd, J₁ = 3.5 Hz, J₂ = 9.1 Hz, 1H), 4.03-3.95 (m, 1H), 3.86-3.79 (m, 1H), 3.09 (br s, 2H), 2.84-2.73 (m, 2H), 2.47-2.37 (m, 2H), 1.21-1.17 (t, J = 7.41 Hz, 3H). |

-continued

| Compd. No. | Structure | Salt or FB* | Analytical Data |
|---|---|---|---|
| 31 | 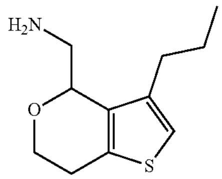 | HCl | $^1$H NMR (DMSO-d$^6$): δ 7.96 (br s, 3H), 7.02 (s, 1H), 4.92-4.90 (d, J = 6.75 Hz, 1H), 4.03-3.95 (m, 1H), 3.86-3.79 (m, 1H), 3.09-3.08 (d, J = 3.96 Hz, 2H), 2.89-2.78 (m, 2H), 2.43-2.38 (t, J = 6.84 Hz, 2H), 1.70-1.54 (m, 2H), 0.97-0.92 (t, J = 7.31 Hz, 3H). |
| 32 | 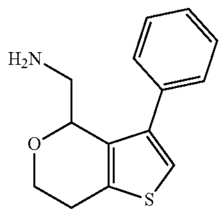 [SMILES: NCC1OCCc2scc(-c3ccccc3)c21] | HCl | $^1$H NMR (DMSO-d$^6$ + D$_2$O): δ 7.46-7.35 (m, 5H), 7.30 (s, 1H), 5.27-5.24 (d, J = 8.49 Hz, 1H), 4.05-3.98 (m, 1H), 3.88-3.82 (m, 1H), 2.88 (s, 2H), 2.71-2.64 (m, 1H), 2.47-2.46 (d, J = 2.85 Hz, 1H). |
| 33 | 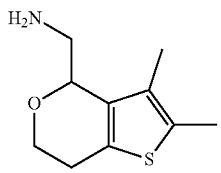 | HCl | GC-MS m/z 197 (M$^+$); $^1$H NMR (D$_2$O): δ 4.95-4.91 (t, J = 5.1 Hz, 1H), 4.04-3.97 (m, 1H), 3.85-3.78 (m, 1H), 3.30-3.28 (d, J = 5.01 Hz, 2H), 2.76-2.72 (t, J = 5.33 Hz, 2H), 2.21 (s, 3H), 1.92 (s, 3H). |
| 34 | 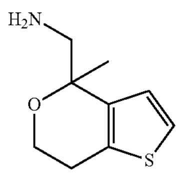 | HCl | LC-MS (6 min method): 0.48 minute, M$^+$ 184 @ 0.48 min.; $^1$H NMR (CD$_3$OD): δ 7.28 (d, J = 5.0 Hz, 1H), 6.90 (d, J = 5.0 Hz, 1H), 4.11-4.07 (m, 1H), 3.97-3.91 (m, 1H), 3.33-3.00 (m, 1H), 3.16 (d, J = 13.0 Hz, 1H), 3.02-2.94 (m, 1H), 2.76 (d, J = 6.1 Hz, 1H), 1.50 (s, 3H). |
| 35 | 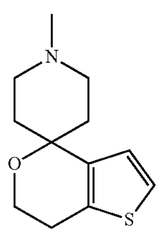 | HCl | $^1$H NMR (CD$_3$OD): δ 7.23 (d, J = 5.0 Hz, 1H), 6.84 (d, J = 5.0 Hz, 1H), 3.97 (t, J = 5.0 Hz, 2H), 3.39 (brs, 4H), 2.92 (s, 3H), 2.84 (t, J = 5.0 Hz, 2H), 2.17-1.18 (m, 4H). |
| 36 | 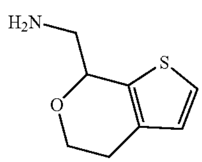 [SMILES: NCC1OCCc2ccsc21] | HCl | $^1$H NMR (CD$_3$OD): δ 7.36 (d, J = 4.4 Hz, 1H), 6.91 (d, J = 4.77 Hz, 1H), 5.08 (d, J = 7.7 Hz, 1H), 4.27-4.23 (m, 1H), 3.84-3.78 (m, 1H), 3.42-3.38 (m, 1H), 3.17-3.12 (m, 1H), 2.91-2.83 (m, 1H), 2.70-2.65 (m, 1H). |
| 37 | 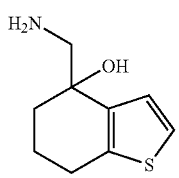 [SMILES: NCC1(O)CCCc2sccc21] | formate | $^1$H NMR (CD$_3$OD): δ 7.20 (d, J = 5.1 Hz, 1H), 7.08 (d, J = 5.1 Hz, 1H), 3.25 (d, J = 13.0 Hz, 1H), 3.07 (d, J = 13.0 Hz, 1H), 2.83-2.79 (m, 2H), 2.04-1.88 (m, 4H). |
| 38 | 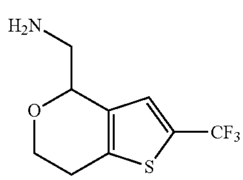 [SMILES: NCC1OCCc2sc(C(F)(F)F)cc21] | HCl | $^1$H NMR (CD$_3$OD): δ 7.44 (s, 1H), 4.96-4.92 (m, 1H), 4.32-4.28 (m, 1H), 3.86 (dt, J = 13.0, 3.5 Hz, 1H), 3.51 (d, J = 13.0 Hz, 1H), 3.20-3.15 (m, 1H), 3.10-3.04 (m, 1H), 2.90-2.86 (m, 1H). |

-continued

| Compd. No. | Structure | Salt or FB* | Analytical Data |
|---|---|---|---|
| 39 | 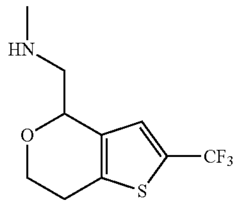 [SMILES: CNCC1OCCc2sc(C(F)(F)F)cc21] | HCl | ¹H NMR (CD₃OD): δ 7.42 (s, 1H), 5.00-4.98 (m, 1H), 4.32-4.28 (m, 1H), 3.84 (t, J = 13.0, 1H), 3.57 (d, J = 13.0 Hz, 1H), 3.30-3.20 (m, 1H), 3.09-3.02 (m, 1H), 2.91-2.86 (m, 1H), 2.74 (s, 3H). |
| 40 | 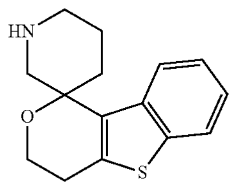 [SMILES: c1ccc2c3c(sc2c1)CCOC31CCCNC1] | HCl | ¹H NMR (CD₃OD): δ 7.91 (d, J = 8.0 Hz, 1H), 7.85 (d, J = 8.0 Hz, 1H), 7.41 (dt, J = 1.0, 7.5 Hz, 1H), 7.33 (dt, J = 1.0 , 7.5 Hz, 1H), 4.08 (dt, J = 1.5, 5.5 Hz, 2H), 3.74 (d, J = 13.0 Hz, 1H), 3.42-3.30 (m, 3H), 3.00 (dt, J = 1.5, 5.5 Hz, 2H), 2.52-2.44 (m, 1H), 2.27 (tq, J = 4.0, 14.0 Hz, 1H), 2.08 (dd, J = 2.0, 14.0 Hz, 1H), 1.89 (d, J = 14.0 Hz, 1H). |
| 41 | 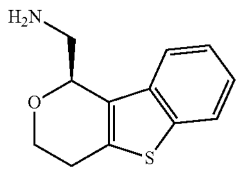 [SMILES: NC[C@@H]1OCCc2sc3ccccc3c21] | HCl | ¹H NMR (CD₃OD): δ 7.86 (d, J = 7.5 Hz, 1H), 7.67 (d, J = 7.5 Hz, 1H), 7.40 (dt, J = 1.0, 7.5 Hz, 1H), 7.34 (dt, J = 1.0, 7.5 Hz, 1H), 5.29-5.25 (m, 1H), 4.28-4.22 (m, 1H), 3.96-3.90 (m, 1H), 3.61 (dd, J = 1.5, 13.5 Hz, 1H), 3.37-3.30 (m, 1H), 3.09-2.91 (m, 2H). |
| 42 | 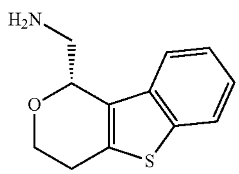 [SMILES: NC[C@H]1OCCc2sc3ccccc3c21] | HCl | ¹H NMR (CD₃OD): δ 7.86 (d, J = 7.5 Hz, 1H), 7.67 (d, J = 7.5 Hz, 1H), 7.40 (dt, J = 1.0, 7.5 Hz, 1H), 7.34 (dt, J = 1.0, 7.5 Hz, 1H), 5.29-5.25 (m, 1H), 4.28-4.22 (m, 1H), 3.96-3.90 (m, 1H), 3.61 (dd, J = 1.5, 13.5 Hz, 1H), 3.37-3.30 (m, 1H), 3.09-2.91 (m, 2H). |
| 43 | 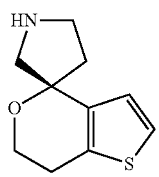 [SMILES: c1cc2c(s1)CCO[C@]21CCNC1] | HCl | ¹H NMR (CD₃OD): δ 7.26 (d, J = 5.1 Hz, 1H), 6.96 (d, J = 5.1 Hz, 1H), 4.01-3.97 (m, 2H), 3.59-3.53 (m, 3H), 3.38 (d, J = = 6.8 Hz, 1H), 2.89 (brs, 2H), 2.38-2.36 (m, 2H). |
| 44 | 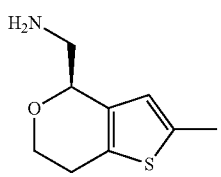 | HCl | ¹H NMR (CD₃OD): δ 6.53 (s, 1H), 4.86 (s, 1H), 4.25-4.20 (m, 1H), 3.82-3.76 (m, 1H), 3.39 (dd, J = 2.93, 13.2 Hz, 1H), 3.08 (dd, J = 8.06, 13.2 Hz, 1H), 2.96-2.88 (m, 1H), 2.70-2.66 (m, 1H), 2.42 (s, 3H). |
| 45 | 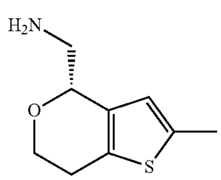 | HCl | ¹H NMR (CD₃OD): δ 6.53 (s, 1H), 4.86 (s, 1H), 4.25-4.20 (m, 1H), 3.82-3.76 (m, 1H), 3.39 (dd, J = 2.93, 13.2 Hz, 1H), 3.08 (dd, J = 8.06, 13.2 Hz, 1H), 2.96-2.88 (m, 1H), 2.70-2.66 (m, 1H), 2.42 (s, 3H). |
| 46 | 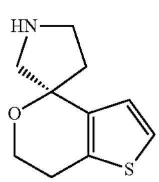 [SMILES: c1cc2c(s1)CCO[C@@]21CCNC1] | HCl | ¹H NMR (CD₃OD): δ 7.26 (d, J = 5.1, Hz, 1H), 6.96 (d, J = 5.1 Hz, 1H), 4.01-3.97 (m, 2H), 3.59-3.53 (m, 3H), 3.38 (d, J = = 6.8 Hz, 1H), 2.89 (brs, 2H), 2.38-2.36 (m, 2H). |

| Compd. No. | Structure | Salt or FB* | Analytical Data |
|---|---|---|---|
| 47 | 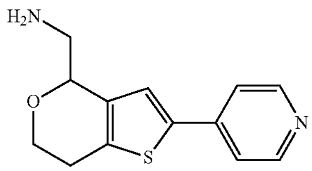 [SMILES: NCC1OCCc2sc(-c3ccncc3)cc21] | HCl | LC-MS m/z 247.2 (MH+); $^1$H NMR (DMSO-d$^6$): δ 8.83-8.81 (d, J = 6.78 Hz, 2H), 8.38 (s, 3H), 8.25 (s, 1H), 8.17-8.14 (d, J = 6.78 Hz, 2H), 5.02-5.00 (d, J = 7.65 Hz, 1H), 4.23-4.17 (m, 1H), 3.94-3.78 (m, 1H), 3.47-3.46 (m, 1H), 3.11-2.90 (m, 3H). |
| 48 | 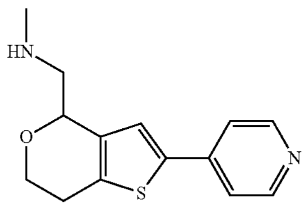 [SMILES: CNCC1OCCc2sc(-c3ccncc3)cc21] | HCl | LC-MS m/z 261.3 (MH+); $^1$H NMR (DMSO-d$^6$): δ 9.61 (br s, 1H), 8.00 (br s, 1H), 8.84-8.82 (d, J = 6.75 Hz, 1H), 8.23 (s, 1H), 8.16-8.13 (d, J = 6.75 Hz, 1H), 5.16-5.13 (d, J = 8.25 Hz, 1H), 4.30-4.17 (m, 1H), 3.88-3.80 (m, 1H), 3.59-3.53 (m, 1H), 3.27-3.16 (m, 1H), 3.08-2.88 (m, 2H), 2.61-2.58 (t, J = 5.19 Hz, 3H). |
| 49 | 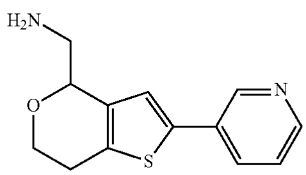 [SMILES: NCC1OCCc2sc(-c3cccnc3)cc21] | HCl | LC-MS m/z 247.2 (MH+); $^1$H NMR (DMSO-d$^6$): δ 9.11 (br s, 1H), 8.98-8.95 (d, J = 4.83 Hz, 1H), 8.51-8.48 (d, J = 8.25 Hz, 1H), 8.35 (br s, 3H), 7.94-7.86 (m, 2H), 4.99-4.97 (d, J = 7.74 Hz, 1H), 4.22-4.15 (m, 1H), 3.85-3.77 (m, 1H), 3.42-3.39 (m, 1H), 3.08-2.89 (m, 3H). |
| 50 | 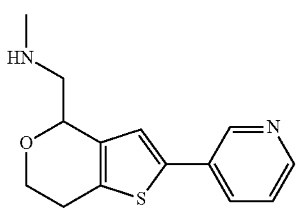 [SMILES: CNCC1OCCc2sc(-c3cccnc3)cc21] | HCl | LC-MS m/z 261.2 (MH+); $^1$H NMR (DMSO-d$^6$): δ 9.37 (br s, 1H), 9.03 (s, 1H), 8.85 (s, 1H), 8.67-8.65 (d, J = 5.01 Hz, 1H), 8.38-8.36 (d, J = 7.86 Hz, 1H), 7.81-7.77 (m, 2H), 5.10-5.08 (d, J = 7.98 Hz, 1H), 4.23-4.16 (m, 1H), 3.87-3.79 (m, 1H), 3.55-3.48 (m, 1H), 3.26-3.17 (m, 1H), 3.03-2.85 (m, 2H), 2.61-2.58 (t, J = 5.31 Hz, 3H). |
| 51 | 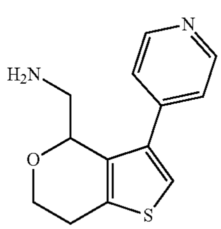 [SMILES: NCC1OCCc2scc(-c3ccncc3)c21] | HCl | LC-MS m/z 247.2 (MH+); $^1$H NMR (DMSO-d$^6$): δ 8.87-8.85 (d, J = 6.69 Hz, 2H), 8.22 (br s, 3H), 8.09-8.07 (d, J = 6.69 Hz, 2H), 8.05 (s, 1H), 5.62-5.60 (d, J = 8.64 Hz, 1H), 4.10-4.02 (m, 1H), 3.93-3.86 (m, 1H), 3.00-2.92 (m, 2H), 2.89-2.77 (m, 1H), 2.57-2.51 (m, 1H). |
| 52 | 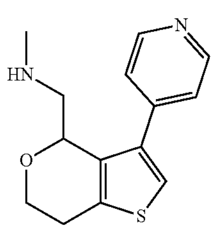 [SMILES: CNCC1OCCc2scc(-c3ccncc3)c21] | HCl | LC-MS m/z 261.3 (MH+); $^1$H NMR (DMSO-d$^6$): δ 9.72 (br s, 1H), 8.88-8.86 (d, J = 6.75 Hz, 2H), 8.69 (br s, 1H), 8.17-8.15 (d, J = 6.75 Hz, 2H), 8.11 (s, 1H), 5.77-5.73 (d, J = 9.24 Hz, 1H), 4.14-4.04 (m, 1H), 3.94-3.87 (m, 1H), 3.06-2.94 (m, 3H), 2.66-2.60 (m, 1H), 2.42-2.41 (t, J = 5.28 Hz, 3H). |
| 53 | 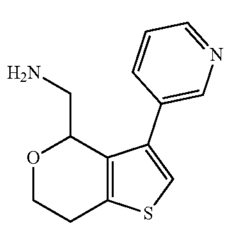 [SMILES: NCC1OCCc2scc(-c3cccnc3)c21] | HCl | LC-MS m/z 247.2 (MH+); $^1$H NMR (DMSO-d$^6$): δ 8.97-8.96 (d, J = 1.77 Hz, 1H), 8.84-8.83 (d, J = 4.53 Hz, 1H), 8.54-8.51 (d, J = 8.22 Hz, 1H), 8.17 (s, 3H), 8.07-7.95 (dd, J$_1$ = 5.49 Hz, J$_2$ = 8.01 Hz, 1H), 7.76 (s, 1H), 5.50-5.47 (d, J = 8.85 Hz, 1H), 4.07-4.01 (m, 1H), 3.91-3.84 (m, 1H), 2.95-2.93 (m, 2H), 2.83-2.74 (m, 1H), 2.45-2.35 (m, 1H). |

| Compd. No. | Structure | Salt or FB* | Analytical Data |
|---|---|---|---|
| 54 | 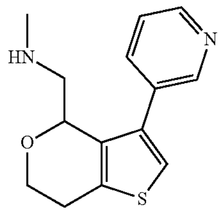 [SMILES: CNCC1OCCc2scc(-c3cccnc3)c21] | HCl | LC-MS m/z 261.3 (MH$^+$); $^1$H NMR (DMSO-d$^6$): δ 9.26 (br s, 1H), 8.90-8.89 (d, J = 1.92 Hz, 1H), 8.79-8.77 (dd, J$_1$ = 1.22 Hz, J$_2$ = 5.27 Hz, 1H), 8.59 (br s, 1H), 8.39-8.36 (d, J = 7.62 Hz, 1H), 7.87-7.83 (dd, J$_1$ =5.43 Hz, J$_2$ = 7.83 Hz, 1H), 7.71 (s, 1H), 5.59-5.56 (d, J = 9.48 Hz, 1H), 4.13-4.08 (m, 1H), 3.94-3.85 (m, 1H), 3.05-2.93 (m, 3H), 2.65-2.60 (m, 1H), 2.39-2.35 (t, J = 5.28 Hz, 3H). |
| 55 | 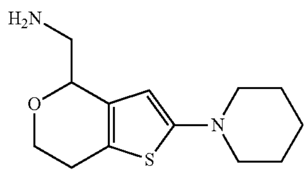 [SMILES: NCC1OCCc2sc(N3CCCCC3)cc21] | HCl | LC-MS m/z 253.3 (MH$^+$); $^1$H NMR (DMSO-d$^6$ + D$_2$O): δ 4.69-4.67 (d, J = 7.68 Hz, 1H), 4.09-4.06 (m, 1H), 3.73-3.71 (m, 2H), 3.28-3.22 (dd, J$_1$ = 2.52 Hz, J$_2$ = 13.30 Hz, 1H), 2.99-2.90 (m, 4H), 2.78-2.68 (m, 1H), 2.56 (s, 1H), 1.56 (s, 5H), 1.47-1.46 (m, 2H). |
| 56 | 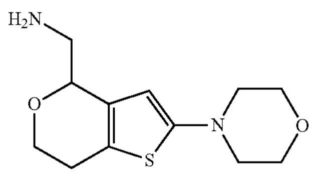 [SMILES: NCC1OCCc2sc(N3CCOCC3)cc21] | HCl | LC-MS m/z 277.3 (M+ Na$^+$); $^1$H NMR (DMSO-d$^6$): δ 8.01 (s, 3H), 6.05 (s, 1H), 4.74-4.72 (d, J = 7.44 Hz, 1H), 4.14-4.08 (m, 1H), 3.78-3.69 (m, 5H), 3.35-3.29 (m, 1H), 3.00-2.97 (m, 5H), 2.77-2.70 (m, 1H), 2.62-2.56 (m, 1H). |
| 57 | 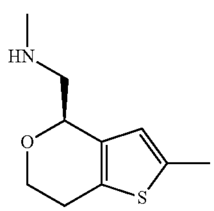 | HCl | $^1$H NMR (CD$_3$OD): δ 6.54 (s, 1H), 4.91-4.85 (m, 1H), 4.26-4.21 (m, 1H), 3.80 (td, J = 3.5, 10.0 Hz, 1H), 3.47 (dd, J = 3.0, 13.0 Hz, 1H), 3.20 (dd, J = 8.5, 13.0 Hz, 1H), 2.93-2.88 (m, 1H), 2.72 (s, 3H), 2.71-2.66 (m, 1H), 2.42 (s, 3H). |
| 58 | 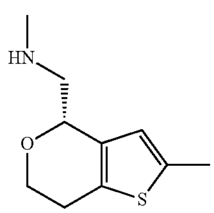 | HCl | $^1$H NMR (CD$_3$OD): δ 6.54 (s, 1H), 4.91-4.85 (m, 1H), 4.26-4.21 (m, 1H), 3.80 (td, J = 3.5, 10.0 Hz, 1H), 3.47 (dd, J = 3.0, 13.0 Hz, 1H), 3.20 (dd, J = 8.5, 13.0 Hz, 1H), 2.93-2.88 (m, 1H), 2.72 (s, 3H), 2.71-2.66 (m, 1H), 2.42 (s, 3H). |
| 59 | 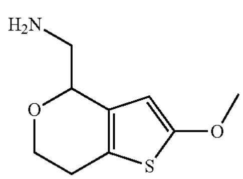 | HCl | LC-MS m/z 200.3 (MH$^+$); $^1$H NMR (DMSO-d$^6$): δ 8.11 (s, 3H), 6.21 (s, 1H), 4.76-4.73 (d, J = 7.14 Hz, 1H), 4.15-4.08 (m, 1H), 3.79-3.72 (m, 4H), 3.31-3.26 (m, 1H), 2.98-2.89 (m, 1H), 2.78-2.68 (m, 1H), 2.60-2.54 (m, 1H). |
| 60 | 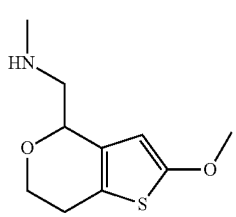 | HCl | LC-MS m/z 214.3 (MH$^+$); $^1$H NMR (DMSO-d$^6$): δ 9.09 (br s, 1H), 8.67 (br s, 1H), 6.15 (s, 1H), 4.87-4.85 (d, J = 7.7 Hz, 1H), 4.15-4.08 (m, 1H), 3.80-3.73 (m, 4H), 3.34 (s, 1H), 3.15-3.05 (m, 1H), 2.77-2.68 (m, 1H), 2.61-2.55 (m, 4H). |

-continued

| Compd. No. | Structure | Salt or FB* | Analytical Data |
|---|---|---|---|
| 61 | 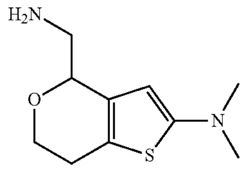 | HCl | LC-MS m/z 213.3 (MH+); $^1$H NMR (DMSO-d$^6$ + D$_2$O): δ 5.74 (s, 1H), 4.71-4.68 (d, J = 7.03 Hz, 1H), 4.12-4.05 (m, 1H), 3.79-3.68 (m, 1H), 3.33-3.25 (m, 1H), 2.95-2.88 (m, 1H), 2.78 (s, 6H), 2.71-2.67 (m, 1H), 2.59-2.58 (m, 1H). |
| 62 | 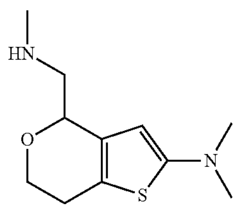 | HCl | LC-MS m/z 227.3 (MH+); $^1$H NMR (DMSO-d$^6$): δ 9.11 (br s, 1H), 8.65 (br s, 1H), 5.73 (s, 1H), 4.87-4.83 (d, J = 9.54 Hz, 1H), 4.13-4.07 (m, 1H), 3.78-3.72 (m, 1H), 3.43-3.39 (m, 1H), 3.16-3.06 (m, 1H), 2.79-2.71 (m, 7H), 2.58-2.55 (m, 4H). |
| 63 | 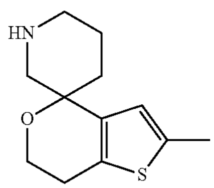 | HCl | $^1$H NMR (CD$_3$OD): δ 6.59 (s, 1H), 3.97 (t, J = 5.0 Hz, 2H), 3.33-3.24 (m, 3H), 3.05 (dt, J = 3.0, 13.0 Hz, 1H), 2.77 (t, J = 5.0 Hz, 2H), 2.41 (s, 3H), 2.16-2.08 (m, 1H), 2.00-1.88 (m, 2H), 1.80 (d, J = 14.0 Hz, 1H). |
| 64 | 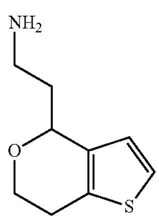 [SMILES: NCCC1OCCc2sccc21] | HCl | LC-MS m/z 184.3 (MH+); $^1$H NMR (DMSO-d$^6$): δ 8.04 (s, 3H), 7.36-7.34 (d, J = 5.07 Hz, 1H), 6.85-6.84 (d, J = 5.07 Hz, 1H), 4.76-4.74 (d, J = 7.38 Hz, 1H), 4.14-4.09 (m, 1H), 3.71-3.64 (m, 1H), 2.87-2.69 (m, 4H), 2.24-2.15 (m, 1H), 2.00-1.88 (m, 1H). |
| 65 | 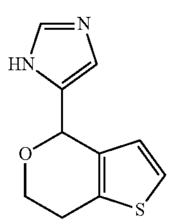 [SMILES: c1ncc(C2OCCc3sccc32)[nH]1] | HCl | LC-MS m/z 207.3 (MH+); $^1$H NMR (DMSO-d$^6$): δ 14.65 (s, 2H), 9.12 (s, 1H), 7.50 (s, 1H), 7.40-7.38 (d, J = 5.20 Hz, 1H), 6.74-6.72 (d, J = 5.20 Hz, 1H), 5.95 (s, 1H), 4.03-3.85 (m, 2H), 2.98-2.84 (m, 2H). |
| 66 | 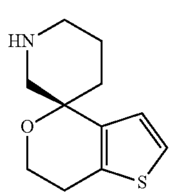 | HCl | $^1$H NMR (CD$_3$OD): δ 7.26 (d, J = 5.0 Hz, 1H), 6.94 (d, J = 5.0 Hz, 1H), 4.00 (t, J = 5.1 Hz, 2H), 3.33-3.21 (m, 3H), 3.08 (apt, J = 2.8 Hz, 1H), 2.87 (t, J = 5.1 Hz, 2H), 2.18-2.11 (m, 1H), 2.04-1.97 (m, 2H), 1.84-1.80 (m, 1H). |
| 67 | 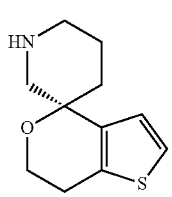 [SMILES: c1cc2c(s1)CCO[C@@]21CCCNC1] | HCl | $^1$H NMR (CD$_3$OD): δ 7.26 (d, J = 5.0 Hz, 1H), 6.94 (d, J = 5.0 Hz, 1H), 4.00 (t, J = 5.1 Hz, 2H), 3.33-3.21 (m, 3H), 3.08 (apt, J = 2.8 Hz, 1H), 2.87 (t, J = 5.1 Hz, 2H), 2.18-2.11 (m, 1H), 2.04-1.97 (m, 2H), 1.84-1.80 (m, 1H). |

-continued

| Compd. No. | Structure | Salt or FB* | Analytical Data |
|---|---|---|---|
| 68 | 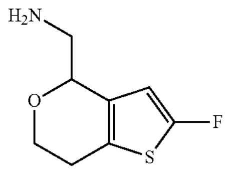 [SMILES: NCC1OCCc2sc(F)cc21] | HCl | ¹H NMR (CD₃OD): δ 6.40 (d, J = 2.0 Hz, 1H), 4.80 (dd, J = 3.0, 5.5 Hz, 1H), 4.27-4.22 (m, 1H), 3.89-3.83 (m, 1H), 3.37 (dd, J = 3.0, 13.0 Hz, 1H), 3.11 (dd, J = 8.0, 13.0 Hz, 1H), 2.93-2.85 (m, 1H), 2.61 (dd, J = 2.0 16.0 Hz, 1H). |
| 69 | 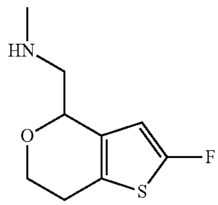 | HCl | ¹H NMR (CD₃OD): δ 6.40 (d, J = 2.0 Hz, 1H), 4.86 (m, 1H), 4.28-4.23 (m, 1H), 3.90-3.84 (m, 1H), 3.45 (dd, J = 2.5, 13.0 Hz, 1H), 3.23 (dd, J = 8.5, 13.0 Hz, 1H), 2.93-2.85 (m, 1H), 2.73 (s, 3H), 2.63 (dd, J = 2.0, 6.0 Hz, 1H). |
| 70 | 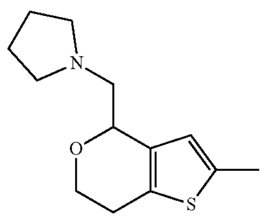 [SMILES: Cc1cc2c(s1)CCOC2CN1CCCC1] | HCl | LC-MS m/z 238.3 (MH⁺); ¹H NMR (CD₃OD): δ 6.57 (s, 1H), 5.03-5.00 (d, J = 9.62 Hz, 1H), 4.30-4.23 (m, 1H), 3.89-3.55 (m, 4H), 3.46-3.38 (m, 1H), 3.28-3.08 (m, 2H), 2.99-2.89 (m, 1H), 2.75-2.70 (d, J = 16.44 Hz, 1H), 2.43 (s, 3H), 2.25-2.01 (m, 4H). |
| 71 | 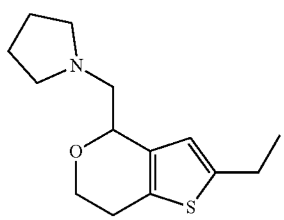 [SMILES: CCc1cc2c(s1)CCOC2CN1CCCC1] | HCl | LC-MS m/z 252.3 (MH⁺); ¹H NMR (DMSO-d⁶): δ 10.36 (s, 1H), 6.68 (s, 1H), 5.07-5.04 (d, J = 8.61 Hz, 1H), 4.15-4.08 (m, 1H), 3.82-3.66 (m, 2H), 3.57-3.55 (m, 2H), 3.40-3.30 (m, 1H), 3.17-3.01 (m, 2H), 2.86-2.68 (m, 4H), 2.00-1.88 (m, 4H), 1.23-1.18 (t, J = 7.49 Hz, 3H). |
| 72 | 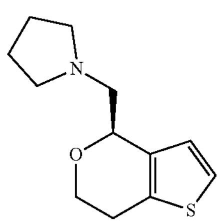 [SMILES: c1cc2c(s1)CCO[C@H]2CN1CCCC1] | HCl | LC-MS (6 min method): broad peak at 0.23-0.67 minute, M⁺ 224 @ 0.56 min.; ¹H NMR (CD₃OD): δ 7.28 (d, J = 5.13 Hz, 1H), 6.94 (d, J = 5.13 Hz, 1H), 5.15-5.12 (m, 1H), 4.30-4.26 (m, 1H), 3.89-3.74 (m, 3H), 3.68-3.63 (m, 1H), 3.44 (dd, J = 9.90, 12.8 Hz, 1H), 3.34-3.29 (m, 1H), 3.19-3.12 (m, 1H), 3.04-2.99 (m, 1H), 2.84-2.79 (m, 1H), 2.24-2.03 (m, 4H). |
| 73 | 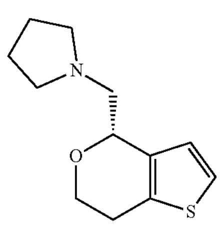 [SMILES: c1cc2c(s1)CCO[C@@H]2CN1CCCC1] | HCl | LC-MS (6 minute method on lab 209 instrument): broad peak at 0.23-0.67 minute, M⁺ 224 @ 0.56 min.; ¹H NMR (CD₃OD): δ 7.28 (d, J = 5.13 Hz, 1H), 6.94 (d, J = 5.13 Hz, 1H), 5.15-5.12 (m, 1H), 4.30-4.26 (m, 1H), 3.89-3.74 (m, 3H), 3.68-3.63 (m, 1H), 3.44 (dd, J = 9.90, 12.8 Hz, 1H), 3.34-3.29 (m, 1H), 3.19-3.12 (m, 1H), 3.04-2.99 (m, 1H), 2.84-2.79 (m, 1H), 2.24-2.03 (m, 4H). |
| 74 | 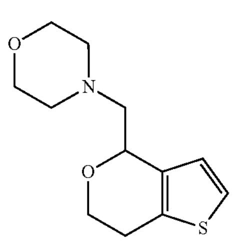 [SMILES: c1cc2c(s1)CCOC2CN1CCOCC1] | HCl | LC-MS (6 min method): 2.24 minute, M⁺ 240 @ 2.25 min.; ¹H NMR (CD₃OD): δ 7.30 (d, J = 5.13 Hz, 1H), 6.90 (d, J = 5.13 Hz, 1H), 5.24 (dd, J = 2.57, 10.3 Hz, 1H), 4.31-4.27 (m, 1H), 4.12-4.03 (m, 2H), 3.89-3.81 (m, 4H), 3.75 (dd, J = 2.93, 13.2 Hz, 1H), 3.70-3.66 (d, J = 13.2 Hz, 1H), 3.55 (d, J = 12.5 Hz, 1H), 3.41-3.35 (m, 1H), 3.26-3.22 (m, 1H), 3.06-2.98 (m, 1H), 2.86-2.82 (m, 1H). |

| Compd. No. | Structure | Salt or FB* | Analytical Data |
|---|---|---|---|
| 75 | 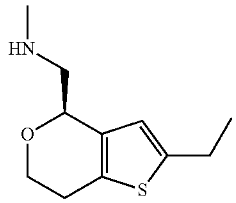 | HCl | LC-MS (6 minute method): 1.6 min, M+ 212 @ 1.71 min; ¹H NMR (CD₃OD): δ 6.59 (s, 1H), 4.91 (d, J = 8.43 Hz, 1H), 4.27-4.22 (m, 1H), 3.84-3.78 (m, 1H), 3.50 (dd, J = 2.93, 12.8 Hz, 1H), 3.24-3.19 (m, 1H), 2.98-2.92 (m, 1H), 2.79 (q, 2H), 2.80-2.68 (m, 1H), 2.73 (s, 3H), 1.27 (t, 3H). |
| 76 | 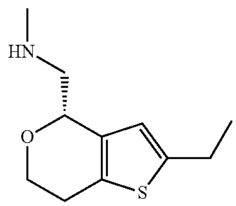 | HCl | LC-MS (6 minute method): 1.6 min, M+ 212 @ 1.71 min; ¹H NMR (CD₃OD): δ 6.59 (s, 1H), 4.91 (d, J = 8.43 Hz, 1H), 4.27-4.22 (m, 1H), 3.84-3.78 (m, 1H), 3.50 (dd, J = 2.93, 12.8 Hz, 1H), 3.24-3.19 (m, 1H), 2.98-2.92 (m, 1H), 2.79 (q, 2H), 2.80-2.68 (m, 1H), 2.73 (s, 3H), 1.27 (t, 3H). |
| 77 | 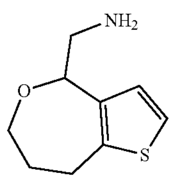 [SMILES: NCC1OCCCc2sccc21] | HCl | ¹H NMR (CD₃OD): δ 7.10 (d, J = 5.5 Hz, 1H), 6.83 (d, J = 5.5 Hz, 1H), 4.73 (dd, J = 3.5, 10.0 Hz, 1H), 4.33 (dt, J = 5.0, 12.5 Hz, 1H), 3.92-3.85 (m, 1H), 3.52 (dd, J = 3.0, 13.0 Hz, 1H), 3.25-3.19 (m, 1H), 3.15-3.08 (m, 1H), 3.00-2.93 (m, 1H), 1.99-1.88 (m, 2H). |
| 78 | 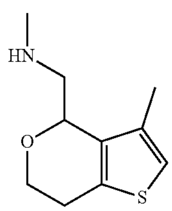 | HCl | LC-MS m/z 198.3 (MH+); ¹H NMR (DMSO-d⁶): δ 9.11 (br s, 1H), 8.59 (br s, 1H), 7.00 (s, 1H), 5.05-5.03 (d, J = 6.63 Hz, 1H), 4.04-3.96 (m, 1H), 3.87-3.80 (m, 1H), 3.28-3.21 (m, 2H), 2.83-2.74 (m, 2H), 2.61-2.59 (d, J = 1.68 Hz, 3H), 2.13 (s, 3H). |
| 79 | 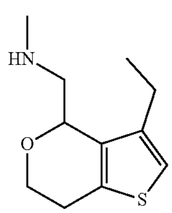 | HCl | LC-MS m/z 212.3 (MH+); ¹H NMR (DMSO-d⁶): δ 9.16 (br s, 1H), 8.58 (s, 1H), 7.02 (s, 1H), 5.07-5.05 (d, J = 8.07 Hz, 1H), 4.05-3.97 (m, 1H), 3.87-3.80 (m, 1H), 3.27-3.15 (m, 2H), 2.90-2.73 (m, 2H), 2.60 (s, 3H), 2.47-2.41 (m, 2H), 1.22-1.17 (t, J = 7.40 Hz, 3H). |
| 80 | 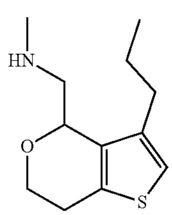 | HCl | LC-MS m/z 226.0 (MH+); ¹H NMR (DMSO-d⁶): δ 8.99 (br s, 1H), 8.54 (br s, 1H), 7.02 (s, 1H), 5.04-5.01 (d, J = 8.85 Hz, 1H), 4.05-3.97 (m, 1H), 3.87-3.80 (m, 1H), 3.18 (s, 2H), 2.90-2.72 (m, 2H), 2.61 (s, 3H), 2.46-2.40 (t, J = 7.80 Hz, 2H), 1.67-1.55 (m, 2H), 0.97-0.92 (t, J = 7.31 Hz, 3H). |
| 81 | 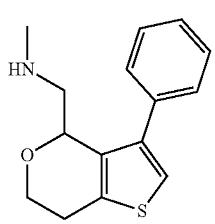 [SMILES: CNCC1OCCc2scc(-c3ccccc3)c21] | HCl | LC-MS m/z 260.3 (MH+); ¹H NMR (CD₃OD): δ 7.55-7.39 (m, 5H), 7.23 (s, 1H), 5.41-5.38 (m, 1H), 4.28-4.21 (m, 1H), 3.98-3.90 (m, 1H), 3.11-3.01 (m, 1H), 2.96-2.92 (m, 2H), 2.80-2.75 (dd, J₁ = 3.3 Hz, J₂ = 12.9 Hz, 1H), 2.47 (s, 3H). |

| Compd. No. | Structure | Salt or FB* | Analytical Data |
|---|---|---|---|
| 82 | 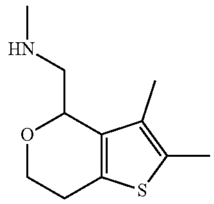 | HCl | LC-MS m/z 212.3 (MH$^+$); $^1$H NMR (DMSO-d$^6$): δ 9.10 (br s, 1H), 8.57 (br s, 1H), 4.98-4.95 (d, J = 8.28 Hz, 1H), 4.03-3.95 (m, 1H), 3.85-3.78 (m, 1H), 3.21-3.17 (m, 2H), 2.79-2.65 (m, 2H), 2.60 (s, 3H), 2.25 (s, 3H), 1.99 (s, 3H). |
| 83 | 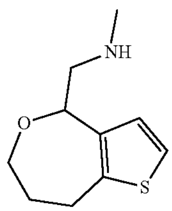 | HCl | $^1$H NMR (CD$_3$OD): δ 7.10 (d, J = 5.0 Hz, 1H), 6.84 (d, J = 5.0 Hz, 1H), 4.82 (dd, J = 3.0, 10.5 Hz, 1H), 4.33 (dt, J = 4.5, 12.5 Hz, 1H), 3.93-3.86 (m, 1H), 3.59 (dd, J = 2.5, 12.5 Hz, 1H), 3.39-3.33 (m, 1H), 3.15-3.08 (m, 1H), 3.01-2.80 (m, 1H), 2.78 (s, 3H), 1.99-1.88 (m, 2H). |
| 84 | 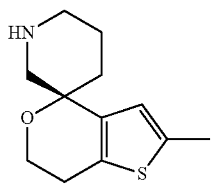 | HCl | $^1$H NMR (CD$_3$OD): δ 6.59 (s, 1H), 3.97 (t, J = 5.0 Hz, 2H), 3.33-3.24 (m, 3H), 3.05 (dt, J = 3.0, 13.0 Hz, 1H), 2.77 (t, J = 5.0 Hz, 2H), 2.41 (s, 3H), 2.16-2.08 (m, 1H), 2.00-1.88 (m, 2H), 1.80 (d, J = 14.0 Hz, 1H). |
| 85 | 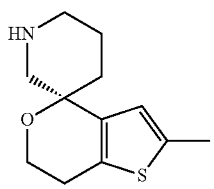 | HCl | $^1$H NMR (CD$_3$OD): δ 6.59 (s, 1H), 3.97 (t, J = 5.0 Hz, 2H), 3.33-3.24 (m, 3H), 3.05 (dt, J = 3.0, 13.0 Hz, 1H), 2.77 (t, J = 5.0 Hz, 2H), 2.41 (s, 3H), 2.16-2.08 (m, 1H), 2.00-1.88 (m, 2H), 1.80 (d, J = 14.0 Hz, 1H). |
| 86 | 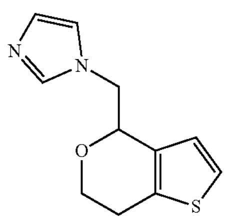 [SMILES: c1cn(CC2OCCc3sccc32)cn1] | HCl | LC-MS (6 minute method): 1.85 min, M$^+$ 221 @ 1.83 min; $^1$H NMR (CD$_3$OD): δ 8.91 (s, 1H), 7.57 (s, 1H), 7.49 (s, 1H), 7.29 (d, J = 5.13 Hz, 1H), 7.09 (d, J = 5.50 Hz, 1H), 5.13-5.10 (m, 1H), 4.80 (dd, J = 2.57, 14.3 Hz, 1H), 4.60 (dd, J = 6.60, 14.3 Hz, 1H), 4.26-4.22 (m, 1H), 3.79-3.73 (m, 1H), 2.87-2.79 (m, 1H), 2.74-2.70 (m, 1H). |
| 87 | 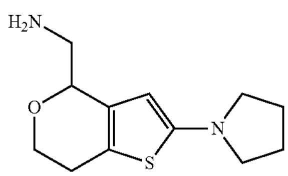 [SMILES: NCC1OCCc2sc(N3CCCC3)cc21] | HCl | $^1$H NMR (CD$_3$OD): δ 4.64 (dd, J = 3.0. 9.5 Hz, 1H), 4.23 (dd, J = 3.5, 11.5 Hz, 1H), 4.16-4.08 (m, 2H), 3.87 (td, J = 1.5, 12.0 Hz, 1H), 3.82-3.78 (m, 2H), 3.68 (dd, J = 2.5, 13.0 Hz, 1H), 3.40 (dd, J = 9.5, 13.0 Hz, 1H), 3.30 (bs, 1H), 2.74 (d, J = 13.0 Hz, 1H), 2.29-2.20 (m, 4H), 1.96-1.89 (td, J = 5.0, 12.5 Hz, 1H). |
| 88 | 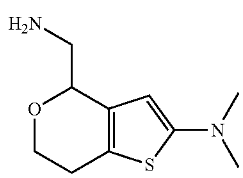 | HCl | LC-MS (6 min method): 0.28 minute, M$^+$ 213 @ 0.33 min.; $^1$H NMR (CD$_3$OD): δ 4.61 (dd, J = 3.0, 10.0 Hz, 1H), 4.26-4.20 (m, 1H), 3.86 (td, J = 2.0, 12.5 Hz, 1H), 3.69 (s, 3H), 3.66 (d, J = 2.0 Hz, 1H), 3.57 (s, 3H), 3.45-3.35 (m, 1H), 3.13-2.97 (m, 1H), 2.74 (d, J = 13.0 Hz, 1H), 1.92 (td, J = 4.0, 13.0 Hz, 1H). |
| 89 | 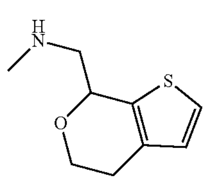 | HCl | LC-MS (6 min method): 0.27-0.45 min, M$^+$ 184 @ 0.38 min; $^1$H NMR (CD$_3$OD): δ 7.36 (d, J = 4.76 Hz, 1H), 6.90 (d, J = 5.13 Hz, 1H), 5.16 (d, J = 8.06 Hz, 1H), 4.28-4.23 (m, 1H), 3.85-3.79 (m, 1H), 3.51-3.47 (m, 1H), 3.26-3.23 (m, 1H), 2.86-2.82 (m, 1H), 2.75 (s, 3H), 2.71-2.66 (m, 1H). |

-continued

| Compd. No. | Structure | Salt or FB* | Analytical Data |
|---|---|---|---|
| 90 | 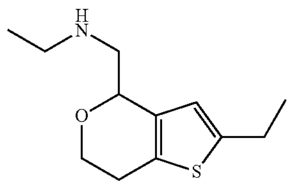 | HCl | LC-MS (6 min method): 1.37 min, M⁺ 226 @ 1.44 min; ¹H NMR (CD₃OD): δ 6.60 (s, 1H), 4.94-4.91 (m, 1H), 4.26-4.21 (m, 1H), 3.84-3.78 (m, 1H), 3.50 (dd, J = 2.2, 12.8 Hz, 1H), 3.19-3.09 (m, 3H), 2.93-2.89 (m, 1H), 2.81-2.69 (m, 3H), 1.33 (t, 3H), 1.27 (t, 3H). |
| 91 | 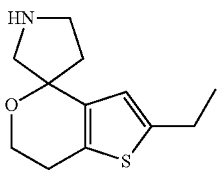 | HCl | LC-MS m/z 224.3 (MH⁺); ¹H NMR (DMSO-d⁶ + D₂O): δ 6.75 (s, 1H), 3.90-3.85 (m, 2H), 3.45-3.41 (m, 2H), 3.26-3.22 (m, 2H), 2.77-2.69 (m, 4H), 2.23-2.18 (m, 2H), 1.22-1.17 (t, J = 7.52 Hz, 3H). |
| 92 | 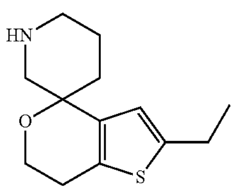 [SMILES: CCc1cc2c(s1)CCOC21CCCNC1] | HCl | LC-MS m/z 238.3 (MH⁺); ¹H NMR (DMSO-d⁶): δ 9.04 (br s, 1H), 8.31 (s, 1H), 6.76 (s, 1H), 3.93-3.89 (t, J = 5.10 Hz, 2H), 3.25-3.15 (m, 3H), 2.93-2.90 (m, 1H), 2.81-2.70 (m, 4H), 1.94-1.80 (m, 3H), 1.69-1.67 (m, 1H), 1.24-1.19 (t, J = 7.52 Hz, 3H). |
| 93 | 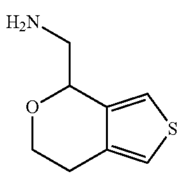 [SMILES: NCC1OCCc2cscc21] | HCl | ¹H NMR (CD₃OD): δ 7.23 (d, J = 2.0 Hz, 1H), 7.14 (d, J = 2.5 Hz, 1H), 4.93 (d, J = 7.0 Hz, 1H), 4.24-4.19 (m, 1H), 3.71 (td, J = 4.0, 11.0 Hz, 1H), 3.52 (dd, J = 2.5, 13.0 Hz, 1H), 3.19 (dd, J = 7.5, 13.0 Hz, 1H), 2.96-2.87 (m, 1H), 2.81-2.75 (m, 1H). |
| 94 | 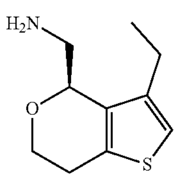 | HCl | LC-MS (6 min method): 0.49-1.01 min, M⁺ 198 @ 0.73 min; ¹H NMR (DMSO-d⁶): δ 8.06 (br s, 1H), 7.02 (s, 1H), 4.97-4.93 (dd, J₁ = 3.5 Hz, J₂ = 9.1 Hz, 1H), 4.03-3.95 (m, 1H), 3.86-3.79 (m, 1H), 3.09 (br s, 2H), 2.84-2.73 (m, 2H), 2.47-2.37 (m, 2H), 1.21-1.17 (t, J = 7.41 Hz, 3H). |
| 95 | 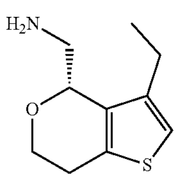 | HCl | LC-MS (6 min method): 0.49-1.01 min, M⁺ 198 @ 0.73 min; ¹H NMR (DMSO-d⁶): δ 8.06 (br s, 1H), 7.02 (s, 1H), 4.97-4.93 (dd, J₁ = 3.5 Hz, J₂ = 9.1 Hz, 1H), 4.03-3.95 (m, 1H), 3.86-3.79 (m, 1H), 3.09 (br s, 2H), 2.84-2.73 (m, 2H), 2.47-2.37 (m, 2H), 1.21-1.17 (t, J = 7.41 Hz, 3H). |
| 96 | 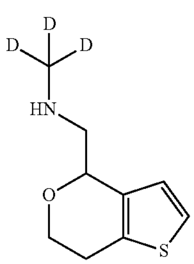 [SMILES: [2H]C([2H])([2H])NCC1OCCc2sccc21] | HCl | LC-MS (6 min method): 0.37 min, M⁺ 187 @ 0.35 min.; ¹H NMR (CD₃OD): δ 7.27 (d, J = 5.13 Hz, 1H), 6.87 (d, J = 5.13 Hz, 1H), 4.98 (d, J = 8.43 Hz, 1H), 4.28-4.23 (m, 1H), 3.84-3.78 (m, 1H), 3.54-3.51 (m, 1H), 3.22 (dd, J = 8.43, 12.8 Hz, 1H), 3.03-2.95 (m, 1H), 2.80 (d, J = 16.1 Hz, 1H). |

-continued

| Compd. No. | Structure | Salt or FB* | Analytical Data |
|---|---|---|---|
| 97 | (structure) | HCl | ¹H NMR (CD₃OD): δ 7.20 (d, J = 2.0 Hz, 1H), 7.13 (d, J = 2.5 Hz, 1H), 4.96 (d, J = 7.0 Hz, 1H), 4.23-4.19 (m, 1H), 3.70 (td, J = 4.0, 11.0 Hz, 1H), 3.49 (dd, J = 3.0, 13.0 Hz, 1H), 3.22 (dd, J = 8.5, 13.0 Hz, 1H), 2.936-2.86 (m, 1H), 2.81-2.75 (m, 1H), 2.69 (s, 3H). |
| 98 | (structure) | HCl | ¹H NMR (CD₃OD): δ 6.50 (s, 1H), 4.66 (dd, J = 2.5, 0.7 Hz, 1H), 4.30 (dt, J = 2.5, 1.2 Hz, 1H), 3.85 (ddd, J = 3.0, 2.5, 1.2 Hz, 1H), 3.46 (dd, J = 3.0, 0.7 Hz, 1H), 3.33-3.29 (m, 1H), 3.17 (dd, J = 3.0, 2.5 Hz, 1H), 3.00 (ddd, J = 4.0, 2.0, 0.7 Hz, 1H), 2.86 (ddd, J = 4.0, 2.0, 0.7 Hz, 1H), 2.37 (s, 3H), 1.96-1.86 (m, 2H). |
| 99 | (structure) | HCl | ¹H NMR (CD₃OD): δ 6.51 (s, 1H), 4.74 (dd, J = 2.5, 0.8 Hz, 1H), 4.30 (dt, J = 3.0, 1.5 Hz, 1H), 3.86 (ddd, J = 3.0, 2.0, 1.0 Hz, 1H), 3.53 (dd, J = 3.0, 1.0 Hz, 1H), 3.01 (ddd, J = 4.0, 2.0, 1.0 Hz, 1H), 2.87 (ddd, J = 4.0, 2.0, 1.0 Hz, 1H), 2.76 (s, 3H), 2.37 (s, 3H), 1.98-1.85 (m, 2H). |
| 100 | (structure) | HCl | ¹H NMR (CD₃OD): δ 6.53 (s, 1H), 4.66 (dd, J = 2.5, 0.7 Hz, 1H), 4.30 (dt, J = 3.0, 1.2 Hz, 1H), 3.85 (ddd, J = 3.2, 2.7, 1.2 Hz, 1H), 3.48 (dd, J = 3.2, 0.7 Hz, 1H), 3.17 (dd, J = 3.2, 2.7 Hz, 1H), 3.03 (ddd, J = 4.0, 2.0, 1.0 Hz, 1H), 2.88 (ddd, J = 4.0, 2.0, 1.0 Hz, 1H), 2.74 (q, J = 1.9 Hz, 2H), 1.96-1.88 (m, 2H), 1.24 (t, J = 3H). |
| 101 | (structure) | HCl | ¹H NMR (CD₃OD): δ 6.54 (s, 1H), 4.75 (dd, J = 2.5, 0.7 Hz, 1H), 4.31 (dt, J = 3.0, 1.2 Hz, 1H), 3.86 (ddd, J = 3.2, 2.2, 1.0 Hz, 1H), 3.55 (dd, J = 3.0, 0.7 Hz, 1H), 3.34-3.28 (m, 1H), 3.02 (ddd, J = 4.0, 2.0, 1.0 Hz, 1H), 2.89 (ddd, J = 4.0, 2.0, 1.0 Hz, 1H), 2.77 (s, 3H), 2.74 (q, J = 1.9 Hz, 2H), 1.98-1.86 (m, 2H), 1.25 (t, J = 1.9 Hz, 3H). |
| 102 | (structure) | HCl | LC-MS: m/z 210 (MH⁺); ¹H NMR (DMSO-d₆): δ 10.05 (s, 1H), 8.79 (s, 1H), 7.41-7.39 (d, J = 5.19 Hz, 1H), 6.99-6.98 (d, J = 5.22 Hz, 1H), 5.06-5.05 (d, J = 2.10 Hz, 1H), 4.28-4.17 (m, 2H), 3.75-3.67 (m, 1H), 3.22-3.05 (m, 2H), 2.96-2.90 (m, 1H), 2.79-2.73 (m, 1H), 1.91-1.74 (m, 2H), 1.65-1.55 (m, 2H). |
| 103 | (structure) | HCl | LC-MS: m/z 210 (MH⁺); ¹H NMR (DMSO-d₆): δ 9.69 (s, 1H), 8.51 (s, 1H), 7.41-7.40 (d, J = 4.50 Hz, 1H), 6.97-6.96 (d, J = 4.20 Hz, 1H), 4.89-4.88 (d, J = 4.20 Hz, 1H), 4.19-4.15 (m, 1H), 3.92-3.90 (m, 1H), 3.76 (s, 1H), 3.10-2.95 (m, 3H), 2.80-2.75 (m, 1H), 2.14-1.84 (m, 4H). |

| Compd. No. | Structure | Salt or FB* | Analytical Data |
|---|---|---|---|
| 104 | 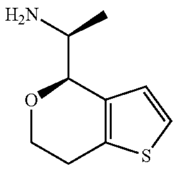 | HCl | LC-MS: m/z 184 (MH$^+$); $^1$H NMR (DMSO-d$_6$): δ 8.39 (s, 3H), 7.40-7.38 (d, J = 5.16 Hz, 1H), 6.99-6.98 (d, J = 5.22 Hz, 1H), 4.99-4.98 (d, J = 1.78 Hz, 1H), 4.27-4.22 (dd, J = 11.24 Hz, 5.12 Hz, 1H), 3.82 (s, 1H), 3.70-3.62 (m, 1H), 2.98-2.87 (m, 1H), 2.77-2.71 (m, 1H), 0.91-0.89 (d, J = 6.69 Hz, 3H). |
| 105 | 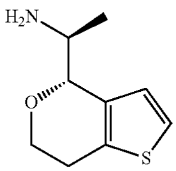 | HCl | LC-MS: m/z 184 (MH$^+$); $^1$H NMR (DMSO-d$_6$): δ 7.84 (s, 3H), 7.41-7.40 (d, J = 5.10 Hz, 1H), 7.00-6.98 (d, J = 5.10 Hz, 1H), 4.71-4.70 (d, J = 2.11 Hz, 1H), 4.20-4.13 (m, 1H), 3.77-3.69 (m, 2H), 2.95-2.76 (m, 2H), 1.36-1.34 (d, J = 6.6 Hz, 3H). |
| 106 | 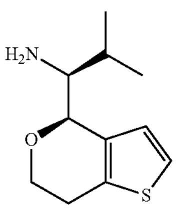 | HCl | LC-MS: m/z 212 (MH$^+$); $^1$H NMR (DMSO-d$_6$): δ 7.59 (s, 3H), 7.43-7.41 (d, J = 5.40 Hz, 1H), 7.01-6.99 (d, J = 5.10 Hz, 1H), 4.95 (s, 1H), 4.24-4.18 (m, 1H), 3.77-3.68 (m, 1H), 2.95-2.91 (m, 1H), 2.77-2.72 (m, 1H), 2.12-2.05 (m, 1H), 1.06-1.03 (m, 6H). |
| 107 | 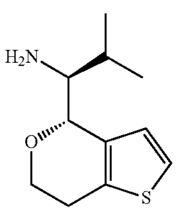 | HCl | LC-MS: m/z 212 (MH$^+$); $^1$H NMR (CD$_3$OD): δ 7.33-7.31 (d, J = 5.40 Hz, 1H), 6.93-6.91 (d, J = 7.56 Hz, 1H), 5.08-5.06 (m, 1H), 4.39-4.33 (m, 1H), 3.76-3.67 (m, 1H), 3.53-3.51 (m, 1H), 3.10-3.07 (m, 1H), 2.81-2.75 (m, 1H), 2.08-2.01 (m, 1H), 1.04-0.97 (m, 6H). |
| 108 | 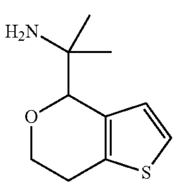 | HCl | LC-MS: m/z 198 (MH$^+$); $^1$H NMR (DMSO-d$_6$): δ 8.16 (s, 3H), 7.41-7.40 (d, J = 5.28 Hz, 1H), 6.98-6.97 (d, J = 5.22 Hz, 1H), 4.80 (s, 1H), 4.25-4.20 (m, 1H), 3.58-3.50 (dd, J = 10.85 Hz, 3.20 Hz, 1H), 2.96-2.74 (m, 2H), 1.48 (s, 3H), 1.01 (s, 3H). |
| 109 | 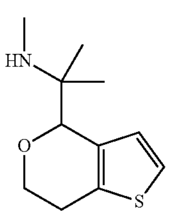 | HCl | LC-MS: m/z 212 (MH$^+$); $^1$H NMR (CD$_3$OD): δ 7.34-7.32 (dd, J = 5.03 Hz, 5.03 Hz, 1H), 6.98-6.96 (d, J = 5.34 Hz, 1H), 4.98-4.97 (m, 1H), 4.38-4.32 (m, 1H), 3.71-3.62 (td, J = 11.13 Hz, 2.94 Hz, 1H), 3.03-2.97 (m, 1H), 2.84-2.78 (m, 1H), 2.69 (s, 3H), 1.59 (s, 3H), 1.14 (s, 3H). |
| 110 | 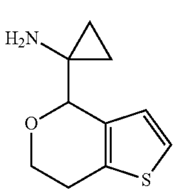 [SMILES: NC1(C2OCCc3sccc32)CC1] | HCl | LC-MS: m/z 196 (MH$^+$); $^1$H NMR (DMSO-d$_6$): δ 8.25-8.21 (brs, 3H), 7.40-7.39 (d, J = 5.10 Hz, 1H), 7.25-7.23 (d, J = 5.40 Hz, 1H), 4.10-4.03 (m, 2H), 3.90-3.82 (m, 1H), 2.93-2.73 (m, 2H), 2.29-2.21 (m, 2H), 2.18-2.02 (m, 2H). |

| Compd. No. | Structure | Salt or FB* | Analytical Data |
|---|---|---|---|
| 111 | | HCl | LC-MS: m/z 210 (MH$^+$); $^1$H NMR (DMSO-d$_6$): | | δ 9.03 (s, 2H), 7.41-7.40 (d, J = 4.51 Hz, 1H), 7.22-7.20 (d, J = 3.92 Hz, 1H), 4.13-4.04 (m, 2H), 3.86-3.79 (m, 1H), 2.96-2.91 (m, 1H), 2.78-2.73 (m, 1H), 2.31 (s, 3H), 2.26-2.01 (m, 4H). |
| 112 | 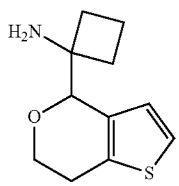 [SMILES: NC1(C2OCCc3sccc32)CCC1] | HCl | LC-MS: m/z 210 (MH$^+$); $^1$H NMR (DMSO-d$_6$): δ 7.86 (s, 3H), 7.37-7.36 (d, J = 5.10 Hz, 1H), 7.05-7.04 (d, J = 5.31 Hz, 1H), 4.10-4.05 (dd, J = 11.49 Hz, 4.71 Hz, 1H), 3.81-3.71 (m, 2H), 2.98-2.87 (m, 1H), 2.89-2.87 (m, 1H), 2.17-2.10 (m, 2H), 1.88-1.82 (m, 4H). |
| 113 | | HCl | LC-MS: m/z 224 (MH$^+$); $^1$H NMR (DMSO-d$_6$): | | δ 9.20 (s, 1H), 8.17 (s, 1H), 7.40-7.38 (d, J = 5.1 Hz, 1H), 7.06-7.05 (d, J = 5.4 Hz, 1H), 4.13-4.07 (m, 1H), 3.84-3.70 (m, 2H), 3.02-2.89 (m, 1H), 2.77-2.71 (m, 1H), 2.26-2.16 (m, 5H), 1.89-1.80 (m, 4H). |
| 114 | 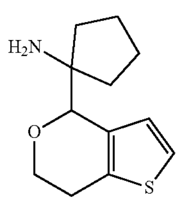 | HCl | LC-MS: m/z 224 (MH$^+$); $^1$H NMR (DMSO-d$_6$): δ 7.85 (s, 3H), 7.41-7.39 (d, J = 4.82 Hz, 1H), 7.00-6.98 (d, J = 4.83 Hz, 1H), 4.85 (s, 1H), 4.23-4.17 (m, 1H), 3.61-3.54 (t, J = 10.24 Hz, 1H), 3.01-2.92 (m, 1H), 2.79-2.74 (m, 1H), 2.17-2.12 (m, 1H), 1.87-1.77 (m, 5H), 1.54 (s, 2H). |
| 115 | | HCl | LC-MS: m/z 238 (MH$^+$); $^1$H NMR (DMSO-d$_6$): | δ 8.66 (s, 2H), 7.41-7.40 (d, J = 3.95 Hz, 1H), 7.00-9.99 (d, J = 3.96 Hz, 1H), 5.03 (s, 1H), 4.20-4.17 (m, 1H), 3.62-3.55 (m, 1H), 2.93-2.82 (m, 1H), 2.76-2.74 (m, 1H), 2.50 (s, 3H), 2.20-2.15 (m, 1H), 1.96-1.89 (m, 1H), 1.74-1.61 (m, 4H), 1.49-1.38 (m, 2H). |
| 116 | | HCl | LC-MS: m/z 238 (MH$^+$); $^1$H NMR (DMSO-d$_6$): | δ 7.73 (s, 3H), 7.43-7.41 (d, J = 4.84 Hz, 1H), 6.97-6.95 (d, J = 4.85 Hz, 1H), 4.94 (s, 1H), 4.22-4.19 (m, 1H), 3.57-3.51 (m, 1H), 2.98-2.90 (m, 1H), 2.78-2.74 (m, 1H), 1.94-1.91 (m, 1H), 1.77-1.42 (m, 8H), 1.26 (s, 1H). |
| 117 | | HCl | LC-MS: m/z 252 (MH$^+$); $^1$H NMR (DMSO-d$_6$): | δ 8.47 (s, 1H), 8.36 (s, 1H), 7.45-7.44 (d, J = 4.88 Hz, 1H), 6.99-6.97 (d, J = 1.86 Hz, 1H), 5.05 (s, 1H), 4.24-4.19 (m, 1H), 3.58-3.51 (m, 1H), 2.97-2.90 (m, 1H), 2.80-2.75 (m, 1H), 2.34 (s, 3H), 1.95-1.32 (m, 10H). |

-continued

| Compd. No. | Structure | Salt or FB* | Analytical Data |
|---|---|---|---|
| 118 | 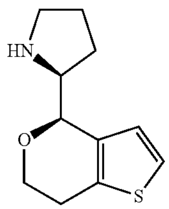 [SMILES: c1cc2c(s1)CCO[C@H]2[C@@H]1CCCN1] | HCl | LC-MS: m/z 210 (MH$^+$); $^1$H NMR (DMSO-d$_6$): δ 9.48-9.47 (d, J = 2.07 Hz, 1H), 8.40-8.39 (d, J = 3.54 Hz, 1H), 7.42-7.40 (d, J = 3.54 Hz, 1H), 6.98-6.96 (d, J = 5.22 Hz, 1H), 4.89-4.87 (d, J = 5.31 Hz, 1H), 4.22-4.15 (m, 1H), 3.95-3.89 (m, 1H), 3.80-3.72 (m, 1H), 3.13-3.06 (m, 2H), 2.97-2.75 (m, 1H), 2.50-2.49 (m, 1H), 2.13-1.84 (m, 4H). |
| 119 | 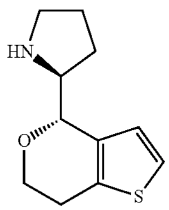 [SMILES: c1cc2c(s1)CCO[C@@H]2[C@@H]1CCCN1] | HCl | LC-MS: m/z 210 (MH$^+$); $^1$H NMR (DMSO-d$_6$): δ 9.94 (s, 1H), 8.76-8.75 (d, J = 4.20 Hz, 1H), 7.41-7.39 (d, J = 5.19 Hz, 1H), 6.99-6.98 (d, J = 5.22 Hz, 1H), 5.05-5.04 (d, J = 2.07 Hz, 1H), 4.28-4.15 (m, 2H), 3.75-3.70 (m, 1H), 3.20-3.10 (m, 2H), 2.96-2.92 (m, 1H), 2.79-2.73 (m, 1H), 1.90-1.56 (m, 4H). |
| 120 | 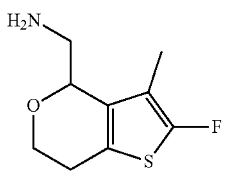 | HCl | LC-MS: m/z 202 (MH$^+$); $^1$H NMR (DMSO-d$_6$): δ 8.19 (s, 3H), 4.89-4.86 (d, J = 7.25 Hz, 1H), 4.06-4.00 (m, 1H), 3.98-3.79 (m, 1H), 3.16-3.06 (m, 2H), 2.76-2.62 (m, 2H), 1.99-1.98 (d, J = 2.14 Hz, 3H). |
| 121 | 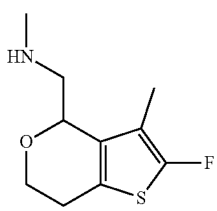 | HCl | LC-MS: m/z 216 (MH$^+$); $^1$H NMR (DMSO-d$_6$): δ 9.25 (s, 1H), 8.67 (s, 1H), 5.00-4.97 (d, J = 8.10 Hz, 1H), 4.08-4.00 (m, 1H), 3.88-3.79 (m, 1H), 3.41-3.14 (m, 2H), 2.77-2.65 (m, 5H), 2.01-2.00 (d, J = 2.10 Hz, 3H). |
| 122 | 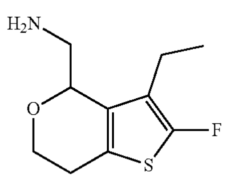 | HCl | LC-MS: m/z 216 (MH$^+$); $^1$H NMR (CD$_3$OD): δ 4.91-4.85 (m, 1H), 4.20-4.12 (m, 1H), 3.91-3.84 (m, 1H), 3.29-3.17 (m, 2H), 2.79-2.72 (m, 2H), 2.57-2.43 (m, 2H), 1.22-1.15 (m, 3H). |
| 123 | 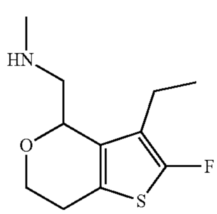 | HCl | LC-MS: m/z 230 (MH$^+$); $^1$H NMR (CD$_3$OD): δ 4.98-4.94 (m, 1H), 4.22-4.14 (m, 1H), 3.92-3.84 (m, 1H), 3.36-3.33 (m, 2H), 2.80-2.69 (m, 5H), 2.62-2.51 (m, 1H), 2.50-2.35 (m, 1H), 1.22-1.17 (t, J = 7.55 Hz, 3H). |
| 124 | 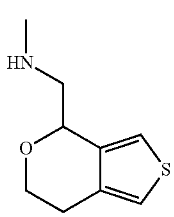 | HCl | $^1$H NMR (CD$_3$OD): δ 7.20 (d, J = 2.0 Hz, 1H), 7.13 (d, J = 2.5 Hz, 1H), 4.96 (d, J = 7.0 Hz, 1H), 4.23-4.19 (m, 1H), 3.70 (td, J = 4.0, 11.0 Hz, 1H), 3.49 (dd, J = 3.0, 13.0 Hz, 1H), 3.22 (dd, J = 8.5, 13.0 Hz, 1H), 2.94-2.86 (m, 1H), 2.81-2.75 (m, 1H) 2.69 (s, 3H). |

-continued

| Compd. No. | Structure | Salt or FB* | Analytical Data |
|---|---|---|---|
| 125 | 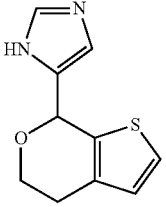 [SMILES: c1ncc(C2OCCc3ccsc32)[nH]1] | HCl | LC-MS (6 minute method): 1.17 min, M⁺ 207 @ 1.1 min; $^1$H NMR (CD$_3$OD-d$^4$): δ 7.61 (s, 1H), 7.16 (d, J = 4.76 Hz, 1H), 7.03 (s, 1H), 6.81 (d, J = 5.13 Hz, 1H), 5.94 (s, 1H), 4.16-4.12 (m, 1H), 3.93-3.86 (m, 1H), 2.87-2.80 (m, 1H), 2.74-2.68 (m, 1H). |
| 126 | 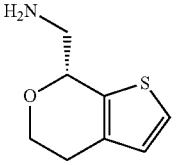 [SMILES: NC[C@H]1OCCc2ccsc21] | HCl | $^1$H NMR (CD$_3$OD): δ 7.34 (d, J = 5.13 Hz, 1H), 6.89 (d, J = 5.13 Hz, 1H), 5.06 (s, 1H), 4.25-4.22 (m, 1H), 3.83-3.77 (m, 1H), 3.38 (d, J = 13.2 Hz, 1H), 3.16-3.12 (m, 1H), 2.85-2.83 (m, 1H), 2.68-2.65 (m, 1H). |
| 127 | 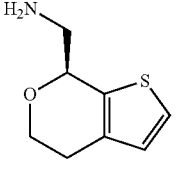 [SMILES: NC[C@@H]1OCCc2ccsc21] | HCl | $^1$H NMR (CD$_3$OD): δ 7.34 (d, J = 5.13 Hz, 1H), 6.89 (d, J = 5.13 Hz, 1H), 5.06 (s, 1H), 4.25-4.22 (m, 1H), 3.83-3.77 (m, 1H), 3.38 (d, J = 13.2 Hz, 1H), 3.16-3.12 (m, 1H), 2.85-2.83 (m, 1H), 2.68-2.65 (m, 1H). |
| 128 | 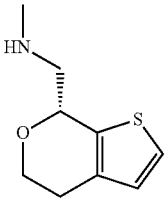 | HCl | $^1$H NMR (CD$_3$OD): δ 7.36 (d, J = 5.13 Hz, 1H), 6.89 (d, J = 4.76 Hz, 1H), 5.14-5.11 (m, 1H), 4.27-4.22 (m, 1H), 3.84-3.77 (m, 1H), 3.49-3.45 (m, 1H), 3.26-3.23 (m, 1H), 2.89-2.81 (m, 1H), 2.73 (s, 3H), 2.70-2.64 (m, 1H). |
| 129 | 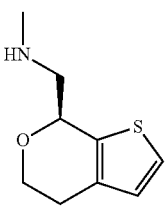 | HCl | $^1$H NMR (CD$_3$OD): δ 7.36 (d, J = 5.13 Hz, 1H), 6.89 (d, J = 4.76 Hz, 1H), 5.14-5.11 (m, 1H), 4.27-4.22 (m, 1H), 3.84-3.77 (m, 1H), 3.49-3.45 (m, 1H), 3.26-3.23 (m, 1H), 2.89-2.81 (m, 1H), 2.73 (s, 3H), 2.70-2.64 (m, 1H). |
| 130 | 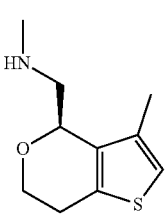 | HCl | $^1$H NMR (DMSO-d$^6$): δ 9.11 (br s, 1H), 8.59 (br s, 1H), 7.00 (s, 1H), 5.05-5.03 (d, J = 6.63 Hz, 1H), 4.04-3.96 (m, 1H), 3.87-3.80 (m, 1H), 3.28-3.21 (m, 2H), 2.83-2.74 (m, 2H), 2.61-2.59 (d, J = 1.68 Hz, 3H), 2.13 (s, 3H). |
| 131 | 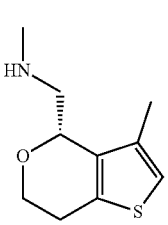 | HCl | $^1$H NMR (DMSO-d$^6$): δ 9.11 (br s, 1H), 8.59 (br s, 1H), 7.00 (s, 1H), 5.05-5.03 (d, J = 6.63 Hz, 1H), 4.04-3.96 (m, 1H), 3.87-3.80 (m, 1H), 3.28-3.21 (m, 2H), 2.83-2.74 (m, 2H), 2.61-2.59 (d, J = 1.68 Hz, 3H), 2.13 (s, 3H). |

-continued

| Compd. No. | Structure | Salt or FB* | Analytical Data |
|---|---|---|---|
| 132 | 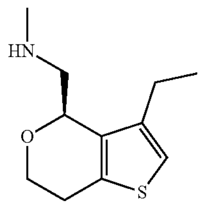 | HCl | ¹H NMR (DMSO-d⁶): δ 9.16 (br s, 1H), 8.58 (s, 1H), 7.02 (s, 1H), 5.07-5.05 (d, J = 8.07 Hz, 1H), 4.05-3.97 (m, 1H), 3.87-3.80 (m, 1H), 3.27-3.15 (m, 2H), 2.90-2.73 (m, 2H), 2.60 (s, 3H), 2.47-2.41 (m, 2H), 1.22-1.17 (t, J = 7.40 Hz, 3H). |
| 133 | 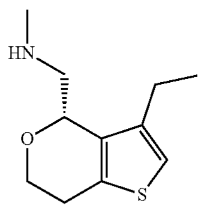 | HCl | ¹H NMR (DMSO-d⁶): δ 9.16 (br s, 1H), 8.58 (s, 1H), 7.02 (s, 1H), 5.07-5.05 (d, J = 8.07 Hz, 1H), 4.05-3.97 (m, 1H), 3.87-3.80 (m, 1H), 3.27-3.15 (m, 2H), 2.90-2.73 (m, 2H), 2.60 (s, 3H), 2.47-2.41 (m, 2H), 1.22-1.17 (t, J = 7.40 Hz, 3H). |
| 134 | 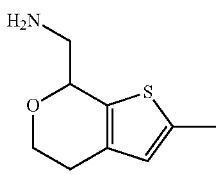 | HCl | LC-MS: m/z 184 (MH⁺); ¹H NMR (DMSO-d₆): δ 8.15 (s, 3H), 6.61 (s, 1H), 4.98-4.96 (d, J = 8.10 Hz, 1H), 4.12-4.03 (m, 1H), 3.77-3.66 (m, 1H), 3.23-3.14 (m, 1H), 2.98 (s, 1H), 2.85-2.62 (m, 2H), 2.40 (s, 3H). |
| 135 | 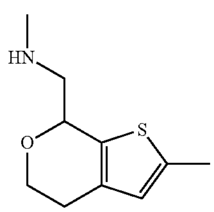 | HCl | LC-MS: m/z 198 (MH⁺); ¹H NMR (DMSO-d₆): δ 9.17 (s, 1H), 8.75 (s, 1H), 6.62-6.61 (s, J = 0.95 Hz, 1H), 4.13-4.06 (m, 1H), 5.09-5.06 (d, J = 9.06 Hz, 1H), 3.78-3.70 (m, 1H), 3.30-3.08 (m, 2H), 2.69-2.52 (m, 5H), 2.40 (s, 3H). |
| 136 | 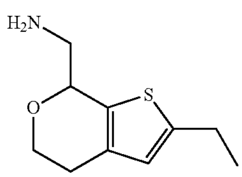 | HCl | LC-MS: m/z 198 (MH⁺); ¹H NMR (DMSO-d₆): δ 8.23 (s, 3H), 6.65 (s, 1H), 5.00-4.97 (d, J = 7.85 Hz, 1H), 4.13-4.06 (m, 1H), 3.77-3.69 (m, 1H), 3.16-3.11 (m, 1H), 3.03-2.93 (m, 1H), 2.79-2.70 (m, 2H), 2.67-2.58 (m, 2H), 1.23-1.18 (t, J = 7.50 Hz, 3H). |
| 137 | 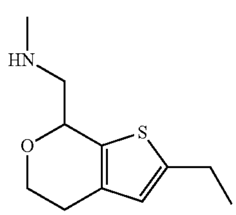 | HCl | LC-MS: m/z 212 (MH⁺); ¹H NMR (DMSO-d₆ + D₂O): δ 6.64 (s, 1H), 5.02-5.00 (d, J = 7.82 Hz, 1H), 4.10-4.05 (m, 1H), 3.77-3.69 (m, 1H), 3.31-3.26 (m, 1H), 3.18-3.11 (m, 1H), 2.78-2.70 (m, 2H), 2.66-2.63 (m, 5H), 1.21-1.16 (t, J = 7.56 Hz, 3H). |
| 138 | 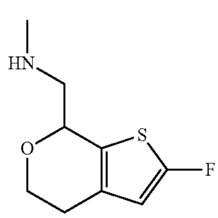 | HCl | LC-MS: m/z 202 (MH⁺); ¹H NMR (DMSO-d₆): δ 9.31-9.29 (d, J = 6.24 Hz, 1H), 8.85 (s, 1H), 6.59 (s, 1H), 5.06-5.03 (d, J = 8.79 Hz, 1H), 4.13-4.09 (m, 1H), 3.81-3.79 (m, 1H), 3.25-3.20 (m, 2H), 2.72-2.57 (m, 5H). |

| Compd. No. | Structure | Salt or FB* | Analytical Data |
|---|---|---|---|
| 139 | 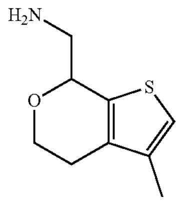 | HCl | LC-MS: m/z 184 (MH$^+$); $^1$H NMR (DMSO-d$_6$): δ 8.06 (s, 3H), 7.10 (s, 1H), 5.02-4.99 (d, J = 8.93 Hz, 1H), 4.19-1.13 (m, 1H), 3.80-3.72 (m, 1H), 3.22-3.14 (m, 1H), 2.99-2.89 (m, 1H), 2.65-2.60 (m, 2H), 2.05 (s, 3H). |
| 140 | 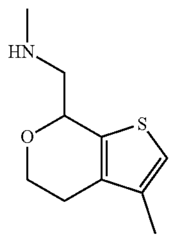 | HCl | LC-MS: m/z 198 (MH$^+$); $^1$H NMR (DMSO-d$_6$): δ 8.87 (s, 2H), 7.11 (s, 1H), 5.11-5.08 (d, J = 9.64 Hz, 1H), 4.02-4.13 (m, 1H), 3.82-3.74 (m, 1H), 3.35 (s, 1H), 3.20-3.12 (m, 1H), 2.60-2.50 (m, 5H), 2.09 (s, 3H). |
| 141 | 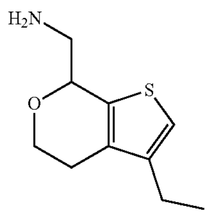 | HCl | LC-MS: m/z 198 (MH$^+$); $^1$H NMR (DMSO-d$_6$): δ 8.21 (s, 3H), 7.10 (s, 1H), 5.03-5.00 (d, J = 8.15 Hz, 1H), 4.18-4.12 (m, 1H), 3.80-3.72 (m, 1H), 3.20-3.18 (m, 1H), 2.99 (s, 1H), 2.68-2.60 (m, 3H), 2.45-2.43 (m, 1H), 1.18-1.14 (t, J = 7.59 Hz, 3H). |
| 142 | 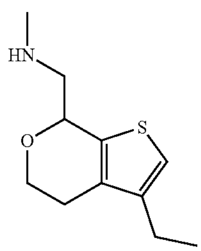 | HCl | LC-MS: m/z 212 (MH$^+$); $^1$H NMR (DMSO-d$_6$ + D$_2$O): δ 7.08 (s, 1H), 5.05 (d, J = 10 Hz, 1H), 4.21-4.11 (m, 1H), 3.80-3.65 (m, 2H), 3.35-3.12 (m, 2H), 2.67-2.35 (m, 6H), 1.19-1.14 (t, J = 7.49 Hz, 3H). |
| 143 | 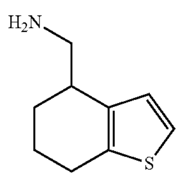 [SMILES: NCC1CCCc2sccc21] | HCl | $^1$H NMR (CD$_3$OD): δ 7.20 (d, J = 1.5 Hz, 1H), 6.90 (d, J = 1.5 Hz, 1H), 3.33-3.30 (m, 1H), 3.08 (m, 1H), 2.99 (dd, J = 2.5, 3.0 Hz, 1H), 2.80 (apt, J = 1.5 Hz, 2H), 2.02-1.87 (m, 2H), 1.85-1.81 (m, 1H), 1.71-1.64 (m, 1H). |
| 144 | 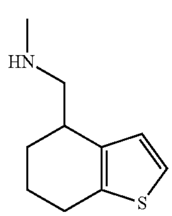 | HCl | $^1$H NMR (CD$_3$OD): δ 7.21 (d, J = 1.5 Hz, 1H), 6.92 (d, J = 1.5 Hz, 1H), 3.36 (dd, J = 3.0, 1.0 Hz, 1H), 3.14 (m, 1H), 3.09 (dd, J = 3.0, 2.5 Hz, 1H), 2.80 (apt, J = 1.5 Hz, 2H), 2.75 (s, 3H), 2.03-1.95 (m, 2H), 1.88-1.81 (m, 1H), 1.72-1.65 (m, 1H). |
| 145 | 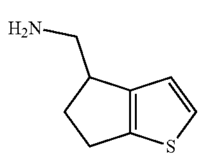 | HCl | LC-MS: m/z 154 (MH$^+$); $^1$H NMR (DMSO-d$_6$) δ 8.10-7.98 (d, J = 9.68 Hz, 2H), 7.39-7.38 (d, J = 3.95 Hz, 1H), 6.98-6.96 (d, J = 5.10 Hz, 1H), 3.35-3.30 (m, 1H), 3.16-3.11 (m, 1H), 2.97-2.79 (m, 3H), 2.70-2.61 (m, 1H), 2.27-2.22 (m, 1H). |

| Compd. No. | Structure | Salt or FB* | Analytical Data |
|---|---|---|---|
| 146 | | HCl | LC-MS: m/z 168 (MH⁺); ¹H NMR (CD₃OD): | δ 7.33-7.31 (d, J = 4.20 Hz, 1H), 6.91-6.90 (d, J = 4.52 Hz, 1H), 3.49-3.32 (m, 2H), 3.11-2.80 (m, 4H), 2.76 (s, 3H), 2.35-2.24 (m, 1H). |
| 147 | | HCl | LC-MS: m/z 228 (MH⁺); ¹H NMR (DMSO-d₆): | ⌐ δ 9.56-9.53 (d, J = 7.21 Hz, 1H), 8.38-8.29 (m, 1H), 6.76-6.75 (d, J = 2.46 Hz, 1H), 3.96-3.92 (t, J = 5.45 Hz, 2H), 3.33-3.13 (m, 3H), 2.87-2.81 (m, 1H), 2.74-2.62 (m, 2H), 1.93-1.83 (m, 3H), 1.72-1.67 (m, 1H). |
| 148 | 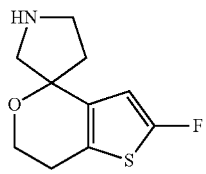 [SMILES: Fc1cc2c(s1)CCOC21CCNC1] | HCl | LC-MS: m/z 214 (MH⁺); ¹H NMR (CD₃OD): ⁻ δ 9.90 (s, 1H), 9.40 (s, 1H), 6.80-6.79 (d, J = 2.42 Hz, 1H), 3.98-3.86 (t, J = 5.51 Hz, 2H), 3.44-3.39 (m, 2H), 2.30-3.21 (m, 2H), 2.71-2.67 (t, J = 5.01 Hz, 2H), 2.26-2.21 (m, 2H). |
| 149 | 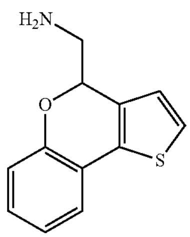 [SMILES: NCC1Oc2ccccc2-c2sccc21] | HCl | LC-MS: m/z 218 (MH⁺); ¹H NMR (D₂O): ⌐δ 7.35-7.30 (m, 2H), 7.16-7.11 (m, 1H), 6.97-6.87 (m, 3H), 5.65-5.63 (m, 1H), 3.33-3.31 (m, 3H). |
| 150 | | HCl | LC-MS: m/z 232 (MH⁺); ¹H NMR (DMSO-d₆): | δ 9.25 (s, 1H), 8.99 (s, 1H), 7.70-7.62 (d, J = 5.10 Hz, 1H), 7.12-7.33 (dd, J = 7.47 Hz, 1.50 Hz, 1H), 7.22-7.17 (m, 1H), 7.13-7.10 (d, J = 5.07 Hz, 1H), 7.07-7.00 (m, 2H), 5.85-5.81 (dd, J = 9.36 Hz, 2.75 Hz, 1H), 3.50-3.39 (m, 2H), 2.80 (s, 3H). |
| 151 | 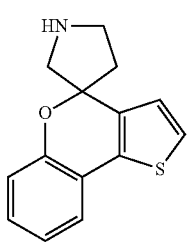 [SMILES: c1ccc2c(c1)OC1(CCNC1)c1ccsc1-2] | HCl | LC-MS: m/z 244 (MH⁺); ¹H NMR (DMSO-d₆): ⌐ δ 10.16-10.14 (d, J = 3.60 Hz, 1H), 9.97 (s, 1H), 7.66-7.64 (d, J = 5.13 Hz, 1H), 7.41-7.38 (m, 1H), 7.25-7.20 (m, 1H), 7.05-7.01 (m, 2H), 3.67-3.63 (m, 1H), 3.59-3.43 (m, 3H), 2.44-2.33 (m, 2H). |
| 152 | 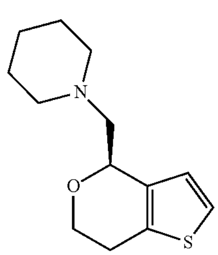 [SMILES: c1cc2c(s1)CCO[C@H]2CN1CCCCC1] | HCl | LC-MS (6 minute method): 1.17 min, M⁺ 238 @ 1.21 min; ¹H NMR (CDCl₃): δ 7.10-7.09 (d, J = 5.1 Hz, 1H), 6.91-6.89 (d, J = 5.1 Hz, 1H), 4.90-4.84 (m, 1H), 4.27-4.21 (m, 1H), 3.81-3.73 (m, 1H), 3.04-2.94 (m, 1H), 2.78-2.70 (m, 1H), 2.67-2.62 (m, 2H), 2.55-2.52 (m, 4H), 1.69-1.59 (m, 4H), 1.50-1.43 (m, 2H). |

-continued

| Compd. No. | Structure | Salt or FB* | Analytical Data |
|---|---|---|---|
| 153 | 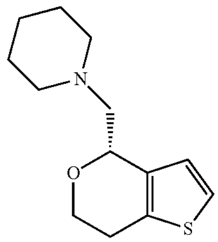 [SMILES: c1cc2c(s1)CCO[C@@H]2CN1CCCCC1] | HCl | LC-MS (6 minute method): 1.17 min, M+ 238 @ 1.21 min; ¹H NMR (CDCl₃): δ 7.10-7.09 (d, J = 5.1 Hz, 1H), 6.91-6.89 (d, J = 5.1 Hz, 1H), 4.90-4.84 (m, 1H), 4.27-4.21 (m, 1H), 3.81-3.73 (m, 1H), 3.04-2.94 (m, 1H), 2.78-2.70 (m, 1H), 2.67-2.62 (m, 2H), 2.55-2.52 (m, 4H), 1.69-1.59 (m, 4H), 1.50-1.43 (m, 2H). |
| 154 | 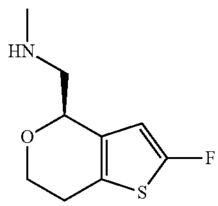 | HCl | ¹H NMR (CD₃OD): δ 6.40 (d, J = 2.0 Hz, 1H), 4.86 (m, 1H), 4.28-4.23 (m, 1H), 3.90-3.84 (m, 1H), 3.45 (dd, J = 2.5, 13.0 Hz, 1H), 3.23 (dd, J = 8.5, 13.0 Hz, 1H), 2.93-2.85 (m, 1H), 2.73 (s, 3H), 2.63 (dd, J = 2.0, 6.0 Hz, 1H). |
| 155 | 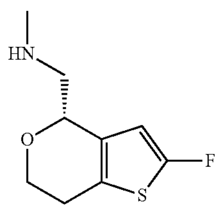 | HCl | ¹H NMR (CD₃OD): δ 6.40 (d, J = 2.0 Hz, 1H), 4.86 (m, 1H), 4.28-4.23 (m, 1H), 3.90-3.84 (m, 1H), 3.45 (dd, J = 2.5, 13.0 Hz, 1H), 3.23 (dd, J = 8.5, 13.0 Hz, 1H), 2.93-2.85 (m, 1H), 2.73 (s, 3H), 2.63 (dd, J = 2.0, 6.0 Hz, 1H). |
| 156 | 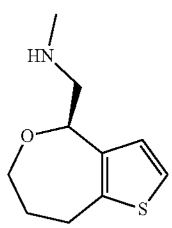 | HCl | ¹H NMR (CD₃OD): δ 7.10 (d, J = 5.0 Hz, 1H), 6.84 (d, J = 5.0 Hz, 1H), 4.82 (dd, J = 3.0, 10.5 Hz, 1H), 4.33 (dt, J = 4.5, 12.5 Hz, 1H), 3.93-3.86 (m, 1H), 3.59 (dd, J = 2.5, 12.5 Hz, 1H), 3.39-3.33 (m, 1H), 3.15-3.08 (m, 1H), 3.01-2.80 (m, 1H), 2.78 (s, 3H), 1.99-1.88 (m, 2H). |
| 157 | 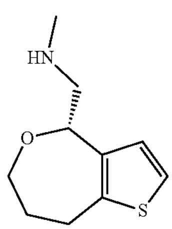 | HCl | ¹H NMR (CD₃OD): δ 7.10 (d, J = 5.0 Hz, 1H), 6.84 (d, J = 5.0 Hz, 1H), 4.82 (dd, J = 3.0, 10.5 Hz, 1H), 4.33 (dt, J = 4.5, 12.5 Hz, 1H), 3.93-3.86 (m, 1H), 3.59 (dd, J = 2.5, 12.5 Hz, 1H), 3.39-3.33 (m, 1H), 3.15-3.08 (m, 1H), 3.01-2.80 (m, 1H), 2.78 (s, 3H), 1.99-1.88 (m, 2H). |
| 158 | 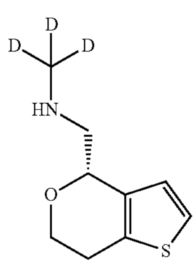 | HCl | LC-MS (6 minute method): 0.19 min, M+ 187 @ 0.38 min; ¹H NMR (CD₃OD): δ 7.28 (d, J = 5.13 Hz, 1H), 6.90 (d, J = 5.13 Hz, 1H), 5.04-5.00 (m, 1H), 4.29-4.24 (m, 1H), 3.85-3.79 (m, 1H), 3.56 (dd, J = 2.57, 12.8 Hz, 1H), 3.31-3.21 (m, 1H), 3.04-2.96 (m, 1H), 2.84-2.78 (m, 1H). |
| 159 | 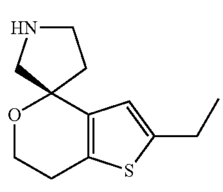 | HCl | LC-MS (6 minute method): 2.03 min, M+ 224 @ 2.13 min; ¹H NMR (CD₃OD): δ 6.65 (s, 1H), 3.97-3.89 (m, 2H), 3.57-3.47 (m, 3H), 3.34 (d, J = 12.1 Hz, 1H), 2.78-2.73 (m, 4H), 2.32-2.28 (m, 2H), 1.24 (t, J = 7.70 Hz, 3H). |

-continued

| Compd. No. | Structure | Salt or FB* | Analytical Data |
|---|---|---|---|
| 160 | 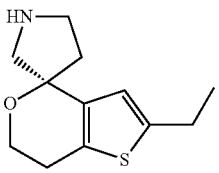 | HCl | LC-MS (6 minute method): 2.03 min, M⁺ 224 @ 2.13 min; $^1$H NMR (CD$_3$OD): δ 6.65 (s, 1H), 3.97-3.89 (m, 2H), 3.57-3.47 (m, 3H), 3.34 (d, J = 12.1 Hz, 1H), 2.78-2.73 (m, 4H), 2.32-2.28 (m, 2H), 1.24 (t, J = 7.70 Hz, 3H). |
| 161 | 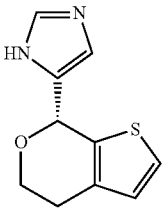 | HCl | LC-MS (6 minute method): 1.42 min, M⁺ 207 @ 1.41 min; $^1$H NMR (CD$_3$OD): δ 7.61 (s, 1H), 7.16 (d, J = 4.76 Hz, 1H), 7.03 (s, 1H), 6.81 (d, J = 5.13 Hz, 1H), 5.94 (s, 1H), 4.16-4.12 (m, 1H), 3.93-3.86 (m, 1H), 2.87-2.80 (m, 1H), 2.74-2.68 (m, 1H). |
| 162 | 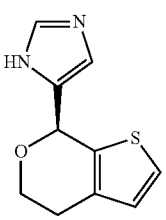 [SMILES: c1ncc([C@@H]2OCCc3ccsc32)[nH]1] | HCl | LC-MS (6 minute method): 1.42 min, M⁺ 207 @ 1.41 min; $^1$H NMR (CD$_3$OD): δ 7.61 (s, 1H), 7.16 (d, J = 4.76 Hz, 1H), 7.03 (s, 1H), 6.81 (d, J = 5.13 Hz, 1H), 5.94 (s, 1H), 4.16-4.12 (m, 1H), 3.93-3.86 (m, 1H), 2.87-2.80 (m, 1H), 2.74-2.68 (m, 1H). |
| 163 | 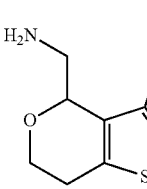 | HCl | LC-MS: m/z 204 (MH⁺); $^1$H NMR (DMSO-d$_6$): δ 8.06 (s, 3H), 7.08 (s, 1H), 4.82-4.80 (d, J = 6.95 Hz, 1H), 4.15-4.11 (m, 1H), 3.80-3.77 (m, 1H), 3.03-2.96 (m, 1H), 2.88-2.68 (m, 3H). |
| 164 | 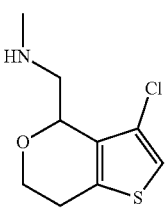 | HCl | LC-MS: m/z 218 (MH⁺); $^1$H NMR (CD$_3$OD):☐δ 6.84 (s, 1H), 4.94-4.91 (m, 1H), 4.31-4.24 (m, 1H), 3.91-3.82 (m, 1H), 3.52-3.48 (m, 1H), 3.29-3.22 (m, 2H), 3.00-2.89 (m, 1H), 2.75 (s, 3H) |
| 165 | 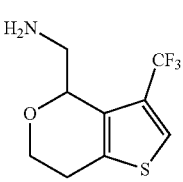 [SMILES: NCC1OCCc2scc(C(F)(F)F)c21] | HCl | LC-MS: m/z 238 (MH⁺); $^1$H NMR (CD$_3$OD): δ 7.45 (s, 1H), 4.97-4.94 (m, 1H), 4.35-4.28 (m, 1H), 3.92-3.83 (m, 1H), 3.56-3.51 (dd, J = 13.12 Hz, 2.68 Hz, 1H), 3.23-3.02 (dd, J = 13.10 Hz, 18.16 Hz, 1H), 3.07-3.04 (m, 1H), 2.92-2.86 (m, 1H). |
| 166 | 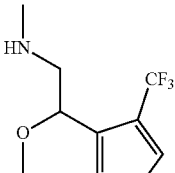 | HCl | LC-MS: m/z 252 (MH⁺); $^1$H NMR (CDCl$_3$): | δ 9.43 (s, 1H), 8.89 (s, 1H), 5.35-5.33 (d, J = 8.46 Hz, 1H), 4.27-4.23 (m, 1H), 3.94-3.86 (m, 1H), 3.55-3.52 (d, J = 9.27 Hz, 1H), 3.17-3.12 (m, 2H), 3.09-3.03 (m, 1H), 2.85 (s, 3H), 2.80 (s, 1H). |

-continued

| Compd. No. | Structure | Salt or FB* | Analytical Data |
|---|---|---|---|
| 167 | 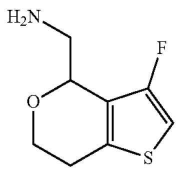 | HCl | LC-MS: m/z 188 (MH+); 1H NMR (D2O): δ 6.27-6.26 (d, J = 2.15 Hz, 1H), 4.85-4.84 (m, 1H), 4.15-4.09 (m, 1H), 3.84-3.76 (m, 1H), 3.34-3.18 (m, 2H), 2.82-2.72 (m, 1H), 2.64-2.50 (m, 1H). |
| 168 | 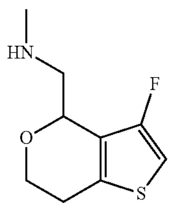 | HCl | LC-MS: m/z 202 (MH+); 1H NMR (DMSO-d6): δ 9.28 (brs, 1H), 8.73 (brs, 1H), 6.64-6.63 (d, J = 2.11 Hz, 1H), 4.93-4.90 (m, 1H), 4.17-4.10 (m, 1H), 3.85-3.77 (m, 1H), 3.17-3.06 (m, 1H), 2.83-2.73 (m, 3H), 2.62-2.51 (m, 3H). |
| 169 | 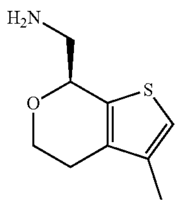 | HCl | LC-MS: m/z 184 (MH+); 1H NMR (DMSO-d6): δ 8.06 (s, 3H), 7.10 (s, 1H), 5.02-4.99 (d, J = 8.93 Hz, 1H), 4.19-1.13 (m, 1H), 3.80-3.72 (m, 1H), 3.22-3.14 (m, 1H), 2.99-2.89 (m, 1H), 2.65-2.60 (m, 2H), 2.05 (s, 3H). |
| 170 | 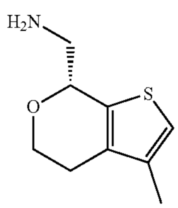 | HCl | LC-MS: m/z 184 (MH+); 1H NMR (DMSO-d6): δ 8.06 (s, 3H), 7.10 (s, 1H), 5.02-4.99 (d, J = 8.93 Hz, 1H), 4.19-1.13 (m, 1H), 3.80-3.72 (m, 1H), 3.22-3.14 (m, 1H), 2.99-2.89 (m, 1H), 2.65-2.60 (m, 2H), 2.05 (s, 3H). |
| 171 | 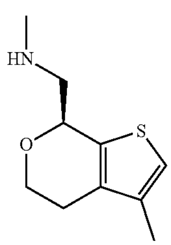 | HCl | LC-MS (6 minute method): 0.46 min, M+ 198 @ 0.48 min; 1H NMR (CD3OD): δ 6.99 (s, 1H), 5.12-5.09 (m, 1H), 4.32-4.27 (m, 1H), 3.86-3.80 (m, 1H), 3.49-3.45 (m, 1H), 3.25 (dd, J = 8.43, 12.83 Hz, 1H), 2.74 (s, 3H), 2.73-2.68 (m, 1H), 2.58-2.52 (m, 1H), 2.15 (s, 3H). |
| 172 | 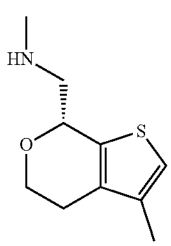 | HCl | LC-MS (6 minute method): 0.46 min, M+ 198 @ 0.48 min; 1H NMR (CD3OD): δ 6.99 (s, 1H), 5.12-5.09 (m, 1H), 4.32-4.27 (m, 1H), 3.86-3.80 (m, 1H), 3.49-3.45 (m, 1H), 3.25 (dd, J = 8.43, 12.83 Hz, 1H), 2.74 (s, 3H), 2.73-2.68 (m, 1H), 2.58-2.52 (m, 1H), 2.15 (s, 3H). |
| 173 | 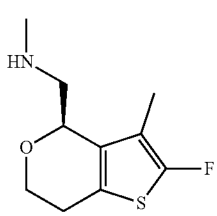 | HCl | LC-MS: m/z 216 (MH+); 1H NMR (DMSO-d6): δ 9.25 (s, 1H), 8.67 (s, 1H), 5.00-4.97 (d, J = 8.10 Hz, 1H), 4.08-4.00 (m, 1H), 3.88-3.79 (m, 1H), 3.41-3.14 (m, 2H), 2.77-2.65 (m, 5H), 2.01-2.00 (d, J = 2.10 Hz, 3H). |

-continued

| Compd. No. | Structure | Salt or FB* | Analytical Data |
|---|---|---|---|
| 174 | 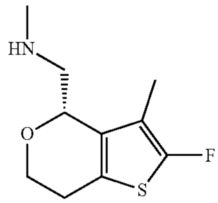 | HCl | LC-MS: m/z 216 (MH+); 1H NMR (DMSO-d6): δ 9.25 (s, 1H), 8.67 (s, 1H), 5.00-4.97 (d, J = 8.10 Hz, 1H), 4.08-4.00 (m, 1H), 3.88-3.79 (m, 1H), 3.41-3.14 (m, 2H), 2.77-2.65 (m, 5H), 2.01-2.00 (d, J = 2.10 Hz, 3H). |
| 175 | 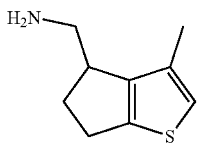 | HCl | LC-MS: m/z 168 (MH+); 1H NMR (DMSO-d6): δ 8.11 (s, 3H), 6.96 (s, 1H), 3.31-3.25 (m, 1H), 3.08-3.02 (m, 1H), 2.97-2.94 (m, 1H), 2.80-2.65 (m, 2H), 2.61-2.53 (m, 1H), 2.43-2.34 (m, 1H), 2.13-2.13 (d, J = 0.84 Hz, 3H). |
| 176 | 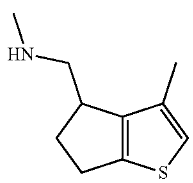 | HCl | LC-MS: m/z 182 (MH+); 1H NMR (CD3OD): δ 6.89 (s, 1H), 3.33-3.32 (m, 1H), 3.31-3.28 (m, 1H), 3.09-2.97 (m, 2H), 2.93-2.83 (m, 1H), 2.81-2.68 (m, 4H), 2.44-2.22 (m, 1H), 2.22 (s, 3H). |
| 177 | 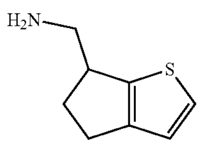 | HCl | LC-MS: m/z 154 (MH+); 1H NMR (DMSO-d6): δ 8.23 (s, 3H), 7.44-7.43 (d, J = 4.50 Hz, 1H), 6.87-6.86 (d, J = 4.85 Hz, 1H), 3.51 (s, 1H), 3.05 (s, 1H), 2.79-2.56 (m, 4H), 2.35-2.24 (m, 1H). |
| 178 | 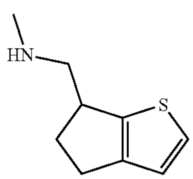 | HCl | LC-MS: m/z 168 (MH+); 1H NMR (DMSO-d6): δ 9.07-9.06 (m, 2H), 7.45-7.44 (d, J = 4.88 Hz, 1H), 6.88-6.86 (d, J = 4.86 Hz, 1H), 3.60-3.58 (d, J = 3.39 Hz, 1H), 3.20-3.13 (m, 1H), 2.97-2.86 (m, 1H), 2.81-2.60 (m, 3H), 2.57-2.53 (m, 3H), 2.43-2.31 (m, 1H). |
| 179 | 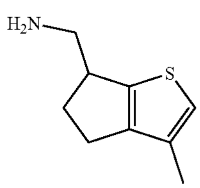 | HCl | LC-MS: m/z 168 (MH+); 1H NMR (DMSO-d6): δ 8.10 (s, 3H), 7.02 (s, 1H), 3.09-3.01 (m, 2H), 2.84-2.75 (m, 2H), 2.69-2.54 (m, 3H), 2.33-2.21 (m, 1H), 2.09-2.08 (d, J = 0.93 Hz, 3H). |
| 180 | 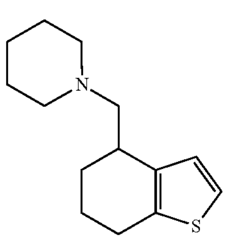 [SMILES: c1cc2c(s1)CCCC2CN1CCCCC1] | HCl | LC-MS: m/z 236 (MH+); 1H NMR (DMSO-d6): δ 7.27-7.26 (d, J = 3.99 Hz, 1H), 6.97-6.96 (d, J = 4.23 Hz, 1H), 3.62-3.57 (m, 1H), 3.34-3.21 (m, 3H), 3.10-3.02 (m, 1H), 2.91 (s, 2H), 2.68 (s, 2H), 1.77-1.72 (m, 9H), 1.38 (s, 1H). |
| 181 | 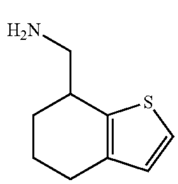 [SMILES: NCC1CCCc2ccsc21] | HCl | LC-MS: m/z 168 (MH+); 1H NMR (CDCl3): δ 7.11-7.10 (d, J = 5.07 Hz, 1H), 6.80-6.78 (d, J = 5.10 Hz, 1H), 2.99-2.89 (m, 3H), 2.70-2.60 (m, 2H), 2.05-1.71 (m, 1H), 1.77-1.59 (m, 1H), 1.44 (s, 2H). |

| Compd. No. | Structure | Salt or FB* | Analytical Data |
|---|---|---|---|
| 182 | | HCl | LC-MS: m/z 182 (MH$^+$); $^1$H NMR (CD$_3$OD): | δ 7.26-7.24 (d, J = 5.10 Hz, 1H), 6.82-6.81 (d, J = 5.10 Hz, 1H), 3.42-3.23 (m, 2H), 3.14-3.06 (m, 1H), 2.74 (s, 3H), 2.69-2.65 (m, 2H), 2.320-2.07 (m, 1H), 2.03-1.96 (m, 1H), 1.82-1.67 (m, 2H). |
| 183 | | HCl | LC-MS: m/z 236 (MH$^+$); $^1$H NMR (CD$_3$OD): | 7.15-7.14 (d, J = 5.15 Hz, 1H), 6.76-6.74 (d, J = 5.17 Hz, 1H), 4.09-4.05 (t, J = 12.90 Hz, 2H), 3.59-3.55 (t, J = 12.90 Hz, 2H), 3.43-3.36 (m, 1H), 3.19-3.17 (m, 1H), 3.12-3.01 (m, 1H), 2.64-2.61 (m, 2H), 1.96-1.90 (m, 2H), 1.72-1.51 (m, 6H), 1.50-1.43 (m, 2H). |
| 184 | 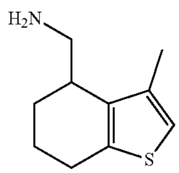 | HCl | LC-MS: m/z 182 (MH$^+$); $^1$H NMR (CD$_3$OD): δ 6.84 (s, 1H), 3.09-2.96 (m, 2H), 2.80-2.73 (m, 2H), 2.18 (s, 3H), 2.05-2.02 (m, 1H), 2.00-1.85 (m, 4H). |
| 185 | 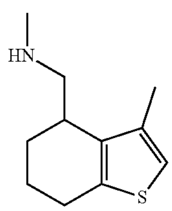 | HCl | LC-MS: m/z 196 (MH$^+$); $^1$H NMR (CD$_3$OD): δ 6.74 (s, 1H), 2.95 (d, J = 11.86 Hz, 1H), 2.83-2.76 (m, 1H), 2.74-2.68 (m, 2H), 2.65-2.60 (m, 1H), 2.52-2.45 (dd, J = 12.55 Hz, 6.96 Hz, 1H), 2.41 (s, 1H), 2.30-2.26 (d, J = 13.27 Hz, 1H), 2.21-2.20 (m, 1H), 2.182-2.179 (m, 3H), 1.89-1.81 (m, 2H), 1.67-1.58 (m, 1H). |
| 186 | 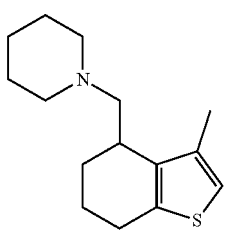 [SMILES: Cc1csc2c1C(CN1CCCCC1)CCC2] | HCl | LC-MS: m/z 250 (MH$^+$); $^1$H NMR (CD$_3$OD): δ 6.72 (s, 1H), 3.01-2.97 (d, J = 10.96 Hz, 1H), 2.82-2.62 (m, 3H), 2.52-2.45 (m, 3H), 2.30-2.20 (m, 2H), 2.17 (s, 3H), 1.91-1.81 (m, 2H), 1.72-1.49 (m, 8H). |
| 187 | 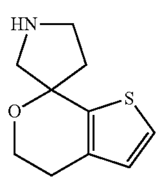 [SMILES: c1cc2c(s1)C1(CCNC1)OCC2] | HCl | LC-MS: m/z 195 (MH$^+$); $^1$H NMR (CD$_3$OD): δ 7.42-7.40 (d, J = 5.1 Hz, 1H), 6.90-6.89 (d, J = 5.1 Hz, 1H), 4.05-3.95 (m, 2H), 3.71-3.70 (m, 1H), 3.67-3.55 (m, 2H), 3.39-3.35 (m, 1H), 2.80-2.79 (m, 2H), 2.55-2.48 (m, 1H), 2.39-2.84 (m, 1H). |
| 188 | 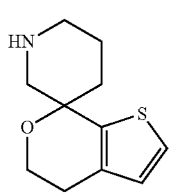 [SMILES: c1cc2c(s1)C1(CCCNC1)OCC2] | HCl | LC-MS: m/z 209 (MH$^+$); $^1$H NMR (DMSO-d$_6$): δ 9.26-9.23 (d, J = 8.75 Hz, 1H), 8.41-8.32 (m, 1H), 7.49-7.44 (dd, J = 8.75 Hz, 5.10 Hz, 1H), 6.91-6.88 (m, 1H), 3.94-3.90 (m, 2H), 3.94-3.92 (m, 1H), 3.19-3.15 (m, 2H), 3.07-2.99 (m, 1H), 2.73-2.61 (m, 2H), 2.01-1.80 (m, 3H), 1.71-1.67 (m, 1H). |

-continued

| Compd. No. | Structure | Salt or FB* | Analytical Data |
|---|---|---|---|
| 189 | 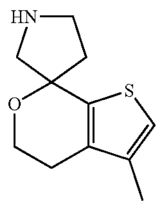 | HCl | LC-MS: m/z 209 (MH+); 1H NMR (D2O): δ 6.94 (s, 1H), 3.99-3.92 (m, 1H), 3.88-3.79 (m, 1H), 3.63-3.58 (m, 1H), 3.55-3.38 (m, 2H), 3.30-3.26 (m, 1H), 2.57-2.44 (m, 2H), 2.38-2.20 (m, 2H), 1.98 (s, 3H). |
| 190 | 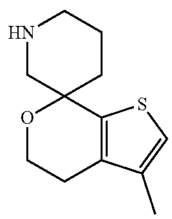 | HCl | LC-MS: m/z 223 (MH+); 1H NMR (D2O): δ 6.89 (s, 1H), 3.96-3.92 (m, 1H), 3.87-3.83 (m, 1H), 3.44-3.39 (d, J = 13.56 Hz, 1H), 3.24-3.20 (d, J = 12.30 Hz, 1H), 3.07-3.03 (d, J = 13.44 Hz, 1H), 2.89-2.81 (m, 1H), 2.48-2.47 (m, 2H), 1.96 (s, 3H), 1.90-1.78 (m, 3H), 1.72-1.67 (m, 1H). |
| 191 | 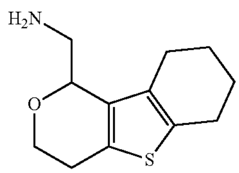 [SMILES: NCC1OCCc2sc3c(c21)CCCC3] | HCl | LC-MS: m/z 224 (MH+); 1H NMR (DMSO-d6): δ 8.22-8.16 (d, J = 13.20 Hz, 3H), 4.90-4.86 (t, J = 12.15 Hz, 1H), 4.01-3.94 (m, 1H), 3.82-3.75 (m, 1H), 3.05 (s, 2H), 2.72-2.66 (m, 4H), 2.41-2.32 (m, 2H), 1.86-1.83 (m, 2H), 1.71-1.53 (m, 2H). |
| 192 | 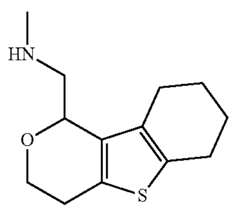 [SMILES: CNCC1OCCc2sc3c(c21)CCCC3] | HCl | LC-MS: m/z 238 (MH+); 1H NMR (DMSO-d6): δ 9.39-9.36 (d, J = 11.15 Hz, 1H), 8.70-8.64 (m, 1H), 5.01-4.98 (m, 1H), 4.03-3.95 (m, 1H), 3.83-3.76 (m, 1H), 3.17-3.02 (m, 2H), 2.79-2.57 (m, 7H), 2.50-2.42 (m, 2H), 1.85-1.82 (m, 2H), 1.70-1.51 (m, 2H). |
| 193 | 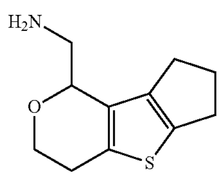 [SMILES: NCC1OCCc2sc3c(c21)CCC3] | HCl | LC-MS: m/z 210 (MH+); 1H NMR (DMSO-d6): δ 8.23 (s, 3H), 4.91-4.88 (d, J = 7.80 Hz, 1H), 4.10-4.03 (m, 1H), 3.79-3.71 (m, 1H), 3.15-3.10 (m, 1H), 3.01-2.92 (m, 1H), 2.88-2.70 (m, 4H), 2.62-2.58 (m, 2H), 2.39-2.31 (m, 2H). |
| 194 | 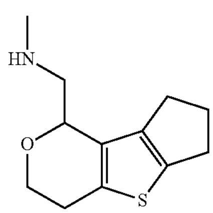 | HCl | LC-MS: m/z 224 (MH+); 1H NMR (DMSO-d6): δ 9.40 (s, 1H), 8.75 (s, 1H), 5.02-4.99 (d, J = 9.05 Hz, 1H), 4.10-4.03 (m, 1H), 3.81-3.73 (m, 1H), 3.24-3.01 (m, 2H), 2.86-2.71 (m, 4H), 2.68-2.50 (m, 5H), 2.42-2.35 (m, 2H). |
| 195 | 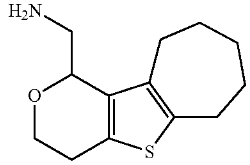 [SMILES: NCC1OCCc2sc3c(c21)CCCCC3] | HCl | LC-MS: m/z 238 (MH+); 1H NMR (DMSO-d6): δ 8.09 (s, 3H), 4.88-4.85 (d, J = 9.81 Hz, 1H), 3.97-3.78 (m, 2H), 3.55 (s, 2H), 3.12-3.06 (m, 1H), 2.91-2.70 (m, 1H), 2.68-2.56 (m, 4H), 1.91-1.73 (m, 2H), 1.56-1.47 (m, 4H). |

| Compd. No. | Structure | Salt or FB* | Analytical Data |
|---|---|---|---|
| 196 | 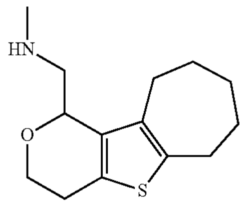 [SMILES: CNCC1OCCc2sc3c(c21)CCCCC3] | HCl | LC-MS: m/z 252 (MH$^+$); $^1$H NMR (D$_2$O): δ 4.91-4.89 (d, J = 7.82 Hz, 1H), 3.88-3.87 (d, J = 4.74 Hz, 1H), 3.74-3.70 (m, 1H), 3.28-3.21 (m, 1H), 3.13-3.08 (m, 1H), 2.63-2.52 (m, 7H), 2.33 (s, 2H), 1.68 (s, 2H), 1.43 (s, 4H). |
| 197 | 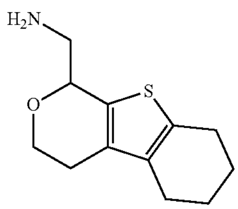 [SMILES: NCC1OCCc2c1sc1c2CCCC1] | HCl | LC-MS: m/z 224 (MH$^+$); $^1$H NMR (D$_2$O): δ 5.02-5.00 (d, J = 5.72 Hz, 1H), 4.13-4.06 (m, 1H), 3.77-3.69 (m, 1H), 3.36-3.30 (m, 1H), 3.19-3.12 (m, 1H), 2.65-2.42 (m, 3H), 2.36-1.68 (m, 3H), 1.66 (s, 4H). |
| 198 | 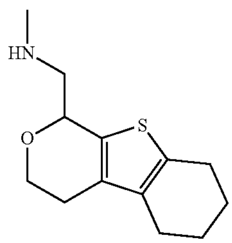 [SMILES: CNCC1OCCc2c1sc1c2CCCC1] | HCl | LC-MS: m/z 238 (MH$^+$); $^1$H NMR (D$_2$O): δ 5.06 (s, 1H), 4.12-4.09 (m, 1H), 3.74 (s, 1H), 3.40-3.36 (m, 1H), 3.27-3.21 (m, 1H), 2.67 (s, 3H), 2.61-2.51 (m, 3H), 2.43-2.33 (m, 3H), 1.68 (m, 4H). |
| 199 | 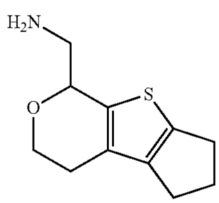 [SMILES: NCC1OCCc2c1sc1c2CCC1] | HCl | LC-MS: m/z 210 (MH$^+$); $^1$H NMR (DMSO-d$_6$): δ 8.14 (s, 3H), 4.98-4.95 (d, J = 8.71 Hz, 1H), 4.15-4.08 (m, 1H), 3.77-3.69 (m, 1H), 3.16-3.12 (m, 1H), 3.03-2.93 (m, 1H), 2.84-2.79 (m, 2H), 2.67-2.52 (m, 4H), 2.42-2.33 (m, 2H). |
| 200 | 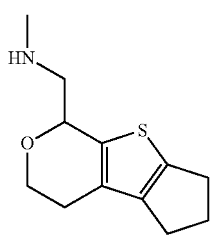 | HCl | LC-MS: m/z 224 (MH$^+$); $^1$H NMR (DMSO-d$_6$): δ 9.13 (s, 1H), 8.74-8.72 (d, J = 6.00 Hz, 1H), 5.09-5.05 (d, J = 9.20 Hz, 1H), 4.15-4.03 (m, 4H), 3.79-3.70 (m, 1H), 3.39-3.10 (m, 2H), 2.84-2.79 (m, 2H), 2.60-2.57 (t, J = 2.57 Hz, 4H), 2.42-2.33 (m, 2H). |
| 201 | 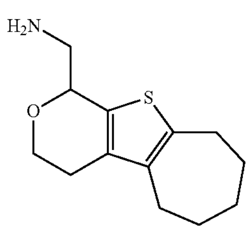 [SMILES: NCC1OCCc2c1sc1c2CCCCC1] | HCl | LC-MS: m/z 238 (MH$^+$); $^1$H NMR (DMSO-d$_6$): δ 8.30 (s, 3H), 4.96-4.93 (d, J = 7.92 Hz, 1H), 4.16-4.09 (m, 1H), 3.78-3.70 (m, 1H), 3.10-3.08 (m, 1H), 3.00-2.91 (m, 1H), 2.76-2.69 (m, 2H), 2.60-2.52 (m, 2H), 2.47-2.42 (m, 2H), 1.83-1.74 (m, 2H), 1.67-1.47 (m, 4H). |
| 202 | 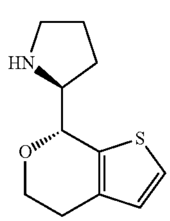 [SMILES: c1cc2c(s1)[C@@H]([C@@H]1CCCN1)OCC2] | HCl | LC-MS: m/z 210 (MH$^+$); $^1$H NMR (DMSO-d$_6$): δ 9.82-9.80 (d, J = 4.11 Hz, 1H), 8.86 (s, 1H), 7.51-7.49 (d, J = 5.04 Hz, 1H), 6.96-6.74 (d, J = 5.04 Hz, 1H), 5.03-5.00 (d, J = 7.17 Hz, 1H), 4.19-4.12 (m, 1H), 3.79-3.71 (m, 2H), 3.13 (s, 2H), 2.86-2.76 (m, 1H), 2.67-2.61 (m, 1H), 2.26-2.22 (m, 1H), 2.04-1.87 (m, 3H). |

-continued

| Compd. No. | Structure | Salt or FB* | Analytical Data |
|---|---|---|---|
| 203 | 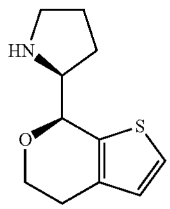 [SMILES: c1cc2c(s1)[C@H]([C@@H]1CCCN1)OCC2] | HCl | LC-MS: m/z 210 (MH$^+$); $^1$H NMR (DMSO-d$_6$): δ 10.19 (s, 1H), 8.90 (brs, 1H), 7.51-7.49 (dd, J = 5.01 Hz, 0.69 Hz, 1H), 6.94-6.93 (d, J = 5.01 Hz, 1H), 5.22-5.21 (d, J = 1.83 Hz, 1H), 4.25-4.20 (dd, J = 11.34 Hz, 5.31 Hz, 1H), 3.95 (s, 1H), 3.75-3.66 (td, J = 11.34 Hz, 3.60 Hz, 1H), 3.19-3.04 (m, 2H), 2.86-2.74 (m, 1H), 2.64-2.59 (m, 1H), 1.90-1.66 (m, 4H). |
| 204 | 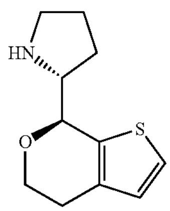 [SMILES: c1cc2c(s1)[C@H]([C@H]1CCCN1)OCC2] | HCl | LC-MS: m/z 210 (MH$^+$); $^1$H NMR (DMSO-d$_6$): δ 9.82 (s, 1H), 8.87 (s, 1H), 4.51-7.49 (d, J = 5.01 Hz, 1H), 6.96-6.94 (d, J = 5.04 Hz, 1H), 5.03-5.01 (d, J = 7.32 Hz, 1H), 4.19-4.12 (m, 1H), 3.79-3.70 (m, 2H), 3.13 (s, 2H), 2.86-2.76 (m, 1H), 2.67-2.61 (m, 1H), 2.26-2.22 (m, 1H), 2.04-1.87 (m, 3H). |
| 205 | 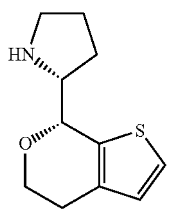 [SMILES: c1cc2c(s1)[C@@H]([C@H]1CCCN1)OCC2] | HCl | LC-MS: m/z 210 (MH$^+$); $^1$H NMR (DMSO-d$_6$): δ 10.23 (s, 1H), 8.90 (s, 1H), 7.51-7.49 (d, J = 5.78 Hz, 1H), 6.94-6.92 (s, J = 5.16 Hz, 1H), 5.22 (s, 1H), 4.25-4.19 (dd, J = 11.24 Hz, 5.45 Hz, 1H), 3.94 (s, 1H), 3.74-3.66 (td, J = 11.31 Hz, 3.57 Hz, 1H), 3.19-3.08 (m, 2H), 2.80-2.75 (m, 1H), 2.64-2.58 (m, 1H), 1.91-1.63 (m, 4H). |
| 206 | 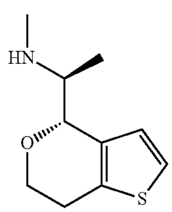 | HCl | LC-MS: m/z 198 (MH$^+$); $^1$H NMR (DMSO-d$_6$): δ 9.02-9.00 (d, J = 5.10 Hz, 1H), 8.14 (s, 1H), 7.43-7.41 (d, J = 5.10 Hz, 1H), 7.04-7.02 (d, J = 5.12 Hz, 1H), 4.82-4.81 (d, J = 2.15 Hz, 1H), 4.22-4.15 (m, 1H), 3.79-3.68 (m, 2H), 2.91-2.77 (m, 2H), 2.40-2.37 (m, 3H), 1.39-1.37 (d, J = 6.96 Hz, 3H). |
| 207 | 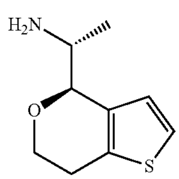 | HCl | LC-MS: m/z 184 (MH$^+$); $^1$H NMR (DMSO-d$_6$): δ 7.90 (s, 3H), 7.41-7.39 (d, J = 5.19 Hz, 1H), 7.00-6.98 (d, J = 5.25 Hz, 1H), 4.72-4.71 (d, J = 2.13 Hz, 1H), 4.70-4.12 (m, 1H), 3.77-3.66 (m, 2H), 3.41-3.34 (m, 2H), 1.36-1.34 (d, J = 6.72 Hz, 3H). |
| 208 | 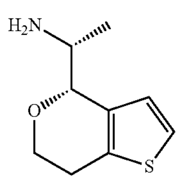 | HCl | LC-MS: m/z 184 (MH$^+$); $^1$H NMR (DMSO-d$_6$): δ 8.38 (s, 3H), 7.43-7.39 (d, J = 5.19 Hz, 1H), 6.70-6.98 (d, J = 5.22 Hz, 1H), 4.98 (s, 1H), 4.97-4.22 (m, 1H), 3.82-3.81 (m, 1H), 3.71-3.62 (td, J = 11.13 Hz, J = 3.53 Hz, 1H), 2.97-2.50 (m, 1H), 2.50-2.49 (m, 1H), 0.91-0.88 (d, J = 6.72 Hz, 3H). |
| 209 | 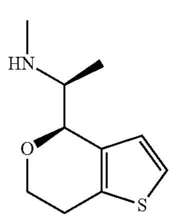 | HCl | LC-MS: m/z 198 (MH$^+$); $^1$H NMR (DMSO-d$_6$): δ 9.24-9.14 (m, 2H), 7.42-7.40 (d, J = 5.17 Hz, 1H), 6.94-6.92 (d, J = 5.42 Hz, 1H), 5.17-5.16 (d, J = 1.80 Hz, 1H), 4.27-4.22 (m, 1H), 3.80 (s, 1H), 3.73-3.65 (m, 1H), 2.98-2.88 (m, 1H), 2.77-2.72 (m, 1H), 2.59 (s, 3H), 0.93-0.91 (d, J = 6.62 Hz, 3H). |

| Compd. No. | Structure | Salt or FB* | Analytical Data |
|---|---|---|---|
| 210 | 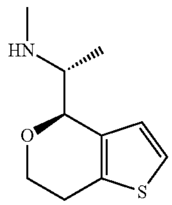 | HCl | LC-MS: m/z 198 (MH+); $^1$H NMR (DMSO-d$_6$): δ 8.91 (s, 1H), 8.08 (s, 1H), 7.43-7.41 (d, J = 5.22 Hz, 1H), 7.04-7.02 (d, J = 5.22 Hz, 1H), 4.81-4.80 (m, 1H), 4.22-4.16 (m, 1H), 3.79-3.67 (m, 2H), 2.97-2.77 (m, 2H), 2.41-2.37 (t, J = 5.42 Hz, 3H), 1.39-1.37 (d, J = 6.75 Hz, 3H). |
| 211 | 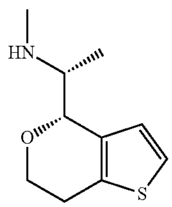 | HCl | LC-MS: m/z 198 (MH+); $^1$H NMR (DMSO-d$_6$): δ 9.20-9.10 (m, 2H), 7.42-7.40 (d, J = 5.10 Hz, 1H), 6.94-6.72 (d, J = 5.16 Hz, 1H), 5.15 (s, 1H), 4.27-4.22 (m, 1H), 3.79-3.65 (m, 2H), 3.74-3.65 (td, J = 11.18 Hz, 3.42 Hz, 2H), 2.98-2.88 (m, 1H), 2.77-2.72 (m, 1H), 2.60 (s, 3H), 0.92-0.90 (d, J = 6.66 Hz, 3H). |
| 212 | 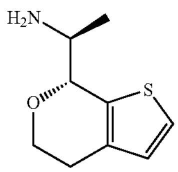 | HCl | LC-MS: m/z 184 (MH+); $^1$H NMR (DMSO-d$_6$): δ 8.03 (s, 3H), 7.52-7.50 (dd, J = 0.58 Hz, J = 5.03 Hz, 1H), 6.96-6.94 (d, J = 5.04 Hz, 1H), 4.83-4.82 (d, J = 5.48 Hz, 1H), 4.17-4.10 (m, 1H), 3.77-3.69 (m, 1H), 3.47 (s, 1H), 2.80-2.61 (m, 2H), 1.43-1.40 (d, J = 6.63 Hz, 3H). |
| 213 | 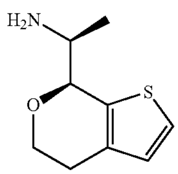 | HCl | LC-MS: m/z 184 (MH+); $^1$H NMR (DMSO-d$_6$): δ 8.42 (s, 3H), 7.51-7.49 (dd, J = 5.11 Hz, J = 0.62 Hz, 1H), 6.94-6.93 (d, J = 5.12 Hz, 1H), 5.14-5.13 (d, J = 1.50 Hz, 1H), 4.25-4.19 (m, 1H), 3.71-3.62 (td, J = 11.12 Hz, 3.64 Hz, 1H), 3.54 (s, 1H), 2.84-2.72 (m, 1H), 2.63-2.57 (m, 1H), 1.01-0.98 (d, J = 6.95 Hz, 3H). |
| 214 | 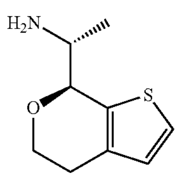 | HCl | LC-MS: m/z 184 (MH+); $^1$H NMR (DMSO-d$_6$): δ 7.87 (s, 3H), 7.53-7.51 (d, J = 4.65 Hz, 1H), 6.97-6.95 (d, J = 5.22 Hz, 1H), 4.82-4.80 (d, J = 5.07 Hz, 1H), 4.18-4.14 (m, 1H), 3.78-3.69 (m, 1H), 3.52-3.44 (m, 1H), 2.78-2.62 (m, 2H), 1.40-1.38 (d, J = 6.57 Hz, 3H). |
| 215 | 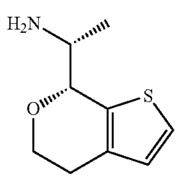 | HCl | LC-MS: m/z 184 (MH+); $^1$H NMR (DMSO-d$_6$): δ 8.32 (s, 3H), 7.51-7.49 (dd, J = 5.01 Hz, J = 0.57 Hz, 1H), 6.95-6.93 (d, J = 5.01 Hz, 1H), 5.11-5.10 (d, J = 1.65 Hz, 1H), 4.25-4.20 (dd, J = 11.34 Hz, 4.98 Hz, 1H), 3.72-3.63 (td, J = 11.27 Hz, 3.51 Hz, 1H), 3.57 (s, 1H), 2.84-2.72 (m, 1H), 2.63-2.58 (m, 1H), 1.01-0.98 (d, J = 6.75 Hz, 3H). |
| 216 | 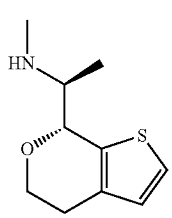 | HCl | LC-MS: m/z 198 (MH+); $^1$H NMR (DMSO-d$_6$): δ 9.09 (s, 1H), 8.35-8.32 (m, 1H), 7.53-7.52 (d, J = 5.12 Hz, 1H), 6.97-6.95 (d, J = 4.80 Hz, 1H), 4.93 (d, J = 1.7 Hz, 1H), 4.19-4.12 (m, 1H), 3.80-3.72 (m, 1H), 3.54-3.51 (m, 1H), 2.77-2.64 (m, 2H), 2.50-2.45 (m, 3H), 1.46-1.43 (d, J = 6.64 Hz, 3H). |
| 217 | 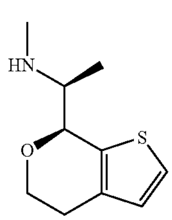 | HCl | LC-MS: m/z 198 (MH+); $^1$H NMR (DMSO-d$_6$): δ 9.42-9.17 (m, 2H), 7.50-7.49 (d, J = 4.85 Hz, 1H), 6.94-6.92 (d, J = 5.18 Hz, 1H), 5.33-5.33 (d, J = 1.27 Hz, 1H), 4.24-4.19 (dd, J = 11.28 Hz, 5.37 Hz, 1H), 3.73-3.64 (td, J = 11.31 Hz, 5.37 Hz, 1H), 3.53 (s, 1H), 2.84-2.72 (m, 1H), 2.63-2.62 (m, 1H), 2.60 (s, 3H), 1.02-1.00 (d, J = 6.9 Hz, 3H). |

| Compd. No. | Structure | Salt or FB* | Analytical Data |
|---|---|---|---|
| 218 | | HCl | LC-MS: m/z 198 (MH⁺); $^1$H NMR (DMSO-$d_6$): | δ 9.07-9.06 (d, J = 5.45 Hz, 1H), 8.31 (s, 1H), 7.53-7.52 (d, J = 5.01 Hz, 1H), 6.97-6.95 (d, J = 5.04 Hz, 1H), 4.94-4.92 (s, J = 5.28 Hz, 1H), 4.19-4.13 (m, 1H), 3.80-3.72 (m, 1H), 3.42-3.49 (m, 1H), 2.82-2.64 (m, 2H), 2.50-2.45 (m, 3H), 1.46-1.43 (d, J = 6.63 Hz, 3H). |
| 219 | 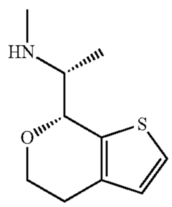 | HCl | LC-MS: m/z 198 (MH⁺); $^1$H NMR (DMSO-$d_6$): ⁂ δ 9.39-9.38 (d, J = 1.17 Hz, 1H), 9.16-9.14 (d, J = 4.92 Hz, 1H), 7.51-7.49 (dd, J = 4.95 Hz, 0.42 Hz, 1H), 6.94-6.93 (d, J = 5.01 Hz, 1H), 5.33-5.32 (d, J = 1.49 Hz, 1H), 4.24-4.19 (dd, J = 11.33 Hz, 5.21 Hz, 1H), 3.73-3.64 (td, J = 11.31 Hz, 3.57 Hz, 1H), 3.55-3.53 (m, 1H), 2.84-2.72 (m, 1H), 2.63-2.58 (m, 4H), 1.10-0.99 (d, J = 6.72 Hz, 3H). |
| 220 | 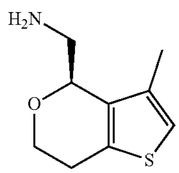 | HCl | $^1$H NMR (DMSO-$d^6$): δ 8.14 (br s, 3H), 7.00 (s, 1H), 4.97-4.90 (m, 1H), 4.02-3.94 (m, 1H), 3.85-3.78 (m, 1H), 3.11-3.08 (t, J = 10.66 Hz, 2H), 2.88-2.73 (m, 2H), 2.13-2.12 (d, J = 0.8 Hz, 3H). |
| 221 | 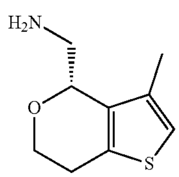 | HCl | $^1$H NMR (DMSO-$d^6$): δ 8.14 (br s, 3H), 7.00 (s, 1H), 4.97-4.90 (m, 1H), 4.02-3.94 (m, 1H), 3.85-3.78 (m, 1H), 3.11-3.08 (t, J = 10.66 Hz, 2H), 2.88-2.73 (m, 2H), 2.13-2.12 (d, J = 0.8 Hz, 3H). |
| 222 | 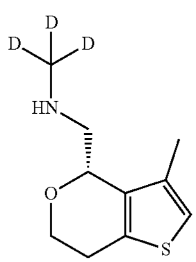 [SMILES: [2H]C([2H])([2H])NC[C@H]1OCCc2scc(C)c21] | HCl | LC-MS (6 minute method): 0.67 min, M⁺ 201 @ 0.63 min; $^1$H NMR (CD$_3$OD): δ 6.90 (s, 1H), 5.05-5.02 (m, 1H), 4.17-4.12 (m, 1H), 3.86-3.81 (m, 1H), 3.46-3.42 (m, 1H), 3.33-3.28 (m, 1H), 2.93-2.81 (m, 1H), 2.19 (s, 3H). |
| 223 | 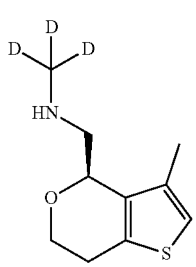 [SMILES: [2H]C([2H])([2H])NC[C@@H]1OCCc2scc(C)c21] | HCl | LC-MS (6 minute method): 0.67 min, M⁺ 201 @ 0.63 min; $^1$H NMR (CD$_3$OD): δ 6.90 (s, 1H), 5.05-5.02 (m, 1H), 4.17-4.12 (m, 1H), 3.86-3.81 (m, 1H), 3.46-3.42 (m, 1H), 3.33-3.28 (m, 1H), 2.93-2.81 (m, 1H), 2.19 (s, 3H). |

-continued

| Compd. No. | Structure | Salt or FB* | Analytical Data |
|---|---|---|---|
| 224 | 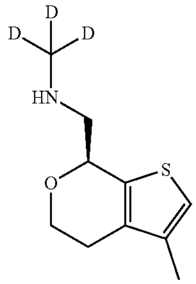 [SMILES: [2H]C([2H])([2H])NC[C@@H]1OCCc2c(C)csc21] | HCl | LC-MS (6 minute method): 0.70 min, M⁺ 201 @ 0.73 min; ¹H NMR (CD₃OD): δ 6.99 (s, 1H), 5.10 (d, J = 8.07 Hz, 1H), 4.32-4.27 (m, 1H), 3.86-3.80 (m, 1H), 3.48-3.44 (m, 1H), 3.27-3.24 (m, 1H), 2.76-2.68 (m, 1H), 2.57-2.52 (m, 1H), 2.14 (s, 3H). |
| 225 | 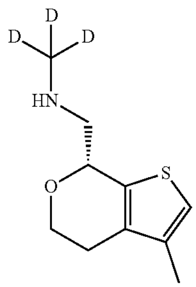 [SMILES: [2H]C([2H])([2H])NC[C@H]1OCCc2c(C)csc21] | HCl | LC-MS (6 minute method): 0.70 min, M⁺ 201 @ 0.73 min; ¹H NMR (CD₃OD): δ 6.99 (s, 1H), 5.10 (d, J = 8.07 Hz, 1H), 4.32-4.27 (m, 1H), 3.86-3.80 (m, 1H), 3.48-3.44 (m, 1H), 3.27-3.24 (m, 1H), 2.76-2.68 (m, 1H), 2.57-2.52 (m, 1H), 2.14 (s, 3H). |
| 226 | 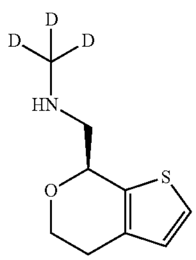 [SMILES: [2H]C([2H])([2H])NC[C@@H]1OCCc2ccsc21] | HCl | LC-MS (6 minute method): 0.17-0.36 min, M⁺ 187 @ 0.35 min; ¹H NMR (CD₃OD): δ 7.37 (d, J = 2.93 Hz, 1H), 6.90 (d, J = 2.93 Hz, 1H), 5.16 (d, J = 7.33 Hz, 1H), 4.28-4.24 (m, 1H), 3.85-3.80 (m, 1H), 3.50 (d, J = 12.8 Hz, 1H), 3.3-3.25 (m, 1H), 2.89-2.84 (m, 1H), 2.71-2.67 (m, 1H). |
| 227 | 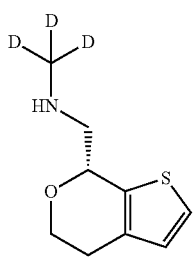 [SMILES: [2H]C([2H])([2H])NC[C@H]1OCCc2ccsc21] | HCl | LC-MS (6 minute method): 0.17-0.36 min, M⁺ 187 @ 0.35 min; ¹H NMR (CD₃OD): δ 7.37 (d, J = 2.93 Hz, 1H), 6.90 (d, J = 2.93 Hz, 1H), 5.16 (d, J = 7.33 Hz, 1H), 4.28-4.24 (m, 1H), 3.85-3.80 (m, 1H), 3.50 (d, J = 12.8 Hz, 1H), 3.3-3.25 (m, 1H), 2.89-2.84 (m, 1H), 2.71-2.67 (m, 1H). |
| 228 | 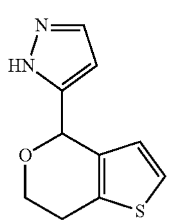 [SMILES: c1cc(C2OCCc3sccc32)[nH]n1] | HCl | LC-MS: m/z 207 (MH⁺); ¹H NMR (CD₃OD): δ 8.20-8.19 (d, J = 2.61 Hz, 1H), 7.30-7.29 (d, J = 5.25 Hz, 1H), 6.79-6.74 (m, 2H), 6.08 (s, 1H), 4.21-4.15 (m, 1H), 4.04-3.96 (m, 1H), 3.11-3.02 (m, 1H), 2.98-2.89 (m, 1H). |
| 229 | 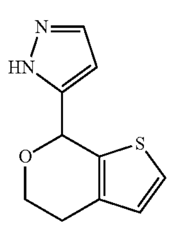 [SMILES: c1cc(C2OCCc3ccsc32)[nH]n1] | HCl | LC-MS: m/z 207 (MH⁺); ¹H NMR (D₂O): δ 7.73 (s, 1H), 7.23-7.22 (d, J = 3.72 Hz, 1H), 6.82 (s, 1H), 6.41 (s, 1H), 6.02 (s, 1H), 4.00-3.95 (m, 1H), 3.85-3.81 (m, 1H), 2.77-2.62 (m, 2H). |

| Compd. No. | Structure | Salt or FB* | Analytical Data |
|---|---|---|---|
| 230 | | HCl | LC-MS: m/z 221 (MH$^+$); $^1$H NMR (CD$_3$OD): | δ 7.31-7.29 (d, J = 5.19 Hz, 1H), 6.81-6.79 (d, J = 5.22 Hz, 1H), 6.56 (s, 1H), 6.09 (s, 1H), 4.21-4.14 (m, 1H), 4.03-3.95 (m, 1H), 3.09-2.90 (m, 2H), 2.46 (s, 3H). |
| 231 | 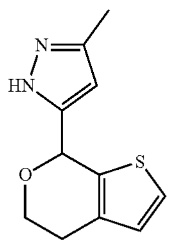 | HCl | LC-MS: m/z 221 (MH$^+$); $^1$H NMR (CD$_3$OD):¯ δ 7.41-7.39 (dd, J = 5.09 Hz, 0.71 Hz, 1H), 6.95-6.93 (d, J = 5.07 Hz, 1H), 6.63 (s, 1H), 6.16 (s, 1H), 4.21-4.14 (m, 1H), 4.02-3.94 (m, 1H), 2.97-2.87 (m, 1H), 2.84-2.75 (m, 1H), 1.19 (s, 3H). |
| 232 | 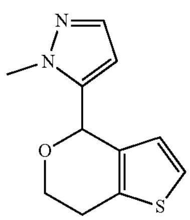 | HCl | LC-MS: m/z 221 (MH$^+$); $^1$H NMR (DMSO-d$_6$): ¯ δ 9.71-9.66 (d, J = 15.52 Hz, 1H), 7.36-7.33 (m, 2H), 6.62-6.61 (d, J = 5.19 Hz, 1H), 5.98 (s, 1H), 5.91-5.90 (d, J = 1.77 Hz, 1H), 3.93-3.79 (m, 2H), 3.76 (s, 3H), 2.89-2.86 (t, J = 5.27 Hz, 2H). |
| 233 | 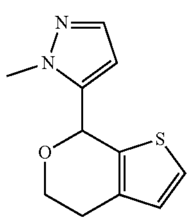 | HCl | LC-MS: m/z 221 (MH$^+$); $^1$H NMR (CDCl$_3$): δ 12.01 (s, 1H), 7.85-7.84 (d, J = 2.40 Hz, 1H), 7.30-7.28 (m, 1H), 6.91-6.87 (d, J = 5.07 Hz, 1H), 6.50-6.49 (d, J = 2.34 Hz, 1H), 6.08 (s, 1H), 4.20 (s, 3H), 4.07-4.00 (m, 1H), 3.96-3.88 (m, 1H), 2.91-2.88 (m, 2H). |
| 234 | 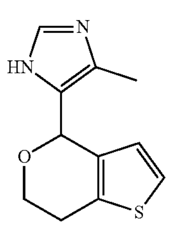 | HCl | LC-MS: m/z 221 (MH$^+$); $^1$H NMR (CD$_3$OD): δ 8.67 (s, 1H), 7.27-7.25 (d, J = 5.25 Hz, 1H), 6.57-6.56 (d, J = 5.28 Hz, 1H), 5.97-5.96 (m, 1H), 4.25-4.19 (m, 1H), 4.01-3.93 (m, 1H), 3.17-3.07 (m, 1H), 2.92-2.86 (m, 1H), 2.29 (s, 3H). |
| 235 | | HCl | LC-MS: m/z 221 (MH$^+$); $^1$H NMR (CD$_3$OD): | δ 8.17 (s, 1H), 7.33-7.31 (dd, J = 5.07 Hz, 0.75 Hz, 1H), 6.92-6.70 (d, J = 5.07 Hz, 1H), 6.02 (s, 1H), 4.27-4.20 (m, 1H), 3.97-3.90 (m, 1H), 3.00-2.92 (m, 1H), 2.78-2.71 (m, 1H), 2.24 (s, 3H). |

-continued

| Compd. No. | Structure | Salt or FB* | Analytical Data |
|---|---|---|---|
| 236 | 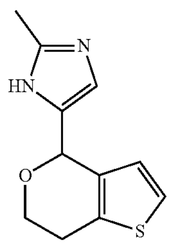 | HCl | LC-MS: m/z 221 (MH⁺); $^1$H NMR (CD$_3$OD): δ 7.16-7.14 (d, J = 5.19 Hz, 1H), 6.68-6.67 (d, J = 0.48 Hz, 1H), 6.64-6.62 (d, J = 5.16 Hz, 1H), 5.71 (s, 1H), 4.11-4.04 (m, 1H), 3.91-3.84 (m, 1H), 2.98-2.82 (m, 2H), 2.33 (s, 3H). |
| 237 | 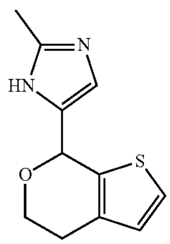 | HCl | LC-MS: m/z 221 (MH⁺); $^1$H NMR (CD$_3$OD): δ 7.27-7.25 (dd, J = 5.07 Hz, 0.75 Hz, 1H), 6.87-6.85 (d, J = 5.04 Hz, 1H), 6.84 (s, 1H), 5.82 (s, 1H), 4.17-4.10 (m, 1H), 3.92-3.86 (m, 1H), 2.89-2.81 (m, 1H), 2.76-2.69 (m, 1H), 2.34 (s, 3H). |
| 238 | 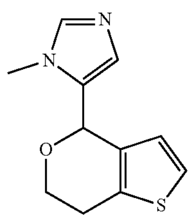 | HCl | LC-MS: m/z 221 (MH⁺); $^1$H NMR (CD$_3$OD): δ 8.95 (s, 1H), 7.35-7.33 (d, J = 5.25 Hz, 1H), 7.29 (s, 1H), 6.75-6.73 (d, J = 5.25 Hz, 1H), 6.10 (s, 1H), 4.02-3.97 (m, 2H), 3.89 (s, 3H), 3.00-2.97 (m, 2H). |
| 239 | 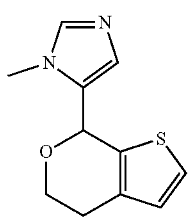 | HCl | LC-MS: m/z 221 (MH⁺); $^1$H NMR (CD$_3$OD): δ 8.96 (s, 1H), 7.48-7.47 (d, J = 1.11 Hz, 1H), 7.45-7.44 (dd, J = 5.07 Hz, 0.69 Hz, 1H), 6.98 (d, J = 1.1 Hz, 1H), 6.25 (s, 1H), 4.09-3.92 (m, 2H), 3.88-3.87 (d, J = 0.45 Hz, 3H), 2.89-2.84 (m, 2H). |
| 240 | 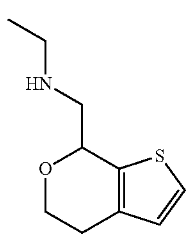 | HCl | $^1$H NMR (CD$_3$OD): δ 7.36 (d, J = 1.5 Hz, 1H), 6.91 (d, J = 1.5 Hz, 1H), 5.13 (d, J = 2.0 Hz, 1H), 4.26 (ddd, J = 3.0, 1.5, 0.7 Hz, 1H), 3.82 (dt, J = 3.0, 1.0 Hz, 1H), 3.46 (dd, J = 3.0, 0.7 Hz, 1H), 3.25 (dd, J = 3.0, 2.0 Hz, 1H), 3.12 (q, J = 1.7 Hz, 2H) 2.91-2.83 (m, 1H), 2.71-2.65 (m, 1H), 1.32 (t, J = 1.7 Hz, 3H). |
| 241 | 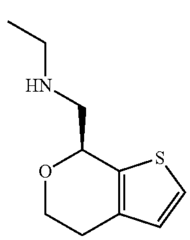 | HCl | $^1$H NMR (CD$_3$OD): δ 7.36 (d, J = 1.5 Hz, 1H), 6.91 (d, J = 1.5 Hz, 1H), 5.13 (d, J = 2.0 Hz, 1H), 4.26 (ddd, J = 3.0, 1.5, 0.7 Hz, 1H), 3.82 (dt, J = 3.0, 1.0 Hz, 1H), 3.46 (dd, J = 3.0, 0.7 Hz, 1H), 3.25 (dd, J = 3.0, 2.0 Hz, 1H), 3.12 (q, J = 1.7 Hz, 2H) 2.91-2.83 (m, 1H), 2.71-2.65 (m, 1H), 1.32 (t, J = 1.7 Hz, 3H). |

| Compd. No. | Structure | Salt or FB* | Analytical Data |
|---|---|---|---|
| 242 | 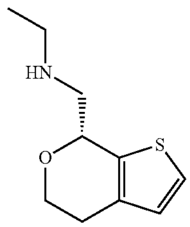 | HCl | ¹H NMR (CD₃OD): δ 7.36 (d, J = 1.5 Hz, 1H), 6.91 (d, J = 1.5 Hz, 1H), 5.13 (d, J = 2.0 Hz, 1H), 4.26 (ddd, J = 3.0, 1.5, 0.7 Hz, 1H), 3.82 (dt, J = 3.0, 1.0 Hz, 1H), 3.46 (dd, J = 3.0, 0.7 Hz, 1H), 3.25 (dd, J = 3.0, 2.0 Hz, 1H), 3.12 (q, J = 1.7 Hz, 2H) 2.91-2.83 (m, 1H), 2.71-2.65 (m, 1H), 1.32 (t, J = 1.7 Hz, 3H). |
| 243 | 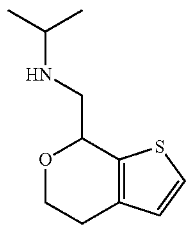 | HCl | ¹H NMR (CD₃OD): δ 7.37 (d, J = 1.2 Hz, 1H), 6.91 (d, J = 1.2 Hz, 1H), 5.12 (apd, J = 1.8 Hz, 1H), 4.26 (ddd, J = 3.0, 1.5, 0.7 Hz, 1H), 3.82 (ddd, J = 3.0, 2.5, 1.0 Hz, 1H), 3.49-3.40 (m, 2H), 3.28-3.21 (m, 1H), 2.92-2.83 (m, 1H), 2.72-2.67 (m, 1H), 1.35 (dd, J = 2.3, 1.6 Hz, 6H). |
| 244 | 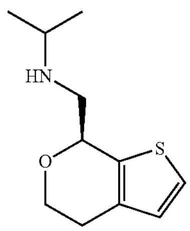 | HCl | ¹H NMR (CD₃OD): δ 7.37 (d, J = 1.2 Hz, 1H), 6.91 (d, J = 1.2 Hz, 1H), 5.12 (apd, J = 1.8 Hz, 1H), 4.26 (ddd, J = 3.0, 1.5, 0.7 Hz, 1H), 3.82 (ddd, J = 3.0, 2.5, 1.0 Hz, 1H), 3.49-3.40 (m, 2H), 3.28-3.21 (m, 1H), 2.92-2.83 (m, 1H), 2.72-2.67 (m, 1H), 1.35 (dd, J = 2.3, 1.6 Hz, 6H). |
| 245 | 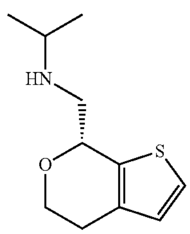 | HCl | ¹H NMR (CD₃OD): δ 7.37 (d, J = 1.2 Hz, 1H), 6.91 (d, J = 1.2 Hz, 1H), 5.12 (apd, J = 1.8 Hz, 1H), 4.26 (ddd, J = 3.0, 1.5, 0.7 Hz, 1H), 3.82 (ddd, J = 3.0, 2.5, 1.0 Hz, 1H), 3.49-3.40 (m, 2H), 3.28-3.21 (m, 1H), 2.92-2.83 (m, 1H), 2.72-2.67 (m, 1H), 1.35 (dd, J = 2.3, 1.6 Hz, 6H). |
| 246 | 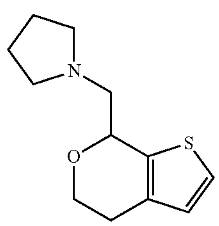 [SMILES: c1cc2c(s1)C(CN1CCCC1)OCC2] | HCl | ¹H NMR (CD₃OD): δ 7.36 (d, J = 1.3 Hz, 1H), 6.91 (d, J = 1.3 Hz, 1H), 5.24 (apd, J = 2.5 Hz, 1H), 4.29-4.25 (m, 1H), 3.85 (dt, J = 2.5, 1.0 Hz, 1H), 3.81-3.67 (m, 1H), 3.66-3.63 (m, 2H), 3.50 (dd, J = 3.0, 2.5 Hz, 1H), 3.31-3.12 (m, 2H), 2.91-2.83 (m, 1H), 2.73-2.68 (m, 1H), 2.19-2.00 (m, 4H). |
| 247 | 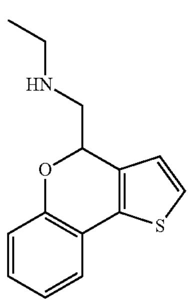 [SMILES: CCNCC1Oc2ccccc2-c2sccc21] | HCl | LC-MS: m/z 246 (MH⁺); ¹H NMR (DMSO-d₆): δ 9.29 (s, 1H), 8.92 (s, 1H), 7.66-7.64 (d, J = 5.10 Hz, 1H), 7.10-7.37 (dd, J = 7.47 Hz, 1.50 Hz, 1H), 7.27-7.21 (m, 1H), 7.13-7.11 (d, J = 5.07 Hz, 1H), 7.07-7.00 (m, 2H), 5.88-5.84 (dd, J = 9.36 Hz, 2.75 Hz, 1H), 3.50-3.39 (m, 2H), 3.07-3.02 (m, 2H), 1.27-1.22 (t, J = 7.23 Hz, 3H). |

-continued

| Compd. No. | Structure | Salt or FB* | Analytical Data |
|---|---|---|---|
| 248 | 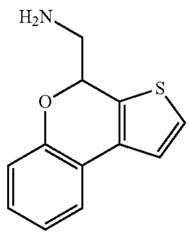 [SMILES: NCC1Oc2ccccc2-c2ccsc21] | HCl | LC-MS: m/z 218 (MH+); 1H NMR (DMSO-d6): δ 8.40 (s, 3H), 7.71-7.64 (m, 2H), 7.59-7.57 (d, J = 5.10 Hz, 1H), 7.26-7.21 (m, 1H), 7.08-7.03 (m, 2H), 5.87-5.82 (dd, J = 8.90 Hz, 3.23 Hz, 1H), 3.31-3.25 (m, 2H). |
| 249 | 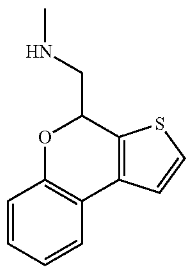 [SMILES: CNCC1Oc2ccccc2-c2ccsc21] | HCl | LC-MS: m/z 232 (MH+); 1H NMR (DMSO-d6): δ 9.36 (s, 1H), 9.09 (s, 1H), 7.72-7.70 (d, J = 5.10 Hz, 1H), 7.67-7.75 (d, J = 6.27 Hz, 1H), 7.59-7.57 (d, J = 5.13 Hz, 1H), 7.27-7.21 (m, 1H), 7.09-7.03 (m, 2H), 6.01-5.96 (dd, J = 8.18 Hz, J = 4.28 Hz, 1H), 3.37 (s, 2H), 2.65 (s, 3H). |
| 250 | 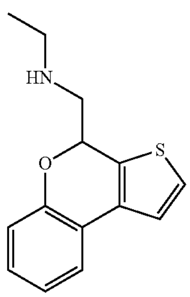 [SMILES: CCNCC1Oc2ccccc2-c2ccsc21] | HCl | LC-MS: m/z 246 (MH+); 1H NMR (DMSO-d6 + D2O): δ 7.69-7.62 (m, 2H), 7.56-7.55 (d, J = 5.07 Hz, 1H), 7.26-7.21 (m, 1H), 7.09-7.03 (m, 2H), 5.93-5.88 (t, J = 12.3 Hz, 1H), 3.44-3.33 (m, 2H), 3.10-3.03 (m, 2H), 1.24-1.19 (t, J = 7.22 Hz, 3H). |
| 251 | 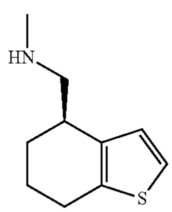 | HCl | 1H NMR (CD3OD): δ 7.21 (d, J = 1.5 Hz, 1H), 6.92 (d, J = 1.5 Hz, 1H), 3.36 (dd, J = 3.0, 1.0 Hz, 1H), 3.14 (m, 1H), 3.09 (dd, J = 3.0, 2.5 Hz, 1H), 2.80 (apt, J = 1.5 Hz, 2H), 2.75 (s, 3H), 2.03-1.95 (m, 2H), 1.88-1.81 (m, 1H), 1.72-1.65 (m, 1H). |
| 252 | 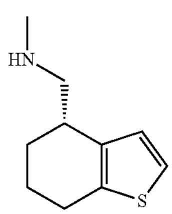 | HCl | 1H NMR (CD3OD): δ 7.21 (d, J = 1.5 Hz, 1H), 6.92 (d, J = 1.5 Hz, 1H), 3.36 (dd, J = 3.0, 1.0 Hz, 1H), 3.14 (m, 1H), 3.09 (dd, J = 3.0, 2.5 Hz, 1H), 2.80 (apt, J = 1.5 Hz, 2H), 2.75 (s, 3H), 2.03-1.95 (m, 2H), 1.88-1.81 (m, 1H), 1.72-1.65 (m, 1H). |
| 253 | 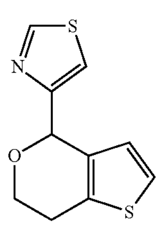 [SMILES: c1nc(C2OCCc3sccc32)cs1] | HCl | 1H NMR (CD3OD): δ 9.85 (d, J = 0.5 Hz, 1H), 7.88 (d, J = 0.5 Hz, 1H), 7.28 (d, J = 1.3, 1H), 6.73 (d, J = 1.3 H, 1H), 6.09 (s, 1H), 4.12-3.95 (m, 2H), 2.99 (ddt, J = 11.0, 4.0, 1.5 Hz, 2H). |

-continued

| Compd. No. | Structure | Salt or FB* | Analytical Data |
|---|---|---|---|
| 254 | 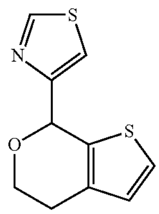 [SMILES: c1nc(C2OCCc3ccsc32)cs1] | HCl | ¹H NMR (CD₃OD): δ 9.52 (d, J = 0.5 Hz, 1H), 7.82 (d, J = 0.5 Hz, 1H), 7.34 (d, J = 1.3, 1H), 6.91 (d, J = 1.3 H, 1H), 6.17 (s, 1H), 4.15 (dt, J = 2.5, 1.3 Hz, 1H), 3.99-3.92 (m, 1H), 2.96-2.87 (m, 1H), 2.81-2.75 (m, 1H). |
| 255 | 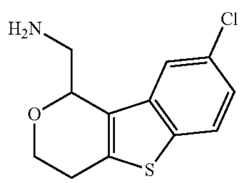 [SMILES: NCC1OCCc2sc3ccc(Cl)cc3c21] | HCl | LC-MS: m/z 254.4 (MH⁺); ¹H NMR (CD₃OD): δ 7.89-7.86 (d, J = 8.61 Hz, 1H), 7.76-7.76 (d, J = 1.89 Hz, 1H), 7.37-7.34 (dd, J = 8.60 Hz, 1.97 Hz, 1H), 5.27-5.23 (m, 1H), 4.30-4.22 (m, 1H), 3.99-3.91 (m, 1H), 3.61-3.56 (m, 1H), 3.38-3.26 (m, 1H), 3.13-2.94 (m, 2H). |
| 256 | 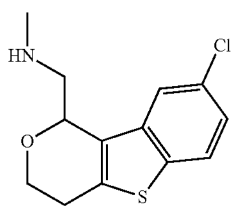 [SMILES: CNCC1OCCc2sc3ccc(Cl)cc3c21] | HCl | LC-MS: m/z 268 (MH⁺); ¹H NMR (DMSO-d₆ + D₂O): δ 7.89-7.85 (d, J = 8.58 Hz, 1H), 7.77-7.76 (d, J = 1.38 Hz, 1H), 7.37-7.34 (dd, J = 8.80 Hz, 1.70 Hz, 1H), 5.34-5.31 (d, J = 7.77 Hz, 1H), 4.30-4.23 (m, 1H), 4.01-3.94 (m, 1H), 3.66- (m, 1H), 3.46-3.36 (m, 1H), 3.12-3.00 (m, 2H), 2.80 (s, 3H). |
| 257 | 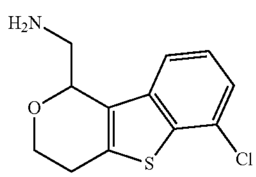 [SMILES: NCC1OCCc2sc3c(Cl)cccc3c21] | HCl | LC-MS: m/z 254 (MH⁺); ¹H NMR (CD₃OD): δ 7.69-7.66 (dd, J = 6.95 Hz, 1.94 Hz, 1H), 7.47-7.40 (m, 2H), 5.30-5.26 (m, 1H), 4.32-4.25 (m, 1H), 3.40-3.92 (m, 1H), 3.64-3.60 (m, 1H), 3.42-3.35 (dd, J = 13.42 Hz, 8.45 Hz, 1H), 3.10-3.02 (m, 2H). |
| 258 | 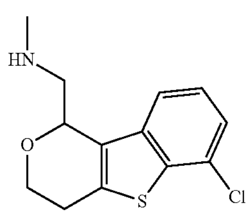 [SMILES: CNCC1OCCc2sc3c(Cl)cccc3c21] | HCl | LC-MS: m/z 268 (MH⁺); ¹H NMR (CD₃OD): 7.72-7.70 (d, J = 1.7 Hz, 1H), 7.48-7.40 (m, 2H), 5.36-5.33 (m, 1H), 4.92-4.26 (m, 1H), 4.01-3.95) m, 1H), 3.73-3.68 (m, 1H), 3.51-3.44 (m, 1H), 3.10-3.03 (m, 2H), 2.80 (s, 3H). |
| 259 | 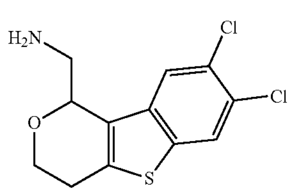 [SMILES: NCC1OCCc2sc3cc(Cl)c(Cl)cc3c21] | HCl | LC-MS: m/z 288 (MH⁺); ¹H NMR (CD₃OD): δ 8.12 (s, 1H), 7.92 (s, 1H), 5.25-5.22 (d, J = 8.50, 1H), 4.30-4.23 (m, 1H), 3.99-3.91 (m, 1H), 3.61-3.40 (m, 1H), 3.37-3.33 (m, 1H), 3.03-2.94 (m, 2H). |
| 260 | 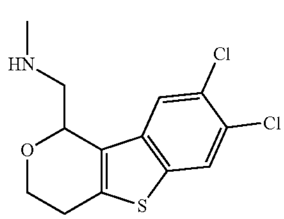 [SMILES: CNCC1OCCc2sc3cc(Cl)c(Cl)cc3c21] | HCl | LC-MS: m/z 302 (MH⁺); ¹H NMR (CD₃OD): δ 8.12 (s, 1H), 7.97 (s, 1H), 5.33-5.29 (m, 1H), 4.31-4.24 (m, 1H), 3.99-3.92 (m, 1H), 3.71-3.65 (m, 1H), 3.48-3.41 (dd, J = 13.10 Hz, 9.17 Hz, 1H), 3.07-2.99 (m, 2H), 2.80 (s, 3H). |

-continued

| Compd. No. | Structure | Salt or FB* | Analytical Data |
|---|---|---|---|
| 261 | (structure) | HCl | LC-MS: m/z 254 (MH+); $^1$H NMR (CD$_3$OD): δ 7.88-7.85 (d, J = 8.61 Hz, 1H), 7.74-7.73 (d, J = 1.65 Hz, 1H), 7.38-7.35 (dd, J = 8.57 Hz, 1.79 Hz, 1H), 5.21-8.19 (m, 1H), 4.43-4.37 (m, 1H), 4.01-3.93 (m, 1H), 3.53-3.46 (m, 1H), 3.33-3.23 (m, 1H), 3.04-2.93 (m, 1H), 2.88-2.82 (m, 1H). |
| 262 | (structure) | HCl | LC-MS: m/z 268 (MH+); $^1$H NMR (CD$_3$OD): δ 7.90-7.87 (d, J = 8.55 Hz, 1H), 7.77-7.76 (d, J = 1.98 Hz, 1H), 7.40-7.36 (dd, J = 8.58 Hz, 2.04 Hz, 1H), 5.28-5.24 (m, 1H), 4.44-4.38 (m, 1H), 4.03-3.94 (m, 1H), 3.62-3.56 (m, 1H), 3.43-3.35 (dd, J = 12.95 Hz, 8.42 Hz, 1H), 3.00-2.96 (m, 1H), 2.90-2.79 (m, 1H), 2.79 (s, 3H). |
| 263 | (structure) | HCl | LC-MS: m/z 254 (MH+); $^1$H NMR (DMSO-d$_6$): δ 8.24 (s, 3H), 7.78-7.75 (dd, J = 7.31 Hz, 1.40 Hz, 1H), 7.54-7.46 (m, 2H), 5.21-2.19 (d, J = 6.24 Hz, 1H), 4.30-4.23 (m, 1H), 3.95-3.87 (m, 1H), 3.37 (s, 1H), 3.19-3.17 (m, 1H), 2.90-2.89 (m, 2H). |
| 264 | (structure) | HCl | LC-MS: m/z 268 (MH+); $^1$H NMR (DMSO-d$_6$): δ 9.44-9.38 (m, 1H), 8.93-8.86 (m, 1H), 7.80-7.75 (dd, J = 7.34 Hz, 1.43 Hz, 1H), 7.55-7.46 (m, 2H), 5.34-5.32 (d, J = 7.65 Hz, 1H), 4.30-4.23 (m, 1H), 3.97-3.89 (m, 1H), 3.53-3.46 (m, 1H), 3.36-3.30 (m, 1H), 2.97-2.83 (m, 2H), 2.62-2.59 (t, J = 4.80 Hz, 3H). |
| 265 | (structure) | HCl | LC-MS: m/z 288 (MH+); $^1$H NMR (MeOD): δ 8.13 (s, 1H), 7.93 (s, 1H), 5.20-5.15 (m, 1H), 4.44-4.37 (m, 1H), 4.01-3.93 (m, 1H), 3.53-3.47 (m, 1H), 3.28-3.26 (m, 1H), 3.00-2.91 (m, 1H), 2.90-2.83 (s, 1H). |
| 266 | (structure) | HCl | LC-MS: m/z 302 (MH+); $^1$H NMR (MeOD): \| δ 8.14 (s, 1H), 7.94 (s, 1H), 5.26-5.22 (dd, J = 8.51 Hz, 2.64 Hz, 1H), 4.43-4.38 (m, 1H), 4.02-3.94 (m, 1H), 3.61-3.56 (m, 1H), 3.43-3.36 (m, 1H), 2.99-2.96 (m, 1H), 2.92-2.90 (m, 1H), 2.79 (s, 3H). |

-continued

| Compd. No. | Structure | Salt or FB* | Analytical Data |
|---|---|---|---|
| 267 | 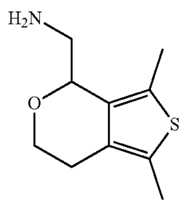 | HCl | $^1$H NMR (CD$_3$OD): δ 4.97 (dd, J = 2.0, 0.7 Hz, 1H), 4.05-3.99 (m, 1H), 3.74-3.68 (m, 1H), 3.34-3.30 (m, 1H), 3.18 (dd, J = 3.3, 2.5 Hz, 1H), 2.64-2.58 (m, 2H), 2.32 (s, 3H), 2.26 (s, 3H). |
| 268 | 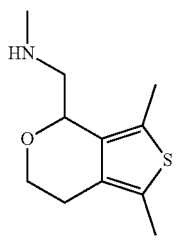 | HCl | $^1$H NMR (CD$_3$OD): δ 5.03 (dd, J = 2.0, 0.7 Hz, 1H), 4.08-4.01 (m, 1H), 3.74-3.67 (m, 1H), 3.39 (dd, J = 3.0, 1.0 Hz, 1H), 3.32-3.26 (m, 1H), 2.75 (s, 3H), 2.69-2.61 (m 2H), 2.33 (s, 3H), 2.26 (s, 3H). |
| 269 | 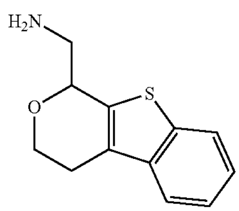 [SMILES: NCC1OCCc2c1sc1ccccc21] | HCl | $^1$H NMR (CD$_3$OD): δ 7.87 (d, J = 2.0 Hz, 1H), 7.72 (d, J = 2.0 Hz, 1H), 7.42 (t, J = 2.0 Hz, 1H), 7.38 (t, J = 2.0 Hz, 1H), 5.19-5.15 (m, 1H), 4.39 (ddd, J = 3.0, 1.5, 0.7 Hz, 1H), 3.97 (ddd, J = 3.0, 2.5, 1.0 Hz, 1H), 3.48 (dd, J = 3.3, 1.0 Hz, 1H), 3.30-3.22 (m, 1H), 3.03-2.96 (m, 1H), 2.91-2.85 (m, 1H). |
| 270 | 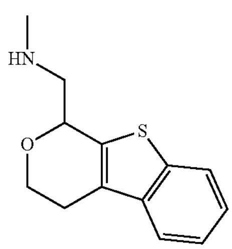 [SMILES: CNCC1OCCc2c1sc1ccccc21] | HCl | $^1$H NMR (CD$_3$OD): δ 7.87 (d, J = 2.0 Hz, 1H), 7.73 (d, J = 2.0 Hz, 1H), 7.42 (t, J = 2.0 Hz, 1H), 7.39 (t, J = 2.0 Hz, 1H), 5.25-5.22 (m, 1H), 4.39 (ddd, J = 3.0, 1.5, 0.7 Hz, 1H), 3.98 (ddd, J = 2.0, 1.7, 1.0 Hz, 1H), 3.57 (dd, J = 3.3, 0.7 Hz, 1H), 3.38 (dd, J = 3.0, 2.0 Hz, 1H), 3.05-2.96 (m, 1H), 2.91-2.86 (m, 1H), 2.77 (s, 3H). |
| 271 | 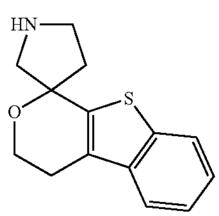 [SMILES: c1ccc2c3c(sc2c1)C1(CCNC1)OCC3] | HCl | $^1$H NMR (CD$_3$OD): δ 7.87 (d, J = 1.7 Hz, 1H), 7.72 (d, J = 1.7 Hz, 1H), 7.43 (t, J = 1.7 Hz, 1H), 7.40 (dt, J = 1.7, 0.7 Hz, 1H), 4.18-3.72 (m, 2H), 3.74 (apd, J = 2.0 Hz, 1H), 3.65-3.58 (m, 2H), 3.47 (d, J = 3.0 Hz, 1H), 2.93 (t, J = 1.0 Hz, 2H), 2.60-2.54 (m, 1H), 2.48-2.39 (m, 1H). |
| 272 | 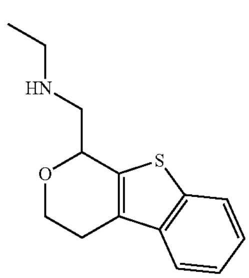 [SMILES: CCNCC1OCCc2c1sc1ccccc21] | HCl | $^1$H NMR (CD$_3$OD): δ 7.87 (d, J = 2.0 Hz, 1H), 7.73 (d, J = 2.0 Hz, 1H), 7.42 (t, J = 2.0 Hz, 1H), 7.38 (dt, J = 2.0, 0.7 Hz, 1H), 5.25-5.22 (m, 1H), 4.40 (ddd, J = 3.0, 1.5, 0.7 Hz, 1H), 3.98 (dt, J = 3.0, 1.0 Hz, 1H), 3.54 (dd, J = 3.3, 1.0 Hz, 1H), 3.36 (dd, J = 3.0, 2.0 Hz, 1H), 3.14 (dq, J = 1.7, 0.7 Hz, 2H), 3.00-2.96 (m, 1H), 2.91-2.87 (m, 1H), 1.34 (t, J = 1.7 Hz, 3H). |

| Compd. No. | Structure | Salt or FB* | Analytical Data |
|---|---|---|---|
| 273 | 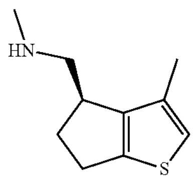 | HCl | $^1$H NMR (CD$_3$OD): δ 6.87 (s, 1H), 3.41-3.35 (m, 1H), 3.33-3.25 (m, 1H), 3.05-2.96 (m, 2H), 2.90-2.83 (m, 1H), 2.77-2.70 (m, 1H), 2.75 (s, 3H), 2.39-2.30 (m, 1H), 2.20 (s, 3H). |
| 274 | 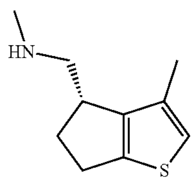 | HCl | $^1$H NMR (CD$_3$OD): δ 6.87 (s, 1H), 3.41-3.35 (m, 1H), 3.33-3.25 (m, 1H), 3.05-2.96 (m, 2H), 2.90-2.83 (m, 1H), 2.77-2.70 (m, 1H), 2.75 (s, 3H), 2.39-2.30 (m, 1H), 2.20 (s, 3H). |
| 275 | 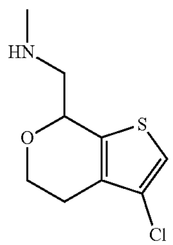 | HCl | LC-MS: m/z 218 (MH$^+$); $^1$H NMR (MeOD): δ 6.84 (s, 1H), 5.08-5.03 (m, 1H), 4.28-4.22 (m, 1H), 3.89-3.81 (m, 1H), 3.47-3.42 (m, 1H), 3.29-3.25 (m, 1H), 2.87-2.78 (m, 1H), 2.78 (s, 3H), 2.66-2.58 (m, 1H). |
| 276 | 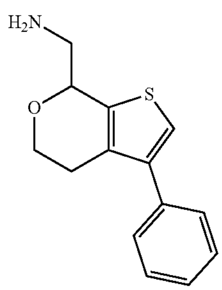 [SMILES: NCC1OCCc2c(-c3ccccc3)csc21] | HCl | LC-MS: m/z 246 (MH$^+$); $^1$H NMR (MeOD): δ 7.49-7.36 (m, 5H), 7.21 (s, 1H), 5.36-5.32 (m, 1H), 4.26-4.17 (m, 1H), 3.97-3.90 (m, 1H), 3.08-3.00 (m, 1H), 2.93-2.88 (m, 1H), 2.81-2.70 (m, 2H). |
| 277 | 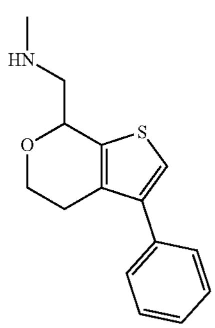 [SMILES: CNCC1OCCc2c(-c3ccccc3)csc21] | HCl | LC-MS: m/z 260 (MH$^+$); $^1$H NMR (MeOD): δ 7.50-7.38 (m, 5H), 7.24 (s, 1H), 5.42-5.38 (m, 1H), 4.27-4.21 (m, 1H), 3.98-3.90 (m, 1H), 2.95-2.93 (m, 1H), 2.92-2.85 (m, 2H), 2.80-2.71 (m, 1H), 2.47 (s, 3H). |
| 278 | 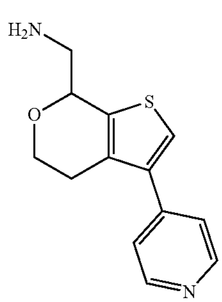 [SMILES: NCC1OCCc2c(-c3ccncc3)csc21] | HCl | LC-MS: m/z 247 (MH$^+$); $^1$H NMR CD$_3$OD): δ 8.90-8.88 (d, J = 6.87 Hz, 2H), 8.22-8.19 (d, J = 6.87 Hz, 2H), 7.99 (s, 1H), 5.67-5.62 (m, 1H), 4.31-4.24 (m, 1H), 4.03-3.91 (m, 1H), 3.22-2.85 (m, 4H). |

-continued

| Compd. No. | Structure | Salt or FB* | Analytical Data |
|---|---|---|---|
| 279 | 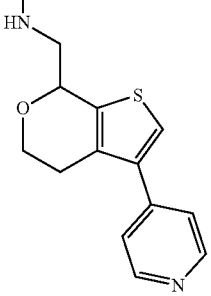 | HCl | LC-MS: m/z 261 (MH$^+$); $^1$H NMR (MeOD): δ 8.90-8.88 (d, J = 6.87 Hz, 2H), 8.22-8.19 (d, J = 6.87 Hz, 2H), 7.99 (s, 1H), 5.74-5.71 (m, 1H), 4.31-4.24 (m, 1H), 4.03-3.95 (m, 1H), 3.32-2.94 (m, 4H), 2.61 (s, 3H). |
| 280 | 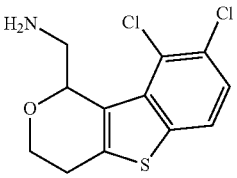 [SMILES: NCC1OCCc2sc3ccc(Cl)c(Cl)c3c21] | HCl | LC-MS: m/z 288 (MH$^+$); $^1$H NMR (MeOD): δ 7.85-7.82 (d, J = 8.40 Hz, 1H), 7.51-7.49 (d, J = 8.40 Hz, 1H), 5.76-5.73 (d, J = 9.92 Hz, 1H), 4.24-4.16 (m, 1H), 4.09-4.00 (m, 1H), 3.67-3.61 (m, 1H), 3.41-3.35 (m, 1H), 3.12-2.99 (m, 2H). |
| 281 | 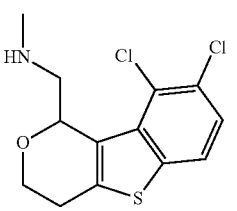 [SMILES: CNCC1OCCc2sc3ccc(Cl)c(Cl)c3c21] | HCl | LC-MS: m/z 302 (MH$^+$); $^1$H NMR (D$_2$O): δ 7.42-7.41 (d, J = 2.42 Hz, 1H), 7.15 (s, 1H), 5.50 (s, 1H), 4.00 (s, 2H), 3.45 (s, 2H), 2.98-2.85 (m, 2H), 2.70 (s, 3H). |
| 282 | 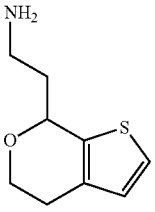 [SMILES: NCCC1OCCc2ccsc21] | HCl | LC-MS: m/z 184 (MH$^+$); $^1$H NMR (MeOD): δ 7.28 (d, J = 1.3 Hz, 1H), 6.85 (d, J = 1.3 Hz, 1H), 5.00-4.96 (m, 1H), 4.24 (ddd, J = 2.8, 1.4, 0.3 Hz, 1H), 3.75 (dt, J = 2.8, 1.0 Hz, 1H), 3.10 (t, J = 1.7 Hz, 2H), 2.90-2.81 (m, 1H), 2.64-2.59 (m, 1H), 2.30-2.22 (m, 1H), 2.09-2.00 (m, 1H). |
| 283 | 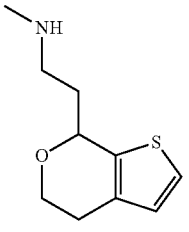 | HCl | LC-MS: m/z 198 (MH$^+$); $^1$H NMR (MeOD): δ 7.29 (d, J = 1.3 Hz, 1H), 6.86 (d, J = 1.3 Hz, 1H), 5.00-4.97 (m, 1H), 4.25 (ddd, J = 2.9, 1.5, 0.4 Hz, 1H), 3.75 (dt, J = 2.9, 0.9 Hz, 1H), 3.23-3.12 (m, 2H), 2.90-2.81 (m, 1H), 2.69 (s, 3H), 2.64-2.59 (m, 1H), 2.33-2.25 (m, 1H), 2.12-2.02 (m, 1H). |
| 284 | 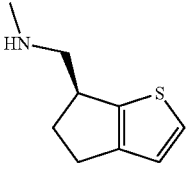 | HCl | $^1$H NMR (CD$_3$OD): δ 7.35 (d, J = 1.3 Hz, 1H), 6.85 (d, J = 1.3 Hz, 1H), 3.62-3.55 (m, 1H), 3.33-3.24 (m, 1H), 3.11-3.05 (m, 1H), 2.90-2.80 (m, 1H), 2.79-2.65 (m, 2H), 2.75 (s, 3H), 2.33-2.25 (m, 1H). |
| 285 | 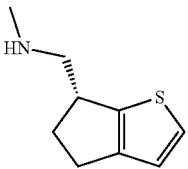 | HCl | $^1$H NMR (CD$_3$OD): δ 7.35 (d, J = 1.3 Hz, 1H), 6.85 (d, J = 1.3 Hz, 1H), 3.62-3.55 (m, 1H), 3.33-3.24 (m, 1H), 3.11-3.05 (m, 1H), 2.90-2.80 (m, 1H), 2.79-2.65 (m, 2H), 2.75 (s, 3H), 2.33-2.25 (m, 1H). |

-continued

| Compd. No. | Structure | Salt or FB* | Analytical Data |
|---|---|---|---|
| 286 | 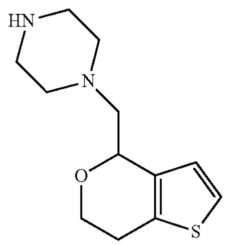 [SMILES: c1cc2c(s1)CCOC2CN1CCNCC1] | HCl | ¹H NMR (CD₃OD): δ 7.30 (d, J = 1.3 Hz, 1H), 6.91 (d, J = 1.3 Hz, 1H), 5.23 (apd, J = 2.3 Hz, 1H), 4.29 (ddd, J = 3.0, 1.5, 0.7 Hz, 1H), 3.88-3.77 (m, 2H), 3.76-3.46 (m, 6H), 3.43-3.29 (m, 2H), 3.25-3.20 (m, 1H), 3.05-2.98 (m, 1H), 2.85-2.80 (m, 1H). |
| 287 | 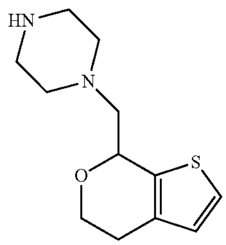 [SMILES: c1cc2c(s1)C(CN1CCNCC1)OCC2] | HCl | ¹H NMR (CD₃OD): δ 7.37 (d, J = 1.3 Hz, 1H), 6.91 (d, J = 1.3 Hz, 1H), 5.40-5.33 (m, 1H), 4.82-4.25 (m, 2H), 3.85 (dt, J = 2.5, 1.0 Hz, 1H), 3.88-3.75 (m, 6H), 3.54-3.44 (m, 1H), 3.28-3.12 (m, 2H), 2.91-2.83 (m, 1H), 2.74-2.67 (m, 1H). |
| 288 | 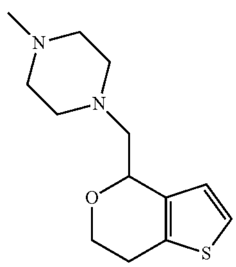 [SMILES: CN1CCN(CC2OCCc3sccc32)CC1] | HCl | ¹H NMR (CD₃OD): δ 7.29 (d, J = 0.7 Hz, 1H), 6.91 (d, J = 0.7 Hz, 1H), 5.18 (d, J = 2.0 Hz, 1H), 4.27 (ddd, J = 3.0, 1.5, 0.7 Hz, 1H), 3.87-3.78 (m, 2H), 3.77-3.40 (m, 6H), 3.39-3.12 (m, 3H), 3.11-2.87 (m, 1H), 2.99 (s, 3H), 2.92-2.82 (m, 1H). |
| 289 | 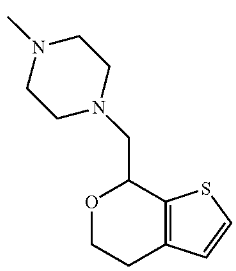 [SMILES: CN1CCN(CC2OCCc3ccsc32)CC1] | HCl | ¹H NMR (CD₃OD): δ 7.35 (d, J = 1. 3 Hz, 1H), 6.90 (d, J = 1.3 Hz, 1H), 5.29 (brd, J = = 2.3 Hz, 1H), 4.26 (ddd, J = 3.0, 1.3, 0.7 Hz, 1H), 3.83 (dt, J = 2.0, 1.0 Hz, 1H), 3.80-3.32 (m, 9H), 3.25 (m, 1H), 3.00 (s, 3H), 2.89-2.82 (m, 1H), 2.72-2.65 (m, 1H). |
| 290 | 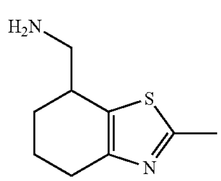 | HCl | LC-MS: m/z 183 (MH⁺); ¹H NMR (CD₃OD): δ 3.47-3.42 (m, 2H), 3.21-3.09 (m, 1H), 2.99 (s, 3H), 2.88 (s, 2H), 2.35-2.14 (m, 2H), 1.97-1.92 (m, 2H). |
| 291 | | HCl | LC-MS: m/z 197 (MH⁺); ¹H NMR (CD₃OD): δ 3.21 (s, 1H), 3.04-2.94 (m, 1H), 2.91-2.87 (m, 1H), 2.73-2.64 (m, 2H), 2.61 (s, 3H), 2.59 (s, 3H), 2.12-1.99 (m, 2H), 1.84-1.79 (m, 2H), 1.72-1.64 (m, 1H). |

| Compd. No. | Structure | Salt or FB* | Analytical Data |
|---|---|---|---|
| 292 | | HCl | LC-MS: m/z 288 (MH+); $^1$H NMR (CD$_3$OD): | δ 7.86-7.83 (d, J = 8.61 Hz, 1H), 7.52-7.49 (d, J= 8.58 Hz, 1H), 5.76-5.73 (d, J = 9.90 Hz, 1H), 4.24-4.17 (m, 1H), 4.07-4.00 (m, 1H), 3.66-3.62 (d, J = 11.19 Hz, 1H), 3.42-3.38 (d, J = 9.48 Hz, 1H), 3.17-3.00 (m, 2H). |
| 293 | 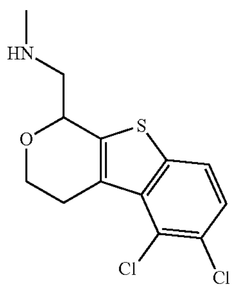 [SMILES: CNCC1OCCc2c1sc1ccc(Cl)c(Cl)c21] | HCl | LC-MS: m/z 302 (MH+); $^1$H NMR (CD$_3$OD): δ 7.85-7.82 (d, J = 8.55, 1H), 7.51-7.49 (d, J = 8.58, 1H), 5.84-5.81 (d, J = 9.55, 1H), 4.25-4.19 (m, 1H), 4.08-4.01 (m, 1H), 3.72-3.67 (dd, J = 13.43 Hz, 2.48 Hz, 1H), 3.54-3.47 (m, 1H), 3.12-3.05 (m, 2H), 2.81 (s, 3H). |
| 294 | 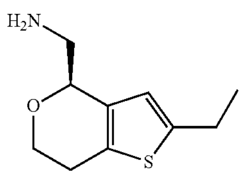 | HCl | $^1$H NMR (DMSO-d$^6$): δ 8.22 (br s, 3H), 6.70 (s, 1H), 4.85-4.83 (d, J = 8.01 Hz, 1H), 4.13-4.07 (m, 1H), 3.78-3.70 (m, 1H), 3.29 (s, 1H), 2.91-2.67 (m, 5H), 1.22-1.18 (t, J = 7.50 Hz, 3H). |
| 295 | 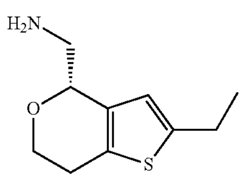 | HCl | $^1$H NMR (DMSO-d$^6$): δ 8.22 (br s, 3H), 6.70 (s, 1H), 4.85-4.83 (d, J = 8.01 Hz, 1H), 4.13-4.07 (m, 1H), 3.78-3.70 (m, 1H), 3.29 (s, 1H), 2.91-2.67 (m, 5H), 1.22-1.18 (t, J = 7.50 Hz, 3H). |
| 296 | 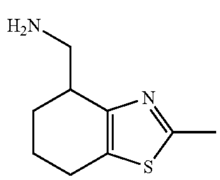 | HCl | LC-MS: m/z 183 (MH+); $^1$H NMR (CD$_3$OD): δ 3.46-3.35 (m, 2H), 3.25-3.19 (m, 1H), 2.93 (s, 3H), 2.89-2.85 (t, J = 5.43 Hz, 2H), 2.12-2.01 (m, 2H), 1.96-1.85 (m, 2H). |
| 297 | 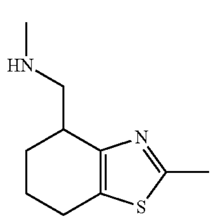 | HCl | LC-MS: m/z 197 (MH+); $^1$H NMR (CD$_3$OD): δ 3.51-3.33 (m, 3H), 2.94 (s, 3H), 2.89-2.85 (m, 2H), 2.83 (s, 3H), 2.13-1.90 (m, 4H). |
| 298 | 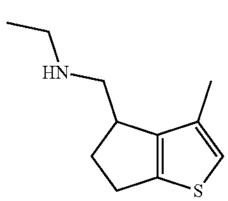 | HCl | LC-MS: m/z 196 (MH+); $^1$H NMR (CD$_3$OD): δ 6.88 (s, 1H), 3.47-3.38 (m, 1H), 3.27-3.26 (m, 1H), 3.18-3.09 (m, 2H), 3.06-2.97 (m, 2H), 2.93-2.83 (m, 1H), 2.80-2.68 (m, 1H), 2.47-2.38 (m, 1H), 8.24-2.22 (m, 3H), 1.39-1.36 (t, J = 7.29 Hz, 3H). |

-continued

| Compd. No. | Structure | Salt or FB* | Analytical Data |
|---|---|---|---|
| 299 | 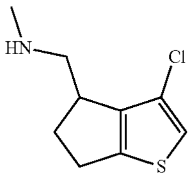 | HCl | LC-MS: m/z 202 (MH$^+$); $^1$H NMR (CD$_3$OD): δ 6.89 (s, 1H), 3.45-3.40 (m, 1H), 3.31-3.29 (m, 1H), 3.09-2.94 (m, 3H), 2.74-2.65 (m, 4H), 2.28-2.17 (m, 1H). |
| 300 | 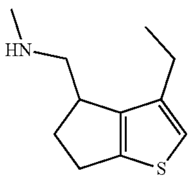 | HCl | LC-MS: m/z 196 (MH$^+$); $^1$H NMR (CD$_3$OD): δ 6.93 (s, 1H), 3.45-3.39 (m, 1H), 3.28-3.24 (m, 1H), 3.08-2.98 (m, 2H), 2.94-2.89 (m, 1H), 2.74-2.68 (m, 4H), 2.64-2.56 (m, 2H), 2.42-2.32 (m, 1H), 1.29-1.24 (t, J = 7.52 Hz, 3H). |
| 301 | 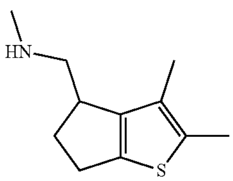 | HCl | LC-MS: m/z 196 (MH$^+$); $^1$H NMR (CD$_3$OD): δ 3.39 (m, 1H), 3.28-3.23 (m, 1H), 3.02-2.93 (m, 2H), 2.87-2.78 (m, 1H), 2.76 (s, 3H), 2.71-2.61 (m, 1H), 2.35-2.22 (m, 1H), 2.31 (s, 3H), 2.10 (s, 3H). |
| 302 | 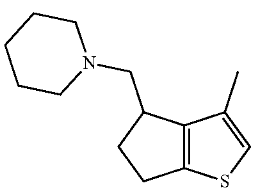 [SMILES: Cc1csc2c1C(CN1CCCCC1)CC2] | HCl | LC-MS: m/z 236 (MH$^+$); $^1$H NMR (CD$_3$OD): δ 6.89 (s, 1H), 3.78-3.75 (m, 1H), 3.58-3.52 (m, 2H), 3.21-3.00 (m, 4H), 2.94-2.72 (m, 3H), 2.50-2.41 (m, 1H), 2.23-2.22 (d, J = 0.96 Hz, 3H), 2.02-1.81 (m, 5H), 1.59 (s, 1H). |
| 303 | 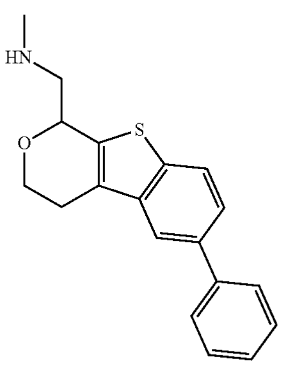 [SMILES: CNCC1OCCc2c1sc1ccc(-c3ccccc3)cc21] | HCl | LC-MS: m/z 310 (MH$^+$); $^1$H NMR (CD$_3$OD): δ 7.98-7.75 (m, 2H), 7.72-7.66 (m, 3H), 7.50-7.45 (t, J = 7.47 Hz, 2H), 7.40-7.37 (m, 1H), 5.29-5.26 (m, 1H), 4.47-4.41 (m, 1H), 4.06-4.00 (m, 1H), 3.63-3.58 (m, 1H), 3.45-3.38 (m, 1H), 3.63-3.38 (m, 2H)), 2.80 (s, 3H). |
| 304 | 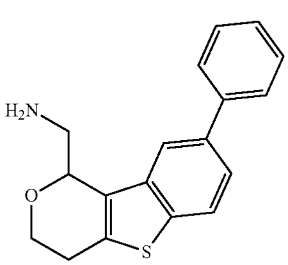 [SMILES: NCC1OCCc2sc3ccc(-c4ccccc4)cc3c21] | HCl | LC-MS: m/z 296 (MH$^+$); $^1$H NMR (CD$_3$OD): δ 7.97-7.94 (d, J = 8.34 Hz, 1H), 7.88-7.87 (d, J = 1.26 Hz, 1H), 7.73-7.70 (m, 2H), 7.65-7.62 (dd, J = 8.37 Hz, 1.65 Hz, 1H), 7.51-7.48 (t, J = 7.47 Hz, 2H), 7.40-7.35 (m, 1H), 5.37-5.34 (d, J = 8.52 Hz, 1H), 4.81-4.25 (m, 1H), 4.02-3.94 (m, 1H), 3.70-3.64 (m, 1H), 3.42-3.37 (m, 1H), 3.32-3.01 (m, 2H). |

-continued

| Compd. No. | Structure | Salt or FB* | Analytical Data |
|---|---|---|---|
| 305 | | HCl | LC-MS: m/z 310 (MH+); $^1$H NMR (CD$_3$OD): | δ 7.96-7.91 (m, 2H), 7.74-7.71 (d, J = 7.11 Hz, 2H), 7.65-7.62 (dd, J = 8.40 Hz, 1.68 Hz, 1H), 7.50-7.48 (t, J = 7.47 Hz, 2H), 7.40-7.37 (m, 1H), 5.43-5.40 (d, J = 6.24 Hz, 1H), 4.84-4.28 (m, 1H), 4.02-3.96 (m, 1H), 3.77-3.72 (dd, J = 13.07 Hz, J = 2.60 Hz, 1H), 3.53-3.33 (m, 1H), 3.32-3.03 (m, 2H), 2.80 (s, 3H). |
| 306 | 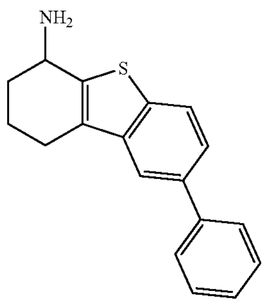 [SMILES: NC1CCCc2c1sc1ccc(-c3ccccc3)cc21] | HCl | LC-MS: m/z 280 (MH+); $^1$H NMR (CD$_3$OD): δ 7.87-7.84 (d, J = 8.34 Hz, 2H), 7.58-7.57 (d, J = 1.80 Hz, 3H), 7.39-7.34 (m, 2H), 7.28-7.24 (m, 1H), 4.63-4.60 (m, 1H), 2.97-2.88 (m, 2H), 2.30-2.21 (m, 1H), 2.08-1.94 (m, 3H). |
| 307 | 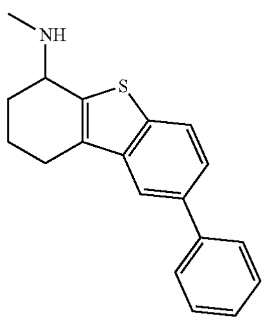 [SMILES: CNC1CCCc2c1sc1ccc(-c3ccccc3)cc21] | HCl | LC-MS: m/z 294 (MH+); $^1$H NMR (DMSO-d$_6$): δ 7.99-7.97 (m, 2H), 7.74-7.69 (m, 3H), 7.51-7.46 (t, J = 7.49 Hz, 2H), 7.40-7.38 (m, 1H), 4.67-4.65 (m, 1H), 2.89 (s, 3H), 2.35-2.29 (m, 1H), 2.23-2.18 (m, 1H), 2.13-2.03 (m, 2H), 1.61 (s, 2H). |
| 308 | 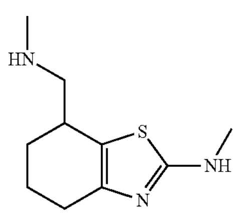 | 2HCl | LC-MS: m/z 212 (MH+); $^1$H NMR (CD$_3$OD): δ 3.49-3.43 (m, 1H), 3.31-3.28 (m, 2H), 3.16 (s, 3H), 2.81 (s, 3H), 2.62-2.61 (m, 2H), 1.96-1.74 (m, 4H). |
| 309 | | formate | LC-MS: m/z 198 (MH+); $^1$H NMR (CD$_3$OD): | δ 7.33 (d, J = 1.2, 0.7 Hz, 1H), 7.15 (brs, 1H), 7.04 (dd, J = 1.2, 0.3 Hz, 1H), 4.82 (t, J = 1.2 Hz, 1H), 4.00-3.94 (m, 1H), 3.88-3.82 (m, 1H), 3.25 (d, J = 1.2 Hz, 2H), 2.96 (t, J = 1.6 Hz, 2H), 2.85 (s, 6H). |
| 310 | 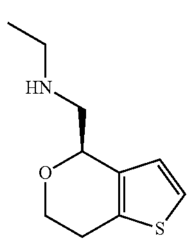 | HCl | GC-MS m/z 139 (M+); $^1$H NMR (DMSO-d$^6$): δ 9.02 (s, 1H), 8.65 (s, 1H), 7.41-7.40 (d, J = 5.19 Hz, 1H), 6.99-6.97 (d, J = 5.19 Hz, 1H), 5.03-5.00 (d, J = 8.13 Hz, 1H), 4.21-4.12 (m, 1H), 3.83-3.75 (m, 1H), 3.52-3.48 (d, J = 12.43 Hz, 1H), 3.13-2.72 (m, 5H), 1.25-1.20 (t, J = 7.26 Hz, 3H). |

-continued

| Compd. No. | Structure | Salt or FB* | Analytical Data |
|---|---|---|---|
| 311 | (structure: ethylamino-substituted dihydrothienopyran) | HCl | GC-MS m/z 139 (M+); $^1$H NMR (DMSO-d$^6$): δ 9.02 (s, 1H), 8.65 (s, 1H), 7.41-7.40 (d, J = 5.19 Hz, 1H), 6.99-6.97 (d, J = 5.19 Hz, 1H), 5.03-5.00 (d, J = 8.13 Hz, 1H), 4.21-4.12 (m, 1H), 3.83-3.75 (m, 1H), 3.52-3.48 (d, J = 12.43 Hz, 1H), 3.13-2.72 (m, 5H), 1.25-1.20 (t, J = 7.26 Hz, 3H). |

*FB is an abbreviation for "free base".

It should be noted that if there is a discrepancy between a depicted structure and a chemical name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it or mixtures thereof. Where the compound provided herein contains an alkenyl or alkenylene group, the compound may exist as one of or a mixture of geometric cis/trans (or Z/E) isomers. Where structural isomers are inter-convertible, the compound may exist as a single tautomer or a mixture of tautomers. This can take the form of proton tautomerism in the compound that contains, for example, an imino, keto, or oxime group; or so-called valence tautomerism in the compound that contains, for example, an aromatic moiety. It follows that a single compound may exhibit more than one type of isomerism.

The compounds provided herein may be enantiomerically pure or diastereomerically pure, such as a single enantiomer or a single diastereomer, or be stereoisomeric mixtures, such as a mixture of enantiomers and/or diastereomers, e.g., a racemic or enantioenriched mixture of two enantiomers; or a mixture of two or more diastereomers. In some instances, for compounds that undergo epimerization in vivo, one of skill in the art will recognize that administration of a compound in its (R) form is equivalent to administration of the compound in its (S) form, and vice versa. Conventional techniques for the preparation/isolation of individual enantiomers or diastereomers include synthesis from a suitable optically pure precursor, asymmetric synthesis from achiral starting materials, or resolution of a stereomeric mixture, for example, by chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, aspartic acid, L-aspartic acid, benzenesulfonic acid, benzoic acid, 4-acetamidobenzoic acid, boric acid, camphoric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, gluconic acid, D-gluconic acid, glucuronic acid, D-glucuronic acid, glutamic acid, L-glutamic acid, α-oxoglutaric acid, glycolic acid, hippuric acid, hydrobromic acid, hydrochloric acid, hydroiodic acid, isoethonic acid; (+)-L-lactic acid, (±)-DL-lactic acid, lactobionic acid, lauric acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, pyroglutamic acid, pyroglutamic acid, L-pyroglutamic acid, saccharic acid, salicylic acid, 4-amino-salicylic acid, sebacic acid, stearic acid, succinic acid, sulfuric acid, tannic acid, tartaric acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, potassium carbonate, zinc hydroxide, sodium hydroxide, or ammonia; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

Unless otherwise specified, the term "compound" referred to herein, such as, e.g., a compound of formula (I), (IIa), (IIb), (IIc), (IIIa), (IIIb), (IIIc), (IVa), (IVb), (IVc), (V), or (VI) is intended to encompass one or more of the following: a free base of the compound or a salt thereof, a stereoisomer or a mixture of two or more stereoisomers, a solid form (e.g., a crystal form or an amorphous form) or a mixture of two or more solid forms thereof, or a solvate (e.g., a hydrate) thereof. In certain embodiments, the term "compound" referred to herein is intended to encompass a pharmaceutical acceptable form of the compound, including but not limited to, a free base, a pharmaceutically acceptable salt, a stereoisomer or a mixture of two or more stereoisomers, a solid form (e.g., a crystal form or an amorphous form) or a mixture of two or more solid forms, a solvate (e.g., a hydrate), or a cocrystal thereof.

The compounds used in the methods provided herein can be made by a variety of methods known to the art, including, but not limited to those, disclosed in U.S. Pat. Nos. 8,710,245 and 9,351,954, the contents of which are incorporated herein by reference in their entirety.

The compounds used in the methods provided herein may also be provided as a prodrug, which is a functional derivative of the compound, for example, of Formula (I) and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

In various embodiments, the compounds used in the methods provided herein are prepared as a mixture of two or more stereoisomers or diastereoisomers. In one embodiment, the stereoisomers or diastereoisomers are separated using techniques known to those skilled in the art, including but not limited to, chiral column chromatography and chiral resolution by forming a salt with a suitable chiral counterion.

In various embodiments, the compounds used in the methods provided herein are provided as pharmaceutical compositions. Pharmaceutical compositions can be used in the preparation of individual, single unit dosage forms. Pharmaceutical compositions and dosage forms provided herein comprise a compound provided herein, or a pharmaceutically acceptable salt, stereoisomer, clathrate, or prodrug thereof. Pharmaceutical compositions and dosage forms can further comprise one or more excipients.

Pharmaceutical compositions and dosage forms provided herein can also comprise one or more additional active ingredients. Examples of optional second, or additional, active ingredients are also disclosed herein.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intra-arterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another and will be readily apparent to those skilled in the art. See, e.g., Remington's Pharmaceutical Sciences, 18th Ed., Mack Publishing, Easton Pa. (1990).

In one embodiment, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and/or magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles &Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In one embodiment, dosage forms comprise a compound provided herein in an amount of from about 0.10 to about 500 mg. In other embodiments, dosage forms comprise a compound provided herein in an amount of about 0.1, 1, 2, 5, 7.5, 10, 12.5, 15, 17.5, 20, 25, 50, 100, 150, 200, 250, 300, 350, 400, 450, or 500 mg.

In other embodiments, dosage forms comprise a second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's The Science and Practice of Pharmacy*, 21st Ed., Lippincott Williams & Wilkins (2005).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific example of a binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W. R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In one embodiment, a solid oral dosage form comprises a compound provided herein, and optional excipients, such as anhydrous lactose, microcrystalline cellulose, polyvinylpyrrolidone, stearic acid, colloidal anhydrous silica, and gelatin.

In various embodiments, the active ingredients of compositions used in the methods provided herein and compounds used in the methods provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In one embodiment, provided are single unit dosage forms suitable for oral administration such as, but not limited to, tablets, capsules, gelcaps, and caplets that are adapted for controlled-release.

In one embodiment, controlled-release pharmaceutical products improve drug therapy over that achieved by their non-controlled counterparts. In another embodiment, the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another embodiment, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In one embodiment, in order to maintain a constant level of drug in the body, the drug can be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral dosage forms can be administered to patients by various routes including, but not limited to, subcutaneous, intravenous (including bolus injection), intramuscular, and intra-arterial. In various embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's The Science and Practice of Pharmacy,* 21st Ed., Lippincott Williams & Wilkins (2005); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., *Remington's The Science and Practice of Pharmacy*, 21st Ed., Lippincott Williams & Wilkins (2005).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, prodrugs, clathrates, or stereoisomers of the active ingredients can be used to further adjust the properties of the resulting composition.

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise one or more second active ingredients as described herein, or a pharmacologically active mutant or derivative thereof, or a combination thereof.

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

VII. EXAMPLES

Various embodiments and aspects of the present inventions are further illustrated by the following non-limiting examples.

Example 1: Validation of Transformation Matrix

The robustness and general applicability of the discovery, was investigated by calculating transformed PANSS factor scores for all subjects in 12 additional clinical trials (the "Validation Study" data set) in the lurasidone database that were not included in the analysis sample (PANSS Analysis Study) used to derive the score matrix of FIG. 4 and Table 4A. Included among the 12 additional clinical trials were short-term acute schizophrenia studies, open-label studies, long-term extension studies, and randomized withdrawal studies. For each study in the Validation Data Set, the transformed PANSS factors were evaluated for their total variance (high r-squared values between sums of the transformed PANSS factors vs. PANSS total score), specificity/orthogonality (low correlation between the individual transformed PANSS factors), and high face validity (high correspondence with the Marder PANSS factors).

All study patients were adults with schizophrenia except for D1050301 which was adolescents (13-17 years) with schizophrenia. The PANSS Analysis Study data set alone was used to derive the score matrix (Table 4A) to transform PANSS items in the Validation Data Set into transformed PANSS factor scores.

Transformed PANSS factors were determined, using the same score matrix established from the PANSS Analysis Study data set operating upon the PANSS data od the Validation Set, to determine transformed PANSS factors data for the Validation Data Set, that is:

$$[\text{PANSS Validation Data}]_{(N \times 30)} * [\text{UPSM Analysis Study}]_{(30 \times 7)} = [\text{Transformed PANSS Factor Validation Data}]_{(N \times 7)}$$

FIG. 5 summarizes the results, for the PANSS Analysis Study dataset (labeled "Analysis" in FIG. 5) and Validation Study dataset (labeled "Validation" in FIG. 5). For each study summarized in FIG. 5, endpoint change scores utilizing the transformed PANSS factors yielded substantially reduced between-factor correlations, regardless of the duration of study treatment (6 weeks to 1 year), or other differences in study design or stage of illness. In addition, a sum of 7 transformed PANSS factors for each patient at endpoint retained over 90% of the variance of untransformed PANSS total.

The transformed PANSS factors also corresponded well to the Marder PANSS factors (r, 0.65-0.94), thus indicating that both factors are measuring very similar schizophrenia symptom domains. Based on the analysis of change, the PANSS negative symptom factor was subdivided into two subfactors, apathy/avolition and deficit of expression (representing these symptom sub-domains), and the PANSS depression/anxiety factor was subdivided into two subfactors, depression and anxiety (representing these symptom sub-domains). The transformed PANSS negative symptom subfactors (apathy/avolition and deficit of expression), correspond to the two subclusters previously identified in a factor analysis by Liemburg et al. (see, *J. Psychiatr Res*, June 2013; 47(6):718-725). The empirically derived PANSS negative symptom subfactors are also consistent with previously reported differences in the clinical presentation of negative symptoms (see, Blanchard J J, Cohen A S., *Schizophr Bull*, April 2006; 32(2):238-245) and with reported differences in outcome for each negative symptom phenotype (see, Strauss G P, Horan W P, Kirkpatrick B, et al., *J. Psychiatr Res*, June 2013; 47(6):783-790). In addition, there is evidence to suggest that these respective negative symptom subfactors may be subserved by distinct neurocircuitry (see, Shaffer J J, Peterson M J, McMahon M A, et al., *Mol Neuropsychiatry*, December 2015; 1(4):191-200). The transformed PANSS depression/anxiety factor, which separates depression and anxiety as two subfactors, is consistent with the view that these subfactors are partially independent of each other.

The transformed PANSS factors of this Example, derived from the weighted score matrix transformation of PANSS items, were found to meet three important criteria: to have good face validity, to account for almost all of the total variance observed in PANSS total score change, and to exhibit minimal between-factor correlation (high specificity/orthogonality). These criteria were met using the 5 lurasidone clinical trials (PANSS Analysis Study data) used to derive the score matrix transformation. The criteria were also met among the 12 additional lurasidone clinical trials, indicating high cross-study stability and general applicability. These criteria are discussed more specifically below.

Face validity. Each of the transformed PANSS factors was found to be strongly correlated with Marder PANSS factor scores, with Pearson's r-values at baseline ranging from 0.65-0.94, indicating that each factor is measuring similar efficacy domains.

Total variance. The transformed PANSS factors retained over 90% of the variance contained in the transformed PANSS total score, thus indicating that there was minimum (but quantifiable) loss of information related to total symptom severity using the transformed, transformed PANSS factors. Thus, the sum of transformed PANSS factor scores accurately captured the overall drug treatment effect sizes.

Specificity. A Pearson's correlation analysis of the transformed PANSS factor change scores at week 6 indicated reduced correlations when compared to the Marder PANSS factors, indicating that the transformed PANSS factors are measuring changes somewhat independent of any changes in correlated scores, reducing pseudospecificity concerns. Accordingly, in various embodiments, analyses using these transformed PANSS factors can be used to determine and/or ensure that improvements in one symptom domain are not largely accounted for by improvements in a cross-correlated domain.

Cross-study stability. In the independent validation sample of 12 clinical studies (Vaidation Study data), the transformed PANSS factor scores, generated using the score matrix, demonstrated similarly low correlations (r<0.25) between the transformed PANSS positive factor change score, and change scores for the other 6 transformed PANSS factors. Notably, the 12 clinical studies used in this Example spanned a diverse range of patient populations, from adolescents, ages 13 to 17 years, to adults, ages 18 to 55 years; and in widely varying geographical regions, including the US, and countries in Europe and Asia. In the analysis of the Validation Study data, the transformed PANSS factors also demonstrated orthogonality and specificity when the score matrix transformation was applied to schizophrenic patient populations, (i.e. patient sub-domains) regardless of whether the patients were acutely ill, chronic, or symptomatically stable. This result indicates that the score matrix formula performs well across studies and across clinical populations, and thus may be pre-specified in the analysis plans.

Example 2: Lurasidone Sub-Domains

The Validation Study data transformed PANSS factors of Example 1 were used to compare treatment effects of an antipsychotic (lurasidone) on established schizophrenia symptom domains with those estimated using Marder PANSS factors. The high degree of total variance explained, effect sizes for the sum of transformed PANSS factors and PANSS total were almost identical (between the transformed PANSS and untransformed PANSS factors), indicating that the estimates of drug effect on schizophrenia symptoms were unchanged between the methods.

FIG. 3A compares baseline to week 6 (within-treatment group) effect sizes for both lurasidone and placebo, as estimated using both the Marder PANSS factors (left panel), and the transformed PANSS factors (right panel). In the left panel, a consistent pattern of moderate-to-high pre-post, within-treatment group, effect sizes (0.5 to 1.1) were observed for lurasidone across all Marder PANSS factors. Pre-post effect sizes for placebo were in the low-to-moderate range across all Marder PANSS factors (effect sizes <0.5, except for the PANSS positive factor change score; FIG. 3A). For both lurasidone and placebo, the transformed PANSS positive factor (right panel) had an endpoint effect size that was similar in magnitude to the Marder PANSS positive factor (left panel). For the other transformed PANSS factors (disorganized, negative-apathy/avolition and deficit of expression, hostility, and depression and anxiety), the endpoint effect sizes were smaller for both lurasidone and placebo.

FIG. 3B presents for the 5 pooled clinical trials (Analysis Study Data), drug vs. placebo effect sizes for baseline-to-endpoint change were calculated using both the Marder PANSS factors (FIG. 3B; left panel) and the transformed PANSS factors (FIG. 3B, right panel). In the left panel, a relatively consistent pattern of moderate effect sizes (ranging from 0.31 to 0.43) were observed for lurasidone across all Marder PANSS factors. In the right panel, the effect size calculated using the transformed PANSS positive factor was approximately similar to the effect size using the Marder PANSS positive factor (left panel). For the other transformed PANSS factors, the endpoint drug effect sizes were smaller when compared to the same Marder PANSS factors. Endpoint effect sizes calculated for the other transformed PANSS factors (right panel) ranged from 0.05 to 0.29. The endpoint effect size for the transformed PANSS hostility factor was larger than the effect sizes observed in the transformed PANSS disorganized, negative apathy/avolition, deficit of expression, and anxiety/depression factors.

Referring again to FIG. 3B, the effect sizes estimated for positive and hostility symptoms were quite similar between the untransformed PANSS method and the present transformed PANSS method. However, the effect sizes were somewhat lower on negative symptoms of apathy/avolition ($r=0.22$) and deficit of expression ($r=0.04$) compared with the effect size observed on Marder negative symptom factor ($r=0.35$). This appears to be a consequence of reducing the correlation between the PANSS positive and negative factors from $1=0.57$ to $r<0.10$. Effect sizes for the other transformed PANSS factor change scores were also reduced compared with the Marder PANSS factor change scores on the positive ($r=0.45$ vs. $0.59$), disorganized ($r=0.23$ vs. $0.48$), hostility ($r=0.31$ vs. $0.43$), and anxiety ($r=0.24$ vs. $0.38$) and depression ($r=0.16$ vs. $0.38$) factors. In traditional PANSS factor use, effect sizes that are similar across symptom domains may be partly attributable to pseudospecificity. In contrast, measuring efficacy using the transformed PANSS factors, in accord with various embodiments of the present inventions, allows for a clearer understanding of the profile of treatment effects across the symptom domains of schizophrenia.

In addition, it was discovered that increasing the orthogonality of PANSS factors (e.g., by the methods of this Example) revealed an effect of placebo on specific clinical domains of schizophrenia. In spite of the large placebo response, the transformed PANSS hostility factor associated with placebo treatment demonstrated a specific worsening in symptoms of hostility (pre-post effect size, −0.10) and revealed that the apparent improvements in the Marder PANSS factor for hostility was likely due to correlations with improvements in other PANSS items.

Example 3: Application to Compound 129

An embodiment of the methods of the present inventions was applied to PANSS data acquired for Compound 129:

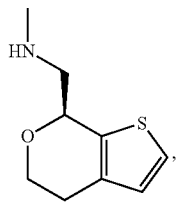

in a study (n=16) of schizophrenic subjects. The study was conducted to test the effects of daily doses of 75 mg Compound 129 for 28 days. PANSS total scores were assessed at baseline ("BL") pre-dose, Day 1 post-dose and on Days 7, 21, and 28 (endpoint). Each of n=16 subjects were classified into distinct subject sub-population types according to the following classifications, subject sub-populations types, subjects with: (1) prominently positive symptoms ("Positive" group in Tables 5A and 5B; subject ID numbers 35, 48, 28, 44, 34, 30, 53 and 56); (2) prominently disorganized symptoms ("Disorganized" group in Tables 5A and 5B; subject ID number 50); (3) prominently affective symptoms ("Affective" group in Tables 5A and 5B; subject ID numbers 54, 51, 47, and 45); or (4) prominently negative symptoms ("Negative" group in Tables 5A and 5B; subject ID numbers 37, 29, and 49).

Subjects were classified using the UPSM (score matrix) of Table 4A on the PANSS factors assessed at baseline ("BL") to produce transformed PANSS factors from which subject classification was made. The classifications were determined using the PANSS Analysis Study data for lurasidone, described elsewhere herein, where each of the subjects' (N=1710) PANSS factor scores at baseline were transformed with the UPSM (score matrix) of Table 4A (see, also FIG. 4). Clustering of the subjects (N=1,710) by k-means was used to identify distinct clusters, each characterized by distinctly prominent baseline transformed PANSS factor scores. A SVM (Support Vector Machine) classifier was trained on these cluster assignments at baseline, and subsequently used to identify subject sub-population types post-baseline and in external data sets. These sub-population types (identified using the PANSS Analysis Study data for lurasidone) where used to classify subject sub-population types for the subjects (N=16) of this study on Compound 129, where the UPSM (score matrix) of Table 4A was used to transform the baseline PANSS factor scores of the subjects in this Example 3 to classify the subjects by sub-population type.

Table 5A shows each subjects total PANSS score (based on untransformed PANSS scores) at baseline (pre-dose) and days 1, 7, 14, 21 and 28 (end-point) post-dose. Table 5B shows change from the % baseline of the untransformed PANSS scores at days 1, 7, 14, 21 and 28 (end-point). It is to be understood that a 20% improvement or decrease from baseline 100% scores is generally considered a clinically significant change in acute schizophrenia trials. It was discovered that Compound 129 provided a clinically significant improvement in overall schizophrenia symptoms (untransformed PANSS total) for the subject sub-population with prominent negative symptoms. These results indicate that Compound 129 was a particularly effective treatment in the patient sub-population type characterized by prominent negative symptoms.

The UPSM transformation of the PANSS factor data shows the specificity of treatment effects within the domains of schizophrenia. A drug with treatment effects on a given symptom domain of schizophrenia (e.g., negative symptoms) would be expected to demonstrate overall improvements (PANSS total) in a patient type characterized by more-prominent symptoms in that specific domain (e.g., negative symptoms). Baseline UPSM factor scores can be used to demonstrate specific schizophrenia patient types having prominence of specific symptoms among the 5 dimensions of schizophrenia.

It is to be understood that the score matrix used in this Example was the one determined, as discussed herein, from lurasidone studies (PANSS Analysis Study data) as was the SVM classifier which was trained on PANSS Analysis Study data transformed with the UPSM (score matrix) of Table 4A (see also FIG. 4). That is, the UPSM of Table 4A was shown in this Example to have general applicability to the assessment of the efficacy of schizophrenia treatments on other subject (e.g. patient) groups with other drugs, even though the UPSM of Table 4A (and FIG. 4) was determined using only data from lurasidone studies.

TABLE 5A

| Subject Sub-Population Type | Subject ID | Untransformed PANSS Total | | | | | |
|---|---|---|---|---|---|---|---|
| | | BL | Day 1 | Day 7 | Day 14 | Day 21 | Day 28 |
| Positive | 35 | 74 | 71 | 70 | 69 | 69 | 68 |
| | 48 | 75 | 74 | 76 | — | — | — |
| | 28 | 66 | 66 | 61 | 57 | 63 | 57 |
| | 44 | 70 | 70 | 67 | 66 | 66 | 63 |
| | 34 | 75 | 75 | 79 | 73 | — | — |
| | 30 | 70 | 69 | 73 | 73 | 67 | 67 |
| | 53 | 73 | 75 | 79 | 78 | 81 | 75 |
| | 56 | 80 | 76 | 74 | 77 | 58 | 57 |
| Disorganized | 50 | 82 | 79 | 86 | 83 | 84 | 89 |
| Affective | 54 | 72 | 62 | 64 | 58 | 62 | 56 |
| | 51 | 70 | 72 | 68 | 64 | 69 | 66 |
| | 47 | 70 | 74 | 65 | 67 | 69 | 71 |
| | 45 | 67 | 66 | 72 | 58 | 69 | 66 |
| Negative | 37 | 76 | 77 | 65 | 59 | 58 | 57 |
| | 29 | 80 | 78 | 85 | 73 | 75 | 68 |
| | 49 | 72 | 72 | 75 | 69 | 58 | 57 |

TABLE 5B

| Subject Sub-Population Type | Subject ID | % of Baseline PANSS Total | | | | | |
|---|---|---|---|---|---|---|---|
| | | BL | Day 1 | Day 7 | Day 14 | Day 21 | Day 28 |
| Positive | 35 | 100% | 96% | 95% | 93% | 93% | 92% |
| | 48 | 100% | 99% | 101% | | | |
| | 28 | 100% | 100% | 92% | 86% | 95% | 86% |
| | 44 | 100% | 100% | 96% | 94% | 94% | 90% |
| | 34 | 100% | 100% | 105% | 97% | | |
| | 30 | 100% | 99% | 104% | 104% | 96% | 96% |
| | 53 | 100% | 103% | 108% | 107% | 111% | 103% |
| | 56 | 100% | 95% | 93% | 96% | 73% | 71% |
| Disorganized | 50 | 100% | 96% | 105% | 101% | 102% | 109% |
| Affective | 54 | 100% | 86% | 89% | 81% | 86% | 78% |
| | 51 | 100% | 103% | 97% | 91% | 99% | 94% |
| | 47 | 100% | 106% | 93% | 96% | 99% | 101% |
| | 45 | 100% | 99% | 107% | 87% | 103% | 99% |

TABLE 5B-continued

| Subject Sub-Population Type | Subject ID | % of Baseline PANSS Total | | | | | |
|---|---|---|---|---|---|---|---|
| | | BL | Day 1 | Day 7 | Day 14 | Day 21 | Day 28 |
| Negative | 37 | 100% | 101% | 86% | 78% | 76% | 75% |
| | 29 | 100% | 98% | 106% | 91% | 94% | 85% |
| | 49 | 100% | 100% | 104% | 96% | 81% | 79% |

Example 4: Animal Models

Anti-psychotic like activity of the compounds was evaluated in mice using the PCP hyperactivity and Pre-Pulse Inhibition (PPI) models of schizophrenia. Tables 6A and 6B summarize the results.

Methods: Animals: Male C57Bl/6J mice from Jackson Laboratories (Bar Harbor, Me.) were used. Upon receipt, mice were assigned unique identification numbers (tail marked) and were group housed with 4 mice per cage in OptiMICE ventilated cages. All animals remained housed in groups of four during the remainder of the study. All mice were acclimated to the colony room for at least two weeks prior to testing. During the period of acclimation, mice were examined on a regular basis, handled, and weighed to assure adequate health and suitability. Animals were maintained on a 12/12 light/dark cycle. The room temperature was maintained between 20 and 23° C. with a relative humidity maintained between 30% and 70%. Chow and water were provided ad libitum for the duration of the study. In each test, animals were randomly assigned across treatment groups.

PCP Hyperactivity: Open field (OF) chambers were Plexiglas square chambers (27.3×27.3×20.3 cm; Med Associates Inc., St Albans, Vt.) surrounded by infrared photobeams (16×16×16) to measure horizontal and vertical activity. The analysis was configured to divide the open field into a center and periphery zone. Distance traveled was measured from horizontal beam breaks as the mouse moved whereas rearing activity was measured from vertical beam breaks.

Mice were injected with vehicle, test compound, or clozapine (1 mg/kg; i.p) and placed in the OF chambers for 30 min measurement of baseline activity. Mice were then injected with either water or PCP (5 mg/kg; i.p) and placed back in the OF chambers for a 60-minute session. At the end of each OF test session the OF chambers were thoroughly cleaned.

Prepulse Inhibition of Startle: The acoustic startle is an unconditioned reflex response to an external auditory stimulus. Prepulse inhibition of startle (PPI) refers to the reduction in the startle response caused by the presentation of a low-intensity auditory stimulus prior to the startle stimulus. The PPI paradigm is used for the study of schizophrenia and antipsychotic action due to the similarities between the results from human and rodent studies. PPI has been used as a tool for the assessment of deficiencies in sensory-motor gating observed in schizophrenia and to screen for potential antipsychotic drugs. Various psychotomimetic drugs such as PCP can disrupt PPI. In mice, antipsychotic drugs such as clozapine can reverse the disruption of PPI induced by PCP.

Mice were placed in the PPI chambers (Med Associates) for a 5 min session of white noise (70 dB) habituation. After the habituation period the test session was initiated. The session started with a habituation block of 6 presentations of the startle stimulus alone, followed by 10 PPI blocks, each of which consisted of 6 different types of trials. Trial types were: 'null' (no stimuli), 'startle' (120 dB), 'startle plus prepulse' (4, 8 and 12 dB over background noise, i.e., 74, 78 or 82 dB) and 'prepulse' (82 dB). Trial types were presented in a random order within each block. Each trial started with a 50 ms stimulus-free period during which baseline movements were recorded. This was followed by a subsequent 20 ms period during which the prepulse stimulus was presented and responses to the prepulse measured. After a further 100 ms period, the startle stimulus was presented for 40 ms and responses recorded for 100 ms from startle onset. Responses were sampled every ms. The inter-trial interval was variable with an average of 15 s (range from 10 to 20 s). In 'startle' trials the basic auditory startle response was measured. The basic startle response was calculated as the mean startle response of all 'startle' trials (i.e., excluding the first habituation block). In 'startle plus prepulse' trials the degree of inhibition of the normal startle was calculated and expressed as a percentage of the basic startle response.

Mice were treated with vehicle, haloperidol (1 mg/kg; i.p) or test compound 30 min prior to PPI test. The PPI enclosures were cleaned following each test.

TABLE 6A

Effects of Compounds on Pre-pulse Inhibition (PPI) in Mice

| Compound/Doses | Effect |
|---|---|
| Compound 5 | |
| 10 mg/kg | − |
| 30 mg/kg | +++ |
| 100 mg/kg | +++ |
| Compound 58 | |
| 10 mg/kg | +++ |
| 30 mg/kg | + |
| 100 mg/kg | +++ |
| Compound 57 | |
| 10 mg/kg | − |
| 30 mg/kg | − |
| 100 mg/kg | ++ |
| Compound 4 | |
| 10 mg/kg | +++ |
| 30 mg/kg | − |
| 100 mg/kg | +++ |
| Compound 27 | |
| 10 mg/kg | − |
| 30 mg/kg | − |
| 100 mg/kg | − |
| Compound 28 | |
| 10 mg/kg | − |
| 30 mg/kg | +++ |
| 100 mg/kg | +++ |
| Compound 1 | |
| 10 mg/kg | − |
| 30 mg/kg | +++ |
| 100 mg/kg | +++ |
| Compound 2 | |
| 10 mg/kg | − |
| 30 mg/kg | − |
| 100 mg/kg | +++ |
| Compound 3 | |
| 10 mg/kg | +++ |
| 30 mg/kg | +++ |
| 100 mg/kg | − |

TABLE 6A-continued

Effects of Compounds on Pre-pulse Inhibition (PPI) in Mice

| Compound/Doses | Effect |
|---|---|
| Compound 10 | |
| 10 mg/kg | +++ |
| 30 mg/kg | +++ |
| 100 mg/kg | +++ |
| Compound 75 | |
| 10 mg/kg | − |
| 30 mg/kg | − |
| 100 mg/kg | − |
| Compound 76 | |
| 10 mg/kg | − |
| 30 mg/kg | − |
| 100 mg/kg | − |
| Compound 13 | |
| 10 mg/kg | − |
| 30 mg/kg | − |
| 100 mg/kg | +++ |
| Compound 140 | |
| 10 mg/kg | − |
| 30 mg/kg | − |
| 100 mg/kg | − |
| Compound 78 | |
| 10 mg/kg | − |
| 30 mg/kg | − |
| 100 mg/kg | − |
| Compound 158 | |
| 3 mg/kg | − |
| 10 mg/kg | − |
| 30 mg/kg | − |
| 100 mg/kg | +++ |
| Compound 130 | |
| 3 mg/kg | − |
| 10 mg/kg | − |
| 30 mg/kg | − |
| Compound 131 | |
| 3 mg/kg | − |
| 10 mg/kg | − |
| 30 mg/kg | − |
| Compound 171 | |
| 3 mg/kg | − |
| 10 mg/kg | − |
| 30 mg/kg | − |
| 100 mg/kg | +++ |
| Compound 172 | |
| 3 mg/kg | − |
| 10 mg/kg | − |
| 30 mg/kg | − |
| 100 mg/kg | − |
| Compound 129 | |
| 3 mg/kg | +++ |
| 10 mg/kg | +++ |
| 30 mg/kg | +++ |
| Compound 310 | |
| 3 mg/kg | − |
| 10 mg/kg | − |
| 30 mg/kg | +++ |
| Compound 205 | |
| 3 mg/kg | − |
| 10 mg/kg | − |
| 30 mg/kg | +++ |

TABLE 6A-continued

Effects of Compounds on Pre-pulse Inhibition (PPI) in Mice

| Compound/Doses | Effect |
|---|---|
| Compound 311 | |
| 3 mg/kg | − |
| 10 mg/kg | − |
| 30 mg/kg | +++ |
| Compound 213 | |
| 3 mg/kg | − |
| 10 mg/kg | +++ |
| 30 mg/kg | +++ |
| Compound 170 | |
| 3 mg/kg | − |
| 10 mg/kg | +++ |
| 30 mg/kg | +++ |
| Compound 242 | |
| 3 mg/kg | − |
| 10 mg/kg | − |
| 30 mg/kg | − |
| Compound 127 | |
| 3 mg/kg | +++ |
| 10 mg/kg | − |
| 30 mg/kg | +++ |
| Compound 102 | |
| 3 mg/kg | − |
| 10 mg/kg | − |
| 30 mg/kg | − |

*$P < 0.05$ vs. vehicle
−: No change in PPI
+: Significant increase in PPI at one pre-pulse intensity (P value < 0.05)
++: Significant increase in PPI at two pre-pulse intensities (P value < 0.05)
+++: Significant increase in PPI at three pre-pulse intensities (P value < 0.05)

TABLE 6B

Effects of Compounds on PCP-Induced Hyperactivity Responses in Mice

| Compound/Doses | Total Distance Traveled (cm) |
|---|---|
| Compound 4 | |
| 0.3 mg/kg Compound + PCP | + |
| 1 mg/kg Compound + PCP | + |
| 3 mg/kg Compound + PCP | + |
| 10 mg/kg Compound + PCP | + |
| 30 mg/kg Compound + PCP | + |
| 100 mg/kg Compound + PCP | + |
| Compound 27 | |
| 0.3 mg/kg Compound + PCP | − |
| 1 mg/kg Compound + PCP | − |
| 3 mg/kg Compound + PCP | − |
| 10 mg/kg Compound + PCP | + |
| 30 mg/kg Compound + PCP | + |
| 100 mg/kg Compound + PCP | + |
| Compound 28 | |
| 0.3 mg/kg Compound + PCP | + |
| 1 mg/kg Compound + PCP | + |
| 3 mg/kg Compound + PCP | + |
| 10 mg/kg Compound + PCP | + |
| 30 mg/kg Compound + PCP | + |
| 100 mg/kg Compound + PCP | + |
| Compound 2 | |
| 10 mg/kg Compound + PCP | + |
| 30 mg/kg Compound + PCP | + |
| 100 mg/kg Compound + PCP | − |

TABLE 6B-continued

Effects of Compounds on PCP-Induced Hyperactivity Responses in Mice

| Compound/Doses | Total Distance Traveled (cm) |
|---|---|
| Compound 3 | |
| 10 mg/kg Compound + PCP | − |
| 30 mg/kg Compound + PCP | − |
| 100 mg/kg Compound + PCP | − |
| Compound 1 | |
| 10 mg/kg Compound + PCP | + |
| 30 mg/kg Compound + PCP | + |
| 100 mg/kg Compound + PCP | − |
| Compound 5 | |
| 10 mg/kg Compound + PCP | + |
| 30 mg/kg Compound + PCP | + |
| 100 mg/kg Compound + PCP | + |
| Compound 57 | |
| 10 mg/kg Compound + PCP | + |
| 30 mg/kg Compound + PCP | + |
| 100 mg/kg Compound + PCP | + |
| Compound 58 | |
| 10 mg/kg Compound + PCP | + |
| 30 mg/kg Compound + PCP | + |
| 100 mg/kg Compound + PCP | + |
| Compound 10 | |
| 10 mg/kg Compound + PCP | + |
| 30 mg/kg Compound + PCP | + |
| 100 mg/kg Compound + PCP | + |
| Compound 75 | |
| 10 mg/kg Compound + PCP | + |
| 30 mg/kg Compound + PCP | − |
| 100 mg/kg Compound + PCP | + |
| Compound 76 | |
| 10 mg/kg Compound + PCP | − |
| 30 mg/kg Compound + PCP | − |
| 100 mg/kg Compound + PCP | + |
| Compound 140 | |
| 10 mg/kg Compound + PCP | − |
| 30 mg/kg Compound + PCP | − |
| 100 mg/kg Compound + PCP | + |
| Compound 78 | |
| 10 mg/kg Compound + PCP | + |
| 30 mg/kg Compound + PCP | + |
| 100 mg/kg Compound + PCP | + |
| Compound 129 | |
| 0.3 mg/kg Compound + PCP | + |
| 1 mg/kg Compound + PCP | + |
| 3 mg/kg Compound + PCP | + |
| 10 mg/kg Compound + PCP | + |
| 30 mg/kg Compound + PCP | + |
| 100 mg/kg Compound + PCP | + |
| Compound 130 | |
| 0.3 mg/kg Compound + PCP | − |
| 1 mg/kg Compound + PCP | − |
| 3 mg/kg Compound + PCP | + |
| 10 mg/kg Compound + PCP | + |
| 30 mg/kg Compound + PCP | + |
| 100 mg/kg Compound + PCP | + |
| Compound 119 | |
| 10 mg/kg Compound + PCP | + |
| 30 mg/kg Compound + PCP | + |
| 100 mg/kg Compound + PCP | + |
| Compound 158 | |
| 1 mg/kg Compound + PCP | + |
| 3 mg/kg Compound + PCP | + |
| 10 mg/kg Compound + PCP | + |
| 30 mg/kg Compound + PCP | + |
| 100 mg/kg Compound + PCP | + |
| Compound 131 | |
| 0.3 mg/kg Compound + PCP | − |
| 1 mg/kg Compound + PCP | + |
| 3 mg/kg Compound + PCP | + |
| Compound 171 | |
| 0.3 mg/kg Compound + PCP | − |
| 1 mg/kg Compound + PCP | − |
| 3 mg/kg Compound + PCP | − |
| 10 mg/kg Compound + PCP | − |
| 30 mg/kg Compound + PCP | + |
| Compound 172 | |
| 0.3 mg/kg Compound + PCP | − |
| 1 mg/kg Compound + PCP | + |
| 3 mg/kg Compound + PCP | + |
| 10 mg/kg Compound + PCP | − |
| 30 mg/kg Compound + PCP | − |
| Compound 127 | |
| 0.3 mg/kg Compound + PCP | − |
| 1 mg/kg Compound + PCP | − |
| 3 mg/kg Compound + PCP | + |
| 10 mg/kg Compound + PCP | + |
| 30 mg/kg Compound + PCP | − |
| Compound 310 | |
| 0.3 mg/kg Compound + PCP | + |
| 1 mg/kg Compound + PCP | − |
| 3 mg/kg Compound + PCP | − |
| 10 mg/kg Compound + PCP | + |
| 30 mg/kg Compound + PCP | + |
| Compound 311 | |
| 0.3 mg/kg Compound + PCP | − |
| 1 mg/kg Compound + PCP | + |
| 3 mg/kg Compound + PCP | + |
| 10 mg/kg Compound + PCP | + |
| 30 mg/kg Compound + PCP | + |
| Compound 205 | |
| 0.3 mg/kg Compound + PCP | + |
| 1 mg/kg Compound + PCP | + |
| 3 mg/kg Compound + PCP | + |
| 10 mg/kg Compound + PCP | + |
| 30 mg/kg Compound + PCP | + |
| Compound 213 | |
| 0.3 mg/kg Compound + PCP | + |
| 1 mg/kg Compound + PCP | + |
| 3 mg/kg Compound + PCP | + |
| 10 mg/kg Compound + PCP | + |
| 30 mg/kg Compound + PCP | + |
| Compound 170 | |
| 0.3 mg/kg Compound + PCP | − |
| 1 mg/kg Compound + PCP | − |
| 3 mg/kg Compound + PCP | − |
| 10 mg/kg Compound + PCP | − |
| 30 mg/kg Compound + PCP | − |
| Compound 242 | |
| 0.3 mg/kg Compound + PCP | − |
| 1 mg/kg Compound + PCP | + |
| 3 mg/kg Compound + PCP | + |
| 10 mg/kg Compound + PCP | + |
| 30 mg/kg Compound + PCP | + |
| Compound 102 | |
| 0.3 mg/kg Compound + PCP | − |
| 1 mg/kg Compound + PCP | + |
| 3 mg/kg Compound + PCP | + |

(Compound 158 continued:)
| 30 mg/kg Compound + PCP | + |
| 100 mg/kg Compound + PCP | + |

TABLE 6B-continued

Effects of Compounds on PCP-Induced Hyperactivity Responses in Mice

| Compound/Doses | Total Distance Traveled (cm) |
|---|---|
| 10 mg/kg Compound + PCP | + |
| 30 mg/kg Compound + PCP | + |

*P < 0.05 vs. vehicle + PCP
−: No inhibition of PCP hyperactivity
+: Significant inhibition of PCP hyperactivity (P value < 0.05)

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure and are encompassed by the appended claims.

All of the patents, patent applications and publications referred to herein are incorporated by reference herein in their entireties. Citation or identification of any reference in this application is not an admission that such reference is available as prior art to this application. The full scope of the disclosure is better understood with reference to the appended claims.

What is claimed:

1. A method for treating a subject having prominently negative symptoms of schizophrenia comprising administering to the subject a therapeutically effective amount of the compound

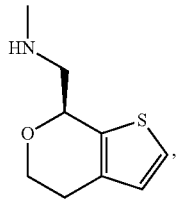

or a pharmaceutically acceptable salt thereof, for four weeks to a subject in need thereof, wherein the subject experiences a decrease in negative PANSS score after four weeks of administration.

2. The method of claim 1, wherein the method further comprises a step of determining if a subject exhibits prominently negative symptoms by:
   (a) transforming baseline PANSS factor scores for the subject using a score matrix in accord with Table 4A;
   (b) determining transformed PANSS symptom domain scores;
   (c) comparing the transformed PANSS symptom domain scores and determining that the subject exhibits prominently negative symptoms if the transformed PANSS negative domain score is the highest transformed PANSS symptom domain score.

3. The method of claim 1, wherein the method further comprises a step of determining if a subject exhibits prominently negative symptoms by:
   (a) transforming baseline PANSS factor scores for the subject using a score matrix in accord with Table 4A;
   (b) determining transformed PANSS symptom domain scores;
   (c) determining a subject has prominently negative symptoms by comparing the transformed PANSS symptom domain scores to a score associated with a prominent negative symptom sub-population.

4. The method of claim 1, wherein the therapeutically effective amount is an amount between about 10 mg and about 300 mg.

5. The method of claim 1, wherein the therapeutically effective amount is an amount between about 20 mg and about 250 mg.

6. The method of claim 1, wherein the therapeutically effective amount is an amount between about 10 mg and about 100 mg.

7. The method of claim 1, wherein the therapeutically effective amount is an amount between about 25 mg and about 50 mg.

8. The method of claim 1, wherein the therapeutically effective amount is provided as a once daily dose.

9. The method of claim 1, further comprising administering to the subject a therapeutically effective amount of a pharmaceutical composition comprising the compound

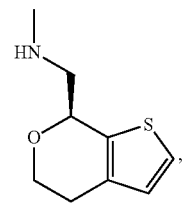

or a pharmaceutically acceptable salt thereof, and a pharmaceutically acceptable excipient or carrier.

10. A method for treating schizophrenia comprising administering a therapeutically effective amount of a compound

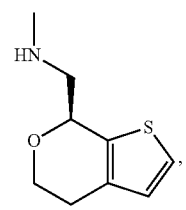

or a pharmaceutically acceptable salt thereof, for four weeks to a subject in need thereof, wherein the subject experiences a decrease in negative PANSS score after four weeks of administration.

11. The method of claim 10, wherein the negative PANSS score is determined by negative PANSS factors N01 Blunted Affect, N02 Emotional Withdrawal, N03 Poor Rapport, N04 Passive/Apathetic Social Withdrawal, N05 Difficulty in Abstract Thinking, N06 Lack of Spontaneity and Flow of Conversation, and N07 Stereotyped Thinking.

12. The method of claim 10, wherein the subject experiences a decrease of at least 10% from baseline in negative PANSS score after four weeks of administration.

13. The method of claim 12, wherein the subject experiences a decrease of at least 20% from baseline in negative PANSS score after four weeks of administration.

14. A method for treating schizophrenia comprising administering a therapeutically effective amount of a compound

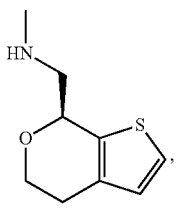

or a pharmaceutically acceptable salt thereof, for four weeks to a subject in need thereof, wherein the subject experiences a decrease in negative symptoms, cognitive dysfunction symptoms, or both, associated with schizophrenia after four weeks of administration.

15. The method of any one of claims 10-14 wherein the compound is administered once daily.

16. The method of any one of claims 10-14 wherein the compound is orally administered once daily.

17. The method of any one of claims 10-14 wherein the therapeutically effective amount is from about 10 mg to about 300 mg per day.

18. The method of any one of claims 10-14 wherein the therapeutically effective amount is from about 20 mg to about 250 mg per day.

19. The method of any one of claims 10-14 wherein the therapeutically effective amount is from about 10 mg to about 100 mg per day.

20. The method of any one of claims 10-14 wherein the compound is a hydrochloride salt of

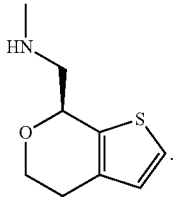

21. The method of any one of claims 10-14 further comprising administering a pharmaceutical composition comprising a therapeutically effective amount of the compound

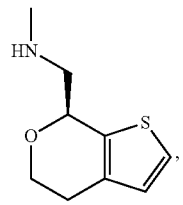

or a pharmaceutically acceptable salt thereof, and one or more pharmaceutically acceptable excipient or carrier.

22. The method of any one of claims 10-14 further comprising administering a pharmaceutical composition comprising a therapeutically effective amount of the compound

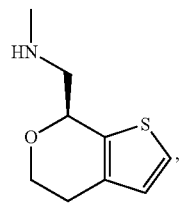

or a pharmaceutically acceptable salt thereof, one or more pharmaceutically acceptable excipient or carrier, and a second active agent.

\* \* \* \* \*